US011051498B2

(12) United States Patent
Murphy et al.

(10) Patent No.: US 11,051,498 B2
(45) Date of Patent: Jul. 6, 2021

(54) MOUSE HAVING AN ENGINEERED IMMUNOGLOBULIN LAMBDA LIGHT CHAIN

(71) Applicant: Regeneron Pharmaceuticals, Inc., Tarrytown, NY (US)

(72) Inventors: Andrew J. Murphy, Croton-on-Hudson, NY (US); Lynn Macdonald, Harrison, NY (US); Chunguang Guo, Thornwood, NY (US); John McWhirter, Hastings-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 16/209,820

(22) Filed: Dec. 4, 2018

(65) Prior Publication Data

US 2019/0223418 A1      Jul. 25, 2019

Related U.S. Application Data

(60) Provisional application No. 62/609,251, filed on Dec. 21, 2017, provisional application No. 62/609,241, filed on Dec. 21, 2017, provisional application No. 62/594,944, filed on Dec. 5, 2017, provisional application No. 62/594,946, filed on Dec. 5, 2017.

(51) Int. Cl.
| | | |
|---|---|---|
| *A01K 67/027* | (2006.01) | |
| *C07K 16/00* | (2006.01) | |
| *C07K 16/46* | (2006.01) | |
| *C12N 9/12* | (2006.01) | |

(52) U.S. Cl.
CPC ......... *A01K 67/0278* (2013.01); *C07K 16/00* (2013.01); *C07K 16/461* (2013.01); *C07K 16/462* (2013.01); *C12N 9/1264* (2013.01); *A01K 2207/15* (2013.01); *A01K 2217/052* (2013.01); *A01K 2217/072* (2013.01); *A01K 2217/15* (2013.01); *A01K 2227/105* (2013.01); *A01K 2267/01* (2013.01); *C07K 2317/10* (2013.01); *C07K 2317/14* (2013.01); *C07K 2317/21* (2013.01); *C07K 2317/24* (2013.01); *C07K 2317/515* (2013.01)

(58) Field of Classification Search
CPC ......... A01K 67/0278; A01K 2217/072; A01K 2217/052; A01K 2227/105; A01K 2267/01; A01K 2217/15; C07K 16/00; C07K 16/462; C07K 2317/10; C12N 9/1264
See application file for complete search history.

(56) References Cited

U.S. PATENT DOCUMENTS

| | | | |
|---|---|---|---|
| 5,670,356 A | 9/1997 | Sherf et al. | |
| 5,874,304 A | 2/1999 | Zolotukhin et al. | |
| 6,300,129 B1 | 10/2001 | Lonberg et al. | |
| 6,586,251 B2 | 7/2003 | Economides et al. | |
| 6,596,541 B2 | 7/2003 | Murphy et al. | |
| 6,998,514 B2 * | 2/2006 | Bruggemann ..... | A01K 67/0278 435/320.1 |
| 7,105,348 B2 * | 9/2006 | Murphy ............. | A01K 67/0275 435/440 |
| 7,435,871 B2 | 10/2008 | Green et al. | |
| 7,582,298 B2 | 9/2009 | Stevens et al. | |
| 8,502,018 B2 | 8/2013 | Murphy et al. | |
| 8,642,835 B2 | 2/2014 | MacDonald et al. | |
| 8,697,940 B2 | 4/2014 | Macdonald et al. | |
| 8,791,323 B2 | 7/2014 | Murphy et al. | |
| 9,006,511 B2 | 4/2015 | Macdonald et al. | |
| 9,012,717 B2 | 4/2015 | Macdonald et al. | |
| 9,029,628 B2 | 5/2015 | Macdonald et al. | |
| 9,035,128 B2 | 5/2015 | MacDonald et al. | |
| 9,066,502 B2 | 6/2015 | Macdonald et al. | |
| 9,150,662 B2 | 10/2015 | Macdonald et al. | |
| 9,163,092 B2 | 10/2015 | Macdonald et al. | |
| 9,738,897 B2 | 8/2017 | Schoenherr et al. | |

(Continued)

FOREIGN PATENT DOCUMENTS

| | | |
|---|---|---|
| EP | 3051942 A2 | 8/2016 |
| WO | WO-2002/036789 A2 | 5/2002 |

(Continued)

OTHER PUBLICATIONS

Munoz et al. Stem Cell Rev. and Rep., vol. 5, 6-9 (Year: 2009).*
Tong et al. Nature, vol. 467(7312), 211-213 (Year: 2010).*
Et al. Amyotroph Lateral Scler. 12(2):79-86, pp. 1-8 (Year: 2011).*
Butler, Rev Scientifique et al Technique Office International Des Epizooties. 17, 1,43-70 (Year: 1998).*
Rougeon et al The Journal of Immunology, 158, 715-723 (Year: 1997).*

(Continued)

*Primary Examiner* — Anoop K Singh
(74) *Attorney, Agent, or Firm* — Choate, Hall & Stewart LLP; Stephanie L. Schonewald; Meaghan E. Bychowski

(57) ABSTRACT

Non-human animals (and/or non-human cells) and methods of using the same are provided, which non-human animals (and/or non-human cells) have a genome comprising human antibody-encoding sequences (i.e., immunoglobulin genes). Non-human animals described herein express antibodies that contain immunoglobulin (Ig) light chains characterized by the presence of human Vλ domains. Non-human animals provided herein are, in some embodiments, characterized by expression of antibodies that contain human Vλ light chains that are encoded by human Igλ light chain-encoding sequences inserted into an endogenous Igκ light chain locus of said non-human animals. Methods for producing antibodies from non-human animals are also provided, which antibodies contain human variable regions and mouse constant regions.

14 Claims, 24 Drawing Sheets

Specification includes a Sequence Listing.

(56) References Cited

U.S. PATENT DOCUMENTS

| | | |
|---|---|---|
| 2002/0088016 A1 | 7/2002 | Bruggemann |
| 2003/0217373 A1 | 11/2003 | Green et al. |
| 2007/0280945 A1 | 12/2007 | Stevens et al. |
| 2011/0236378 A1 | 9/2011 | Green et al. |
| 2013/0096287 A1 | 4/2013 | Macdonald et al. |
| 2014/0235933 A1 | 8/2014 | Lee et al. |
| 2014/0310828 A1 | 10/2014 | Lee et al. |
| 2015/0376628 A1 | 12/2015 | Schoenherr et al. |
| 2016/0145646 A1 | 5/2016 | Frendewey et al. |
| 2016/0177339 A1 | 6/2016 | Voronina et al. |
| 2017/0204430 A1 | 7/2017 | Lee et al. |

FOREIGN PATENT DOCUMENTS

| | | | | |
|---|---|---|---|---|
| WO | WO-02/066630 A1 | | 8/2002 | |
| WO | WO-02066630 A1 | * | 8/2002 | ......... A01K 67/0275 |
| WO | WO-2011/004192 A1 | | 1/2011 | |
| WO | WO-2013/096142 A1 | | 6/2013 | |
| WO | WO-2013096142 A1 | * | 6/2013 | ......... A01K 67/0278 |
| WO | WO-2013/116609 A1 | | 8/2013 | |
| WO | WO-2013116609 A1 | * | 8/2013 | ......... A01K 67/0278 |
| WO | WO-2015/049517 A2 | | 4/2015 | |
| WO | WO-2015049517 A2 | * | 4/2015 | ......... A01K 67/0278 |
| WO | WO-2017/210586 A1 | | 12/2017 | |
| WO | WO-2019/113065 A1 | | 6/2019 | |

OTHER PUBLICATIONS

Montano and Morrison J Immunology, 168:224-231 (Year: 2002).*
Bentolila, L.A. et al., Constitutive expression of terminal Constitutive Expression of Terminal Deoxynucleotidyl Transferase in Transgenic Mice is Sufficient for N Region Diversity to Occur at Any Ig locus Throughout B Cell Differentiation, The Journal of Immunology, 158(2):715-723 (1997).
International Search Report for PCT/US2018/063841 (Non-Human Animals Having an Engineered Immunoglobulin Lambda Light Chain and Uses Thereof, filed Dec. 4, 2018), issued by ISA/EP, 9 pages (Mar. 1, 2019).
Written Opinion for PCT/US2018/063841 (Non-Human Animals Having an Engineered Immunoglobulin Lambda Light Chain and Uses Thereof, filed Dec. 4, 2018), issued by ISA/EP, 9 pages (Mar. 1, 2019).
Altschul, S.F. and Gish, W., Local alignment statistics. Methods Enzymol, 266:460-80 (1996).
Altschul, S.F. et al., Basic local alignment search tool, J Mol Biol, 215(3):403-10 (1990).
Altschul, S.F. et al., Gapped BLAST and PSI-BLAST: a new generation of protein database search programs, Nucleic Acids Res, 25(17):3389-402 (1997).
Araki, K. et al., Site-specific recombination of a transgene in fertilized eggs by transient expression of Cre recombinase, Proc Natl Acad Sci USA, 92(1):160-4 (1995).
Auerbach, W. et al., Establishment and chimera analysis of 129/SvEv- and C57BL/6-derived mouse embryonic stem cell lines, Biotechniques, 29(5):1024-8, 1030, 1032 (2000).
Azzazy, H.M. and Highsmith, W.E. Jr., Phage display technology: clinical applications and recent innovations, Clin Biochem, 35(6):425-45 (2002).
Brüggemann, M. et al., A repertoire of monoclonal antibodies with human heavy chains from transgenic mice, Proc. Natl. Acad. Sci. USA, 86: 6709-6713, 1989.
Brüggemann, M. et al., Human antibody production in transgenic mice: expression from 100 kb of the human IgH locus, Eur J Immunol, 21(5):1323-1326 (1991).
Brüggeman, M. et al., Human antibody production in transgenic animals, Arch Immunol Ther Exp (Warsz), 63(2):101-8 (2015).
Davies, N. et al., Creation of Mice Expressing Human Antibody Light Chains by Introduction of a Yeast Artificial Chromosome Containing the Core Region of the Human Immunoglobulin κ Locus, Nature Biotechnology 11:911-914, (1993).
Dechiara, T.M. et al., Producing fully ES cell-derived mice from eight-cell stage embryo injections, Methods Enzymol, 476:285-94 (2010).
Dechiara, T.M. et al., VelociMouse: fully ES cell-derived F0-generation mice obtained from the injection of ES cells into eight-cell-stage embryos, Methods Mol Biol, 530:311-24 (2009).
Dymecki, S.M., Flp recombinase promotes site-specific DNA recombination in embryonic stem cells and transgenic mice, Proc Natl Acad Sci USA, 93(12):6191-6 (1996).
Festing, M.F. et al., Revised nomenclature for strain 129 mice, Mamm Genome, 10(8):836 (1999).
Fishwild, D.M. et al., High-avidity human IgG kappa monoclonal antibodies from a novel strain of minilocus transgenic mice, Nat Biotechnol, 14(7):845-51 (1996).
Frendewey, D. et al., The loss-of-allele assay for ES cell screening and mouse genotyping, Methods Enzymol, 476:295-307 (2010).
Gavilondo, J.V. and Larrick, J.W., Antibody engineering at the millennium, Biotechniques, 29(1):128-32 (2000).
Gibson, D. et al., Chemical Synthesis of the mouse mitochondrial genome, Nature Methods, 7(11):901-903 (2010).
Gibson, D. et al., Enzymatic assembly of DNA molecules up to several hundred kilobses, Nature Methods, 6(5):343-346 (2009).
Gonnett, G.H. et al., Exhaustive matching of the entire protein sequence database, Science, 256(5062):1443-5 (1992).
Green, L. et al., Antigen-specific human monoclonal antibodies from mice engineered with human Ig heavy and light chain YACs, Nature Genetics, 7(1):13-21 (1994).
Green, L. et al., Regulation of B cell development by variable gene complexity in mice reconstituted with human immunoglobulin yeast artificial chromosomes, J. Exp. Med., 188(3):483-495 (1998).
Gu, H. et al., Independent control of immunoglobulin switch recombination at individual switch regions evidenced through Cre-loxP-mediated gene targeting, Cell, 73(6):1155-64 (1993).
Hoogenboom, H.R., Designing and optimizing library selection strategies for generating high-affinity antibodies, Trends Biotechnol, 15(2):62-70 (1997).
Hoogenboon, H.R. and Chames, P., Natural and designer binding sites made by phage display technology, Immunol Today, 21(8):371-8 (2000).
Ignatovich, O. et al., Dominance of intrinsic genetic factors in shaping the human immunoglobulin Vlambda repertoire, J Mol Biol., 294(2):457-65 (1999).
Ignatovich, O. et al., the creation of diversity in the human immunoglobulin V(lambda) repertoire, J Mol Biol., 268(1):69-77 (1997).
Kellermann, S.A. and Green, L.L., Antibody discovery: the use of transgenic mice to generate human monoclonal antibodies for therapeutics, Curr Opin Biotechnol, 13(6):593-7 (2002).
Kim, U.J. et al., Construction and characterization of a human bacterial artificial chromosome library, Genomics, 34(2):213-8 (1996).
Lakso, M. et al., Targeted oncogene activation by site-specific recombination in transgenic mice, Proc Natl Acad Sci USA, 89(14):6232-6 (1992).
Lee, E.G. et al., Complete humanization of the mouse immunoglobulin loci enables efficient therapeutic antibody discovery, Nat Biotechnol, 32(4):356-363 (2014).
Little, M. et al., Of mice and men: hybridoma and recombinant antibodies, Immunol Today, 21(8):364-70 (2000).
Lonberg, N. et al., Antigen-specific Human Antibodies from Mice Comprising Four Distinct Genetic Modifications, Nature, 368:856-859, (1994).
Macdonald, L.E. et al., Precise and in situ genetic humanization of 6 Mb of mouse immunoglobulin genes, Proc Natl Acad Sci USA, 111(14):5147-52 (2014).
Mendez M.J., et al., Functional transplant of megabase human immunoglobulin loci recapitulates human antibody response in mice, Nat Genet. 15(2):146-56 (1997).
Murphy, A.J. et al., Mice with megabase humanization of their immunoglobulin genes generate antibodies as efficiently as normal mice. Proc Natl Acad Sci USA, 111(14):5153-5158 (2014).
Nicholson, I.C. et al., Antibody Repertoires of Four- and Five-Feature Translocus Mice Carrying Human Immunoglobulin Heavy Chain and kappa and lambda light chain Yeast Artificial Chromosomes. Journal of Immunology 163(12):6898-6906 (1999).

(56) References Cited

OTHER PUBLICATIONS

O'Gorman, S. et al., Recombinase-mediated gene activation and site-specific integration in mammalian cells, Science, 251(4999):1351-5 (1991).
Orban, P.C. et al., Tissue- and site-specific Dna recombination in transgenic mice, Proc Natl Acad Sci USA, 89(15):6861-5 (1992).
Osborn, M.J. et al., High-affinity IgG antibodies develop naturally in Ig-knockout rats carrying germline human IgH/IgK/IgA loci bearing the rat CH region, J Immunol, 190(4):1481-90 (2013).
Osoegawa, K. et al., A bacterial artificial chromosome library for sequencing the complete human genome, Genome Res, 11(3):483-96 (2001).
Osoegawa, K. et al., An improved approach for construction of bacterial artificial chromosome libraries, Genomics, 52(1):1-8 (1998).
Popov, A.V. et al., Assembly and extension of yeast artificial chromosomes to build up a large locus, Gene, 177(1-2):195-201 (1996).
Popov, et al., A Human Immunoglobulin I locus is Similarly Well Expressed in Mice and Humans, J. Exp. Med., 189(10):1611-1619 (1999).
Poueymirou, W.T. et al., F0 generation mice fully derived from gene-targeted embryonic stem cells allowing immediate phenotypic analyses, Nat Biotechnol, 25(1):91-9 (2007).
Rajewsky, K. et al., Conditional gene targeting, J Clin Invest, 98(3):600-3 (1996).
Shizuya, H. et al., Cloning and stable maintenance of 300-kilobase-pair fragments of human DNA in *Escherichia coli* using an F-factor-based vector, Proc Natl Acad Sci USA, 89(18):8794-7 (1992).
Swiatek, P.J. and Gridley, T., Perinatal lethality and defects in hindbrain development in mice homozygous for a targeted mutation of the zinc finger gene Krox20, Genes Dev, 7(11):2071-84 (1993).
Taylor L.D. et al., Human immunoglobulin transgenes undergo rearrangement, somatic mutation and class switching in mice that lack endogenous IgM, Int Immunol. 6(4):579-91 (1994).
Taylor, L.D. et al., A Transgenic Mouse that Expresses a Diversity of Human Sequence Heavy and Light Chain Immunoglobulins, Nucleic Acid Research, 20(23):6287-6295 (1992).
Valenzuela, D.M., et al., High-throughput engineering of the mouse genome coupled with high-resolution expression analysis, Nat Biotechnol, 21(6):652-9 (2003).
Wagner S.D. et al., The diversity of antigen-specific monoclonal antibodies from transgenic mice bearing human immunoglobulin gene miniloci, Eur J Immunol. 24(11):2672-81 (1994).
Wagner, S.D. et al., Antibody expression from the core region of the human IgH locus reconstructed in transgenic mice using bacteriophage P1 clones, Genomics, 35(3):405-14 (1996).
Xian, J. et al., Comparison of the Performance of a Plasmid-Based Human Igk Minilocus and Yac-Based Human Igk Transloci for the Production of Human Antibody Repertoires in Transgenic Mice, Transgenics, 2:333-343 (1998).
Glassy, M. et al., Final Oral Progamme, The Twelfth International Conference on Human Antibodies & Hybridomas, 4 pages (May 10-12, 2006).
Glassy, M. et al., Second Circular and Provisional Conference Program, The Twelfth International Conference on Human Antibodies & Hybridomas, 8 pages (May 10-12, 2006).
Karow, Margaret, Making the VelocImmune mouse using Velocigene technology [abstract], Session 5: Molecular biology—II, Human Antibodies, 15:19-28 (2006).
Murphy, Andrew, Making the VelocImmune Mouse Using VelociGene Technology, Human Antibodies & Hybridomas, 31 pages (May 10-12, 2006).
U.S. Appl. No. 13/166,200, filed Jun. 22, 2011 (Granted).
U.S. Appl. No. 14/715,145, filed May 18, 2015 (Granted).
U.S. Appl. No. 14/715,147, filed May 18, 2015 (Granted).
U.S. Appl. No. 14/800,257, filed Jul. 15, 2015 (Granted).
U.S. Appl. No. 13/166,171, filed Jun. 22, 2011 (Granted).
U.S. Appl. No. 13/716,238, filed Dec. 17, 2012 (Granted).
U.S. Appl. No. 13/945,573, filed Jul. 18, 2013 (Granted).
U.S. Appl. No. 13/945,582, filed Jul. 18, 2013 (Granted).
U.S. Appl. No. 13/951,996, filed Jul. 26, 2013 (Granted).
U.S. Appl. No. 14/132,412, filed Dec. 18, 2013 (Granted).
U.S. Appl. No. 14/561,867, filed Dec. 5, 2014 (Granted).
U.S. Appl. No. 14/636,784, filed Mar. 3, 2015 (Granted).
U.S. Appl. No. 14/638,429, filed Mar. 4, 2015 (Granted).
U.S. Appl. No. 14/800,263, filed Jul. 15, 2015 (Granted).
U.S. Appl. No. 14/943,672, filed Nov. 17, 2015 (Granted).
U.S. Appl. No. 14/943,890, filed Nov. 17, 2015 (Granted).
U.S. Appl. No. 14/638,424, filed Jun. 22, 2011 (Granted).
U.S. Appl. No. 15/398,410, filed Jan. 4, 2017 (Granted).
U.S. Appl. No. 15/585,023, filed May 2, 2017 (Granted).
U.S. Appl. No. 15/604,021, filed May 14, 2017 (Granted).
U.S. Appl. No. 15/810,900, filed Nov. 13, 2017 (Granted).
U.S. Appl. No. 15/803,513, filed Nov. 3, 2017 (Pending).
U.S. Appl. No. 16/269,477, filed Feb. 6, 2019 (Abandoned).
U.S. Appl. No. 16/298,308, filed Mar. 11, 2019 (Abandoned).
U.S. Appl. No. 16/729,798, filed Dec. 30, 2019 (Pending).
U.S. Appl. No. 16/729,852, filed Dec. 30, 2019 (Pending).
U.S. Appl. No. 16/788,532, filed Feb. 12, 2020 (Pending).
U.S. Appl. No. 16/769,821, filed Jun. 4, 2020 (Pending).

\* cited by examiner

MOUSE HAVING AN ENGINEERED IMMUNOGLOBULIN LAMBDA LIGHT CHAIN

CROSS REFERENCE TO RELATED APPLICATIONS

This application claims priority to U.S. Provisional Application No. 62/594,944, filed Dec. 5, 2017; U.S. Provisional Application No. 62/594,946, filed Dec. 5, 2017; U.S. Provisional Application No. 62/609,241, filed Dec. 21, 2017; and U.S. Provisional Application No. 62/609,251, filed Dec. 21, 2017; each of which is incorporated herein by reference.

SEQUENCE LISTING

The instant application contains a Sequence Listing, which has been submitted electronically in ASCII format and is hereby incorporated by reference in its entirety. The ASCII copy, created Jul. 30, 2020, is named 2010794-1443_SL.txt, and is 29,403 bytes in size.

BACKGROUND

Human antibodies are the most rapidly growing class of therapeutics. Of the technologies that are currently used for their production, the development of genetically engineered animals (e.g., rodents) engineered with genetic material encoding human antibodies, in whole or in part, has revolutionized the field of human therapeutic monoclonal antibodies for the treatment of various diseases. Still, development of improved in vivo systems for generating human monoclonal antibodies that maximize human antibody repertoires in host genetically engineered animals is needed.

SUMMARY

In some embodiments, the present disclosure provides a rodent, whose germline genome includes:
an engineered endogenous immunoglobulin κ light chain locus including:
(a) one or more human Vλ gene segments,
(b) one or more human Jλ gene segments, and
(c) one or more Cλ genes,
where the one or more human Vλ gene segments and the one or more human Jλ gene segments are operably linked to the one or more Cλ genes, and where the rodent lacks a rodent Cκ gene at the engineered endogenous immunoglobulin κ locus.

In some embodiments, one or more Cλ genes is a Cλ gene. In some embodiments, a Cλ gene is or includes a rodent Cλ gene. In some embodiments, a rodent Cλ gene has a sequence that is at least 80%, at least 85%, at least 90%, at least 95%, at least 98%, or at least 99% identical to a mouse Cλ1, mouse Cλ2 or a mouse Cλ3 gene. In some embodiments, a rodent Cλ gene is or includes a mouse Cλ1 gene. In some embodiments, a rodent Cλ gene is or includes a rat Cλ gene. In some embodiments, a rat Cλ gene has a sequence that is at least at least 80%, at least 85%, at least 90%, at least 95%, at least 98%, or at least 99% identical to a rat Cλ1, rat Cλ2, rat Cλ3 or a rat Cλ4 gene.

In some embodiments, one or more human Vλ gene segments and one or more human Jλ gene segments are in place of one or more rodent Vκ gene segments, one or more rodent Jκ gene segments, or any combination thereof. In some embodiments, one or more human Vλ gene segments and one or more human Jλ gene segments replace one or more rodent Vκ gene segments, one or more rodent Jκ gene segments, or any combination thereof. In some embodiments, one or more human Vλ gene segments and one or more human Jλ gene segments replace all functional rodent Vκ gene segments and/or all functional rodent Jκ gene segments.

In some embodiments, one or more human Vλ gene segments include Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof. In some embodiments, one or more human Vλ gene segments include Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1- 40, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof. In some embodiments, one or more human Vλ gene segments include Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, and Vλ3-1.

In some embodiments, one or more human Jλ gene segments include Jλ1, Jλ2, Jλ3, Jλ6, Jλ7, or any combination thereof. In some embodiments, one or more human Jλ gene segments include Jλ1, Jλ2, Jλ3, Jλ6, and Jλ7.

In some embodiments, an engineered endogenous immunoglobulin κ light chain locus includes one or more human Vλ non-coding sequences, each of which is adjacent to at least one of the one or more human Vλ gene segments, where the one or more human Vλ non-coding sequences naturally appears adjacent to a human Vλ gene segment in an endogenous human immunoglobulin λ light chain locus. For example, referring to FIG. 20, a first exemplary endogenous human Vλ non-coding sequence naturally appears adjacent (and 3') to a Vλ3-12 gene segment in an endogenous human immunoglobulin λ light chain locus. An engineered endogenous immunoglobulin κ light chain locus including the first exemplary endogenous human Vλ non-coding sequence could include that non-coding sequence at a position that is adjacent (and preferably 3') to a Vλ3-12 gene segment in the engineered endogenous immunoglobulin κ light chain locus. An engineered endogenous immunoglobulin κ light chain locus including the first exemplary endogenous human Vλ non-coding sequence could also include that non-coding sequence at a position that is adjacent (and preferably 5') to a Vλ2-11 gene segment in the engineered endogenous immunoglobulin κ light chain locus. In some instances, an engineered endogenous immunoglobulin κ light chain locus including the first exemplary endogenous human Vλ non-coding sequence could also include that non-coding sequence at a position that is adjacent (and preferably 3') to a Vλ3-12 gene segment and adjacent (and preferably 5') to a Vλ2-11 gene segment in the engineered endogenous immunoglobulin κ light chain locus. In some embodiments, each of the one or more human Vλ non-coding sequences is or includes an intron.

In some embodiments, an engineered endogenous immunoglobulin κ light chain locus includes one or more human Jλ non-coding sequences, each of which is adjacent to at least one of the one or more human Jλ gene segments, where the one or more human Jλ non-coding sequences naturally appears adjacent to a human Jλ gene segment in an endogenous human immunoglobulin λ light chain locus. In some embodiments, each of the one or more human Jλ non-coding sequences is or includes an intron. In some embodiments, an engineered endogenous immunoglobulin κ light chain locus includes one or more human Jκ non-coding sequences, each of which is adjacent to at least one of the one or more human Jλ gene segment, where the one or more human Jκ non-coding sequences naturally appears adjacent to a human Jκ gene segment in an endogenous human immunoglobulin κ light chain locus. For example, referring to FIG. 21, a first exemplary endogenous human Jκ non-coding sequence naturally appears in an endogenous human immunoglobulin κ light chain locus. An engineered endogenous immunoglobulin κ light chain locus including the first exemplary endogenous human Jκ non-coding sequence could be a non-coding sequence at a position that is adjacent to a Jλ gene segment (e.g., Jλ1, Jλ2, Jλ3, Jλ6 or Jλ7) in the engineered endogenous immunoglobulin κ light chain locus. In some embodiments, each of the one or more human Jκ non-coding sequences is or includes an intron.

In some embodiments, an engineered endogenous immunoglobulin κ light chain locus includes one or more human Vλ non-coding sequences, where each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the engineered endogenous immunoglobulin κ light chain locus, and where each of the one or more human Vλ non-coding sequences naturally appear adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus. In some embodiments, an engineered endogenous immunoglobulin κ light chain locus includes one or more human Jλ non-coding sequences, where each of the one or more human Jλ non-coding sequences is adjacent to the Jλ1, Jλ2, Jλ3, Jλ6 or Jλ7 in the engineered endogenous immunoglobulin κ light chain locus, and where each of the one or more human Jλ non-coding sequences naturally appear adjacent to a Jλ1, Jλ2, Jλ3, Jλ6 or Jλ7 of an endogenous human immunoglobulin λ light chain locus. In some embodiments, an engineered endogenous immunoglobulin κ light chain locus includes one or more human Jκ non-coding sequences, where each of the one or more human Jκ non-coding sequences is adjacent to the Jλ1, Jλ2, Jλ3, Jλ6 or Jλ7 in the engineered endogenous immunoglobulin κ light chain locus, and where each of the one or more human Jκ non-coding sequences naturally appear adjacent to a Jκ1, Jκ2, Jκ3, Jκ4, or Jκ5 of an endogenous human immunoglobulin κ light chain locus.

In some embodiments, an engineered endogenous immunoglobulin κ light chain locus includes a κ light chain non-coding sequence between the one or more human Vλ gene segments and the one or more human Jλ gene segments. In some embodiments, a κ light chain non-coding sequence is a human κ light chain non-coding sequence. In some embodiments, a human κ light chain non-coding sequence has a sequence that naturally appears between a human Vκ4-1 gene segment and a human Jκ1 gene segment in an endogenous human immunoglobulin κ light chain locus.

In some embodiments, a rodent described herein is homozygous for an engineered endogenous immunoglobulin κ light chain locus. In some embodiments, a rodent described herein is heterozygous for an engineered endogenous immunoglobulin κ light chain locus. In some embodiments, the germline genome of a rodent includes a second engineered endogenous immunoglobulin κ light chain locus that includes:

(a) one or more human Vκ gene segments, and
(b) one or more human Jκ gene segments, where the one or more human Vκ gene segments and the one or more human Jκ gene segments are operably linked to a Cκ gene.

In some embodiments, the genome of the rodent further includes a nucleic acid sequence encoding an exogenous terminal deoxynucleotidyltransferase (TdT) operably linked to a transcriptional control element. In some embodiments, the transcriptional control element includes a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof. In some embodiments, the nucleic acid sequence encoding an exogenous TdT is located at an immunoglobulin κ light chain locus, an immunoglobulin λ light chain locus, an immunoglobulin heavy chain locus, a RAG1 locus, or a RAG2 locus. In some embodiments, a TdT is a human TdT. In some embodiments, a TdT is a short isoform of TdT (TdTS).

In some embodiments, a rodent described herein includes a nucleic acid sequence encoding an exogenous terminal deoxynucleotidyltransferase (TdT) operably linked to a transcriptional control element in its germline genome and exhibits light chains (e.g., expresses light chain variable domains including) with at least a 1.2-fold, at least a 1.5-fold, at least a 1.75-fold, at least a 2-fold, at least a 3-fold, at least a 4-fold, or a least a 5-fold increase in junctional diversity over a comparable mouse (e.g., littermate) that does not include an exogenous terminal deoxynucleotidyltransferase (TdT) operably linked to a transcriptional control element in its germline genome. In some embodiments, junctional diversity is measured by number of unique CDR3/10,000 reads.

In some embodiments, a rodent described herein includes a nucleic acid sequence encoding an exogenous terminal deoxynucleotidyltransferase (TdT) operably linked to a transcriptional control element in its germline genome and at least 25%, at least 30%, at least 35%, at least 40%, at least 45%, at least 50%, at least 55%, at least 60%, at least 65% of light chains (e.g., lambda and/or kappa light chains) produced by the rodent exhibit non-template additions.

In some embodiments, a germline genome of a rodent described herein includes: an engineered endogenous immunoglobulin heavy chain locus, including:

(a) one or more human $V_H$ gene segments,
(b) one or more human $D_H$ gene segments, and
(c) one or more human $J_H$ gene segments, where the one or more human $V_H$ gene segments, the one or more human $D_H$ gene segments, and the one or more human $J_H$ gene segments are operably linked to a rodent immunoglobulin heavy chain constant region at the engineered endogenous immunoglobulin heavy chain locus.

In some embodiments, one or more human $V_H$ gene segments, one or more human $D_H$ gene segments, and one or more human $J_H$ gene segments are in place of one or more rodent $V_H$ gene segments, one or more rodent $D_H$ gene segments, one or more rodent $J_H$ gene segments, or a combination thereof. In some embodiment, one or more human $V_H$ gene segments, one or more human $D_H$ gene segments, and one or more human $J_H$ gene segments replace one or more rodent $V_H$ gene segments, one or more rodent $D_H$ gene segments, one or more rodent $J_H$ gene segments, or any combination thereof.

In some embodiments, one or more human $V_H$ gene segments include $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, or any combination thereof. In some embodiments, one or more human $V_H$ gene segments include $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, and $V_H6$-1.

In some embodiments, one or more human $D_H$ gene segments include $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof. In some embodiments, one or more human $D_H$ gene segments include $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, and $D_H7$-27.

In some embodiments, one or more human $J_H$ gene segments include $J_H1$, $J_H2$, $J_H3$, $J_H4$, $J_H5$, $J_H6$, or any combination thereof. In some embodiments, one or more human $J_H$ gene segments include $J_H1$, $J_H2$, $J_H3$, $J_H4$, $J_H5$, and $J_H6$.

In some embodiments, an engineered endogenous immunoglobulin heavy chain locus includes one or more human $V_H$ non-coding sequences, each of which is adjacent to at least one of the one or more human $V_H$ gene segments, where each of the one or more $V_H$ non-coding sequences naturally appears adjacent to a human $V_H$ gene segment in an endogenous human immunoglobulin heavy chain locus. In some embodiments, each of the one or more human $V_H$ non-coding sequences is or includes an intron. In some embodiments, an engineered endogenous immunoglobulin heavy chain locus includes one or more human $D_H$ non-coding sequences, each of which is adjacent to at least one of the one or more human $D_H$ gene segments, where each of the one or more $D_H$ non-coding sequences naturally appears adjacent to a human $D_H$ gene segment in an endogenous human immunoglobulin heavy chain locus. In some embodiments, each of the one or more human $D_H$ non-coding sequences is or includes an intron. In some embodiments, an engineered endogenous immunoglobulin heavy chain locus includes one or more human $J_H$ non-coding sequences, each of which is adjacent to at least one of the one or more human $J_H$ gene segments, where each of the one or more $J_H$ non-coding sequences naturally appears adjacent to a human $J_H$ gene segment in an endogenous human immunoglobulin heavy chain locus. In some embodiments, each of the one or more human $J_H$ non-coding sequences is or includes an intron.

In some embodiments, a rodent described herein is homozygous for an engineered endogenous immunoglobulin heavy chain locus.

In some embodiments, a rodent immunoglobulin heavy chain constant region is an endogenous rodent immunoglobulin heavy chain constant region.

In some embodiments, endogenous Vλ gene segments, endogenous Jλ gene segments, and the endogenous Cλ genes are deleted in whole or in part. In some embodiments, a rodent described herein does not detectably express endogenous immunoglobulin λ light chain variable domains. In some embodiments, a rodent described herein does not detectably express endogenous immunoglobulin κ light chain variable domains.

In some embodiments, an engineered endogenous immunoglobulin heavy chain locus lacks a functional endogenous rodent Adam6 gene. In some embodiments, a germline genome of a rodent includes one or more nucleotide sequences encoding one or more rodent ADAM6 polypeptides, functional orthologs, functional homologs, or functional fragments thereof. In some embodiments, one or more rodent ADAM6 polypeptides, functional orthologs, functional homologs, or functional fragments thereof are expressed (e.g., in a cell of the male reproductive system, e.g., a testes cell).

In some embodiments, one or more nucleotide sequences encoding one or more rodent ADAM6 polypeptides, functional orthologs, functional homologs, or functional fragments thereof are included on the same chromosome as the engineered endogenous immunoglobulin heavy chain locus. In some embodiments, one or more nucleotide sequences encoding one or more rodent ADAM6 polypeptides, functional orthologs, functional homologs, or functional fragments thereof are included in the engineered endogenous immunoglobulin heavy chain locus. In some embodiments, one or more nucleotide sequences encoding one or more rodent ADAM6 polypeptides, functional orthologs, functional homologs, or functional fragments thereof are between a first human $V_H$ gene segment and a second human $V_H$ gene segment. In some embodiments, a first human $V_H$ gene segment is $V_H1$-2 and a second human $V_H$ gene segment is $V_H6$-1. In some embodiments, one or more nucleotide sequences encoding one or more rodent ADAM6 polypeptides, functional orthologs, functional homologs, or functional fragments thereof are in place of a human Adam6 pseudogene. In some embodiments, one or more nucleotide sequences encoding one or more rodent ADAM6 polypeptides, functional orthologs, functional homologs, or functional fragments thereof replace a human Adam6 pseudogene. In some embodiments, one or more nucleotide sequences encoding one or more rodent ADAM6 polypeptides, functional orthologs, functional homologs, or functional fragments thereof are between a human $V_H$ gene segment and a human $D_H$ gene segment.

In some embodiments, a rodent described herein includes a population of B cells that express antibodies, including immunoglobulin λ light chains that each include a human immunoglobulin λ light chain variable domain. In some embodiments, a human immunoglobulin λ light chain variable domain is encoded by a rearranged human immunoglobulin λ light chain variable region sequence including (i) one of the one or more human Vλ gene segments or a somatically hypermutated variant thereof, and (ii) one of the one or more human Jλ gene segments or a somatically hypermutated variant thereof.

In some embodiments, a rodent described herein includes a population of B cells that express antibodies, including immunoglobulin heavy chains that each include a human immunoglobulin heavy chain variable domain. In some embodiments, a human immunoglobulin heavy chain variable domain is encoded by a rearranged human immunoglobulin heavy chain variable region sequence including (i) one of the one or more human $V_H$ gene segments or a somatically hypermutated variant thereof, (ii) one of the one or more human $D_H$ gene segments or a somatically hypermutated variant thereof, and (ii) one of the one or more human $J_H$ gene segments or a somatically hypermutated variant thereof.

In some embodiments, a rodent described herein produces a population of B cells in response to immunization with an antigen that includes one or more epitopes. In some embodiments, a rodent produces a population of B cells that express antibodies that bind (e.g., specifically bind) to one or more epitopes of antigen of interest. In some embodiments, antibodies expressed by a population of B cells produced in response to an antigen include a heavy chain having a human heavy chain variable domain encoded by a human heavy chain variable region sequence and/or a lambda light chain having a human lambda light chain variable domain encoded by a human lambda light chain variable region sequence as described herein. In some embodiments, antibodies expressed by a population of B cells produced in response to an antigen include a heavy chain having a human heavy chain variable domain encoded by a human heavy chain variable region sequence and/or a kappa light chain having a human kappa light chain variable domain encoded by a human kappa light chain variable region sequence as described herein.

In some embodiments, a rodent produces a population of B cells that express antibodies that bind to one or more epitopes of antigen of interest, where antibodies expressed by the population of B cells produced in response to an antigen include: (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof.

In some embodiments, a human heavy chain variable region sequence, a human λ light chain variable region sequence, and/or a human κ light chain variable region sequence as described herein is somatically hypermutated. In some embodiments, at least about 5%, 10%, 15%, 20%, 25%, 30%, 35%, 40%, 45%, 50%, 55%, 60%, 65%, 70%, 75%, 80%, 85%, 90% of the B cells in a population of B cells produced in response to an antigen include a human heavy chain variable region sequence, λ light chain variable region sequence, and/or κ light chain variable region sequence that is somatically hypermutated.

In some embodiments, a rodent described herein is a mouse or a rat.

In some embodiments, cells and/or tissues provided (e.g., isolated cells and/or tissues) from a rodent are described herein. In some embodiments, provided cells and tissues include, for example, lymphoid tissue, splenocytes, B cells, stem cells and/or germ cells. In some embodiments, a provided cell is isolated. In some embodiments, an isolated cell is or includes a pro B-cell, a pre-B cell, an immature B cell, a mature naïve B cell, an activated B cell, a memory B cell, a B lineage lymphocyte, and/or a plasma cell. In some embodiments, an isolated cell includes a stem cell (e.g., an embryonic stem cell) and/or a germ cell (e.g., sperm, oocyte).

In some embodiments, the present disclosure provides an isolated rodent cell, whose germline genome includes:
an engineered endogenous immunoglobulin κ light chain locus including:
(a) one or more human Vλ gene segments,
(b) one or more human Jλ gene segments, and
(c) a Cλ gene,
where the one or more human Vλ gene segments and the one or more human Jλ gene segments are operably linked to the Cλ gene.

In some embodiments, an isolated rodent cell described herein lacks a rodent Cκ gene at the engineered endogenous immunoglobulin κ locus.

In some embodiments, an isolated rodent cell described herein is a rodent embryonic stem (ES) cell.

In some embodiments, the present disclosure provides a rodent embryo generated from a rodent ES cell described herein.

In some embodiments, the present disclosure provides an immortalized cell generated from an isolated rodent cell described herein.

In some embodiments, the present disclosure provides a method of making a rodent whose germline genome includes an engineered endogenous immunoglobulin κ light chain locus, the method including the steps of:
(a) introducing one or more DNA fragments into the germline genome of a rodent ES cell, where the one or more DNA fragments comprise:
(i) one or more human Vλ gene segments,
(ii) one or more human Jλ gene segments, and
(iii) one or more Cλ genes,
where the one or more human Vλ gene segments, the one or more human Jλ gene segments, and the one or more Cλ genes are introduced into the germline genome of the rodent ES cell at the endogenous immunoglobulin κ light chain locus, and where the one or more human Vλ gene segments, the one or more human Jλ gene segments, and the one or more Cλ genes are operably linked; and
(b) generating a rodent using the rodent ES cell generated in (a).

In some embodiments, a method of making a rodent whose germline genome includes an engineered endogenous immunoglobulin κ light chain locus, includes the step of introducing a κ light chain non-coding sequence into the germline genome of the rodent ES cell so that the κ light chain non-coding sequence is between the one or more human Vλ gene segments and the one or more human Jλ gene segments in the germline genome of the rodent ES cell.

In some embodiments, the present disclosure provides a method of making a rodent whose germline genome includes an engineered endogenous immunoglobulin κ light chain locus, the method including the steps of:
engineering the endogenous immunoglobulin κ light chain locus in the germline genome to include:
(a) one or more human Vλ gene segments,
(b) one or more human Jλ gene segments, and
(c) one or more Cλ genes,
where the one or more human Vλ gene segments and the one or more human Jλ gene segments are operably linked to the one or more Cλ genes, and
where the one or more Cλ genes are inserted in place of a rodent Cκ gene at the endogenous immunoglobulin κ locus.

In some embodiments, a Cλ gene replaces a rodent Cκ gene at the endogenous immunoglobulin κ locus.

In some embodiments, one or more human Vλ gene segments include Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1, or any combination thereof. In some embodiments, one or more human Vλ gene segments include Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, and Vλ3-1. In some embodiments, one or more human Vλ gene segments include Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, and Vλ3-1.

In some embodiments, one or more human Jλ gene segments includes Jλ1, Jλ2, Jλ3, Jλ6, Jλ7, or any combination thereof. In some embodiments, one or more human Jλ gene segments includes Jλ1, Jλ2, Jλ3, Jλ6, and Jλ7.

In some embodiments, an engineered endogenous immunoglobulin κ light chain locus includes one or more human Vλ non-coding sequences, each of which is adjacent to at least one of the one or more human Vλ gene segments, where the one or more human Vλ non-coding sequences naturally appears adjacent to a human Vλ gene segment in an endogenous human immunoglobulin λ light chain locus. In some embodiments, each of the one or more human Vλ non-coding sequences is or includes an intron. In some embodiments, an engineered endogenous immunoglobulin κ light chain locus includes one or more human Jλ non-coding sequences, each of which is adjacent to at least one of the one or more human Jλ gene segment, where the one or more human Jλ non-coding sequences naturally appears adjacent to a human Jλ gene segment in an endogenous human immunoglobulin λ light chain locus. In some embodiments, each of the one or more human Jλ non-coding sequences is or includes an intron. In some embodiments, an engineered endogenous immunoglobulin κ light chain locus includes one or more human Jκ non-coding sequences, each of which is adjacent to at least one of the one or more human Jλ gene segment, where the one or more human Jκ non-coding sequences naturally appears adjacent to a human Jκ gene segment in an endogenous human immunoglobulin κ light chain locus. In some embodiments, each of the one or more human Jκ non-coding sequences is or includes an intron.

In some embodiments, a Cλ gene is or includes a rodent Cλ gene. In some embodiments, a rodent Cλ gene has a sequence that is at least 80%, at least 85%, at least 90%, at least 95%, at least 98%, or at least 99% identical to a mouse Cλ1, mouse Cλ2 or a mouse Cλ3 gene. In some embodiments, a rodent Cλ gene is or includes a mouse Cλ1 gene. In some embodiments, a rodent Cλ gene is or includes a rat Cλ gene. In some embodiments, a rat Cλ gene has a sequence that is at least at least 80%, at least 85%, at least 90%, at least 95%, at least 98%, or at least 99% identical to a rat Cλ1, rat Cλ2, rat Cλ3 or a rat Cλ4 gene.

In some embodiments, one or more DNA fragments include at least one selection marker. In some embodiments, one or more DNA fragments include at least one site-specific recombination site.

In some embodiments, the germline genome of a rodent includes:

an engineered endogenous immunoglobulin heavy chain locus, including:

(a) one or more human $V_H$ gene segments,
(b) one or more human $D_H$ gene segments, and
(c) one or more human $J_H$ gene segments, where the one or more human $V_H$ gene segments, the one or more human $D_H$ gene segments, and the one or more human $J_H$ gene segments are operably linked to a rodent immunoglobulin heavy chain constant region.

In some embodiments, the step of engineering the endogenous immunoglobulin κ light chain locus in the germline genome is carried out in a rodent ES cell whose germline genome includes an engineered endogenous immunoglobulin heavy chain locus including one or more human $V_H$ gene segments, one or more human $D_H$ gene segments, and one or more human $J_H$ gene segments operably linked to a rodent immunoglobulin heavy chain constant region.

In some embodiments, an engineered endogenous immunoglobulin heavy chain locus includes one or more human $V_H$ non-coding sequences, each of which is adjacent to at least one of the one or more human $V_H$ gene segments, where each of the one or more human $V_H$ non-coding sequences naturally appears adjacent to a human $V_H$ gene segment in an endogenous human immunoglobulin heavy chain locus. In some embodiments, each of the one or more human $V_H$ non-coding sequences is or includes an intron. In some embodiments, an engineered endogenous immunoglobulin heavy chain locus includes one or more human $D_H$ non-coding sequences, each of which is adjacent to at least one of the one or more human $D_H$ gene segments, where each of the one or more $D_H$ non-coding sequences naturally appears adjacent to a human $D_H$ gene segment in an endogenous human immunoglobulin heavy chain locus. In some embodiments, each of the one or more human $D_H$ non-coding sequences is or includes an intron. In some embodiments, an engineered endogenous immunoglobulin heavy chain locus includes one or more human $J_H$ non-coding sequences, each of which is adjacent to at least one of the one or more human $J_H$ gene segments, where each of the one or more $J_H$ non-coding sequences naturally appears adjacent to a human $J_H$ gene segment in an endogenous human immunoglobulin heavy chain locus. In some embodiments, each of the one or more human $J_H$ non-coding sequences is or includes an intron.

In some embodiments, the present disclosure provides a method of producing an antibody in a rodent, the method including the steps of:

(i) immunizing a rodent with an antigen of interest, where the rodent has a germline genome including:

an engineered endogenous immunoglobulin κ light chain locus, including:
  (a) one or more human Vλ gene segments,
  (b) one or more human Jλ gene segments, and
  (c) one or more Cλ genes, where the one or more human Vλ gene segments and the one or more human Jλ gene segments are operably linked to the Cλ gene, and where the one or more Cλ genes are in the place of a rodent Cκ gene at the engineered endogenous immunoglobulin κ locus;

maintaining the rodent under conditions sufficient for the rodent to produce an immune response to the antigen of interest; and recovering an antibody that binds the antigen of interest from the rodent, a cell of the rodent, or a cell derived from a cell of the rodent.

In some embodiments, in response to the step of immunizing, a rodent produces a B cell that expresses an antibody that binds the antigen of interest. In some embodiments, an antibody expressed by a B cell includes a heavy chain having a human heavy chain variable domain encoded by a human heavy chain variable region sequence and/or a lambda light chain having a human lambda light chain variable domain encoded by a human lambda light chain variable region sequence as described herein. In some embodiments, an antibody expressed by a B cell includes (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof.

In some embodiments, in response to the step of immunizing, the rodent produces a population of B cells that expresses antibodies that bind an antigen of interest. In some embodiments, antibodies expressed by a population of B cells produced in response to an antigen include a heavy chain having a human heavy chain variable domain encoded by a human heavy chain variable region sequence and/or a lambda light chain having a human lambda light chain variable domain encoded by a human lambda light chain variable region sequence as described herein. In some embodiments, antibodies expressed by a population of B cells produced in response to an antigen include (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof.

In some embodiments, in response to the step of immunizing, a rodent produces a population of B cells that express antibodies that bind to one or more epitopes of antigen of interest, where antibodies expressed by the population of B cells produced in response to an antigen include: (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof.

In some embodiments, a human heavy chain variable region sequence, a human λ light chain variable region sequence, and/or a human κ light chain variable region sequence as described herein is somatically hypermutated. In some embodiments, at least about 5%, 10%, 15%, 20%, 25%, 30%, 35%, 40%, 45%, 50%, 55%, 60%, 65%, 70%, 75%, 80%, 85%, 90% of the B cells in a population of B cells produced in response to an antigen include a human heavy chain variable region sequence, λ light chain variable region sequence, and/or κ light chain variable region sequence that is somatically hypermutated.

In some embodiments, an antibody that binds the antigen of interest is isolated from, recovered from, or identified from a B cell of the rodent. In some embodiments, an antibody that binds an antigen of interest is isolated from, recovered from, or identified from a hybridoma made with a B cell of the rodent.

In some embodiments, an antigen includes one or more epitopes and an antibody that binds an antigen of interest binds to an epitope of the one or more epitopes.

In some embodiments, a Cλ gene is or includes a rodent Cλ gene. In some embodiments, a rodent Cλ gene has a sequence that is at least 80%, at least 85%, at least 90%, at least 95%, at least 98%, or at least 99% identical to a mouse Cλ1, mouse Cλ2 or a mouse Cλ3 gene. In some embodiments, a rodent Cλ gene is or includes a mouse Cλ1 gene. In some embodiments, a rodent Cλ gene is or includes a rat Cλ gene. In some embodiments, a rat Cλ gene has a sequence that is at least at least 80%, at least 85%, at least 90%, at least 95%, at least 98%, or at least 99% identical to a rat Cλ1, rat Cλ2, rat Cλ3 or a rat Cλ4 gene.

In some embodiments, one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1, or any combination thereof. In some embodiments, one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, and Vλ3-1. In some embodiments, one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, and Vλ3-1.

In some embodiments, one or more human Jλ gene segments comprise Jλ1, Jλ2, Jλ3, Jλ6, Jλ7 or any combination thereof. In some embodiments, one or more human Jλ gene segments includes Jλ1, Jλ2, Jλ3, Jλ6, and Jλ7.

In some embodiments, an engineered endogenous immunoglobulin κ light chain locus includes one or more human Vλ non-coding sequences, where each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the engineered endogenous immunoglobulin κ light chain locus, and where each of the one or more human Vλ non-coding sequences naturally appear adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus. In some embodiments, an engineered endogenous immunoglobulin κ light chain locus includes one or more human Jλ non-coding sequences, where each of the one or more human Jλ non-coding sequences is adjacent to the Jλ1, Jλ2, Jλ3, Jλ6 or Jλ7 in the engineered endogenous immunoglobulin κ light chain locus, and where each of the one or more human Jλ non-coding sequences naturally appear adjacent to a Jλ1, Jλ2, Jλ3, Jλ6 or Jλ7 of an endogenous human immunoglobulin λ light chain locus. In some embodiments, an engineered endogenous immunoglobulin κ light chain locus includes one or more human Jκ non-coding sequences, where each of the one or more human Jκ non-coding sequences is adjacent to the Jλ1, Jλ2, Jλ3, Jλ6 or Jλ7 in the engineered endogenous immunoglobulin κ light chain locus, and where each of the one or more human Jκ non-coding sequences naturally appear adjacent to a Jκ1, Jκ2, Jκ3, Jκ4, or Jκ5 of an endogenous human immunoglobulin κ light chain locus.

In some embodiments, a rodent has a germline genome including an engineered endogenous immunoglobulin heavy chain locus including:
(a) one or more human $V_H$ gene segments,
(b) one or more human $D_H$ gene segments, and
(c) one or more human $J_H$ gene segments,
where the one or more human $V_H$ gene segments, the one or more human $D_H$ gene segments, and the one or more human $J_H$ gene segments are operably linked to a rodent immunoglobulin heavy chain constant region.

In some embodiments, one or more human $V_H$ gene segments comprise $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1 or any combination thereof. In some embodiments, one or more human $V_H$ gene segments comprise $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, and $V_H6$-1.

In some embodiments, one or more human $D_H$ gene segments comprise $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof. In some embodiments, one or more human $D_H$ gene segments comprise $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, and $D_H7$-27.

In some embodiments, one or more human $J_H$ gene segments comprise $J_H1$, $J_H2$, $J_H3$, $J_H4$, $J_H5$, $J_H6$, or any combination thereof. In some embodiments, one or more human $J_H$ gene segments comprise $J_H1$, $J_H2$, $J_H3$, $J_H4$, $J_H5$, and $J_H6$.

In some embodiments, an engineered endogenous immunoglobulin heavy chain locus includes one or more human $V_H$ non-coding sequences, where each of the one or more human $V_H$ non-coding sequences is adjacent to the $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2 or $V_H6$-1 in the engineered endogenous immunoglobulin heavy chain locus, and where each of the one or more human $V_H$ non-coding sequences naturally appear adjacent to a $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2 or $V_H6$-1 of an endogenous human immunoglobulin heavy chain locus. In some embodiments, an engineered endogenous immunoglobulin heavy chain locus includes one or more human $D_H$ non-coding sequences, where each of the one or more human $D_H$ non-coding sequences is adjacent to the $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26 or $D_H7$-27 in the engineered endogenous immunoglobulin heavy chain locus, and where each of the one or more human $D_H$ non-coding sequences naturally appear adjacent to a $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26 or $D_H7$-27 of an endogenous human immunoglobulin heavy chain locus. In some embodiments, an engineered endogenous immunoglobulin heavy chain locus includes one or more human $J_H$ non-coding sequences, where each of the one or more human $J_H$ non-coding sequences is adjacent to the $J_H1$, $J_H2$, $J_H3$, $J_H4$, $J_H5$ or $J_H6$ in the engineered endogenous immunoglobulin heavy chain locus, and where each of the one or more human $J_H$ non-coding sequences naturally appear adjacent to a $J_H1$, $J_H2$, $J_H3$, $J_H4$, $J_H5$ or $J_H6$ of an endogenous human immunoglobulin heavy chain locus. In some embodiments, a cell of the rodent that is recovered is a B cell. In some embodiments, a cell derived from a cell of the rodent is a hybridoma.

In some embodiments, a nucleotide sequence that encodes a human heavy chain variable region sequence, a human lambda light chain variable region sequence, and/or a human kappa light chain variable region sequence is obtained from a B cell.

In some embodiments, an engineered endogenous immunoglobulin heavy chain locus lacks a functional endogenous rodent Adam6 gene. In some embodiments, a germline genome of a rodent includes one or more nucleotide sequences encoding one or more rodent ADAM6 polypeptides, functional orthologs, functional homologs, or functional fragments thereof. In some embodiments, one or more rodent ADAM6 polypeptides, functional orthologs, functional homologs, or functional fragments thereof are expressed (e.g., in a cell of the male reproductive system, e.g., a testes cell).

In some embodiments, one or more nucleotide sequences encoding one or more rodent ADAM6 polypeptides, functional orthologs, functional homologs, or functional fragments thereof are included on the same chromosome as the engineered endogenous immunoglobulin heavy chain locus. In some embodiments, one or more nucleotide sequences encoding one or more rodent ADAM6 polypeptides, functional orthologs, functional homologs, or functional fragments thereof are included in the engineered endogenous immunoglobulin heavy chain locus. In some embodiments, one or more nucleotide sequences encoding one or more rodent ADAM6 polypeptides, functional orthologs, functional homologs, or functional fragments thereof are between a first human $V_H$ gene segment and a second human $V_H$ gene segment. In some embodiments, a first human $V_H$ gene segment is $V_H1$-2 and a second human $V_H$ gene segment is $V_H6$-1. In some embodiments, one or more nucleotide sequences encoding one or more rodent ADAM6 polypeptides, functional orthologs, functional homologs, or functional fragments thereof are in place of a human Adam6 pseudogene. In some embodiments, one or more nucleotide sequences encoding one or more rodent ADAM6 polypeptides, functional orthologs, functional homologs, or functional fragments thereof replace a human Adam6 pseudogene. In some embodiments, one or more nucleotide sequences encoding one or more rodent ADAM6 polypeptides, functional orthologs, functional homologs, or functional fragments thereof are between a human $V_H$ gene segment and a human $D_H$ gene segment.

In some embodiments, a rodent is a mouse or a rat.

In some embodiments, the present disclosure provides a rodent whose germline genome includes a homozygous engineered endogenous immunoglobulin κ light chain locus including:

(i) one or more human Vλ gene segments, where the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1, or any combination thereof, (ii) one or more human Jλ gene segments, where the one or more human Jλ gene segments comprise Jλ1, Jλ2, Jλ3, Jλ6, Jλ7, or any combination thereof, and (iii) a rodent Cλ gene;

where the one or more human Vλ gene segments, the one or more human Jλ gene segments, and the rodent Cλ gene are operably linked to each other, where the rodent Cλ gene is in place of a rodent Cκ gene of the endogenous immunoglobulin κ light chain locus, where the engineered endogenous immunoglobulin κ light chain locus includes:

(a) one or more human Vλ non-coding sequences, where each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the engineered endogenous immunoglobulin κ light chain locus, and where each of the one or more human Vλ non-coding sequences naturally appear adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus, and (b) one or more human Jκ non-coding sequences, where each of the one or more human Jκ non-coding sequences is adjacent to the Jλ1, Jλ2, Jλ3, Jλ6, or Jλ7 in the engineered endogenous immunoglobulin κ light chain locus, and where each of the one or more human Jκ non-coding sequences naturally appear adjacent to a Jκ1, Jκ2, Jκ3, Jκ4, or Jκ5 of an endogenous human immunoglobulin κ light chain locus, and where the immunoglobulin κ light chain locus includes a human κ light chain non-coding sequence between the one or more human Vλ gene segments and the one or more human Jλ gene segments that has a sequence that naturally appears between a human Vκ4-1 gene segment and a human Jκ1 gene segment in an endogenous human immunoglobulin κ light chain locus.

In some embodiments, a rodent Cλ gene is a mouse Cλ1 gene.

In some embodiments, an engineered endogenous immunoglobulin κ light chain locus includes rodent immunoglobulin κ light chain enhancers Eκ$_i$ and Eκ3'.

In some embodiments, an engineered endogenous immunoglobulin κ light chain locus includes a deletion of one or more rodent Vκ gene segments and/or one or more Jκ gene segments. In some embodiments, an engineered endogenous immunoglobulin κ light chain locus includes a deletion of all functional rodent Vκ and/or Jκ gene segments.

In some embodiments, the present disclosure provides a rodent whose germline genome includes:

(a) a homozygous endogenous immunoglobulin heavy chain locus including one or more human V$_H$ gene segments, one or more human D$_H$ gene segments, and one or more human J$_H$ gene segments operably linked to one or more endogenous immunoglobulin heavy chain constant region genes such that the rodent expresses immunoglobulin heavy chains that each comprise a human heavy chain variable domain sequence and a rodent heavy chain constant domain sequence, (b) a first engineered endogenous immunoglobulin κ light chain locus including one or more human Vκ gene segments and one or more Jκ gene segments operably linked to an endogenous rodent Cκ region gene such that the rodent expresses immunoglobulin light chains that each includes a human κ light chain variable domain sequence and a rodent κ light chain constant domain sequence, and (c) a second engineered endogenous immunoglobulin κ light chain locus including:

(i) one or more human Vλ gene segments, where the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1, or any combination thereof, (ii) one or more human Jλ gene segments, where the one or more human Jλ gene segments comprise Jλ1, Jλ2, Jλ3, Jλ6, Jλ7, or any combination thereof, and (iii) a rodent Cλ gene;

where the one or more human Vλ gene segments, the one or more human Jλ gene segments, and the rodent Cλ gene are operably linked to each other, where the rodent Cλ gene is in place of a rodent Cκ gene of the endogenous immunoglobulin κ light chain locus, where the engineered endogenous immunoglobulin κ light chain locus includes:

(a) one or more human Vλ non-coding sequences, where each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the engineered endogenous immunoglobulin κ light chain locus, and where each of the one or more human Vλ non-coding sequences naturally appear adjacent to a Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus, and (b) one or more human Jκ non-coding sequences, where each of the one or more human Jκ non-coding sequences is adjacent to the Jλ1, Jλ2, Jλ3, Jλ6 or Jλ7 in the engineered endogenous immunoglobulin κ light chain locus, and where each of the one or more human Jκ non-coding sequences naturally appear adjacent to a Jκ1, Jκ2, Jκ3, Jκ4, or Jκ5 of an endogenous human immunoglobulin κ light chain locus, and where the immunoglobulin κ light chain locus includes a human κ light chain non-coding sequence between the one or more human Vλ gene segments and the one or more human Jλ gene segments that has a sequence that naturally appears between a human Vκ4-1 gene segment and a human Jκ1 gene segment in an endogenous human immunoglobulin κ light chain locus;

such that the rodent expresses immunoglobulin light chains that each comprise a human λ light chain variable domain sequence and a rodent λ light chain constant domain sequence.

In some embodiments, a rodent described herein includes an inactivated endogenous immunoglobulin λ light chain locus. In some embodiments, a rodent described herein is heterozygous for the inactivated endogenous immunoglobulin λ light chain locus. In some embodiments, a rodent described herein is homozygous for the inactivated endogenous immunoglobulin λ light chain locus.

In some embodiments, the genome of the rodent further includes a nucleic acid sequence encoding an exogenous terminal deoxynucleotidyltransferase (TdT) operably linked to a transcriptional control element. In some embodiments, the transcriptional control element includes a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof. In some embodiments, the nucleic acid sequence encoding an exogenous TdT is located at an immunoglobulin κ light chain locus, an immunoglobulin λ light chain locus, an immunoglobulin heavy chain locus, a RAG1 locus, or a RAG2 locus. In some embodiments, a TdT is a human TdT. In some embodiments, a TdT is a short isoform of TdT (TdTS).

In some embodiments, a rodent described herein includes a nucleic acid sequence encoding an exogenous terminal deoxynucleotidyltransferase (TdT) operably linked to a transcriptional control element in its germline genome and exhibits light chains (e.g., expresses light chain variable domains including) with at least a 1.2-fold, at least a 1.5-fold, at least a 1.75-fold, at least a 2-fold, at least a 3-fold, at least a 4-fold, or a least a 5-fold increase in junctional diversity over a comparable mouse (e.g., littermate) that does not include an exogenous terminal deoxynucleotidyltransferase (TdT) operably linked to a transcriptional control element in its germline genome. In some embodiments, junctional diversity is measured by number of unique CDR3/10,000 reads. In some embodiments, junctional diversity is measured by number of unique CDR3/10,000 reads.

In some embodiments, a rodent described herein includes a nucleic acid sequence encoding an exogenous terminal deoxynucleotidyltransferase (TdT) operably linked to a transcriptional control element in its germline genome and at least 25%, at least 30%, at least 35%, at least 40%, at least 45%, at least 50%, at least 55%, at least 60%, at least 65% of light chains (e.g., lambda and/or kappa light chains) produced by the rodent exhibit non-template additions.

In some embodiments, a rodent described herein is a rat or a mouse.

In some embodiments, the present disclosure provides an antibody prepared by a method including the steps of:
 (a) providing a rodent described herein;
 (b) immunizing the rodent with an antigen of interest;
 (c) maintaining the rodent under conditions sufficient for the rodent to produce an immune response to the antigen of interest; and
 (d) recovering an antibody that binds the antigen of interest from the rodent, or a cell of the rodent, or a cell derived from a cell of the rodent,
 where the antibody of (d) includes human heavy chain variable and human λ light chain variable domains.

In some embodiments, the present disclosure provides an antibody prepared by a method including the steps of:
 (a) immunizing a rodent described herein with an antigen of interest;
 (b) maintaining the rodent under conditions sufficient for the rodent to produce an immune response to the antigen of interest; and
 (c) recovering an antibody that binds the antigen of interest from the rodent, or a cell of the rodent, or a cell derived from a cell of the rodent,
 where the antibody of (c) includes human heavy chain variable and human λ light chain variable domains.

In some embodiments, a rodent does not detectably express endogenous immunoglobulin κ light chain variable domains. In some embodiments, a rodent rodent does not detectably express endogenous immunoglobulin λ light chain variable domains.

In some embodiments, a rodent described herein produces a population of B cells in response to immunization with an antigen that includes one or more epitopes. In some embodiments, a rodent produces a population of B cells that express antibodies that bind (e.g., specifically bind) to one or more epitopes of antigen of interest. In some embodiments, antibodies expressed by a population of B cells produced in response to an antigen include a heavy chain having a human heavy chain variable domain encoded by a human heavy chain variable region sequence and/or a lambda light chain having a human lambda light chain variable domain encoded by a human lambda light chain variable region sequence as described herein. In some embodiments, antibodies expressed by a population of B cells produced in response to an antigen include (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof.

In some embodiments, a rodent produces a population of B cells that express antibodies that bind to one or more epitopes of antigen of interest, where antibodies expressed by the population of B cells produced in response to an antigen include: (i) a heavy chain having a human heavy chain variable domain encoded by a human heavy chain variable region sequence, (ii) a lambda light chain having a human lambda light chain variable domain encoded by a human lambda light chain variable region sequence as described herein, and/or (iii) a kappa light chain having a human kappa light chain variable domain encoded by a human kappa light chain variable region sequence as described herein.

In some embodiments, a human heavy chain variable region sequence, a human λ light chain variable region sequence, and/or a human κ light chain variable region sequence as described herein is somatically hypermutated. In some embodiments, at least about 5%, 10%, 15%, 20%, 25%, 30%, 35%, 40%, 45%, 50%, 55%, 60%, 65%, 70%, 75%, 80%, 85%, 90% of the B cells in a population of B cells produced in response to an antigen include a human heavy chain variable region sequence, λ light chain variable region sequence, and/or κ light chain variable region sequence that is somatically hypermutated.

In some embodiments, the present disclosure provides a method of making an antibody, including:

(i) expressing a first nucleotide sequence that encodes an immunoglobulin heavy chain in a host cell, where the first nucleotide sequence includes a human heavy chain variable region sequence;

(ii) expressing a second nucleotide sequence that encodes an immunoglobulin λ light chain in a host cell, where the second nucleotide sequence includes a human λ light chain variable region sequence that was identified (e.g., expressed and/or isolated) from a rodent whose germline genome includes:
- an engineered endogenous immunoglobulin κ light chain locus including:
  - (a) one or more human Vλ gene segment,
  - (b) one or more human Jλ gene segment, and
  - (c) one or more Cλ genes,
- where the one or more human Vλ gene segment and the one or more human Jλ gene segment are operably linked to the one or more Cλ genes, and
- where the rodent lacks a rodent Cκ gene at the engineered endogenous immunoglobulin κ locus;

(iii) culturing the host cell so that immunoglobulin light chains and immunoglobulin heavy chains are expressed and form an antibody; and (iv) obtaining the antibody from the host cell and/or host cell culture.

In some embodiments, a first nucleotide sequence includes a human heavy chain constant region. In some embodiments, an antibody is a fully human antibody.

In some embodiments, a second nucleotide includes a human λ light chain constant region sequence.

In some embodiments, an antibody is a reverse chimeric antibody. In some embodiments, a first nucleotide sequence includes a rodent heavy chain constant region. In some embodiments, a second nucleotide sequence includes a rodent λ light chain constant region sequence.

In some embodiments, the present disclosure provides a rodent, whose germline genome includes:
(a) a first engineered endogenous immunoglobulin κ light chain locus comprising:
  (i) one or more human Vλ gene segments,
  (ii) one or more human Jλ gene segments, and
  (iii) a Cλ gene,
  where the one or more human Vλ gene segments and the one or more human Jλ gene segments are operably linked to the Cλ gene, and
  where the rodent lacks a rodent Cκ gene at the first engineered endogenous immunoglobulin κ locus; and
(b) a second engineered endogenous immunoglobulin κ light chain locus further includes:
  (i) one or more human Vκ gene segments, and
  (ii) one or more human Jκ gene segments,
  where the one or more human Vκ gene segments and the one or more human Jκ gene segments are operably linked to a Cκ gene.

In some embodiments, a Cκ gene is an endogenous rodent Cκ gene.

In some embodiments, the genome of the rodent further includes a nucleic acid sequence encoding an exogenous terminal deoxynucleotidyltransferase (TdT) operably linked to a transcriptional control element. In some embodiments, the transcriptional control element includes a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof. In some embodiments, the nucleic acid sequence encoding an exogenous TdT is located at an immunoglobulin κ light chain locus, an immunoglobulin λ light chain locus, an immunoglobulin heavy chain locus, a RAG1 locus, or a RAG2 locus. In some embodiments, a TdT is a human TdT. In some embodiments, a TdT is a short isoform of TdT (TdTS).

In some embodiments, the genome of the rodent further includes a nucleic acid sequence encoding an exogenous terminal deoxynucleotidyltransferase (TdT) operably linked to a transcriptional control element. In some embodiments, the transcriptional control element includes a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof. In some embodiments, the nucleic acid sequence encoding an exogenous TdT is located at an immunoglobulin κ light chain locus, an immunoglobulin λ light chain locus, an immunoglobulin heavy chain locus, a RAG1 locus, or a RAG2 locus. In some embodiments, a TdT is a human TdT. In some embodiments, a TdT is a short isoform of TdT (TdTS).

In some embodiments, a rodent described herein includes a nucleic acid sequence encoding an exogenous terminal deoxynucleotidyltransferase (TdT) operably linked to a transcriptional control element in its germline genome and exhibits light chains (e.g., expresses light chain variable domains including) with at least a 1.2-fold, at least a 1.5-fold, at least a 1.75-fold, at least a 2-fold, at least a 3-fold, at least a 4-fold, or a least a 5-fold increase in junctional diversity over a comparable mouse (e.g., littermate) that does not include an exogenous terminal deoxynucleotidyltransferase (TdT) operably linked to a transcriptional control element in its germline genome. In some embodiments, junctional diversity is measured by number of unique CDR3/10,000 reads. In some embodiments, junctional diversity is measured by number of unique CDR3/10,000 reads.

In some embodiments, a rodent described herein includes a nucleic acid sequence encoding an exogenous terminal deoxynucleotidyltransferase (TdT) operably linked to a transcriptional control element in its germline genome and at least 25%, at least 30%, at least 35%, at least 40%, at least 45%, at least 50%, at least 55%, at least 60%, at least 65% of light chains (e.g., lambda and/or kappa light chains) produced by the rodent exhibit non-template additions.

In various embodiments, a non-human animal, non-human cell or non-human tissue as described herein is a rodent, rodent cell or rodent tissue; in some embodiments, a mouse, mouse cell or mouse tissue; in some embodiments, a rat, rat cell or rat tissue. In some embodiments, a mouse, mouse cell or mouse tissue as described herein comprises a genetic background that includes a 129 strain, a BALB/c strain, a C57BL/6 strain, a mixed 129xC57BL/6 strain, or combinations thereof.

BRIEF DESCRIPTION OF THE DRAWINGS

The Drawings included herein, which are composed of the following Figures, is for illustration purposes only and not for limitation.

FIG. 20 includes a first arrow pointing to a representation of a first exemplary endogenous human Vλ non-coding sequence in the endogenous human immunoglobulin λ light chain locus. As illustrated, the first exemplary endogenous human Vλ non-coding sequence (represented by a line) in the endogenous human immunoglobulin λ light chain locus naturally appears adjacent to a human Vλ3-12 gene segment (represented by a dark grey square) and a human Vλ2-11 gene segment (represented by a dark grey square) in the endogenous human immunoglobulin Igλ light chain locus. FIG. 20 also includes a second arrow pointing to a representation of a second exemplary endogenous human Vλ non-coding sequence in the endogenous human immunoglobulin λ light chain locus. As illustrated, the second exemplary endogenous human Vλ non-coding sequence (represented by a line) in the endogenous human immunoglobulin λ light chain locus naturally appears adjacent to a human Vλ2-11 gene segment (represented by a dark grey square) and a human Vλ3-10 gene segment (represented by a dark grey square) in the endogenous human immunoglobulin λ light chain locus.

FIG. 21 includes a first arrow pointing to a representation of a first exemplary endogenous human Jκ non-coding sequence in the endogenous human immunoglobulin κ light chain locus. As illustrated, the first exemplary endogenous human Jκ non-coding sequence (represented by a line) in the endogenous human immunoglobulin κ light chain locus naturally appears adjacent to a human Jκ1 gene segment (represented by a dark grey square) and a human Jκ2 gene segment (represented by a dark grey square) in the endogenous human immunoglobulin κ light chain locus. FIG. 21 also includes a second arrow pointing to a representation of a second exemplary endogenous human Jκ non-coding sequence in the endogenous human immunoglobulin κ light chain locus. As illustrated, the second exemplary endogenous human Jκ non-coding sequence (represented by a line) in the endogenous human immunoglobulin κ light chain locus naturally appears adjacent to a human Jκ2 gene segment (represented by a dark grey square) and a human Jκ3 gene segment (represented by a dark grey square) in the endogenous human immunoglobulin κ light chain locus.

BRIEF DESCRIPTION OF SELECTED SEQUENCES IN THE SEQUENCE LISTING

Figure 1A:
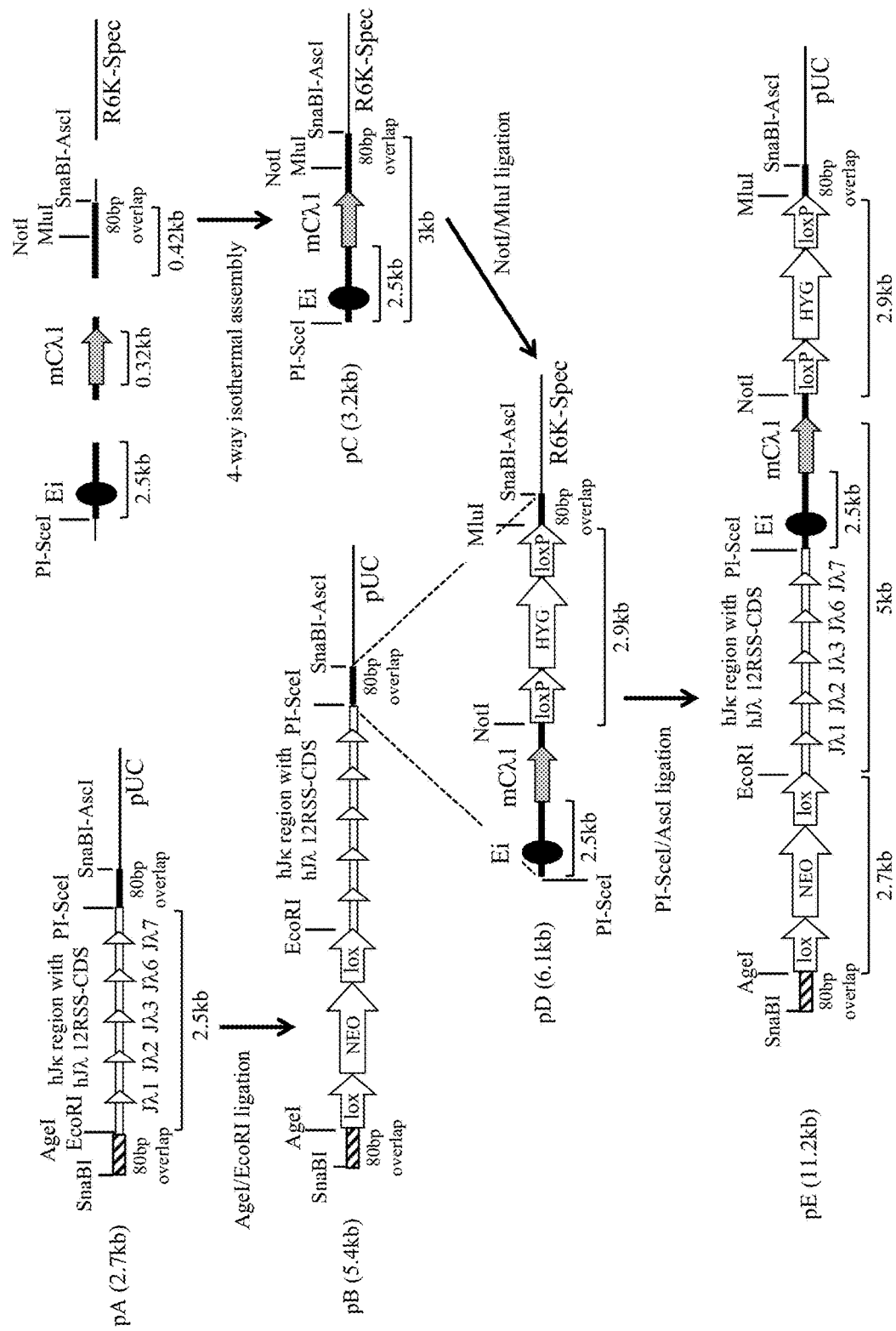
FIGS. 1A and 1B show illustrations of an exemplary embodiment, not to scale, of a strategy for constructing a targeting vector (described in Example 1.1) used in generating an embodiment of the rodent according to the present disclosure.

The following are representative nucleic acid and amino acid sequence of various immunoglobulin constant regions of the mouse, rat, or human lambda genes. Nucleic acid and amino acid sequences of immunoglobulin genes and polypeptides are available from the

```
Mouse Cλ1 DNA (SEQ ID NO: 1):
GCCAGCCCAAGTCTTCGCCATCAGTCACCCTGTTTCCACCTTCCTCTGAAGAGCTCGAGACTAACAAGGCCACACTGGTG

TGTACGATCACTGATTTCTACCCAGGTGTGGTGACAGTGGACTGGAAGGTAGATGGTACCCCTGTCACTCAGGGTATGGA

GACAACCCAGCCTTCCAAACAGAGCAACAACAAGTACATGGCTAGCAGCTACCTGACCCTGACAGCAAGAGCATGGGAAA

GGCATAGCAGTTACAGCTGCCAGGTCACTCATGAAGGTCACACTGTGGAGAAGAGTTTGTCCCGTGCTGACTGTTCC

Mouse Cλ1 amino acid (SEQ ID NO: 2):
GQPKSSPSVTLFPPSSEELETNKATLVCTITDFYPGVVTVDWKVDGTPVTQGMETTQPSKQSNNKYMASSYLTLTARAWE

RHSSYSCQVT HEGHTVEKSL SRADCS

Mouse Cλ2 DNA (SEQ ID NO: 3):
GTCAGCCCAAGTCCACTCCCACTCTCACCGTGTTTCCACCTTCCTCTGAGGAGCTCAAGGAAAACAAAGCCACACTGGTG

TGTCTGATTTCCAACTTTTCCCCGAGTGGTGTGACAGTGGCCTGGAAGGCAAATGGTACACCTATCACCCAGGGTGTGGA

CACTTCAAATCCCACCAAAGAGGGCAACAAGTTCATGGCCAGCAGCTTCCTACATTTGACATCGGACCAGTGGAGATCTC

ACAACAGTTTTACCTGTCAAGTTACACATGAAGGGGACACTGTGGAGAAGAGTCTGTCTCCTGCAGAATGTCTC

Mouse Cλ2 amino acid (SEQ ID NO: 4):
GQPKSTPTLTVFPPSSEELKENKATLVCLISNFSPSGVTVAWKANGTPITQGVDTSNPTKEGNKFMASSFLHLTSDQWRS

HNSFTCQVTHEGDTVEKSLSPAECL

Mouse Cλ3 DNA (SEQ ID NO: 5):
GTCAGCCCAAGTCCACTCCCACACTCACCATGTTTCCACCTTCCCCTGAGGAGCTCCAGGAAAACAAAGCCACACTCGTG

TGTCTGATTTCCAATTTTTCCCCAAGTGGTGTGACAGTGGCCTGGAAGGCAAATGGTACACCTATCACCCAGGGTGTGGA

CACTTCAAATCCCACCAAAGAGGACAACAAGTACATGGCCAGCAGCTTCTTACATTTGACATCGGACCAGTGGAGATCTC

ACAACAGTTTTACCTGCCAAGTTACACATGAAGGGGACACTGTGGAGAAGAGTCTGTCTCCTGCAGAATGTCTC
```

```
Mouse Cλ3 amino acid (SEQ ID NO: 6):
GQPKSTPTLTMFPPSPEELQENKATLVCLISNFSPSGVTVAWKANGTPITQGVDTSNPTKEDNKYMASSFLHLTSDQWRS

HNSFTCQVTHEGDTVEKSLSPAECL

Rat Cλ1 DNA (SEQ ID NO: 7):
GTCAGCCCAAGTCCACTCCCACACTCACAGTATTTCCACCTTCAACTGAGGAGCTCCAGGGAAACAAAGCCACACTGGTG

TGTCTGATTTCTGATTTCTACCCGAGTGATGTGGAAGTGGCCTGGAAGGCAAATGGTGCACCTATCTCCCAGGGTGTGGA

CACTGCAAATCCCACCAAACAGGGCAACAAATACATCGCCAGCAGCTTCTTACGTTTGACAGCAGAACAGTGGAGATCTC

GCAACAGTTTTACCTGCCAAGTTACACATGAAGGGAACACTGTGGAGAAGAGTCTGTCTCCTGCAGAATGTGTC

Rat Cλ1 amino acid (SEQ ID NO: 8):
GQPKSTPTLTVFPPSTEELQGNKATLVCLISDFYPSDVEVAWKANGAPISQGVDTANPTKQGNKYIASSFLRLTAEQWRS

RNSFTCQVTHEGNTVEKSLSPAECV

Rat Cλ2 DNA (SEQ ID NO: 9):
ACCAACCCAAGGCTACGCCCTCAGTCACCCTGTTCCCACCTTCCTCTGAAGAGCTCAAGACTGACAAGGCTACACTGGTG

TGTATGGTGACAGATTTCTACCCTGGTGTTATGACAGTGGTCTGGAAGGCAGATGGTACCCCTATCACTCAGGGTGTGGA

GACTACCCAGCCTTTCAAACAGAACAACAAGTACATGGCTACCAGCTACCTGCTTTTGACAGCAAAAGCATGGGAGACTC

ATAGCAATTACAGCTGCCAGGTCACTCACGAAGAGAACACTGTGGAGAAGAGTTTGTCCCGTGCTGAGTGTTCC

Rat Cλ2 amino acid (SEQ ID NO: 10):
DQPKATPSVTLFPPSSEELKTDKATLVCMVTDFYPGVMTVVWKADGTPITQGVETTQPFKQNNKYMATSYLLLTAKAWET

HSNYSCQVTHEENTVEKSLSRAECS

Rat Cλ3 DNA (SEQ ID NO: 11):
GTCAGCCCAAGTCCACTCCCACACTCACAGTATTTCCACCTTCAACTGAGGAGCTCCAGGGAAACAAAGCCACACTGGTG

TGTCTGATTTCTGATTTCTACCCGAGTGATGTGGAAGTGGCCTGGAAGGCAAATGGTGCACCTATCTCCCAGGGTGTGGA

CACTGCAAATCCCACCAAACAGGGCAACAAATACATCGCCAGCAGCTTCTTACGTTTGACAGCAGAACAGTGGAGATCTC

GCAACAGTTTTACCTGCCAAGTTACACATGAAGGGAACACTGTGGAAAAGAGTCTGTCTCCTGCAGAGTGTGTC

Rat Cλ3 amino acid (SEQ ID NO: 12):
GQPKSTPTLTVFPPSTEELQGNKATLVCLISDFYPSDVEVAWKANGAPISQGVDTANPTKQGNKYIASSFLRLTAEQWRS

RNSFTCQVTHEGNTVEKSLSPAECV

Rat Cλ4 DNA (SEQ ID NO: 13):
ACCAACCCAAGGCTACGCCCTCAGTCACCCTGTTCCCACCTTCCTCTGAAGAGCTCAAGACTGACAAGGCTACACTGGTG

TGTATGGTGACAGATTTCTACCCTGGTGTTATGACAGTGGTCTGGAAGGCAGATGGTACCCCTATCACTCAGGGTGTGGA

GACTACCCAGCCTTTCAAACAGAACAACAAGTACATGGCTACCAGCTACCTGCTTTTGACAGCAAAAGCATGGGAGACTC

ATAGCAATTACAGCTGCCAGGTCACTCACGAAGAGAACACTGTGGAGAAGAGTTTGTCCCGTGCTGAGTGTTCC

Rat Cλ4 amino acid (SEQ ID NO: 14):
DQPKATPSVTLFPPSSEELKTDKATLVCMVTDFYPGVMTVVWKADGTPITQGVETTQPFKQNNKYMATSYLLLTAKAWET

HSNYSCQVTHEENTVEKSLSRAECS

Human Cλ1 DNA (SEQ ID NO: 15):
CCCAAGGCCAACCCCACGGTCACTCTGTTCCCGCCCTCCTCTGAGGAGCTCCAAGCCAACAAGGCCACACTAGTGTGTCT

GATCAGTGACTTCTACCCGGGAGCTGTGACAGTGGCCTGGAAGGCAGATGGCAGCCCCGTCAAGGCGGGAGTGGAGACGA

CCAAACCCTCCAAACAGAGCAACAACAAGTACGCGGCCAGCAGCTACCTGAGCCTGACGCCCGAGCAGTGGAAGTCCCAC

AGAAGCTACAGCTGCCAGGTCACGCATGAAGGGAGCACCGTGGAGAAGACAGTGGCCCCTACAGAATGTTCATAG

Human Cλ1 amino acid (SEQ ID NO: 16):
PKANPTVTLFPPSSEELQANKATLVCLISDFYPGAVTVAWKADGSPVKAGVETTKPSKQSNNKYAASSYLSLTPEQWKSH

RSYSCQVTHEGSTVEKTVAPTECS
```

-continued

Human Cλ2 DNA (SEQ ID NO: 17):
GTCAGCCCAAGGCTGCCCCCTCGGTCACTCTGTTCCCGCCCTCCTCTGAGGAGCTTCAAGCCAACAAGGCCACACTGGTG

TGTCTCATAAGTGACTTCTACCCGGGAGCCGTGACAGTGGCTTGGAAAGCAGATAGCAGCCCCGTCAAGGCGGGAGTGGA

GACCACCACACCCTCCAAACAAAGCAACAACAAGTACGCGGCCAGCAGCTATCTGAGCCTGACGCCTGAGCAGTGGAAGT

CCCACAGAAGCTACAGCTGCCAGGTCACGCATGAAGGGAGCACCGTGGAGAAGACAGTGGCCCCTACAGAATGTTCA

Human Cλ2 amino acid (SEQ ID NO: 18):
QPKAAPSVTLFPPSSEELQANKATLVCLISDFYPGAVTVAWKADSSPVKAGVETTTPSKQSNNKYAASSYLSLTPEQWKS

HRSYSCQVTHEGSTVEKTVAPTECS

Human Cλ3 DNA (SEQ ID NO: 19):
CCCAAGGCTGCCCCCTCGGTCACTCTGTTCCCACCCTCCTCTGAGGAGCTTCAAGCCAACAAGGCCACACTGGTGTGTCT

CATAAGTGACTTCTACCCGGGAGCCGTGACAGTTGCCTGGAAGGCAGATAGCAGCCCCGTCAAGGCGGGGGTGGAGACCA

CCACACCCTCCAAACAAAGCAACAACAAGTACGCGGCCAGCAGCTACCTGAGCCTGACGCCTGAGCAGTGGAAGTCCCAC

AAAAGCTACAGCTGCCAGGTCACGCATGAAGGGAGCACCGTGGAGAAGACAGTTGCCCCTACGGAATGTTCATAG

Human Cλ3 amino acid (SEQ ID NO: 20):
PKAAPSVTLFPPSSEELQANKATLVCLISDFYPGAVTVAWKADSSPVKAGVETTTPSKQSNNKYAASSYLSLTPEQWKSH

KSYSCQVTHEGSTVEKTVAPTECS

Human Cλ6 DNA (SEQ ID NO: 21):
GGTCAGCCCAAGGCTGCCCCATCGGTCACTCTGTTCCCGCCCTCCTCTGAGGAGCTTCAAGCCAACAAGGCCACACTGGT

GTGCCTGATCAGTGACTTCTACCCGGGAGCTGTGAAAGTGGCCTGGAAGGCAGATGGCAGCCCCGTCAACACGGGAGTGG

AGACCACCACACCCTCCAAACAGAGCAACAACAAGTACGCGGCCAGCAGCTACCTGAGCCTGACGCCTGAGCAGTGGAAG

TCCCACAGAAGCTACAGCTGCCAGGTCACGCATGAAGGGAGCACCGTGGAGAAGACAGTGGCCCCTGCAGAATGTTCATA

G

Human Cλ6 amino acid (SEQ ID NO: 22):
QPKAAPSVTLFPPSSEELQANKATLVCLISDFYPGAVKVAWKADGSPVNTGVETTTPSKQSNNKYAASSYLSLTPEQWKS

HRSYSCQVTHEGSTVEKTVAPAECS

Human Cλ7 DNA (SEQ ID NO: 23):
GTCAGCCCAAGGCTGCCCCCTCGGTCACTCTGTTCCCACCCTCCTCTGAGGAGCTTCAAGCCAACAAGGCCACACTGGTG

TGTCTCGTAAGTGACTTCTACCCGGGAGCCGTGACAGTGGCCTGGAAGGCAGATGGCAGCCCCGTCAAGGTGGGAGTGGA

GACCACCAAACCCTCCAAACAAAGCAACAACAAGTATGCGGCCAGCAGCTACCTGAGCCTGACGCCCGAGCAGTGGAAGT

CCCACAGAAGCTACAGCTGCCGGGTCACGCATGAAGGGAGCACCGTGGAGAAGACAGTGGCCCCTGCAGAATGCTCT

Human Cλ7 amino acid (SEQ ID NO: 24):
QPKAAPSVTLFPPSSEELQANKATLVCLVSDFYPGAVTVAWKADGSPVKVGVETTKPSKQSNNKYAASSYLSLTPEQWKS

HRSYSCRVTHEGSTVEKTVAPAECS

Definitions

The scope of the present invention is defined by the claims appended hereto and is not limited by certain embodiments described herein. Those skilled in the art, reading the present specification, will be aware of various modifications that may be equivalent to such described embodiments, or otherwise within the scope of the claims. In general, terms used herein are in accordance with their understood meaning in the art, unless clearly indicated otherwise. Explicit definitions of certain terms are provided below; meanings of these and other terms in particular instances throughout this specification will be clear to those skilled in the art from context. Additional definitions for the following and other terms are set forth throughout the specification. Patent and non-patent literature references cited within this specification, or relevant portions thereof, are incorporated herein by reference in their entireties.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used in this application, the terms "about" and "approximately" are used as equivalents. Any numerals used in this application with or without about or approximately are meant to cover any normal fluctuations appreciated by one of ordinary skill in the relevant art.

The articles "a" and "an" in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Administration: as used herein, includes the administration of a composition to a subject or system (e.g., to a cell, organ, tissue, organism, or relevant component or set of components thereof). The skilled artisan will appreciate that route of administration may vary depending, for example, on the subject or system to which the composition is being administered, the nature of the composition, the purpose of the administration, etc. For example, in certain embodiments, administration to an animal subject (e.g., to a human or a rodent) may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and/or vitreal. In some embodiments, administration may involve intermittent dosing. In some embodiments, administration may involve continuous dosing (e.g., perfusion) for at least a selected period of time.

Amelioration: as used herein, includes the prevention, reduction or palliation of a state, or improvement of the state of a subject. Amelioration includes but does not require complete recovery or complete prevention of a disease, disorder or condition.

Approximately: as applied to one or more values of interest, includes to a value that is similar to a stated reference value. In certain embodiments, the term "approximately" or "about" refers to a range of values that fall within ±10% (greater than or less than) of the stated reference value unless otherwise stated or otherwise evident from the context (except where such number would exceed 100% of a possible value).

Biologically active: as used herein, refers to a characteristic of any agent that has activity in a biological system, in vitro or in vivo (e.g., in an organism). For instance, an agent that, when present in an organism, has a biological effect within that organism is considered to be biologically active. In particular embodiments, where a protein or polypeptide is biologically active, a portion of that protein or polypeptide that shares at least one biological activity of the protein or polypeptide is typically referred to as a "biologically active" portion.

Comparable: as used herein, refers to two or more agents, entities, situations, sets of conditions, etc. that may not be identical to one another but that are sufficiently similar to permit comparison there between so that conclusions may reasonably be drawn based on differences or similarities observed. Persons of ordinary skill in the art will understand, in context, what degree of identity is required in any given circumstance for two or more such agents, entities, situations, sets of conditions, etc. to be considered comparable.

Conservative: as used herein, refers to instances when describing a conservative amino acid substitution, including a substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include: aliphatic side chains such as glycine (Gly, G), alanine (Ala, A), valine (Val, V), leucine (Leu, L), and isoleucine (Ile, I); aliphatic-hydroxyl side chains such as serine (Ser, S) and threonine (Thr, T); amide-containing side chains such as asparagine (Asn, N) and glutamine (Gln, Q); aromatic side chains such as phenylalanine (Phe, F), tyrosine (Tyr, Y), and tryptophan (Trp, W); basic side chains such as lysine (Lys, K), arginine (Arg, R), and histidine (His, H); acidic side chains such as aspartic acid (Asp, D) and glutamic acid (Glu, E); and sulfur-containing side chains such as cysteine (Cys, C) and methionine (Met, M). Conservative amino acids substitution groups include, for example, valine/leucine/isoleucine (Val/Leu/Ile, V/L/I), phenylalanine/tyrosine (Phe/Tyr, F/Y), lysine/arginine (Lys/Arg, K/R), alanine/valine (Ala/Val, A/V), glutamate/aspartate (Glu/Asp, E/D), and asparagine/glutamine (Asn/Gln, N/Q). In some embodiments, a conservative amino acid substitution can be a substitution of any native residue in a protein with alanine, as used in, for example, alanine scanning mutagenesis. In some embodiments, a conservative substitution is made that has a positive value in the PAM250 log-likelihood matrix disclosed in Gonnet, G. H. et al., 1992, Science 256:1443-1445, which is incorporated herein by reference in its entirety. In some embodiments, a substitution is a moderately conservative substitution wherein the substitution has a nonnegative value in the PAM250 log-likelihood matrix.

Control: as used herein, refers to the art-understood meaning of a "control" being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. A "control" also includes a "control animal." A "control animal" may have a modification as described herein, a modification that is different as described herein, or no modification (i.e., a wild-type animal). In one experiment, a "test" (i.e., a variable being tested) is applied. In a second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Disruption: as used herein, refers to the result of a homologous recombination event with a DNA molecule (e.g., with an endogenous homologous sequence such as a gene or gene locus). In some embodiments, a disruption may achieve or represent an insertion, deletion, substitution, replacement, missense mutation, or a frame-shift of a DNA sequence(s), or any combination thereof. Insertions may include the insertion of entire genes or gene fragments, e.g., exons, which may be of an origin other than the endogenous sequence (e.g., a heterologous sequence). In some embodiments, a disruption may increase expression and/or activity of a gene or gene product (e.g., of a polypeptide encoded by a gene). In some embodiments, a disruption may decrease expression and/or activity of a gene or gene product. In some embodiments, a disruption may alter sequence of a gene or an encoded gene product (e.g., an encoded polypeptide). In some embodiments, a disruption may truncate or fragment a gene or an encoded gene product (e.g., an encoded polypeptide). In some embodiments, a disruption may extend a gene or an encoded gene product. In some such embodiments, a disruption may achieve assembly of a fusion polypeptide. In some embodiments, a disruption may affect level, but not activity, of a gene or gene product. In some embodiments, a disruption may affect activity, but not level, of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

Determining, measuring, evaluating, assessing, assaying and analyzing: are used interchangeably herein to refer to any form of measurement, and include determining if an element is present or not. These terms include both quantitative and/or qualitative determinations. Assaying may be relative or absolute. "Assaying for the presence of" can be determining the amount of something present and/or determining whether or not it is present or absent.

Endogenous promoter: as used herein, refers to a promoter that is naturally associated, e.g., in a wild-type organism, with an endogenous gene.

Engineered: as used herein refers, in general, to the aspect of having been manipulated by the hand of man. For example, in some embodiments, a polynucleotide may be considered to be "engineered" when two or more sequences that are not linked together in that order in nature are manipulated by the hand of man to be directly linked to one another in the engineered polynucleotide. In some embodiments, an engineered polynucleotide may comprise a regulatory sequence that is found in nature in operative association with a first coding sequence but not in operative association with a second coding sequence, is linked by the hand of man so that it is operatively associated with the second coding sequence. Alternatively, or additionally, in some embodiments, first and second nucleic acid sequences that each encode polypeptide elements or domains that in nature are not linked to one another may be linked to one another in a single engineered polynucleotide. Comparably, in some embodiments, a cell or organism may be considered to be "engineered" if it has been manipulated so that its genetic information is altered (e.g., new genetic material not previously present has been introduced, or previously present genetic material has been altered or removed). As is common practice and is understood by persons of skill in the art, progeny of an engineered polynucleotide or cell are typically still referred to as "engineered" even though the actual manipulation was performed on a prior entity. Furthermore, as will be appreciated by persons of skill in the art, a variety of methodologies are available through which "engineering" as described herein may be achieved. For example, in some embodiments, "engineering" may involve selection or design (e.g., of nucleic acid sequences, polypeptide sequences, cells, tissues, and/or organisms) through use of computer systems programmed to perform analysis or comparison, or otherwise to analyze, recommend, and/or select sequences, alterations, etc.). Alternatively, or additionally, in some embodiments, "engineering" may involve use of in vitro chemical synthesis methodologies and/or recombinant nucleic acid technologies such as, for example, nucleic acid amplification (e.g., via the polymerase chain reaction) hybridization, mutation, transformation, transfection, etc., and/or any of a variety of controlled mating methodologies. As will be appreciated by those skilled in the art, a variety of established such techniques (e.g., for recombinant DNA, oligonucleotide synthesis, and tissue culture and transformation (e.g., electroporation, lipofection, etc.) are well known in the art and described in various general and more specific references that are cited and/or discussed throughout the present specification. See e.g., Sambrook et al., Molecular Cloning: A Laboratory Manual 2nd ed., Cold Spring Harbor Laboratory Press, Cold Spring Harbor, N.Y., 1989 and Principles of Gene Manipulation: An Introduction to Genetic Manipulation, 5th Ed., ed. By Old, R. W. and S. B. Primrose, Blackwell Science, Inc., 1994, incorporated herein by reference in their entireties.

Functional: as used herein, refers to a form or fragment of an entity (e.g., a gene or gene segment) that exhibits a particular property (e.g., forms part of a coding sequence) and/or activity. For example, in the context of immunoglobulins, variable regions are encoded by unique gene segments (i.e., V, D and/or J) that are assembled (or recombined) to form functional coding sequences. When present in the genome, gene segments are organized in clusters, although variations do occur. A "functional" gene segment is a gene segment represented in an expressed sequence (i.e., a variable region) for which the corresponding genomic DNA has been isolated (i.e., cloned) and identified by sequence. Some immunoglobulin gene segment sequences contain open reading frames and are considered functional although not represented in an expressed repertoire, while other immunoglobulin gene segment sequences contain mutations (e.g., point mutations, insertions, deletions, etc.) resulting in a stop codon and/or truncated sequence which subsequently render(s) such gene segment sequences unable to perform the property/ies and/or activity/ies associated with a non-mutated sequence(s). Such sequences are not represented in expressed sequences and, therefore, categorized as pseudogenes.

Gene: as used herein, refers to a DNA sequence in a chromosome that codes for a product (e.g., an RNA product and/or a polypeptide product). In some embodiments, a gene includes coding sequence (i.e., sequence that encodes a particular product). In some embodiments, a gene includes non-coding sequence. In some particular embodiments, a gene may include both coding (e.g., exonic) and non-coding (e.g., intronic) sequence. In some embodiments, a gene may include one or more regulatory sequences (e.g., promoters, enhancers, etc.) and/or intron sequences that, for example, may control or impact one or more aspects of gene expression (e.g., cell-type-specific expression, inducible expression, etc.). For the purpose of clarity, we note that, as used in the present disclosure, the term "gene" generally refers to a portion of a nucleic acid that encodes a polypeptide or fragment thereof; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a polypeptide-coding nucleic acid.

Heterologous: as used herein, refers to an agent or entity from a different source. For example, when used in reference to a polypeptide, gene, or gene product present in a particular cell or organism, the term clarifies that the relevant polypeptide, gene, or gene product: 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type). "Heterologous" also includes a polypeptide, gene or gene product that is normally present in a particular native cell or organism, but has been altered or modified, for example, by mutation or placement under the control of non-naturally associated and, in some embodiments, non-endogenous regulatory elements (e.g., a promoter).

Host cell: as used herein, refers to a cell into which a nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the phrase "host cell." In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *Escherichia coli, Bacillus* spp., *Streptomyces* spp., etc.), mycobacteria cells, fungal cells, yeast cells (e.g., *Saccharomyces cerevisiae, Schizosaccharomyces pombe, Pichia pastoris, Pichia methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, a cell is a human, monkey, ape, hamster, rat, or mouse cell. In some embodiments, a cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, a cell comprises one or more viral genes, e.g., a retinal cell that expresses a viral gene (e.g., a PER.C6® cell). In some embodiments, a host cell is or comprises an isolated cell. In some embodiments, a host cell is part of a tissue. In some embodiments, a host cell is part of an organism.

Identity: as used herein in connection with a comparison of sequences, refers to identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

In place of: as used herein, refers to a positional substitution in which a first nucleic acid sequence is located at the position of a second nucleic acid sequence in a chromosome (e.g., where the second nucleic acid sequence was previously (e.g., originally) located in a chromosome, e.g., at the endogenous locus of the second nucleic acid sequence). The phrase "in place of" does not require that the second nucleic acid sequence be removed from, e.g., a locus or chromosome. In some embodiments, the second nucleic acid sequence and the first nucleic acid sequence are comparable to one another in that, for example, the first and second sequences are homologous to one another, contain corresponding elements (e.g., protein-coding elements, regulatory elements, etc.), and/or have similar or identical sequences. In some embodiments, a first and/or second nucleic acid sequence includes one or more of a promoter, an enhancer, a splice donor site, a splice acceptor site, an intron, an exon, an untranslated region (UTR); in some embodiments, a first and/or second nucleic acid sequence includes one or more coding sequences. In some embodiments, a first nucleic acid sequence is a homolog or variant (e.g., mutant) of the second nucleic acid sequence. In some embodiments, a first nucleic acid sequence is an ortholog or homolog of the second sequence. In some embodiments, a first nucleic acid sequence is or comprises a human nucleic acid sequence. In some embodiments, including where the first nucleic acid sequence is or comprises a human nucleic acid sequence, the second nucleic acid sequence is or comprises a rodent sequence (e.g., a mouse or rat sequence). In some embodiments, including where the first nucleic acid sequence is or comprises a human nucleic acid sequence, the second nucleic acid sequence is or comprises a human sequence. In some embodiments, a first nucleic acid sequence is a variant or mutant (i.e., a sequence that contains one or more sequence differences, e.g., substitutions, as compared to the second sequence) of the second sequence. The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, a first nucleic acid sequence is a substitution of an endogenous sequence with a heterologous sequence that results in the production of a gene product from the nucleic acid sequence so placed (comprising the heterologous sequence), but not expression of the endogenous sequence; a first nucleic acid sequence is of an endogenous genomic sequence with a nucleic acid sequence that encodes a polypeptide that has a similar function as a polypeptide encoded by the endogenous sequence (e.g., the endogenous genomic sequence encodes a non-human variable region polypeptide, in whole or in part, and the DNA fragment encodes one or more human variable region polypeptides, in whole or in part). In various embodiments, a human immunoglobulin gene segment or fragment thereof is in place of an endogenous non-human immunoglobulin gene segment or fragment.

In vitro: as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and/or a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are separated from 10% to 100%, 15%-100%, 20%-100%, 25%-100%, 30%-100%, 35%-100%, 40%-100%, 45%-100%, 50%-100%, 55%-100%, 60%-100%, 65%-100%, 70%-100%, 75%-100%, 80%-100%, 85%-100%, 90%-100%, 95%-100%, 96%-100%, 97%-100%, 98%-100%, or 99%-100% of the other components with which they were initially associated. In some embodiments, isolated agents are separated from 10% to 100%, 10%-99%, 10%-98%, 10%-97%, 10%-96%, 10%-95%, 10%-90%, 10%-85%, 10%-80%, 10%-75%, 10%-70%, 10%-65%, 10%-60%, 10%-55%, 10%-50%, 10%-45%, 10%-40%, 10%-35%, 10%-30%, 10%-25%, 10%-20%, or 10%-15% of the other components with which they were initially associated. In some embodiments, isolated agents are separated from 11% to 99%, 12%-98%, 13%-97%, 14%-96%, 15%-95%, 20%-90%, 25%-85%, 30%-80%, 35%-75%, 40%-70%, 45%-65%, 50%-60%, or 55%-60% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. In some embodiments, isolated agents are 80%-99%, 85%-99%, 90%-99%, 95%-99%, 96%-99%, 97%-99%, or 98%-99% pure. In some embodiments, isolated agents are 80%-99%, 80%-98%, 80%-97%, 80%-96%, 80%-95%, 80%-90%, or 80%-85% pure. In some embodiments, isolated agents are 85%-98%, 90%-97%, or 95%-96% pure. In some embodiments, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when: a) by virtue of its origin or source of derivation is not associated with some or all of the components that accompany it in its native state in nature; b) it is substantially free of other polypeptides or nucleic acids of the same species from the species that produces it in nature; or c) is expressed by or is otherwise in association with components from a cell or other expression system that is not of the species that produces it in nature. Thus, for instance, in some embodiments, a polypeptide that is chemically synthesized, or is synthesized in a cellular system different from that which produces it in nature, is considered to be an "isolated" polypeptide. Alternatively, or additionally, in some embodiments, a polypeptide that has been subjected to one or more purification techniques may be considered to be an "isolated" polypeptide to the extent that it has been separated from other components: a) with which it is associated in nature; and/or b) with which it was associated when initially produced.

Locus or loci: as used herein, refers to a location(s) of a gene (or significant sequence), DNA sequence, polypeptide-encoding sequence, or position on a chromosome of the genome of an organism. For example, an "immunoglobulin locus" may refer to the location of an immunoglobulin gene segment (e.g., V, D, J or C), immunoglobulin gene segment DNA sequence, immunoglobulin gene segment-encoding sequence, or immunoglobulin gene segment position on a chromosome of the genome of an organism that has been identified as to where such a sequence resides. An "immunoglobulin locus" may comprise a regulatory element of an immunoglobulin gene segment, including, but not limited to, an enhancer, a promoter, 5' and/or 3' regulatory sequence or region, or a combination thereof. An "immunoglobulin locus" may comprise intergenic DNA, e.g., DNA that normally resides or appears between gene segments in a wild-type locus. Persons of ordinary skill in the art will appreciate that chromosomes may, in some embodiments, contain hundreds or even thousands of genes and demonstrate physical co-localization of similar genetic loci when comparing between different species. Such genetic loci can be described as having shared synteny.

Naturally appears: as used herein in reference to a biological element (e.g., a nucleic acid sequence) means that the biological element can be found in a specified context and/or location, absent engineering (e.g., genetic engineering), in a cell or organism (e.g., an animal). In other words, a sequence that naturally appears in a specified context and/or location is not in the specified context and/or location as the result of engineering (e.g., genetic engineering). For example, a sequence that naturally appears adjacent to a human Jκ 1 gene segment in an endogenous human immunoglobulin kappa light chain locus is a sequence that can be found adjacent to a human Jκ1 gene segment in an endogenous human immunoglobulin kappa light chain locus, absent genetic engineering, in a human. In some embodiments, a sequence can be obtained, derived, and/or isolated from where it naturally appears in a cell or organism. In some embodiments, a cell or organism is not a direct source of a sequence that naturally appears in the cell or organism. For example, a corresponding sequence in a cell or organism could be identified and then produced or replicated by mechanisms known in the art.

Non-human animal: as used herein, refers to any vertebrate organism that is not a human. In some embodiments, a non-human animal is a cyclostome, a bony fish, a cartilaginous fish (e.g., a shark or a ray), an amphibian, a reptile, a mammal, and a bird. In some embodiments, a non-human animal is a mammal. In some embodiments, a non-human mammal is a primate, a goat, a sheep, a pig, a dog, a cow, or a rodent. In some embodiments, a non-human animal is a rodent such as a rat or a mouse.

Nucleic acid: as used herein, refers to any compound and/or substance that is or can be incorporated into an oligonucleotide chain. In some embodiments, a "nucleic acid" is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a "nucleic acid" is, comprises, or consists of one or more natural nucleic acid residues. In some embodiments, a "nucleic acid" is, comprises, or consists of one or more nucleic acid analogs. In some embodiments, a nucleic acid analog differs from a "nucleic acid" in that it does not utilize a phosphodiester backbone. For example, in some embodiments, a "nucleic acid" is, comprises, or consists of one or more "peptide nucleic acids", which are known in the art and have peptide bonds instead of phosphodiester bonds in the backbone. Alternatively, or additionally, in some embodiments, a "nucleic acid" has one or more phosphorothioate and/or 5'-N-phosphoramidite linkages rather than phosphodiester bonds. In some embodiments, a "nucleic acid" is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a "nucleic acid" is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a "nucleic acid" comprises one or more modified sugars (e.g., 2'-fluororibose, ribose, 2'-deoxyribose, arabinose, and hexose) as compared with those in natural nucleic acids. In some embodiments, a "nucleic acid" has a nucleotide sequence that encodes a functional gene product such as an RNA or polypeptide. In some embodiments, a "nucleic acid" includes one or more introns. In some embodiments, a "nucleic acid" includes one or more exons. In some embodiments, a "nucleic acid" is prepared by one or more of isolation from a natural source, enzymatic synthesis by polymerization based on a complementary template (in vivo or in vitro), reproduction in a recombinant cell or system, and chemical synthesis. In some embodiments, a "nucleic acid" is at least, e.g., but not limited to, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a "nucleic acid" is single stranded; in some embodiments, a "nucleic acid" is double stranded. In some embodiments, a "nucleic acid" has a nucleotide sequence comprising at least one element that encodes, or is the complement of a sequence that encodes, a polypeptide. In some embodiments, a "nucleic acid" has enzymatic activity.

Operably linked: as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with a gene of interest and expression control sequences that act in trans or at a distance to control a gene of interest (or sequence of interest). The term "expression control sequence" includes polynucleotide sequences, which are necessary to affect the expression and processing of coding sequences to which they are ligated. "Expression control sequences" include: appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance polypeptide stability; and when desired, sequences that enhance polypeptide secretion. The nature of such control sequences differs depending upon the host organism. For example, in prokaryotes, such control sequences generally include promoter, ribosomal binding site and transcription termination sequence, while in eukaryotes typically such control sequences include promoters and transcription termination sequence. The term "control sequences" is intended to include components whose presence is essential for expression and processing, and can also include additional components whose presence is advantageous, for example, leader sequences and fusion partner sequences.

Physiological conditions: as used herein, refers to its art-understood meaning referencing conditions under which cells or organisms live and/or reproduce. In some embodiments, the term includes conditions of the external or internal milieu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Polypeptide: as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that contains portions that occur in nature separately from one another (i.e., from two or more different organisms, for example, human and non-human portions). In some embodiments, a polypeptide has an amino acid sequence that is engineered in that it is designed and/or produced through action of the hand of man. In some embodiments, a polypeptide has an amino acid sequence encoded by a sequence that does not occur in nature (e.g., a sequence that is engineered in that it is designed and/or produced through action of the hand of man to encode said polypeptide).

Recombinant: as used herein, refers to polypeptides that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom, H. R., 1997, TIB Tech. 15:62-70; Azzazy, H. and W. E. Highsmith, 2002, Clin. Biochem. 35:425-45; Gavilondo, J. V. and J. W. Larrick, 2002, BioTechniques 29:128-45; Hoogenboom H., and P. Chames, 2000, Immunol. Today 21:371-8, incorporated herein by reference in their entireties), antibodies isolated from an animal (e.g., a mouse) that has been genetically engineered to include human immunoglobulin genes (see e.g., Taylor, L. D. et al., 1992, Nucl. Acids Res. 20:6287-95; Kellermann, S-A. and L. L. Green, 2002, Curr. Opin. Biotechnol. 13:593-7; Little, M. et al., 2000, Immunol. Today 21:364-70; Osborn, M. J. et al., 2013, J. Immunol. 190:1481-90; Lee, E-C. et al., 2014, Nat. Biotech. 32(4):356-63; Macdonald, L. E. et al., 2014, Proc. Natl. Acad. Sci. U.S.A. 111(14):5147-52; Murphy, A. J. et al., 2014, Proc. Natl. Acad. Sci. U.S.A. 111(14):5153-8, each of which is incorporated herein by reference in its entirety) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements result from mutagenesis (e.g., in vivo or in vitro) of a known sequence element, e.g., from a natural or synthetic (e.g., man-made) source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example, in a non-human animal), so that the amino acid sequences of the recombinant polypeptides are sequences that, while originating from and related to polypeptides sequences, may not naturally exist within the genome of a non-human animal in vivo.

Reference: as used herein, refers to a standard or control agent, animal, cohort, individual, population, sample, sequence or value against which an agent, animal, cohort, individual, population, sample, sequence or value of interest is compared. In some embodiments, a reference agent, animal, cohort, individual, population, sample, sequence or value is tested and/or determined substantially simultaneously with the testing or determination of an agent, animal, cohort, individual, population, sample, sequence or value of interest. In some embodiments, a reference agent, animal, cohort, individual, population, sample, sequence or value is a historical reference, optionally embodied in a tangible medium. In some embodiments, a reference may refer to a control. A "reference" also includes a "reference animal." A "reference animal" may have a modification as described herein, a modification that is different as described herein or no modification (i.e., a wild-type animal). Typically, as would be understood by persons of skill in the art, a reference agent, animal, cohort, individual, population, sample, sequence or value is determined or characterized under conditions comparable to those utilized to determine or characterize an agent, animal (e.g., a mammal), cohort, individual, population, sample, sequence or value of interest.

Replacement: as used herein, refers to a process through which a "replaced" nucleic acid sequence (e.g., a gene) found in a host locus (e.g., in a genome) is removed from that locus, and a different, "replacement" nucleic acid is located in its place. In some embodiments, the replaced nucleic acid sequence and the replacement nucleic acid sequences are comparable to one another in that, for example, they are homologous to one another, contain corresponding elements (e.g., protein-coding elements, regulatory elements, etc.), and/or have similar or identical sequences. In some embodiments, a replaced nucleic acid sequence includes one or more of a promoter, an enhancer, a splice donor site, a splice acceptor site, an intron, an exon, an untranslated region (UTR); in some embodiments, a replacement nucleic acid sequence includes one or more coding sequences. In some embodiments, a replacement nucleic acid sequence is a homolog or variant (e.g., mutant) of the replaced nucleic acid sequence. In some embodiments, a replacement nucleic acid sequence is an ortholog or homolog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse or rat sequence). In some embodiments, including where the replacement nucleic acid sequence is or comprises a human nucleic acid sequence, the replaced nucleic acid sequence is or comprises a human sequence. In some embodiments, a replacement nucleic acid sequence is a variant or mutant (i.e., a sequence that contains one or more sequence differences, e.g., substitutions, as compared to the replaced sequence) of the replaced sequence. The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, a replacement is a substitution of an endogenous sequence with a heterologous sequence that results in the production of a gene product from the nucleic acid sequence so placed (comprising the heterologous sequence), but not expression of the endogenous sequence; a replacement is of an endogenous genomic sequence with a nucleic acid sequence that encodes a polypeptide that has a similar function as a polypeptide encoded by the endogenous sequence (e.g., the endogenous genomic sequence encodes a non-human variable region polypeptide, in whole or in part, and the DNA fragment encodes one or more human variable region polypeptides, in whole or in part). In various embodiments, an endogenous non-human immunoglobulin gene segment or fragment thereof is replaced with a human immunoglobulin gene segment or fragment thereof.

Substantially: as used herein, refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantial similarity: as used herein, refers to a comparison between amino acid or nucleic acid sequences. As will be appreciated by those of ordinary skill in the art, two sequences are generally considered to be "substantially similar" if they contain similar residues (e.g., amino acids or nucleotides) in corresponding positions. As is understood in the art, while similar residues may be identical residues (see also Substantial Identity, below), similar residues may also be non-identical residues with appropriately comparable structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "conservative" substitution. Typical amino acid categorizations are summarized in the table below.

| Alanine | Ala | A | Nonpolar | Neutral | 1.8 |
| Arginine | Arg | R | Polar | Positive | −4.5 |

-continued

| | | | | | |
|---|---|---|---|---|---|
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-10; Altschul, S. F. et al., 1996, Meth. Enzymol. 266:460-80; Altschul, S. F. et al., 1997, Nucleic Acids Res., 25:3389-402; Baxevanis, A. D. and B. F. F. Ouellette (eds.) Bioinformatics: A Practical Guide to the Analysis of Genes and Proteins, Wiley, 1998; and Misener et al. (eds.) Bioinformatics Methods and Protocols, Methods in Molecular Biology, Vol. 132, Humana Press, 1998, incorporated herein by reference in their entireties. In addition to identifying similar sequences, the programs mentioned above typically provide an indication of the degree of similarity. In some embodiments, two sequences are considered to be substantially similar if at least, e.g., but not limited to, 80%, 85%, 90%, 91%, 92%, 93%, 94%, 95%, 96%, 97%, 98%, 99% or more of their corresponding residues are similar (e.g., identical or include a conservative substitution) over a relevant stretch of residues. In some embodiments, the relevant stretch is a complete sequence (e.g. a sequence of a gene, a gene segment, a sequence encoding a domain, a polypeptide, or a domain). In some embodiments, the relevant stretch is at least 9, 10, 11, 12, 13, 14, 15, 16, 17 or more residues. In some embodiments, the relevant stretch is at least 10, 15, 20, 25, 30, 35, 40, 45, 50, or more residues. In some embodiments, the relevant stretch includes contiguous residues along a complete sequence. In some embodiments, the relevant stretch includes discontinuous residues along a complete sequence, for example, noncontiguous residues brought together by the folded conformation of a polypeptide or a portion thereof.

Substantial identity: as used herein, refers to a comparison between amino acid or nucleic acid sequences. As will be appreciated by those of ordinary skill in the art, two sequences are generally considered to be "substantially identical" if they contain identical residues (e.g., amino acids or nucleotides) in corresponding positions. As is well-known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, S. F. et al., 1990, J. Mol. Biol., 215(3): 403-10; Altschul, S. F. et al., 1996, Meth. Enzymol. 266:460-80; Altschul, S. F. et al., 1997, Nucleic Acids Res., 25:3389-402; Baxevanis, A. D. and B. F. F. Ouellette (eds.) Bioinformatics: A Practical Guide to the Analysis of Genes and Proteins, Wiley, 1998; and Misener et al. (eds.) Bioinformatics Methods and Protocols, Methods in Molecular Biology, Vol. 132, Humana Press, 1998, each of which is incorporated herein by reference in its entirety. In addition to identifying identical sequences, the programs mentioned above typically provide an indication of the degree of identity. In some embodiments, two sequences are considered to be substantially identical if at least 80%, 85%, 90%, 91%, 92%, 93%, 94%, 95%, 96%, 97%, 98%, 99% or more of their corresponding residues are identical over a relevant stretch of residues. In some embodiments, a relevant stretch of residues is a complete sequence. In some embodiments, a relevant stretch of residues is, e.g., but not limited to, at least 10, 15, 20, 25, 30, 35, 40, 45, 50, or more residues.

Targeting construct or targeting vector: as used herein, refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included and described herein. In some embodiments, a targeting construct as described herein further comprises a nucleic acid sequence or gene of particular interest, a selectable marker, control and/or regulatory sequences, and other nucleic acid sequences that allow for recombination mediated through exogenous addition of proteins that aid in or facilitate recombination involving such sequences. In some embodiments, a targeting construct as described herein further comprises a gene of interest in whole or in part, wherein the gene of interest is a heterologous gene that encodes a polypeptide, in whole or in part, that has a similar function as a protein encoded by an endogenous sequence. In some embodiments, a targeting construct as described herein further comprises a humanized gene of interest, in whole or in part, wherein the humanized gene of interest encodes a polypeptide, in whole or in part, that has a similar function as a polypeptide encoded by an endogenous sequence. In some embodiments, a targeting construct (or targeting vector) may comprise a nucleic acid sequence manipulated by the hand of man. For example, in some embodiments, a targeting construct (or targeting vector) may be constructed to contain an engineered or recombinant polynucleotide that contains two or more sequences that are not linked together in that order in nature yet manipulated by the hand of man to be directly linked to one another in the engineered or recombinant polynucleotide.

Transgene or transgene construct: as used herein, refers to a nucleic acid sequence (encoding e.g., a polypeptide of interest, in whole or in part) that has been introduced into a cell by the hand of man such as by the methods described herein. A transgene could be partly or entirely heterologous, i.e., foreign, to the genetically engineered animal or cell into which it is introduced. A transgene can include one or more transcriptional regulatory sequences and any other nucleic acid, such as introns or promoters, which may be necessary for expression of a selected nucleic acid sequence.

Genetically modified non-human animal or genetically engineered non-human animal: are used interchangeably herein and refer to any non-naturally occurring non-human animal in which one or more of the cells of the non-human animal contain heterologous nucleic acid and/or gene encoding a polypeptide of interest, in whole or in part. For example, in some embodiments, a "genetically modified non-human animal" or "genetically engineered non-human animal" refers to non-human animal that contains a transgene or transgene construct as described herein. In some embodiments, a heterologous nucleic acid and/or gene is introduced into the cell, directly or indirectly by introduction into a precursor cell, by way of deliberate genetic manipulation, such as by microinjection or by infection with a recombinant virus. The term genetic manipulation does not include classic breeding techniques, but rather is directed to introduction of recombinant DNA molecule(s). This molecule may be integrated within a chromosome, or it may be extrachromosomally replicating DNA. The phrases "genetically modified non-human animal" or "genetically engineered non-human animal" refers to animals that are heterozygous or homozygous for a heterologous nucleic acid and/or gene, and/or animals that have single or multi-copies of a heterologous nucleic acid and/or gene.

Vector: as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operably linked genes are referred to herein as "expression vectors."

Wild-type: as used herein, refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION

The present disclosure provides, among other things, engineered non-human animals having heterologous genetic material encoding human Vλ domains, which heterologous genetic material comprises human Vλ and Jλ gene sequences (i.e., gene segments) and other human sequences that provide for proper rearrangement (e.g., recombination signal sequence (RSS)) and expression of antibodies having Igλ light chains that include a human portion and a non-human portion, or antibodies having Igλ light chains that are fully human. For example, in various embodiments, when a human gene segment is present in a genome of an engineered non-human animal, the corresponding recombination signal sequence(s) can also be present (e.g., Vλ RSS with Vλ gene segment, Jλ RSS with Jλ gene segment, Vκ RSS with Vκ gene segment, Jκ RSS with Jκ gene segment, etc.). In various embodiments, provided engineered non-human animals contain heterologous genetic material that is inserted in such a way so that antibodies containing light chains that have a human Vλ domain and a non-human or human CX domain are expressed in the antibody repertoire of the non-human animal. Further, provided engineered non-human animals contain heterologous genetic material that is inserted in such a way so that antibodies containing light chains that have a human Vλ domain and a non-human or human CX domain are expressed from engineered Igκ light chain loci that include human and non-human Igλ gene sequences (e.g., gene segments) and, in some embodiments, human Igκ light chain sequences, in the germline genome of the non-human animal.

Without wishing to be bound by any particular theory, it is contemplated that non-human animals as described herein provide an improved in vivo system that exploits the expression of antibodies containing human Vλ domains for the production of therapeutic antibodies. It is also contemplated that non-human animals as described herein, in some embodiments, provide alternate engineered forms of light chain loci (e.g., Igκ light chain loci) that contain heterologous genetic material for the development of human antibody-based therapeutics (e.g., human monoclonal antibodies, multi-specific binding agents, scFvs, fusion polypeptides, etc.) to disease targets that are associated with biased antibody responses (e.g., antibody responses characterized by an overwhelming proportion of either K or λ light chains). Thus, provided non-human animals are particularly useful for the development of human antibodies and human antibody-based molecules (e.g., multi-specific binding agents, scFvs, fusion polypeptides, etc.) against targets associated with poor immunogenicity (e.g., viruses) due, in part, to skewed antibody repertoires and/or responses.

The present disclosure describes, among other things, an immunoglobulin κ light chain locus that includes one or more human Vλ gene segments, one or more human Jλ gene segments, and a Cλ gene. Such a locus is referred to as a "lambda in kappa" locus or "LiK".

In particular, the present disclosure describes the production of a non-human animal (e.g., a rodent) having a germline genome that contains an engineered Igκ light chain locus that is, in some embodiments, characterized by the introduction of a plurality of human Vλ and Jλ gene segments and introduction of a non-human or human Cλ gene in the place of a non-human Cκ gene, so that said plurality of human Vλ and Jλ gene segments are operably linked to said non-human or human Cλ gene. As described herein, the production of such an engineered Igκ light chain locus results in the expression of antibodies that contain light chains that include a human Vλ domain and a non-human or human Cλ domain from said engineered Igκ light chain locus in the germline genome of the non-human animal. In some embodiments, the germline genome of provided non-human animals comprises an Igκ light chain locus including human Igλ light chain sequences. In some embodiments, the germline genome of provided non-human animals comprises (i) an Igκ light chain locus including human Igλ light chain sequences, and (ii)(a) an Igκ light chain locus including human Igλ light chain sequences or (ii)(b) an Igκ light chain locus including human Igκ light chain sequences. The germline genome of provided non-human animals, in some embodiments, comprises an Igλ light chain locus as described herein and further comprises (i) a humanized IgH locus or (ii) a humanized IgH locus and functionally silenced or otherwise rendered non-functional endogenous Igλ light chain locus. Provided non-human animals, as described herein, express antibody repertoires that contain Igλ light chains that include human Vλ domains.

In some embodiments, non-human animals as described herein contain human Igλ light chain sequences within an Igκ light chain locus. In some embodiments, non-human animals as described herein contain human and non-human Igλ light chain sequences within an Igκ light chain locus. In some embodiments, non-human animals as described herein contain human Igλ and human Igκ light chain sequences within an Igκ light chain locus. In some embodiments, non-human animals as described herein contain human Igλ, human Igκ and murine Igκ and/or murine Igλ light chain sequences within an Igκ light chain locus. In some embodiments, non-human animals as described herein contain human Igλ light chain sequences, non-human Igλ light chain sequences, human Igκ light chain sequences, non-human Igκ light chain sequences, or combinations thereof within an Igκ light chain locus. In many embodiments of non-human animals as described herein, non-human sequences are or comprise murine sequences (e.g., mouse or rat).

In some embodiments, Igκ and/or Igλ light chain sequences include intergenic DNA that is of human and/or murine origin. In some embodiments, Igκ and/or Igλ light chain sequences include intergenic DNA that is engineered and based on a source sequence that is of human or murine origin. In some embodiments, said intergenic DNA is of the same immunoglobulin locus in which the intergenic DNA is so placed, inserted, positioned or engineered (e.g., Igκ intergenic DNA in an Igκ light chain locus). In some embodiments, said intergenic DNA is of a different immunoglobulin locus in which the intergenic DNA is so placed, inserted, positioned or engineered (e.g., Igλ intergenic DNA in an Igκ light chain locus). In some certain embodiments, non-human animals as described herein contain an engineered Igκ light chain locus that contains intergenic DNA that includes Igκ light chain sequence(s), Igλ light chain sequence(s) and/or combinations thereof.

In various embodiments, a humanized immunoglobulin heavy chain locus contains at least one human $V_H$, at least one human $D_H$ and at least one human $J_H$ gene segment operably linked to to a non-human immunoglobulin heavy chain constant region (e.g., an endogenous non-human immunoglobulin heavy chain constant region that includes one or more immunoglobulin heavy chain constant region genes such as, for example, IgM, IgD, IgG, IgE, IgA, etc.), e.g., a plurality of human $V_H$, $D_H$ and $J_H$ gene segments operably linked to a non-human immunoglobulin heavy chain constant region. In some embodiments, provided non-human animals have a germline genome that includes one or more immunoglobulin loci depicted in the Drawings. Such engineered non-human animals provide a source of human antibodies and human antibody fragments, and provide an improved in vivo system suitable for exploiting human Vλ sequences for the production of human therapeutic antibodies.

As described in the Examples section below, non-human animals are provided that have a genome that contains at least one of each human heavy (i.e., $V_H$, $D_H$ and $J_H$) and light chain (e.g., Vλ and Jλ at the endogenous kappa locus) variable region gene segments, e.g., a plurality of human heavy (i.e., $V_H$, $D_H$ and $J_H$) and light chain (e.g., Vλ and Jλ at the endogenous kappa locus) variable region gene segments, in the place of non-human variable region gene segments at endogenous immunoglobulin loci, and include human non-coding intergenic DNA between the human variable region gene segments. Such intergenic DNA includes, for example, promoters, leader sequences and recombination signal sequences that allow for proper recombination and expression of the human gene segments in the context of variable domains of antibodies. Persons of skill understand that non-human immunoglobulin loci also contain such non-coding intergenic DNA. Upon reading this disclosure, persons of skill will understand that other human or non-human intergenic DNA can be employed in constructing such loci resulting in the same expression of human variable domains in the context of antibodies in the non-human animal. Such similar loci need only contain the human coding sequences (i.e., exons) of the desired human gene segments to achieve expression of antibodies that contain human variable domains.

Various aspects of certain embodiments are described in detail in the following sections, each of which can apply to any aspect or embodiment as described herein. The use of sections is not for limitation.

Antibody Repertoires in Non-Human Animals

Immunoglobulins (also called antibodies) are large (~150 kD), Y-shaped glycoproteins that are produced by B cells of a host immune system to neutralize pathogens (e.g., viruses, bacteria, etc.). Each immunoglobulin (Ig) is composed of two identical heavy chains and two identical light chains, each of which has two structural components: a variable domain and a constant domain. The heavy and light chain variable regions differ in antibodies produced by different B cells, but are the same for all antibodies produced by a single B cell or B cell clone. The heavy and light chain variable regions of each antibody together comprise the antigen-binding region (or antigen-binding site). Immunoglobulins can exist in different varieties that are referred to as isotypes or classes based on the heavy chain constant regions (or domains) that they contain. The heavy chain constant region is identical in all antibodies of the same isotype, but differs in antibodies of different isotypes. The table below summarizes the nine antibody isotypes in mouse and human.

| Mouse | Human |
|-------|-------|
| IgM   | IgM   |
| IgD   | IgD   |
| IgG1  | IgG1  |
| IgG2a | IgG2  |
| IgG2b | IgG3  |
| IgG2c | IgG4  |
| IgG3  | IgE   |
| IgE   | IgA1  |
| IgA   | IgA2  |

Additional isotypes have been identified in other species. Isotypes confer specialized biological properties on the antibody due to the different structural characteristics among the different isotypes and are found in different locations (cells, tissues, etc.) within an animal body. Initially, B cells produce IgM and IgD with identical antigen-binding regions. Upon activation, B cells switch to different isotypes by a process referred to as class switching, which involves a change of the constant region of the antibody produced by the B cell while the variable regions remain the same, thereby preserving antigen specificity of the original antibody (B cell).

Two separate loci (Igκ and Igλ) contain the gene segments that, upon rearrangement, encode the light chains of antibodies, and exhibit both allelic and isotypic exclusion. The expression ratios of κ⁺ to λ⁺ B cells vary among species. For example, humans demonstrate a ratio of about 60:40 (κ:λ). In mice and rats, a ratio of 95:5 (κ:λ) is observed. Interestingly, the κ:λ ratio observed in cats (5:95) is opposite of mice and rats. Several studies have been conducted to elucidate the possible reasons behind these observed ratios, and both the complexity of the locus (i.e., number of gene segments, in particular, V gene segments) and the efficiency of gene segment rearrangement have been proposed as rationale. The human Igλ light chain locus extends over 1,000 kb and contains approximately 70 Vλ gene segments (29 to 33 functional) and seven Jλ-Cλ gene segment pairs (four to five functional) organized into three clusters (see, e.g., FIG. 1 of U.S. Pat. No. 9,006,511, which is incorporated herein by reference in its entirety). The majority of the observed Vλ regions in the expressed antibody repertoire are encoded by gene segments contained within the most proximal cluster (referred to as cluster A). The mouse Igλ light chain locus is strikingly different than the human locus and, depending on the strain, contains only a few Vλ and Jλ gene segments organized in two distinct gene clusters (see, e.g., FIG. 2 of U.S. Pat. No. 9,006,511, which is incorporated herein by reference in its entirety).

Development of therapeutic antibodies for the treatment of various human diseases has largely been centered on the creation of engineered non-human animal lines, in particular, engineered rodent lines, harboring varying amounts of genetic material in their genomes corresponding to human immunoglobulin genes (reviewed in, e.g., Bruggemann, M. et al., 2015, Arch. Immunol. Ther. Exp. 63:101-8, which is incorporated herein by reference in its entirety). Initial efforts in creating such genetically engineered rodent lines focused on integration of portions of human immunoglobulin loci that could, by themselves, support recombination of gene segments and production of heavy and/or light chains that were entirely human while having endogenous immunoglobulin loci inactivated (see e.g., Bruggemann, M. et al., 1989, Proc. Nat. Acad. Sci. U.S.A. 86:67-09-13; Bruggemann, M. et al., 1991, Eur. J. Immunol. 21:1323-6; Taylor, L. D. et al., 1992, Nucl. Acids Res. 20:6287-6295; Davies, N. P. et al., 1993, Biotechnol. 11:911-4; Green, L. L. et al., 1994, Nat. Genet. 7:13-21; Lonberg, N. et al., 1994, Nature 368:856-9; Taylor, L. D. et al., 1994, Int. Immunol. 6:579-91; Wagner, S. D. et al., 1994, Eur. J. Immunol. 24:2672-81; Fishwild, D. M. et al., 1996, Nat. Biotechnol. 14:845-51; Wagner, S. D. et al., 1996, Genomics 35:405-14; Mendez, M. J. et al., 1997, Nat. Genet. 15:146-56; Green, L. L. et al., 1998, J. Exp. Med. 188:483-95; Xian, J. et al., 1998, Transgenics 2:333-43; Little, M. et al., 2000, Immunol. Today 21:364-70; Kellermann, S. A. and L. L. Green, 2002, Cur. Opin. Biotechnol. 13:593-7, each of which is incorporated by reference in their entirety). In particular, some efforts have included integration of human Igλ light chain sequences (see, e.g., U.S. Patent Application Publication Nos. 2002/0088016 A1, 2003/0217373 A1 and 2011/0236378 A1; U.S. Pat. Nos. 6,998,514 and 7,435,871; Nicholson, I. C. et al., 1999, J. Immunol. 163:6898-906; Popov, A. V et al., 1999, J. Exp. Med. 189(10): 1611-19, each of which is incorporated herein by reference in its entirety). Such efforts have focused on the random integration of yeast artificial chromosomes containing human Vλ, Jλ and Cλ sequences thereby creating mouse strains that express fully human Igλ light chains (i.e., human Vλ and Cλ domains). More recent efforts have employed similar strategies using constructs that also contain human Vλ, Jλ and Cλ sequences (Osborn, M. J. et al., 2013, J. Immunol. 190:1481-90; Lee, E-C. et al., 2014, Nat. Biotech. 32(4): 356-63, each of which is incorporated herein by reference in its entirety).

Figure 11:
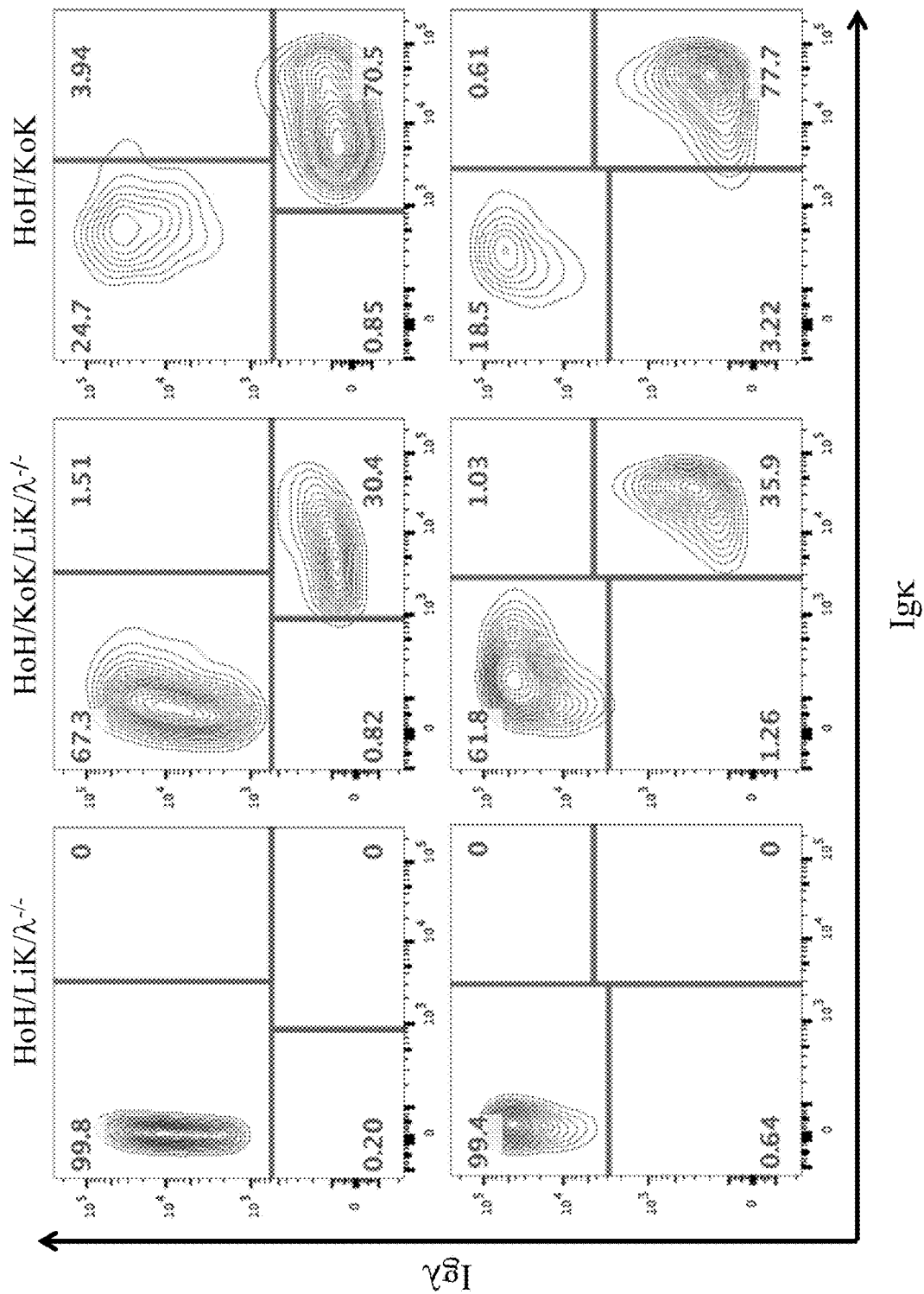
FIG. 11 shows results derived from a representative embodiment according to the present disclosure, including representative single cell-gated bone marrow harvested from various indicated humanized mice illustrating expression of immunoglobulin light chains containing mouse Igλ (y-axis) or mouse Igκ (x-axis) constant regions in immature (top row) and mature (bottom row) B cells.
Figure 12:
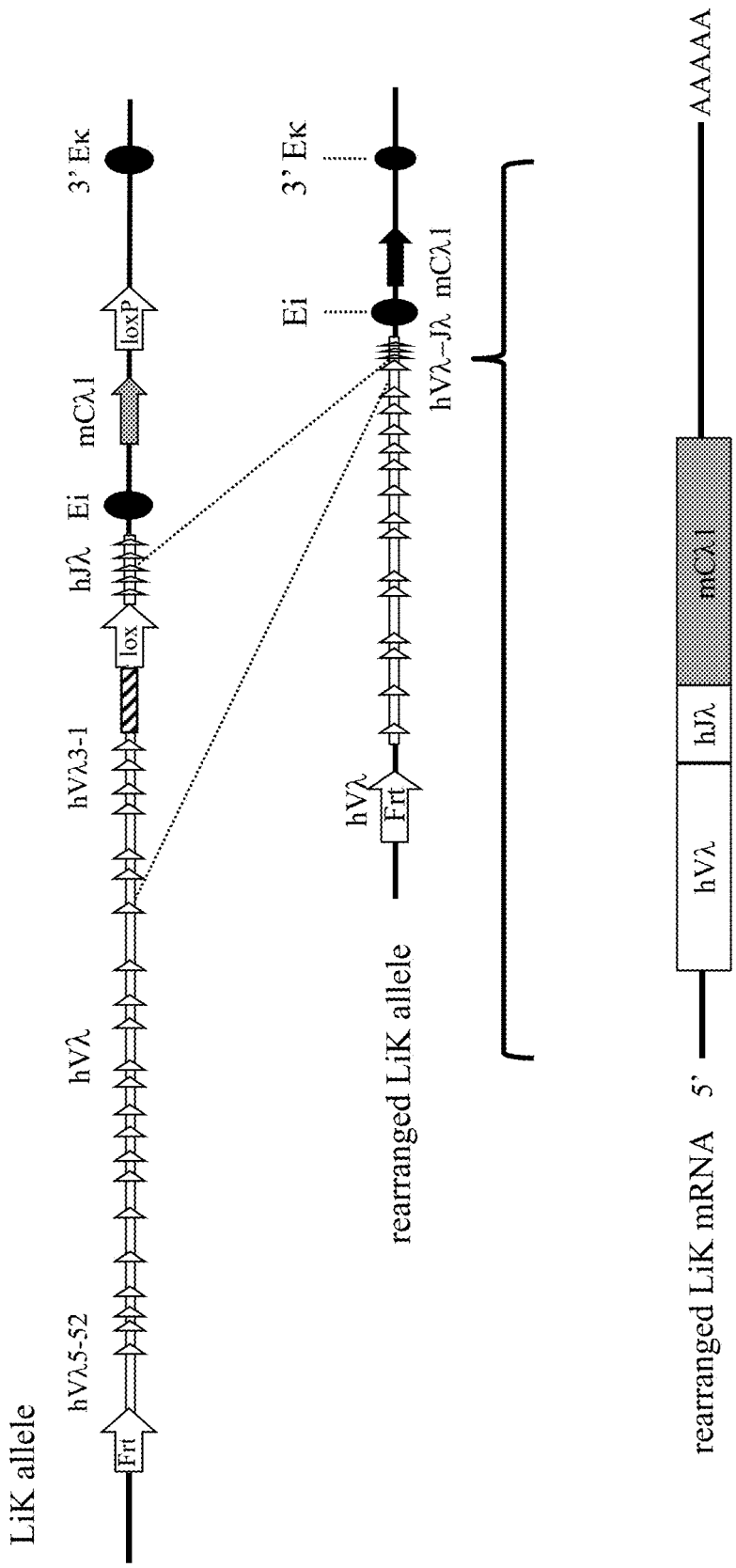
FIG. 12 shows a schematic illustration of an exemplary embodiment, according to the present disclosure, not to scale, of an engineered immunoglobulin κ light chain locus as described herein and the rearrangement of the locus to form an mRNA molecule.

Yet other efforts have included the specific insertion of human Vλ and Jλ gene segments into endogenous rodent Ig light chain loci (κ and λ) so that said human Vλ and Jλ gene segments are operably linked to endogenous Ig light chain constant region genes (see, e.g., U.S. Pat. Nos. 9,006,511, 9,012,717, 9,029,628, 9,035,128, 9,066,502, 9,150,662 and 9,163,092; all of which are incorporated herein by reference in their entireties). In such animals, all of the human Vλ gene segments from clusters A and B and either one or four human Jλ gene segments were inserted into endogenous Igκ and Igλ light chain loci. As a result, several different human Vλ and Jλ gene segments demonstrated proper rearrangement at both engineered rodent Ig light chain loci to form functional light chains expressed in the rodent antibody repertoire, which light chains included human Vλ domains in the context of either endogenous Cκ and Cλ regions (see, e.g., Table 7 and FIGS. 11-13 of U.S. Pat. No. 9,006,511, which is incorporated herein by reference in its entirety). In particular, mice having engineered Igκ light chain loci harboring human Vλ and Jλ gene segments demonstrated a human lambda to endogenous lambda ratio (as measured by IgCκ to IgCλ ratio) of about 1:1 in the splenic compartment (see, e.g., Table 4 of U.S. Pat. No. 9,006,511, which is incorporated herein by reference in its entirety). Indeed, both engineered mouse strains (i.e., engineered Igκ or engineered Igλ light chain loci) demonstrated that human Vλ domains could be expressed from endogenous Ig light chain loci in rodents, which normally display a large bias in light chain expression (see above). The present disclosure provides the recognition that alternate engineered Ig light chain locus structures can be produced to maximize usage of human Vλ and Jλ gene segments in antibody repertoires to therapeutic targets in non-human animals, in particular, as compared to non-human animals that contain an Igλ light chain locus that lacks the complexity and robust quality (e.g., mice and rats) that is normally associated with a human Igλ light chain locus (i.e., such a locus that appears in a human cell). Such alternate engineered Ig light chain locus structures provide the capacity for unique antibody repertoires resulting from their design.

The present disclosure exemplifies the successful production of a non-human animal whose germline genome contains an engineered endogenous Igκ light chain locus comprising a plurality of human Vλ and Jλ gene segments in operable linkage to a non-human or human Igλ light chain constant region gene, which non-human or human Igλ light chain constant region gene is inserted in the place of a non-human Igκ light chain constant region gene of the endogenous Igκ light chain locus. In particular, the present disclosure specifically demonstrates the successful production of (1) an engineered non-human animal that expresses antibodies having human variable regions and non-human constant regions, which antibodies include light chains that contain a human Vλ domain and a non-human Cλ domain, and (2) an engineered non-human animal that expresses antibodies having human variable regions and human constant regions, which antibodies include light chains that contain human Vλ and Cλ domains. As specifically exemplified herein, expression of such light chains is achieved by insertion of said plurality of human Vλ and Jλ gene segments into an endogenous Igκ light chain locus (or allele). In some embodiments, provided non-human animals are engineered so that expression of endogenous Igλ light chain variable regions is inactivated (e.g., by gene deletion).

In some embodiments, provided non-human animals are engineered so that expression of endogenous Igκ light chain variable regions is inactivated (e.g., by replacement or substitution). In some embodiments, provided non-human animals are engineered so that the non-human animals express human Igλ light chain variable regions from an engineered endogenous Igκ light chain locus and human Igκ light chain variable regions from an engineered endogenous Igκ light chain locus. Thus, the present disclosure, in at least some embodiments, embraces the development of an improved in vivo system for the production of human antibodies by providing an engineered non-human animal containing an alternatively engineered Igκ light chain locus that results in an expressed antibody repertoire containing human Vλ domains and non-human or human Cλ domains.

Nucleic Acid Constructs

Typically, a polynucleotide molecule containing human Igλ light chain sequences (e.g., human Vλ and Jλ gene segments) or portion(s) thereof linked with (e.g., is inserted into) a vector, preferably a DNA vector, in order to replicate the polynucleotide molecule in a host cell.

Human Igλ light chain sequences can be cloned directly from known sequences or sources (e.g., libraries) or synthesized from germline sequences designed in silico based on published sequences available from GenBank or other publically available databases (e.g., IMGT). Alternatively, bacterial artificial chromosome (BAC) libraries can provide immunoglobulin DNA sequences of interest (e.g., human Vλ and Jλ sequences and combinations thereof). BAC libraries can contain an insert size of 100-150 kb and are capable of harboring inserts as large as 300 kb (Shizuya, et al., 1992, Proc. Natl. Acad. Sci., USA 89:8794-8797; Swiatek, et al., 1993, Genes and Development 7:2071-2084; Kim, et al., 1996, Genomics 34 213-218; incorporated herein by reference in their entireties). For example, a human BAC library harboring average insert sizes of 164-196 kb has been described (Osoegawa, K. et al., 2001, Genome Res. 11(3):483-96; Osoegawa, K. et al., 1998, Genomics 52:1-8, Article No. GE985423, each of which is incorporated herein by reference in its entirety). Human and mouse genomic BAC libraries have been constructed and are commercially available (e.g., ThermoFisher). Genomic BAC libraries can also serve as a source of immunoglobulin DNA sequences as well as transcriptional control regions.

Alternatively, immunoglobulin DNA sequences may be isolated, cloned and/or transferred from yeast artificial chromosomes (YACs). For example, the nucleotide sequence of the human Igλ light chain locus has been determined (see, e.g., Dunham, I. et al., 1999, Nature 402:489-95, which is incorporated herein by reference in its entirety). Further, YACs have previously been employed to assemble a human Igλ light chain locus transgene (see, e.g., Popov, A. V. et al., 1996, Gene 177:195-201; Popov, A. V. et al., 1999, J. Exp. Med. 189(10):1611-19, each of which is incorporated herein by reference in its entirety). An entire Igλ light chain locus (human or rodent) can be cloned and contained within several YACs. If multiple YACs are employed and contain regions of overlapping similarity, they can be recombined within yeast host strains to produce a single construct representing the entire locus or desired portions of the locus (e.g., a region to targeted with a targeting vector). YAC arms can be additionally modified with mammalian selection cassettes by retrofitting to assist in introducing the constructs into embryonic stems cells or embryos by methods known in the art and/or described herein.

DNA and amino acid sequences of human Igλ light chain gene segments for use in constructing an engineered Igκ light chain locus as described herein may be obtained from published databases (e.g., GenBank, IMGT, etc.) and/or published antibody sequences. In some embodiments, nucleic acid constructs containing human Igλ light chain gene segments comprise a J region (i.e., a genomic sequence that includes a plurality of light chain J gene segments), where the J region comprises coding sequences of human Jλ gene segments with their corresponding 12RSS, where the 12RSS have been positioned among non-coding intergenic DNA typically associated with coding sequences of human Jκ gene segments with their corresponding 23RSS.

In some embodiments, such a sequence may be referred to as an engineered light chain J region. In some certain embodiments, nucleic acid constructs containing human Igλ light chain gene segments comprise human Vλ and Jλ sequences operably linked to a human or non-human Igλ light chain constant region (Cλ) gene. In some certain embodiments, nucleic acid constructs containing human Igλ light chain gene segments comprise human Vλ and Jλ sequences operably linked to one or more non-human Igκ light chain enhancer regions (or enhancer sequences). In some certain embodiments, nucleic acid constructs containing human Igλ light chain gene segments comprise human Vλ and Jλ sequences operably linked to a non-human or human Cλ region gene and non-human Igκ light chain enhancer regions (or enhancer sequences).

In some embodiments, nucleic acid constructs containing human Vλ and Jλ sequences further comprises intergenic DNA that is of human and/or murine origin. In some embodiments, intergenic DNA is or comprises non-coding murine Igκ light chain sequence, non-coding human Igκ light chain sequence, non-coding murine Igλ light chain sequence, non-coding human Igλ light chain sequence, or combinations thereof.

Nucleic acid constructs can be prepared using methods known in the art. For example, a nucleic acid construct can be prepared as part of a larger plasmid. Such preparation allows the cloning and selection of the correct constructions in an efficient manner as is known in the art. Nucleic acid constructs containing human Igλ light chain sequences, in whole or in part, as described herein can be located between restriction sites on the plasmid so that they can be isolated from the remaining plasmid sequences for incorporation into a desired non-human animal.

Various methods employed in preparation of nucleic acid constructs (e.g., plasmids) and transformation of host organisms are known in the art. For other suitable expression systems for both prokaryotic and eukaryotic cells, as well as general recombinant procedures, see Principles of Gene Manipulation: An Introduction to Genetic Manipulation, 5th Ed., ed. By Old, R. W. and S. B. Primrose, Blackwell Science, Inc., 1994 and Molecular Cloning: A Laboratory Manual, 2nd Ed., ed. by Sambrook, J. et al., Cold Spring Harbor Laboratory Press: 1989, each of which is incorporated herein by reference in its entirety.

Targeting Vectors

Targeting vectors can be employed to introduce a nucleic acid construct into a genomic target locus and comprise a nucleic acid construct and homology arms that flank said nucleic acid construct; those skilled in the art will be aware of a variety of options and features generally applicable to the design, structure, and/or use of targeting vectors. For example, targeting vectors can be in linear form or in circular form, and they can be single-stranded or double-stranded. Targeting vectors can be deoxyribonucleic acid (DNA) or ribonucleic acid (RNA). For ease of reference, homology arms are referred to herein as 5' and 3' (i.e., upstream and downstream) homology arms. This terminology relates to the relative position of the homology arms to a nucleic acid construct within a targeting vector. 5' and 3' homology arms correspond to regions within a targeted locus or to a region within another targeting vector, which are referred to herein as "5' target sequence" and "3' target sequence," respectively. In some embodiments, homology arms can also function as a 5' or a 3' target sequence.

In some embodiments, methods described herein employ two, three or more targeting vectors that are capable of recombining with each other. In various embodiments, targeting vectors are large targeting vectors (LTVEC) as described elsewhere herein. In such embodiments, first, second, and third targeting vectors each comprise a 5' and a 3' homology arm. The 3' homology arm of the first targeting vector comprises a sequence that overlaps with the 5' homology arm of the second targeting vector (i.e., overlapping sequences), which allows for homologous recombination between first and second LTVECs.

In the case of double targeting methods, a 5' homology arm of a first targeting vector and a 3' homology arm of a second targeting vector can be similar to corresponding segments within a target genomic locus (i.e., a target sequence), which can promote homologous recombination of the first and the second targeting vectors with corresponding genomic segments and modifies the target genomic locus.

In the case of triple targeting methods, a 3' homology arm of a second targeting vector can comprise a sequence that overlaps with a 5' homology arm of a third targeting vector (i.e., overlapping sequences), which can allow for homologous recombination between the second and the third LTVEC. The 5' homology arm of the first targeting vector and the 3' homology arm of the third targeting vector are similar to corresponding segments within the target genomic locus (i.e., the target sequence), which can promote homologous recombination of the first and the third targeting vectors with the corresponding genomic segments and modifies the target genomic locus.

A homology arm and a target sequence or two homology arms "correspond" or are "corresponding" to one another when the two regions share a sufficient level of sequence identity to one another to act as substrates for a homologous recombination reaction. The sequence identity between a given target sequence and the corresponding homology arm found on a targeting vector (i.e., overlapping sequence) or between two homology arms can be any degree of sequence identity that allows for homologous recombination to occur. To give but one example, an amount of sequence identity shared by a homology arm of a targeting vector (or a fragment thereof) and a target sequence of another targeting vector or a target sequence of a target genomic locus (or a fragment thereof) can be, e.g., but not limited to, at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination.

Moreover, a corresponding region of similarity (e.g., identity) between a homology arm and a corresponding target sequence can be of any length that is sufficient to promote homologous recombination at the target genomic locus. For example, a given homology arm and/or corresponding target sequence can comprise corresponding regions of similarity that are, e.g., but not limited to, about 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length (such as described elsewhere herein) such that a homology arm has sufficient similarity to undergo homologous recombination with a corresponding target sequence(s) within a target genomic locus of the cell or within another targeting vector. In some embodiments, a given homology arm and/or corresponding target sequence comprise corresponding regions of similarity that are, e.g., but not limited to, about 10-100 kb, 15-100 kb, 20-100 kb, 25-100 kb, 30-100 kb, 35-100 kb, 40-100 kb, 45-100 kb, 50-100 kb, 55-100 kb, 60-100 kb, 65-100 kb, 70-100 kb, 75-100 kb, 80-100 kb, 85-100 kb, 90-100 kb, or 95-100 kb in length (such as described elsewhere herein) such that a homology arm has sufficient similarity to undergo homologous recombination with a corresponding target sequence(s) within a target genomic locus of the cell or within another targeting vector.

Overlapping sequences of a 3' homology arm of a first targeting vector and a 5' homology arm of a second targeting vector or of a 3' homology arm of a second targeting vector and a 5' homology arm of a third targeting vector can be of any length that is sufficient to promote homologous recombination between said targeting vectors. For example, a given overlapping sequence of a homology arm can comprise corresponding overlapping regions that are about 1-5 kb, 5-10 kb, 5-15 kb, 5-20 kb, 5-25 kb, 5-30 kb, 5-35 kb, 5-40 kb, 5-45 kb, 5-50 kb, 5-55 kb, 5-60 kb, 5-65 kb, 5-70 kb, 5-75 kb, 5-80 kb, 5-85 kb, 5-90 kb, 5-95 kb, 5-100 kb, 100-200 kb, or 200-300 kb in length such that an overlapping sequence of a homology arm has sufficient similarity to undergo homologous recombination with a corresponding overlapping sequence within another targeting vector. In some embodiments, a given overlapping sequence of a homology arm comprises an overlapping region that is about 1-100 kb, 5-100 kb, 10-100 kb, 15-100 kb, 20-100 kb, 25-100 kb, 30-100 kb, 35-100 kb, 40-100 kb, 45-100 kb, 50-100 kb, 55-100 kb, 60-100 kb, 65-100 kb, 70-100 kb, 75-100 kb, 80-100 kb, 85-100 kb, 90-100 kb, or 95-100 kb in length such that an overlapping sequence of a homology arm has sufficient similarity to undergo homologous recombination with a corresponding overlapping sequence within another targeting vector. In some embodiments, an overlapping sequence is from 1-5 kb, inclusive. In some embodiments, an overlapping sequence is from about 1 kb to about 70 kb, inclusive. In some embodiments, an overlapping sequence is from about 10 kb to about 70 kb, inclusive. In some embodiments, an overlapping sequence is from about 10 kb to about 50 kb, inclusive. In some embodiments, an overlapping sequence is at least 10 kb. In some embodiments, an overlapping sequence is at least 20 kb. For example, an overlapping sequence can be from about 1 kb to about 5 kb, inclusive, from about 5 kb to about 10 kb, inclusive, from about 10 kb to about 15 kb, inclusive, from about 15 kb to about 20 kb, inclusive, from about 20 kb to about 25 kb, inclusive, from about 25 kb to about 30 kb, inclusive, from about 30 kb to about 35 kb, inclusive, from about 35 kb to about 40 kb, inclusive, from about 40 kb to about 45 kb, inclusive, from about 45 kb to about 50 kb, inclusive, from about 50 kb to about 60 kb, inclusive, from about 60 kb to about 70 kb, inclusive, from about 70 kb to about 80 kb, inclusive, from about 80 kb to about 90 kb, inclusive, from about 90 kb to about 100 kb, inclusive, from about 100 kb to about 120 kb, inclusive, from about 120 kb to about 140 kb, inclusive, from about 140 kb to about 160 kb, inclusive, from about 160 kb to about 180 kb, inclusive, from about 180 kb to about 200 kb, inclusive, from about 200 kb to about 220 kb, inclusive, from about 220 kb to about 240 kb, inclusive, from about 240 kb to about 260 kb, inclusive, from about 260 kb to about 280 kb, inclusive, or about 280 kb to about 300 kb, inclusive. To give but one example, an overlapping sequence can be from about 20 kb to about 60 kb, inclusive. Alternatively, an overlapping sequence can be at least 1 kb, at least 5 kb, at least 10 kb, at least 15 kb, at least 20 kb, at least 25 kb, at least 30 kb, at least 35 kb, at least 40 kb, at least 45 kb, at least 50 kb, at least 60 kb, at least 70 kb, at least 80 kb, at least 90 kb, at least 100 kb, at least 120 kb, at least 140 kb, at least 160 kb, at least 180 kb, at least 200 kb, at least 220 kb, at least 240 kb, at least 260 kb, at least 280 kb, or at least 300 kb. In some embodiments, an overlapping sequence can be at most 400 kb, at most 350 kb, at most 300 kb, at most 280 kb, at most 260 kb, at most 240 kb, at most 220 kb, at most 200 kb, at most 180 kb, at most 160 kb, at most 140 kb, at most 120 kb, at most 100 kb, at most 90 kb, at most 80 kb, at most 70 kb, at most 60 kb or at most 50 kb.

Homology arms can, in some embodiments, correspond to a locus that is native to a cell (e.g., a targeted locus), or alternatively they can correspond to a region of a heterologous or exogenous segment of DNA that was integrated into the genome of the cell, including, for example, transgenes, expression cassettes, or heterologous or exogenous regions of DNA. In some embodiments, homology arms can, in some embodiments, correspond to a region on a targeting vector in a cell. In some embodiments, homology arms of a targeting vector may correspond to a region of a yeast artificial chromosome (YAC), a bacterial artificial chromosome (BAC), a human artificial chromosome, or any other engineered region contained in an appropriate host cell. Still further, homology arms of a targeting vector may correspond to or be derived from a region of a BAC library, a cosmid library, or a P1 phage library. In some certain embodiments, homology arms of a targeting vector correspond to a locus that is native, heterologous, or exogenous to a prokaryote, a yeast, a bird (e.g., chicken), a non-human mammal, a rodent, a human, a rat, a mouse, a hamster a rabbit, a pig, a bovine, a deer, a sheep, a goat, a cat, a dog, a ferret, a primate (e.g., marmoset, rhesus monkey), a domesticated mammal, an agricultural mammal, or any other organism of interest. In some embodiments, homology arms correspond to a locus of the cell that shows limited susceptibility to targeting using a conventional method or that has shown relatively low levels of successful integration at a targeted site, and/or significant levels of off-target integration, in the absence of a nick or double-strand break induced by a nuclease agent (e.g., a Cas protein). In some embodiments, homology arms are designed to include engineered DNA.

In some embodiments, 5' and 3' homology arms of a targeting vector(s) correspond to a targeted genome. Alternatively, homology arms correspond to a related genome. For example, a targeted genome is a mouse genome of a first strain, and targeting arms correspond to a mouse genome of a second strain, wherein the first strain and the second strain are different. In certain embodiments, homology arms correspond to the genome of the same animal or are from the genome of the same strain, e.g., the targeted genome is a mouse genome of a first strain, and the targeting arms correspond to a mouse genome from the same mouse or from the same strain.

A homology arm of a targeting vector can be of any length that is sufficient to promote a homologous recombination event with a corresponding target sequence, including, for example, 1-5 kb, inclusive, 5-10 kb, inclusive, 5-15 kb, inclusive, 5-20 kb, inclusive, 5-25 kb, inclusive, 5-30 kb, inclusive, 5-35 kb, inclusive, 5-40 kb, inclusive, 5-45 kb, inclusive, 5-50 kb, inclusive, 5-55 kb, inclusive, 5-60 kb, inclusive, 5-65 kb, inclusive, 5-70 kb, inclusive, 5-75 kb, inclusive, 5-80 kb, inclusive, 5-85 kb, inclusive, 5-90 kb, inclusive, 5-95 kb, inclusive, 5-100 kb, inclusive, 100-200 kb, inclusive, or 200-300 kb, inclusive, in length. In some embodiments, a homology arm of a targeting vector has a length that is sufficient to promote a homologous recombination event with a corresponding target sequence that is 1-100 kb, inclusive, 5-100 kb, inclusive, 10-100 kb, inclusive, 15-100 kb, inclusive, 20-100 kb, inclusive, 25-100 kb, inclusive, 30-100 kb, inclusive, 35-100 kb, inclusive, 40-100 kb, inclusive, 45-100 kb, inclusive, 50-100 kb, inclusive, 55-100 kb, inclusive, 60-100 kb, inclusive, 65-100 kb, inclusive, 70-100 kb, inclusive, 75-100 kb, inclusive, 80-100 kb, inclusive, 85-100 kb, inclusive, 90-100 kb, inclusive, or 95-100 kb, inclusive, in length. As described herein, large targeting vectors can employ targeting arms of greater length.

Nuclease agents (e.g., CRISPR/Cas systems) can be employed in combination with targeting vectors to facilitate the modification of a target locus (e.g., modification of an Igκ light chain locus, or modification of a previously modified or engineered Igκ light chain locus). Such nuclease agents may promote homologous recombination between a targeting vector and a target locus. When nuclease agents are employed in combination with a targeting vector, the targeting vector can comprise 5' and 3' homology arms corresponding to 5' and 3' target sequences located in sufficient proximity to a nuclease cleavage site so as to promote the occurrence of a homologous recombination event between target sequences and homology arms upon a nick or double-strand break at the nuclease cleavage site. The term "nuclease cleavage site" includes a DNA sequence at which a nick or double-strand break is created by a nuclease agent (e.g., a Cas9 cleavage site). Target sequences within a targeted locus that correspond to 5' and 3' homology arms of a targeting vector are "located in sufficient proximity" to a nuclease cleavage site if the distance is such as to promote the occurrence of a homologous recombination event between 5' and 3' target sequences and homology arms upon a nick or double-strand break at the recognition site. Thus, in certain embodiments, target sequences corresponding to 5' and/or 3' homology arms of a targeting vector are within at least one nucleotide of a given recognition site or are within at least 10 nucleotides to about 14 kb of a given recognition site. In some embodiments, a nuclease cleavage site is immediately adjacent to at least one or both of the target sequences.

The spatial relationship of target sequences that correspond to homology arms of a targeting vector and a nuclease cleavage site can vary. For example, target sequences can be located 5' to a nuclease cleavage site, target sequences can be located 3' to a recognition site, or target sequences can flank a nuclease cleavage site.

Combined use of a targeting vector (including, for example, a large targeting vector) with a nuclease agent can result in an increased targeting efficiency compared to use of a targeting vector alone. For example, when a targeting vector is used in conjunction with a nuclease agent, targeting efficiency of a targeting vector can be increased by at least two-fold, at least three-fold, at least four-fold, at least five-fold, at least six-fold, at least seven-fold, at least eight-fold, at least nine-fold, at least ten-fold or within a range formed from these integers, such as 2-10-fold when compared to use of a targeting vector alone.

Some targeting vectors are "large targeting vectors" or "LTVECs," which includes targeting vectors that comprise homology arms that correspond to and are derived from nucleic acid sequences larger than those typically used by other approaches intended to perform homologous recombination in cells. A LTVEC can be, for example, at least 10 kb in length, or the sum total of a 5' homology arm and a 3' homology arm can be, for example, at least 10 kb. LTVECs also include targeting vectors comprising nucleic acid constructs larger than those typically used by other approaches intended to perform homologous recombination in cells. For example, LTVECs make possible the modification of large loci that cannot be accommodated by traditional plasmid-based targeting vectors because of their size limitations. For example, a targeted locus can be (i.e., 5' and 3' homology arms can correspond to) a locus of a cell that is not targetable using a conventional method or that can be targeted only incorrectly or only with significantly low efficiency in the absence of a nick or double-strand break induced by a nuclease agent (e.g., a Cas protein).

In some embodiments, methods described herein employ two or three LTVECs that are capable of recombining with each other and with a target genomic locus in a three-way or a four-way recombination event. Such methods make possible the modification of large loci that cannot be achieved using a single LTVEC.

Examples of LTVECs include vectors derived from a bacterial artificial chromosome (BAC), a human artificial chromosome, or a yeast artificial chromosome (YAC). LTVECs can be in linear form or in circular form. Examples of LTVECs and methods for making them are described, e.g., in U.S. Pat. Nos. 6,586,251, 6,596,541 and 7,105,348; and International Patent Application Publication No. WO 2002/036789, each of which is incorporated herein by reference in their entireties.

Provided Non-Human Animals, Cells and Tissues

Non-human animals are provided that express (e.g., whose B cells express) antibodies that contain light chains that include a human Vλ domain resulting from integration of genetic material that corresponds to at least a portion of a human Igλ light chain locus (i.e., at least a portion of human Vλ and Jλ gene segments), and which encodes a human Vλ domain (i.e., a rearranged human Vλ-Jλ sequence), in the place of corresponding non-human Igκ light chain variable region sequences in the germline genome of the non-human animal. Suitable examples described herein include, but are not limited to, rodents, in particular, mice.

The present disclosure provides improved in vivo systems for identifying and developing new antibodies, antibody components (e.g., antigen-binding portions and/or compositions or formats that include them), and/or antibody-based therapeutics that can be used, for example, in the treatment of a variety of diseases that affect humans. Further, the present disclosure also encompasses the recognition that non-human animals (e.g., rodents) having engineered immunoglobulin loci, such as engineered immunoglobulin (Ig) kappa (κ) light chain loci and/or otherwise expressing, producing or containing antibody repertoires characterized by light chains having human V lambda (λ) regions are useful. For example, in some embodiments, such non-human animals may be used for exploiting the diversity of human Vλ sequences in the identification and development of new antibody-based therapeutics. In some embodiments, non-human animals described herein provide improved in vivo systems for development of antibodies and/or antibody-based therapeutics for administration to humans. In some embodiments, non-human animals described herein provide improved in vivo systems for development of antibodies and/or antibody-based therapeutics that contain human Vλ domains characterized by improved performance (e.g., expression and/or representation in an antigen-specific antibody repertoire) as compared to antibodies and/or antibody-based therapeutics obtained from existing in vivo systems that contain human Vλ region sequences.

The present disclosure provides, among other things, a non-human animal having an Igκ light chain locus that contains an engineered immunoglobulin light chain variable region and an engineered immunoglobulin light chain constant region gene. As described herein, provided non-human animals, contain in their germline genome an immunoglobulin κ light chain locus comprising an engineered immunoglobulin κ light chain variable region characterized by the presence of one or more human Vλ gene segments and one or more human Jλ gene segments, which one or more human Vλ and one or more human Jλ gene segments are operably linked to an immunoglobulin λ light chain constant region (Cλ) gene, which immunoglobulin λ light chain constant region (Cλ) gene is positioned in the place of a non-human immunoglobulin κ light chain constant region (Cκ) gene at the endogenous immunoglobulin κ locus of the non-human animal. In some embodiments, provided non-human animals comprise an Igκ light chain locus that contains intergenic DNA that is immunoglobulin λ light chain and/or immunoglobulin κ light chain in origin, and combinations thereof.

In many embodiments, an engineered immunoglobulin κ light chain variable region further comprises an immunoglobulin κ light chain sequence positioned or inserted between said one or more human Vλ gene segments and one or more human Jλ gene segments. In some embodiments, said immunoglobulin κ light chain sequence positioned or inserted between said one or more human Vλ gene segments and one or more human Jλ gene segments is or comprises a murine (e.g., rat or mouse) sequence. In some embodiments, said immunoglobulin κ light chain sequence positioned or inserted between said one or more human Vλ gene segments and one or more human Jλ gene segments is or comprises a human sequence. For example, in some embodiments, a human immunoglobulin κ light chain sequence is or comprises a genomic sequence that naturally appears between a human Vκ4-1 gene segment and a human Jκ1 gene segment of a human immunoglobulin κ light chain locus.

In some embodiments, provided non-human animals comprise at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 or at least 25 functional human Vλ gene segments. In some embodiments, provided non-human animals comprise 5 to 25, 5 to 24, 5 to 23, 5 to 22, 5 to 21, 5 to 20, 5 to 19, 5 to 18, 5 to 17, 5 to 16, 5 to 15, 5 to 14, 5 to 13, 5 to 12, 5 to 11, 5 to 10, 5 to 9, 5 to 8, 5 to 7, or 5 to 6 functional human Vλ gene segments. In some embodiments, provided non-human animals comprise 6 to 25, 7 to 25, 8 to 25, 9 to 25, 10 to 25, 11 to 25, 12 to 25, 13 to 25, 14 to 25, 15 to 25, 16 to 25, 17 to 25, 18 to 25, 19 to 25, 20 to 25, 21 to 25, 22 to 25, 23 to 25 or 24 to 25 functional human Vλ gene segments. In some embodiments, provided non-human animals comprise 6 to 24, 7 to 23, 8 to 22, 9 to 21, 10 to 20, 11 to 19, 12 to 18, 13 to 17, 14 to 16, or 15 to 16 functional human Vλ gene segments. In some embodiments, provided non-human animals comprise 6 to 24, 7 to 23, 8 to 22, 9 to 21, 10 to 20, 11 to 19, 12 to 18, 13 to 17, or 14 to 16 functional human Vλ gene segments.

In some embodiments, provided non-human animals comprise 10 to 70, 10 to 65, 10 to 60, 10 to 55, 10 to 50, 10 to 45, 10 to 40, 10 to 35, 10 to 30, 10 to 25, 10 to 20, or 10 to 15 total human Vλ gene segments. In some embodiments, provided non-human animals comprise 15 to 70, 20 to 70, 25 to 70, 30 to 70, 35 to 70, 40 to 70, 45 to 70, 50 to 70, 55 to 70, 60 to 70, or 65 to 70 total human Vλ gene segments. In some embodiments, provided non-human animals comprise 15 to 65, 20 to 60, 25 to 55, 20 to 50, 25 to 45, 30 to 40, 30 to 35, or 35 to 40 total human Vλ gene segments.

In some embodiments, provided non-human animals contain human Vλ and/or Jλ gene segments in natural or germline configuration (e.g., a DNA sequence containing a plurality of human Vλ and/or Jλ gene segment coding sequences interspersed with non-coding human immunoglobulin λ light chain sequence light chain sequence). In some embodiments, provided non-human animals contain human Vλ and/or Jλ gene segments in configuration that departs or deviates from a natural or germline configuration (e.g., a DNA sequence containing a plurality of human Vλ and/or Jλ gene segment coding sequences interspersed with non-coding immunoglobulin κ light chain sequence (e.g., human or murine]). In some embodiments, provided non-human animals contain human Vλ and/or Jλ gene segments in a configuration that does not naturally appear in a human immunoglobulin λ light chain locus of the germline genome of a human cell.

In some embodiments, provided non-human animals contain a DNA sequence at an endogenous non-human Igκ light chain locus that includes a plurality of human Vλ and Jλ coding sequences interspersed (or juxtaposed, associated, etc.) with non-coding human immunoglobulin light chain sequence (e.g., κ, λ and combinations thereof). In some embodiments, provided non-human animals contain a DNA sequence at an endogenous non-human Igλ light chain locus that includes a plurality of human Vλ and Jλ coding sequences interspersed with non-coding non-human (e.g., murine) immunoglobulin λ light chain sequence.

In some embodiments, provided non-human animals are characterized by expression of antibodies from endogenous immunoglobulin κ light chain loci in the germline genome of said non-human animals, which antibodies contain (1) human Vλ domains and (2) non-human or human Cλ domains. In some embodiments, provided non-human animals are characterized by an improved usage of human Vλ regions from engineered immunoglobulin κ light chain loci (e.g., but not limited to, about 2-fold) as compared to one or more reference engineered non-human animals.

In some embodiments, a non-human animal, non-human cell or non-human tissue is provided whose germline genome comprises an endogenous immunoglobulin κ light chain locus comprising: (a) one or more human Vλ gene segments, (b) one or more human Jλ gene segments, and (c) a Cλ gene, wherein (a) and (b) are operably linked to (c), and wherein the rodent lacks a rodent Cκ gene at the endogenous immunoglobulin κ light chain locus.

In some embodiments, a non-human animal, non-human cell or non-human tissue is provided whose germline genome comprises an endogenous immunoglobulin κ light chain locus comprising insertion of one or more human Vλ gene segments, one or more human Jλ gene segments and a Cλ gene, which human Vλ and Jλ gene segments are operably linked to said Cλ gene, and which Cλ gene is inserted in the place of a non-human Cκ gene at the endogenous immunoglobulin κ light chain locus. In many embodiments of a non-human animal, non-human cell or non-human tissue, a Cλ gene inserted in the place of a non-human Cκ gene at an endogenous immunoglobulin κ light chain locus is a non-human or human Cλ gene. In some embodiments, a non-human Cλ gene is or comprises a mammalian Cλ gene selected from the group consisting of a primate, goat, sheep, pig, dog, cow, or rodent Cλ gene.

In some embodiments, a non-human Cλ gene is or comprises a rodent Cλ gene.

In some embodiments, a rodent Cλ gene is or comprises a mouse Cλ gene. In some embodiments, a mouse Cλ gene comprises a sequence that is at least 80%, at least 85%, at least 90%, at least 95%, or at least 98% identical to a mouse Cλ gene selected from the group consisting of a mouse Cλ1, mouse Cλ2 and a mouse Cλ3. In some embodiments, a mouse Cλ gene comprises a sequence that is substantially identical or identical to a mouse Cλ gene selected from the group consisting of a mouse Cλ1, mouse Cλ2 and a mouse Cλ3. In some embodiments, a mouse Cλ1 gene is or comprises SEQ ID NO: 1. In some certain embodiments, a mouse Cλ2 gene is or comprises SEQ ID NO:3. In some certain embodiments, a mouse Cλ3 gene is or comprises SEQ ID NO:5. In some certain embodiments, a mouse Cλ gene comprises a sequence that is identical to a mouse Cλ1 gene.

In some embodiments, a mouse Cλ gene comprises a sequence that is 80% to 100%, 85% to 100%, 90% to 100%, 95% to 100%, or 98% to 100% identical to a mouse Cλ gene selected from the group consisting of a mouse Cλ1, mouse Cλ2 and a mouse Cλ3. In some embodiments, a mouse Cλ gene comprises a sequence that is 80% to 98%, 80% to 95%, 80% to 90%, or 80% to 85% identical to a mouse Cλ gene selected from the group consisting of a mouse Cλ1, mouse Cλ2 and a mouse Cλ3. In some embodiments, a mouse Cλ gene comprises a sequence that is 85% to 98%, 90% to 95%, or 88% to 93% identical to a mouse Cλ gene selected from the group consisting of a mouse Cλ1, mouse Cλ2 and a mouse Cλ3.

In some embodiments, a rodent Cλ gene is or comprises a rat Cλ gene. In some embodiments, a rat Cλ gene comprises a sequence that is at least 80%, at least 85%, at least 90%, at least 95%, or at least 98% identical to a rat Cλ gene selected from the group consisting of a rat Cλ1, rat Cλ2, rat Cλ3 and a rat Cλ4 gene. In some embodiments, a rat Cλ gene comprises a sequence that is substantially identical or identical to a rat Cλ gene selected from the group consisting of a rat Cλ1, rat Cλ2, rat Cλ3 and a rat Cλ4 gene. In some certain embodiments, a rat Cλ1 gene is or comprises SEQ ID NO:7. In some certain embodiments, a rat Cλ2 gene is or comprises SEQ ID NO:9. In some certain embodiments, a rat Cλ3 gene is or comprises SEQ ID NO: 11. In some certain embodiments, a rat Cλ4 gene is or comprises SEQ ID NO:13.

In some embodiments, a rat Cλ gene comprises a sequence that is 80% to 100%, 85% to 100%, 90% to 100%, 95% to 100%, or 98% to 100% identical to a rat Cλ gene selected from the group consisting of a rat Cλ1, rat Cλ2, rat Cλ3 and a rat Cλ4 gene. In some embodiments, a rat Cλ gene comprises a sequence that is 80% to 98%, 80% to 95%, 80% to 90%, or 80% to 85% identical to a rat Cλ gene selected from the group consisting of a rat Cλ1, rat Cλ2, rat Cλ3 and a rat Cλ4 gene. In some embodiments, a rat Cλ gene comprises a sequence that is 85% to 98%, 90% to 95%, or 88% to 93%, identical to a rat Cλ gene selected from the group consisting of a rat Cλ1, rat Cλ2, rat Cλ3 and a rat Cλ4 gene.

In some embodiments, a human Cλ gene comprises a sequence that is at least 80%, at least 85%, at least 90%, at least 95%, or at least 98% identical to a human Cλ gene selected from the group consisting of a human Cλ1, human Cλ2, human Cλ3, human Cλ6 and a human Cλ7 gene. In some embodiments, a human Cλ gene comprises a sequence that is substantially identical or identical to a human Cλ gene selected from the group consisting of a human Cλ, human Cλ2, human Cλ3, human Cλ6 and a human Cλ7 gene. In some embodiments, a human Cλ gene comprises a sequence that is identical to a human Cλ gene selected from the group consisting of a human Cλ1, human Cλ2, human Cλ3, human Cλ6 and a human Cλ7 gene. In some certain embodiments, a human Cλ1 gene is or comprises SEQ ID NO:15. In some certain embodiments, a human Cλ2 gene is or comprises SEQ ID NO:17. In some certain embodiments, a human Cλ3 gene is or comprises SEQ ID NO: 19. In some certain embodiments, a human Cλ6 gene is or comprises SEQ ID NO:21. In some certain embodiments, a human Cλ7 gene is or comprises SEQ ID NO:23. In some certain embodiments, a human Cλ gene is or comprises a human Cλ2 gene.

In some embodiments, a human Cλ gene comprises a sequence that is 80% to 100%, 85% to 100%, 90% to 100%, 95% to 100%, or 98% to 100% identical to a human Cλ gene selected from the group consisting of a human Cλ1, human Cλ2, human Cλ3, human Cλ6 and a human Cλ7 gene. In some embodiments, a human Cλ gene comprises a sequence that is 80% to 98%, 80% to 95%, 80% to 90%, or 80% to 85% identical to a human Cλ gene selected from the group consisting of a human Cλ1, human Cλ2, human Cλ3, human Cλ6 and a human Cλ7 gene. In some embodiments, a human Cλ gene comprises a sequence that is 85% to 98%, 90% to 95%, or 88% to 93%, identical to a human Cλ gene selected from the group consisting of a human Cλ1, human Cλ2, human Cλ3, human Cλ6 and a human Cλ7 gene.

In some embodiments of a provided non-human animal, non-human cell or non-human tissue, insertion of one or more human Vλ gene segments and one or more human Jλ gene segments replace non-human Vκ and Jκ gene segments at the endogenous immunoglobulin κ light chain locus. In some embodiments, insertion includes human non-coding DNA that naturally appears between human Vλ and Jλ gene segments, and combinations thereof. In some embodiments of a provided non-human animal, non-human cell or non-human tissue, insertion of one or more human Vλ gene segments and one or more human Jλ gene segments are in place of or replace non-human Vκ and Jκ gene segments at the endogenous immunoglobulin κ light chain locus. In some embodiments of a provided non-human animal, non-human cell or non-human tissue, an immunoglobulin κ light chain locus comprises insertion of at least 24, at least 34, at least 52, at least 61, or at least 70 human Vλ gene segments and at least 1, at least 2, at least 3, at least 4 or at least 5 human Jλ gene segments. In some certain embodiments of a provided non-human animal, non-human cell or non-human tissue, an immunoglobulin κ light chain locus comprises insertion of 39 human Vλ gene segments and at least 5 human Jλ gene segments. In some embodiments of a provided non-human animal, non-human cell or non-human tissue, an immunoglobulin κ light chain locus comprises insertion of human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, V,3-1 or any combination thereof, and human J Jλ1, Jλ2, Jλ3, Jλ6, Jλ7, or any combination thereof. In some embodiments, insertion includes human non-coding DNA that naturally appears adjacent to a human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in an endogenous human λ light chain locus, and human non-coding DNA (in whole or in part) that naturally appears adjacent to a human Jλ1, Jλ2, Jλ3, Jλ6 or Jλ7 in an endogenous human λ light chain locus. In some certain embodiments, insertion includes human non-coding DNA that naturally appears adjacent to a human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in an endogenous human λ light chain locus, and human non-coding DNA that naturally appears adjacent to a human Jκ1, Jκ2, Jκ3, Jκ4, or Jκ5 in an endogenous human κ light chain locus. In some certain embodiments, insertion of human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1 or any combination thereof includes human non-coding DNA that naturally appears adjacent to a human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in an endogenous human λ light chain locus, and the insertion of human Jλ1, Jλ2, Jλ3, Jλ6, Jλ7, or any combination thereof includes human non-coding DNA (in whole or in part) that naturally appears adjacent to a human Jλ1, Jλ2, Jλ3, Jλ6, Jλ7 in an endogenous human λ light chain locus. In some certain embodiments, the insertion of human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1 or any combination thereof includes human non-coding DNA that naturally appears adjacent to a human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in an endogenous human λ light chain locus, and the insertion of human Jλ1, Jλ2, Jλ3, Jλ6, Jλ7, or any combination thereof includes human non-coding DNA (in whole or in part) that naturally appears adjacent to a human Jκ1, Jκ2, Jκ3, Jκ4, or Jκ5 in an endogenous human κ light chain locus.

In some embodiments of a provided non-human animal, non-human cell or non-human tissue, an immunoglobulin κ light chain locus as described herein further comprises a human immunoglobulin κ light chain sequence between the one or more human Vλ gene segments, the one or more human Jλ gene segments, the one or more human Vλ gene segments and the one or more human Jλ gene segments, and combinations thereof. In some embodiments, a human immunoglobulin κ light chain sequence as described herein is or comprises a genomic sequence that naturally appears between a human Vκ4-1 gene segment and a human Jκ1 gene segment of a human immunoglobulin κ light chain locus.

In some embodiments of a provided non-human animal, non-human cell or non-human tissue, the germline genome of said non-human animal, non-human cell or non-human tissue further comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region at the endogenous immunoglobulin heavy chain locus (see, e.g., U.S. Pat. Nos. 8,502,018, 8,642,835, 8,697,940 and 8,791,323, each of which is incorporated herein by reference in its entirety).

In some embodiments, insertion of one or more human $V_H$ gene segments, one or more human $D_H$ gene segments and one or more human $J_H$ gene segments are in place of or replace, in whole or in part, non-human $V_H$, $D_H$ and $J_H$ gene segments (e.g., positionally replace or substitute coding sequences of non-human $V_H$, $D_H$ and $J_H$ gene segments with coding sequences of human $V_H$, $D_H$ and $J_H$ gene segments). In some certain embodiments, insertion includes human non-coding DNA that naturally appears between human $V_H$, $D_H$ and $J_H$ gene segments, and combinations thereof. In some embodiments, a non-human immunoglobulin heavy chain constant region is or comprises an endogenous non-human immunoglobulin heavy chain constant region. In many embodiments, a non-human immunoglobulin heavy chain constant region (e.g., endogenous) includes one or more non-human immunoglobulin heavy chain constant region genes or gene segments (e.g., IgM, IgD, IgG, IgE, IgA, etc.). In some certain embodiments, an immunoglobulin heavy chain locus as described herein comprises insertion of the human $V_H$ gene segments $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, or any combination thereof, the human $D_H$ gene segments $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof, and the human $J_H$ gene segments $J_H1$, $J_H2$, $J_H3$, $J_H4$, $J_H5$, $J_H6$, or any combination thereof. In some certain embodiments, insertion includes human non-coding DNA that naturally appears adjacent to a human $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, or $V_H6$-1 in an endogenous heavy chain locus, human non-coding DNA that naturally appears adjacent to a human $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, or $D_H7$-27, and human non-coding DNA that naturally appears adjacent to a human $J_H1$, $J_H2$, $J_H3$, $J_H4$, $J_H5$, or $J_H$ in an endogenous heavy chain locus.

In some embodiments, a non-human animal described herein includes an Adam6 gene in its genome (e.g., its germline genome), which encodes an ADAM6 polypeptide, functional ortholog, functional homolog, or functional fragment thereof (see, e.g., U.S. Pat. Nos. 8,642,835 and 8,697,940, each of which is incorporated herein by reference in its entirety). In some embodiments, an ADAM6 polypeptide, functional ortholog, functional homolog, or functional fragment thereof is expressed from an Adam6 gene. In some embodiments, an Adam6 gene is does not originate from the non-human animal that includes an Adam6 gene (e.g., a mouse that includes a rat Adam6 gene or a mouse Adam6 gene obtained from another strain of mouse). In some embodiments, a non-human animal described herein includes an ectopic Adam6 gene. An "ectopic" Adam6 gene, as used herein, refers to an Adam6 gene that is in a different context than the Adam6 gene appears in a wild-type non-human animal. For example, the Adam6 gene could be located on a different chromosome, located at a different locus, or positioned adjacent to different sequences. An exemplary ectopic Adam6 gene is a mouse Adam6 gene located within human immunoglobulin sequences (e.g., human heavy chain variable region gene segments). In some embodiments, a non-human animal described herein includes an inserted or integrated Adam6 gene.

In some embodiments, a non-human animal described herein includes an insertion of one or more nucleotide sequences encoding one or more non-human Adam6 polypeptides, functional orthologs, functional homologs, or functional fragments thereof in its genome (e.g., its germline genome).

In some embodiments, a non-human animal described herein includes one or more nucleotide sequences encoding one or more non-human ADAM6 polypeptides, functional orthologs, functional homologs, or functional fragments thereof in its genome (e.g., its germline genome). In some embodiments, a non-human animal described herein includes a mouse Adam6a gene and/or a mouse Adam6b gene in its genome (e.g. its germline genome). In some embodiments, a non-human animal described herein includes one or more nucleotide sequences a mouse ADAM6a, functional ortholog, functional homolog, or functional fragment thereof, and/or a mouse ADAM6b, functional ortholog, functional homolog, or functional fragment thereof.

In some embodiments, one or more nucleotide sequences encoding one or more non-human ADAM6 polypeptides, functional orthologs, functional homologs, or functional fragments thereof are inserted and/or are located on the same chromosome as the endogenous immunoglobulin heavy chain locus. In some embodiments, one or more nucleotide sequences encoding one or more non-human ADAM6 polypeptides, functional orthologs, functional homologs, or functional fragments thereof are inserted and/or are located in a position so that the one or more nucleotide sequences encoding one or more non-human ADAM6 polypeptides, functional orthologs, functional homologs, or functional fragments thereof are contiguous with human immunoglobulin heavy chain variable region gene segments. In some embodiments, one or more nucleotide sequences encoding one or more non-human ADAM6 polypeptides, functional orthologs, functional homologs, or functional fragments thereof are inserted and/or are located in a position so that the one or more nucleotide sequences encoding one or more non-human ADAM6 polypeptides, functional orthologs, functional homologs, or functional fragments thereof are adjacent to human immunoglobulin heavy chain variable region gene segments. In some embodiments, one or more nucleotide sequences encoding one or more non-human ADAM6 polypeptides, functional orthologs, functional homologs, or functional fragments thereof are inserted and/or are located in a position so that the one or more nucleotide sequences encoding one or more non-human ADAM6 polypeptides, functional orthologs, functional homologs, or functional fragments thereof are located in between human immunoglobulin heavy chain variable region gene segments. In some embodiments, one or more nucleotide sequences encoding one or more non-human ADAM6 polypeptides, functional orthologs, functional homologs, or functional fragments thereof are inserted and/ or are located between a first and a second human $V_H$ gene segment. In some embodiments, a first human $V_H$ gene segment is human $V_H1$-2 and a second human $V_H$ gene segment is human $V_H6$-1. In some embodiments, one or more nucleotide sequences encoding one or more non-human ADAM6 polypeptides, functional orthologs, functional homologs, or functional fragments thereof are inserted and/or are located in the place of a human Adam6 pseudogene. In some embodiments, one or more nucleotide sequences encoding one or more non-human ADAM6 polypeptides, functional orthologs, functional homologs, or functional fragments thereof are inserted between a human $V_H$ gene segment and a human $D_H$ gene segment.

In some embodiments, a non-human animal described herein includes an Adam6 gene that restores or enhances ADAM6 activity. In some embodiments, the Adam6 gene restores ADAM6 activity to the level of a comparable non-human animal that includes a functional, endogenous Adam6 gene. In some embodiments, the Adam6 gene enhances ADAM6 activity to a level that is at least 2 times, at least 3 times, at least 4 times, at least 5 times, at least 6 times, at least 7 times, at least 8 times, at least 9 times, or at least 10 times the ADAM6 activity of a comparable non-human animal that does not include a functional Adam6 gene.

In some embodiments, a non-human animal described herein includes an Adam6 gene that restores or enhances fertility in a male non-human animal. In some embodiments, the Adam6 gene restores fertility in a male non-human animal to a level of a comparable non-human animal that includes a functional, endogenous Adam6 gene. In some embodiments, the Adam6 gene restores fertility in a male non-human animal so that the number of pups produced by mating the male non-human animal is at least 70%, at least 80%, at least 90%, at least 95% the number of pups produced from a comparable mating of a comparable, male non-human animal that does not include a functional Adam6 gene. In some embodiments, the Adam6 gene enhances fertility in a male non-human animal so that number of pups produced by the mating of the male non-human animal include at least 2 times, at least 3 times, at least 4 times, at least 5 times, at least 6 times, at least 7 times, at least 8 times, at least 9 times, or at least 10 times the number of pups produced from a comparable mating of a comparable, male non-human animal that does not include a functional Adam6 gene.

In some embodiments, a non-human immunoglobulin heavy chain locus as described herein lacks at least one endogenous non-human Adam6 gene. In some embodiments, the lack of the at least one endogenous non-human Adam6 gene reduces ADAM6 activity and/or fertility in a male mouse that lacks an endogenous non-human Adam6 gene. In some embodiments, a non-human immunoglobulin heavy chain locus as described herein includes a disruption of at least one endogenous non-human Adam6 gene. In some embodiments, the disruption of at least one endogenous non-human Adam6 gene reduces ADAM6 activity and/or fertility in a male mouse that lacks an endogenous non-human Adam6 gene.

In some embodiments of a non-human animal, non-human cell or non-human tissue, the non-human animal, non-human cell or non-human tissue is homozygous or heterozygous for an endogenous immunoglobulin heavy chain locus as described herein.

In some embodiments of a non-human animal, non-human cell or non-human tissue, the non-human animal, non-human cell or non-human tissue is homozygous or heterozygous for an endogenous immunoglobulin κ light chain locus as described herein.

In some embodiments of a provided non-human animal, non-human cell or non-human tissue, the endogenous immunoglobulin λ light chain locus is deleted in whole or in part. In some embodiments of a provided non-human animal, non-human cell or non-human tissue, the endogenous immunoglobulin λ light chain locus is functionally silenced or otherwise non-functional (e.g., by gene targeting). In some certain embodiments of a provided non-human animal, non-human cell or non-human tissue, the non-human animal, non-human cell or non-human tissue is homozygous or heterozygous for a functionally silenced or otherwise non-functional endogenous immunoglobulin λ light chain locus as described herein.

In some embodiments, a non-human animal, non-human cell or non-human tissue as described herein does not detectably express endogenous immunoglobulin λ light chains, endogenous immunoglobulin κ light chains, or endogenous immunoglobulin λ light chains and endogenous immunoglobulin κ light chains.

In some embodiments, a non-human animal, non-human cell or non-human tissue as described herein has a genome further comprising a nucleic acid sequence encoding an exogenous terminal deoxynucleotidyltransferase (TdT) operably linked to a transcriptional control element.

In some embodiments, a transcriptional control element includes a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof.

In some embodiments, a nucleic acid sequence encoding an exogenous TdT is located at an immunoglobulin κ light chain locus, an immunoglobulin λ light chain locus, an immunoglobulin heavy chain locus, a RAG1 locus, or a RAG2 locus.

In some embodiments, the TdT is a human TdT. In some embodiments, the TdT is a short isoform of TdT (TdTS).

A human Igλ light chain sequence, in some embodiments, comprises genetic material from (e.g., isolated or obtained from) or identical to a human Igλ light chain locus, wherein the human Igλ light chain sequence encodes an Ig light chain that comprises the encoded portion of the genetic material from the human Igλ light chain locus. In some embodiments, a human Igλ light chain sequence as described herein comprises at least one human Vλ gene segment and at least one human Jλ gene segment, and one or more sequences necessary to promote rearrangement (e.g., recombination signal sequence(s)) of said at least one human Vλ gene segment with said at least one human Jλ gene segment to form a functional rearranged Vλ-Jλ sequence that encodes a human Vλ domain. In many embodiments, a human Igλ light chain sequence comprises a plurality of human Vλ and Jλ gene segments and one or more sequences necessary to promote rearrangement of said human Vλ gene segments with said human Jλ gene segments. In many embodiments, a human Igλ light chain sequence comprises at least the coding sequences (e.g., exons) of one or more human Vλ gene segments and at least the coding sequences (e.g., exons) of one or more human Jλ gene segments. In some embodiments, a human Igλ light chain sequence as described herein is a genomic sequence of a human Igλ light chain locus (e.g., isolated and/or cloned from a bacterial artificial chromosome) and contains a plurality of human Vλ gene segments in germline configuration. In some embodiments, a human Igλ light chain sequence comprises human Vλ and Jλ sequences (i.e., gene segments) in germline configuration (i.e., a plurality of human Vλ gene segments separated by intervening DNA that includes sequences necessary for and that promote recombination, and a plurality of Jλ gene segments separated by intervening DNA that incudes sequences necessary for and that promote recombination).

In some embodiments, a human Igλ light chain sequence as described herein is an engineered sequence and contains a plurality of human Jλ gene segments in a configuration that is different than that which appears in a human Igλ light chain locus in a human cell. In some embodiments, a human Igλ light chain sequence as described herein is an engineered sequence and contains a plurality of human Vλ and Jλ gene segments in a configuration that resembles or is similar to that which appears in an Igκ light chain locus of a wild-type murine or human cell. In some embodiments, a human Igλ light chain sequence comprises engineered human Jλ sequences (i.e., coding sequences of human Jλ gene segments made by de novo DNA synthesis that includes sequences necessary for and that promote recombination with one or more human Vλ gene segments). In some embodiments, a human Igλ light chain sequence comprises Igκ and Igx sequences that naturally appear separately in Igκ and Igλ genomic sequences, respectively. In some certain embodiments, a human Igλ light chain sequence comprises a Igκ sequence(s), in particular, a Jκ region (i.e., a sequence that contains coding and non-coding sequences that appear in a region containing a plurality of Jκ gene segments), that naturally appears in an Igκ light chain locus except that said Igκ sequence contains coding sequences of Jλ gene segments and Jλ 12RSS in the place of corresponding coding sequences of Jκ gene segments and Jκ 23RSS, respectively. In some certain embodiments, a human Igλ light chain sequence comprises a plurality of Jλ gene segments and Jλ 12RSS in the place of Jκ gene segments and Jκ 23RSS of a Jκ region sequence. In various embodiments, intervening (or intergenic) DNA that includes sequences necessary for and that promote recombination includes human Igκ and/or human Igλ genomic sequence(s). Alternatively, and in some embodiments, intervening (or intergenic) DNA that includes sequences necessary for and that promote recombination includes murine Igκ and/or murine Igλ genomic sequence(s).

In some certain embodiments, a human Igλ light chain sequence is or comprises a sequence that appears in the Drawing. In some embodiments, a human Igλ light chain sequence encodes, or is capable of encoding (e.g., after rearrangement of human gene segments), a Vλ domain polypeptide, which Vλ domain polypeptide appears in an immunoglobulin, in particular, an immunoglobulin that is expressed by a human B cell. Non-human animals, embryos, cells and targeting constructs for making non-human animals, non-human embryos, and cells containing said human Igλ light chain sequence in the place of a corresponding non-human Igκ light chain sequence (e.g., an endogenous rodent Igκ light chain locus) are also provided.

In some embodiments, a human Igλ light chain sequence is inserted in the place of a corresponding non-human Igκ light chain sequence within the germline genome of a non-human animal. In some embodiments, a human Igλ light chain sequence is inserted upstream of a non-human Igλ light chain sequence (e.g., a non-human Igλ light chain constant region gene sequence), which non-human Igλ light chain sequence is positioned in the place of a non-human Igκ light chain sequence (e.g., a non-human Igκ light chain constant region gene sequence). In some embodiments, a human Igκ light chain sequence is inserted in the midst of said human Igλ light chain sequence (i.e., between human Vλ and Jλ gene segments) so that said human Igκ light chain sequence is juxtaposed by human Igλ light chain sequences.

In some embodiments, all or substantially all of the variable region of a non-human Igκ light chain locus is replaced or substituted with one or more human Igλ light chain sequences (as described herein), and said one or more human Igλ light chain sequences are operably linked to a non-human or human Igλ light chain constant region gene. In some embodiments, a non-human Igκ light chain constant region gene is deleted or replaced in a non-human animal that includes a human Igλ light chain sequence as described herein. In one non-limiting example, in the instance of an insertion of a human Igλ light chain sequence that is inserted into a non-human Igκ light chain locus, said insertion is made in manner to maintain the integrity of non-human Igκ light chain enhancer regions (or enhancer sequences) near the insertion point (e.g., a non-human Igκ intronic enhancer and/or a non-human Igκ 3' enhancer). Thus, such non-human animals have wild-type Igλ light chain enhancer regions (or enhancer sequences) operably linked to human and non-human Igλ light chain sequences (e.g., human Vλ and Jλ gene segments, and a non-human Cλ region gene) or operably linked to human Igλ light chain sequences (e.g., human Vλ and Jλ gene segments, and a human Cλ region gene). In some embodiments, a non-human Igκ light chain locus that is altered, displaced, disrupted, deleted, replaced or engineered with one or more human Igλ light chain sequences as described herein is a murine Igκ light chain locus. In some embodiments, one or more human Igλ light chain sequences as described herein is inserted into one copy (i.e., allele) of a non-human Igκ light chain locus of the two copies of said non-human Igκ light chain locus, giving rise to a non-human animal that is heterozygous with respect to the human Igκ light chain sequence. In some embodiments of a non-human animal that is heterozygous with respect to the human Igκ light chain sequence, the non-human animal includes one or more human Igκ light chain sequences inserted into the other copy (i.e., allele) of the non-human Igκ light chain locus. In some embodiments, a non-human animal is provided that is homozygous for an Igκ light chain locus that includes one or more human Igλ light chain sequences as described herein.

In some embodiments, an engineered non-human Igκ light chain locus as described herein comprises human Vλ and Jλ gene segments operably linked to a non-human or human Igλ light chain constant region gene, wherein said non-human or human Igλ light chain constant region gene is located in the place of a non-human Igκ light chain constant region gene that appears in a wild-type Igκ light chain locus of a non-human animal of the same species.

In some embodiments, one or more endogenous non-human Igλ light chain sequences (or portions thereof) of an endogenous non-human Igλ light chain locus are not deleted. In some embodiments, one or more endogenous non-human Igλ light chain sequences (or portions thereof) of an endogenous non-human Igλ light chain locus are deleted. In some embodiments, one or more endogenous non-human Igλ light chain sequences (e.g., V, J and/or C or any combination thereof) of an endogenous non-human Igλ light chain locus is altered, displaced, disrupted, deleted or replaced so that said non-human Igλ light chain locus is functionally silenced. In some embodiments, one or more endogenous non-human Igλ light chain sequences (e.g., V, J and/or C or any combination thereof) of an endogenous non-human Igλ light chain locus is altered, displaced, disrupted, deleted or replaced with a targeting vector so that said non-human Igλ light chain locus is functionally inactivated (i.e., unable to produce a functional light chain of an antibody that is expressed and/or detectable in the antibody repertoire of the non-human animal). Guidance for inactivation of an endogenous non-human Igλ light chain locus is provided in, e.g., U.S. Pat. No. 9,006,511 (see, e.g., FIG. 2), which is incorporated herein by reference in its entirety.

In some embodiments, a non-human animal contains an engineered Igκ light chain locus as described herein that is randomly integrated into its genome (e.g., as part of a randomly integrated human Igλ light chain sequence). Thus, such non-human animals can be described as having a human Igλ light chain transgene containing a plurality of human Vλ and Jλ gene segments operably linked to a non-human or human Igλ light chain constant region gene and non-human Igκ light chain enhancer regions (or enhancer sequences), so that that said human Vλ and Jλ gene segments are capable of rearrangement and encoding an Ig light chain of an antibody in the expressed repertoire of the non-human animal, which Ig light chain includes a human Vλ domain and a non-human Cλ domain or which Ig light chain includes human Vλ and Cλ domains. An engineered Igκ light chain locus or transgene as described herein can be detected using a variety of methods including, for example, PCR, Western blot, Southern blot, restriction fragment length polymorphism (RFLP), or a gain or loss of allele assay. In some embodiments, a non-human animal as described herein is heterozygous with respect to an engineered Igκ light chain locus as described herein. In some embodiments, a non-human animal as described herein is hemizygous with respect to an engineered Igκ light chain locus as described herein. In some embodiments, a non-human animal as described herein contains one or more copies of an engineered Igκ light chain locus or transgene as described herein. In some embodiments, a non-human animal as described herein contains an Igκ light chain locus as depicted in the Drawing.

The present disclosure recognizes that a non-human animal as described herein will utilize human heavy chain, λ light chain, and κ light chain variable region gene segments included in its genome in its antibody selection and generation mechanisms (e.g., recombination and somatic hypermutation). As such, in various embodiments, human immunoglobulin human heavy chain, λ light chain, and κ light chain variable domains generated by non-human animals described herein are encoded by the human heavy, λ light chain, and κ light chain variable region gene segments included in their genome or somatically hypermutated variants thereof, respectively.

In some embodiments, a non-human animal is provided whose genome comprises an engineered immunoglobulin κ light chain locus, where the non-human animal includes a B cell that includes a human heavy variable region sequence, a human λ light chain variable region sequence, and/or a human κ light chain variable region sequence that is somatically hypermutated. In some embodiments, a human heavy variable region sequence, a human λ light chain, and/or a human κ light chain variable region sequence present in a B cell of a mouse of the present disclosure has 1, 2, 3, 4, 5, or more somatic hypermutations. Those skilled in the art are aware of methods for identifying source gene segments in a mature antibody sequence. For example, various tools are available to aid in this analysis, such as, for example, DNAPLOT, IMGT/V-QUEST, JOINSOLVER, SoDA, and Ab-origin.

The present disclosure provides, among other things, cells and tissues from non-human animals described herein. In some embodiments, provided are splenocytes (and/or other lymphoid tissue) from a non-human animal as described herein. In some embodiments, provided is a B cell from a non-human animal as described herein. In some embodiments, provided is a pro-B cell from a non-human animal as described herein. In some embodiments, provided is a pre-B cell from a non-human animal as described herein. In some embodiments, provided is an immature B cell from a non-human animal as described herein. In some embodiments, provided is a mature naïve B cell from a non-human animal as described herein. In some embodiments, provided is an activated B cell from a non-human animal as described herein. In some embodiments, provided is a memory B cell from a non-human animal as described herein. In some embodiments, provided is a B lineage lymphocyte from a non-human animal as described herein. In some embodiments, provided is plasma or a plasma cell from a non-human animal as described herein. In some embodiments, provided is a stem cell from a non-human animal as described herein. In some embodiments, a stem cell is an embryonic stem cell. In some embodiments, provided is a germ cell from a non-human animal as described herein. In some embodiments, a germ cell is an oocyte. In some embodiments, a germ cell is a sperm cell. In some embodiments, a sperm cell from a non-human animal as described herein expresses one or more ADAM6 polypeptides, functional orthologs, functional homologs, or functional fragments thereof. In some embodiments, any cell or tissue from a non-human animal as described herein may be isolated. In some embodiments, provided is an isolated cell and/or an isolated tissue from a non-human animal as described herein. In some embodiments, a hybridoma is provided, wherein the hybridoma is made with a B cell of a non-human animal as described herein. In some embodiments, a hybridoma is made with a B cell of a non-human animal that has been immunized with an antigen of interest. In some embodiments, a hybridoma is made with a B cell of a non-human animal that expresses an antibody that binds (e.g., specifically binds) to an epitope on an antigen of interest.

Any of the non-human animals as described herein may be immunized with one or more antigens of interest under conditions and for a time sufficient that the non-human animal develops an immune response to said one or more antigens of interest. Those skilled in the art are aware of methods for immunizing non-human animals. An exemplary, non-limiting method for immunizing non-human animals can be found in US 2007/0280945A1, incorporated herein by reference in its entirety.

The present disclosure provides, among other things, immunized non-human animals as described herein, and cells and tissues isolated from the same. In some embodiments, a non-human animal described herein produces a population of B cells in response to immunization with an antigen that includes one or more epitopes. In some embodiments, a non-human animal produces a population of B cells that express antibodies that bind (e.g., specifically bind) to one or more epitopes of antigen of interest. In some embodiments, antibodies expressed by a population of B cells produced in response to an antigen include a heavy chain having a human heavy chain variable domain encoded by a human heavy chain variable region sequence and/or a lambda light chain having a human lambda light chain variable domain encoded by a human lambda light chain variable region sequence as described herein. In some embodiments, antibodies expressed by a population of B cells produced in response to an antigen include (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof.

In some embodiments, a non-human animal produces a population of B cells that express antibodies that bind to one or more epitopes of antigen of interest, where antibodies expressed by the population of B cells produced in response to an antigen include: (i) a heavy chain having a human heavy chain variable domain encoded by a human heavy chain variable region sequence, (ii) a lambda light chain having a human lambda light chain variable domain encoded by a human lambda light chain variable region sequence as described herein, (iii) a kappa light chain having a human kappa light chain variable domain encoded by a human kappa light chain variable region sequence as described herein, or (iv) any combination thereof. In some embodiments, a human heavy chain variable region sequence, a human λ light chain variable region sequence, and/or a human κ light chain variable region sequence as described herein is somatically hypermutated. In some embodiments, at least about 5%, 10%, 15%, 20%, 25%, 30%, 35%, 40%, 45%, 50%, 55%, 60%, 65%, 70%, 75%, 80%, 85%, 90% of the B cells in a population of B cells produced in response to an antigen include a human heavy chain variable region sequence, a human λ light chain variable region sequence, and/or a human κ light chain variable region sequence that is somatically hypermutated.

In some embodiments, non-human animals provided herein, in their germline genome, (1) include an engineered endogenous immunoglobulin κ light chain locus comprising (a) one or more human Vλ gene segments, (b) one or more human Jλ gene segments, and (c) a Cλ gene, where the one or more human Vλ gene segments and one or more human Jλ gene segments are operably linked to the Cλ gene, (2) lack a rodent Cκ gene at the engineered endogenous immunoglobulin κ locus, and (3) include an engineered endogenous immunoglobulin κ light chain locus comprising (a) one or more human Vκ gene segments, (b) one or more human Jκ gene segments, and (c) a Cκ gene, where the one or more human Vκ gene segments and one or more human Jκ gene segments are operably linked to the Cκ gene. In some embodiments, the percentage of light chains in splenocytes (e.g., as detected or observed, e.g., by flow cytometry (see, e.g., Example 3)) of such non-human animals that are λ light chains is at least 35%, at least 40%, at least 45%, at least 50%, at least 55%, at least 60%, at least 65%, at least 70%, or at least 75%. In some embodiments, the percentage of light chains in splenocytes (e.g., as detected or observed, e.g., by flow cytometry (see, e.g., Example 3)) of such non-human animals that are λ light chains is between 35-80%, between 35-75%, between 40-80%, between 40-75%, between 50-80%, between 50-75%, between 55-80%, between 55-75%, between 60-80%, or between 60-75%. In some embodiments, the percentage of light chains in splenocytes (e.g., as detected or observed, e.g., by flow cytometry (see, e.g., Example 3)) of such non-human animals that are κ light chains is at most 65%, at most 60%, at most 55%, at most 50%, at most 45%, at most 40%, or at most 35%. In some embodiments, the percentage of light chains in splenocytes (e.g., as detected or observed, e.g., by flow cytometry (see, e.g., Example 3)) of such non-human animals that are κ light chains is between 20-65%, between 25-65%, between 20-60%, between 25-60%, between 20-55%, between 25-55%, between 20-50%, between 25-50%, between 20-45%, between 25-45%, between 20-40%, or between 25-40%. In some embodiments, the ratio of κ:λ light chains in splenocytes (e.g., as detected or observed, e.g., by flow cytometry (see, e.g., Example 3)) of such non-human animals is between 0.5:1 and 3:1, 0.65:1 and 3:1, between 0.8:1 and 3:1, between 1:1 and 3:1, between 1.2:1 and 3:1, between 1:1 and 2.3:1, between 1.1:1 and 1.8:1, between 1.2:1 and 2.3:1, or between 1.2:1 and 1.8:1.

Methods of Making Provided Non-Human Animals

Compositions and methods for making non-human animals whose germline genome comprises an engineered Igκ light chain locus that includes one or more human Igλ light chain sequences (e.g., human Vλ and Jλ gene segments) in the place of non-human Igκ light chain sequences, including human Igλ light chain encoding sequences that include specific polymorphic forms of human Vλ and Jλ segments (e.g., specific V and/or J alleles or variants) are provided, including compositions and methods for making non-human animals that express antibodies comprising Igλ light chains that contain human variable regions and non-human or human constant regions, assembled from an Igκ light chain locus that contains human Vλ and Jλ gene segments operably linked to a non-human or human Igλ light chain constant region gene, which non-human or human Igλ light chain constant region gene is located in the place of a non-human Igκ light chain constant region gene that normally appears in a wild-type non-human Igκ light chain locus. In some embodiments, compositions and methods for making non-human animals that express such antibodies under the control of an endogenous Igκ enhancer(s) and/or an endogenous Igκ regulatory sequence(s) are also provided. In some embodiments, compositions and methods for making non-human animals that express such antibodies under the control of a heterologous Igκ enhancer(s) and/or a heterologous Igκ regulatory sequence(s) are also provided.

Methods described herein include inserting human Vλ and Jλ sequences encoding human Vλ domains upstream of a non-human or human Igλ light chain constant region gene (e.g., a murine or human Cλ region gene), which non-human or human Igλ light chain constant region gene is located in the place of a non-human Igκ light chain constant region gene that normally appears in a wild-type non-human Igκ light chain locus, so that an antibody is expressed, which antibody is characterized by the presence of a light chain that contains a human Vλ domain and a non-human Cλ domain (e.g., a rodent Cλ domain) or by the presence of a light chain that contains human Vλ and non-human Cλ domains (e.g., one or more rodent Cλ domains), and is expressed both on the surface of B cells and in the blood serum of a non-human animal.

In some embodiments, methods include insertion of genetic material that contains human Vλ and Jλ gene segments into an Igκ light chain locus (e.g., a wild-type, modified or engineered Igκ light chain locus). In some certain embodiments, methods include insertion of genetic material that contains human Jλ gene segments into an Igκ light chain locus of a modified or engineered strain. In some embodiments, genetic material that contains human Igλ light chain sequences can be engineered or genomic (e.g., cloned from a bacterial artificial chromosome). In some embodiments, genetic material that contains human Igλ light chain sequences can be designed from published sources and/or bacterial artificial chromosomes so that said genetic material contains human Vλ and Jλ segments in an orientation that is different from that which appears in a human Igλ light chain locus yet said genetic material still contains sequences to support rearrangement of said human Vλ and Jλ segments to encode a functional human Vλ domain of an Ig light chain. To give but one example, genetic material corresponding to a plurality of human Vλ and Jλ gene segments can be designed using the guidance provided herein to construct a human Igλ light chain sequence that contains human Vλ and Jλ segments in an order and/or arrangement that is different than that which appears in a human Igλ light chain locus of a human cell (e.g., an arrangement that resembles or is similar to a human or rodent Igκ light chain locus, such as, a series of V gene segments, followed 3' by intervening DNA, followed 3' by a series of J gene segments). In such an example, genetic content of human Vλ and Jλ gene segments would be equivalent to the corresponding segments in a human cell, however, the order and arrangement would be different. When constructing an engineered Igκ light chain locus for generation of a non-human animal as described herein, the requisite recombination signal sequences can be configured so that the human V and J gene segments can correctly rearrange and form a functional human Vλ domain. Guidance for germline configuration of human Vλ and Jλ gene segments and sequences necessary for proper recombination can be found in, e.g., Molecular Biology of B Cells, London: Elsevier Academic Press, 2004, Ed. Honjo, T., Alt, F. W., Neuberger, M. Chapters 4 (pp. 37-59) and 5 (61-82); incorporated herein by reference in their entireties.

In some embodiments, methods include multiple insertions in a single ES cell clone. In some embodiments, methods include sequential insertions made in a successive ES cell clones. In some embodiments, methods include a single insertion made in an engineered ES cell clone.

In some embodiments, methods include DNA insertion(s) upstream of a murine Cλ1 gene (or human Cλ2 gene) so that said DNA insertion(s) is operably linked to said murine Cλ1 gene (or human Cλ2 gene), which DNA insertion(s) comprise human Vλ gene segments Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1- 44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1 or any combination thereof, and human Jλ gene segments Jλ1, Jλ2, Jλ3, Jλ6, Jλ7, or any combination thereof, and which murine Cλ1 gene (or human Cλ2 gene) is located in the place of a murine Cκ gene of an endogenous Igκ light chain locus.

In some embodiments, methods include DNA insertion(s) downstream of a human Vλ3-1 gene segment and upstream of a non-human Igκ intronic enhancer region (or enhancer sequence) of an engineered Igκ light chain locus, so that said DNA insertion(s) is operably linked to a murine Cλ1 gene (or human Cλ2 gene), which DNA insertion(s) comprises a human Igκ genomic sequence that naturally appears between a human Vκ4-1 gene segment and a human Jκ1 gene segment of a human Igκ light chain locus, and one or more human Jλ gene segments (e.g., one, two, three, four, five, six or seven), which murine Cλ1 gene (or human Cλ2 gene) is located in the place of a murine Cκ gene of an endogenous non-human Igκ light chain locus. In some certain embodiments, methods include DNA insertion(s) between a human Vλ3-1 gene segment and a non-human Igκ intronic enhancer, which DNA insertion(s) includes human Vκ-Jκ sequence that naturally appears between human Vκ4-1 and Jκ1 gene segments of a human Igκ light chain locus and five human Jλ gene segments (e.g., Jλ1, Jλ2, Jλ3, Jλ6 and Jλ7). In various embodiments, DNA insertion(s) including human Jλ gene segments comprises human Jκ genomic DNA with coding sequences of human Jλ gene segments and human Jλ 12RSS.

Insertion of additional human Vλ and Jλ segments may be achieved using methods described herein to further supplement the diversity of an engineered Igλ light chain locus. For example, in some embodiments, methods can include insertion of about 270 kb of DNA upstream of a murine Cλ1 gene (or human Cλ2 gene) of an engineered Igκ light chain locus so that said DNA is operably linked to said murine Cλ1 gene (or human Cλ2 gene), which DNA includes human Vλ gene segments Vλ10-54, Vλ6-57, Vλ4-60, Vλ8-61 and Vλ4-69. In such embodiments, said DNA is inserted upstream of a human Vλ5-52 gene segment that is operably linked to a murine Cλ1 gene (or human Cλ2 gene) of an engineered Igκ light chain locus, which DNA includes human Vλ gene segments Vλ10-54, Vλ6-57, Vλ4-60, Vλ8-61 and Vλ4-69. In some certain embodiments, said DNA includes a human VpreB gene. Additional human Vλ gene segments described above may be cloned directly from commercially available BAC clones and arranged in smaller DNA fragment using recombinant techniques described herein or otherwise known in the art. Alternatively, additional human Vλ gene segments described above can be synthesized as an engineered DNA fragment and added to an engineered Igκ light chain locus as described above using molecular biology techniques known in the art. Likewise, additional human Jλ gene segments may be obtained from commercially available BAC clones or synthesized directly from published sequences. An exemplary illustration that shows an engineered Igκ light chain locus of non-human animals as described herein is set forth in FIG. 2B or 4B.

Where appropriate, a human Igλ light chain sequence (i.e., a sequence containing human Vλ and Jλ gene segments) encoding a human Vλ domain may separately be modified to include codons that are optimized for expression in a non-human animal (e.g., see U.S. Pat. Nos. 5,670,356 and 5,874,304). Codon optimized sequences are engineered sequences, and preferably encode the identical polypeptide (or a biologically active fragment of a full-length polypeptide which has substantially the same activity as the full-length polypeptide) encoded by the non-codon optimized parent polynucleotide. In some embodiments, a human Igλ light chain sequence encoding a human Vλ domain may separately include an altered sequence to optimize codon usage for a particular cell type (e.g., a rodent cell). For example, the codons of each nucleotide sequence to be inserted into the genome of a non-human animal (e.g., a rodent) may be optimized for expression in a cell of the non-human animal. Such a sequence may be described as a codon-optimized sequence.

Insertion of nucleotide sequences encoding human Vλ domains employs a minimal modification of the germline genome of a non-human animal as described herein and results in expression of antibodies comprising light chains having human Vλ domains, which human Vλ domains are expressed from endogenous engineered Igκ light chain loci. Methods for generating engineered non-human animals, including knockouts and knock-ins, are known in the art (see, e.g., Gene Targeting: A Practical Approach, Joyner, ed., Oxford University Press, Inc., 2000; incorporated herein by reference in its entirety). For example, generation of genetically engineered rodents may optionally involve disruption of the genetic loci of one or more endogenous rodent genes (or gene segments) and introduction of one or more heterologous genes (or gene segments or nucleotide sequences) into the rodent genome, in some embodiments, at the same location as an endogenous rodent gene (or gene segments).

In some embodiments, nucleotide sequences encoding human Vλ domains are introduced upstream of a murine or human Igλ light chain constant region gene of a randomly inserted engineered light chain transgene in the germline genome of a rodent. In some embodiments, nucleotide sequences encoding human Vλ domains are introduced upstream of a murine or human Igλ light chain constant region gene of an endogenous Igκ light chain locus in the germline genome of a rodent; in some certain embodiments, an endogenous Igκ light chain locus is altered, modified, or engineered to contain human Igλ gene segments (e.g., human V and J) operably linked to a mouse Cλ1 gene or operably linked to a human Cλ2 gene.

Figure 1B:
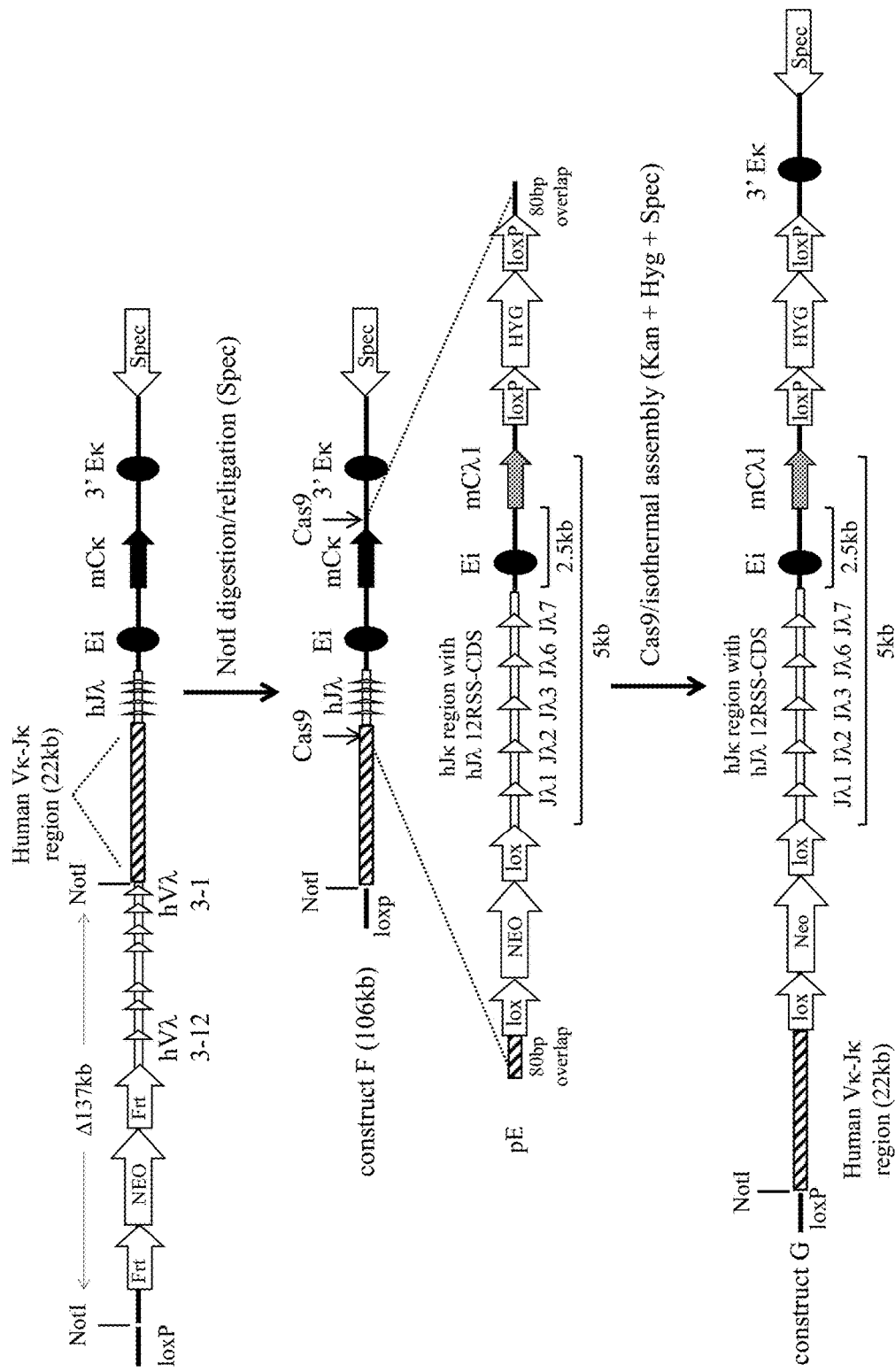
Figure 2A:
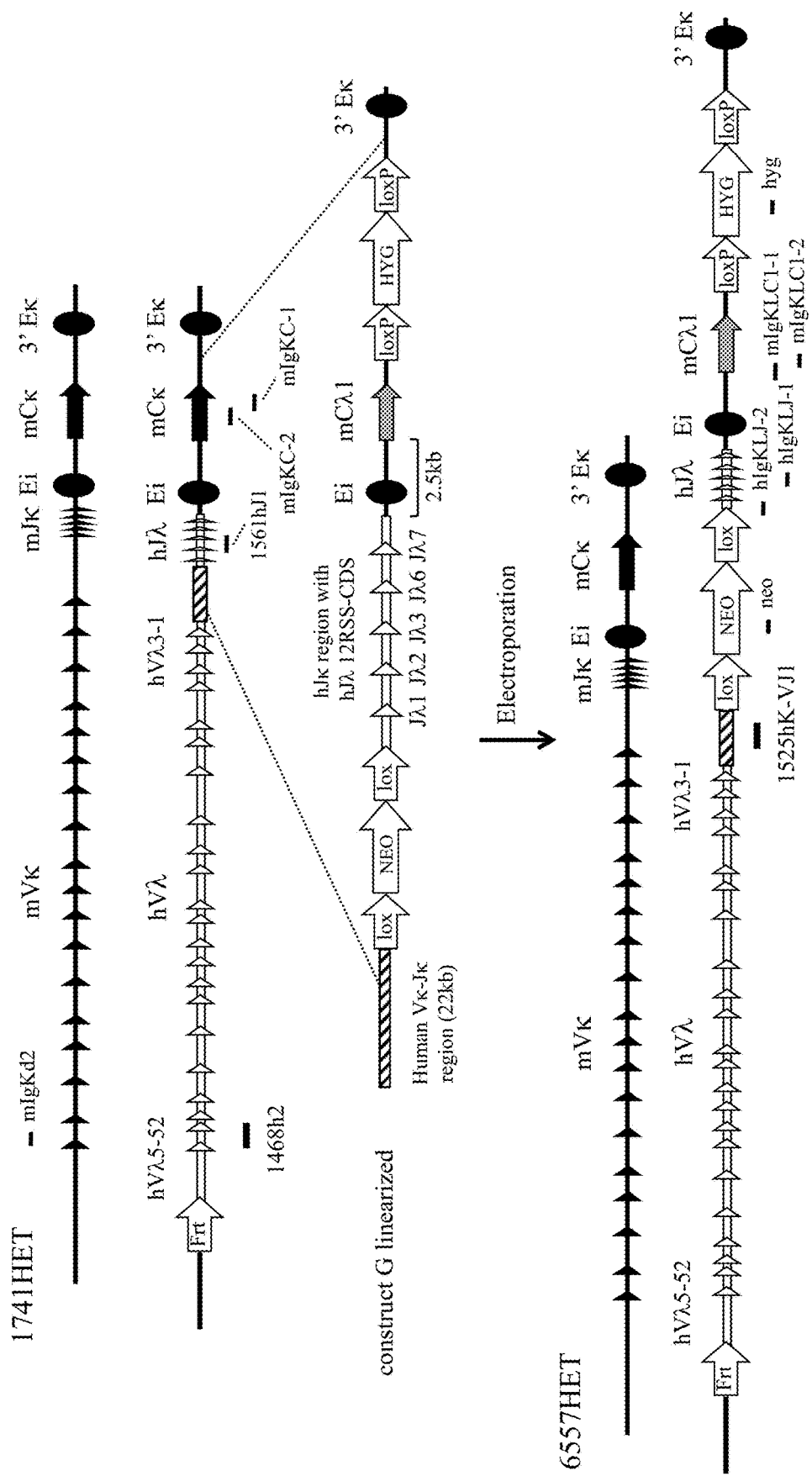
FIG. 2A shows an illustration of an exemplary embodiment, not to scale, of the insertion of a targeting vector (described in Example 1.1) into an engineered Igκ light chain locus of a rodent embryonic stem (ES) cell clone, which ES cell clone was used in generating an embodiment according to the present disclosure.
Figure 2B:
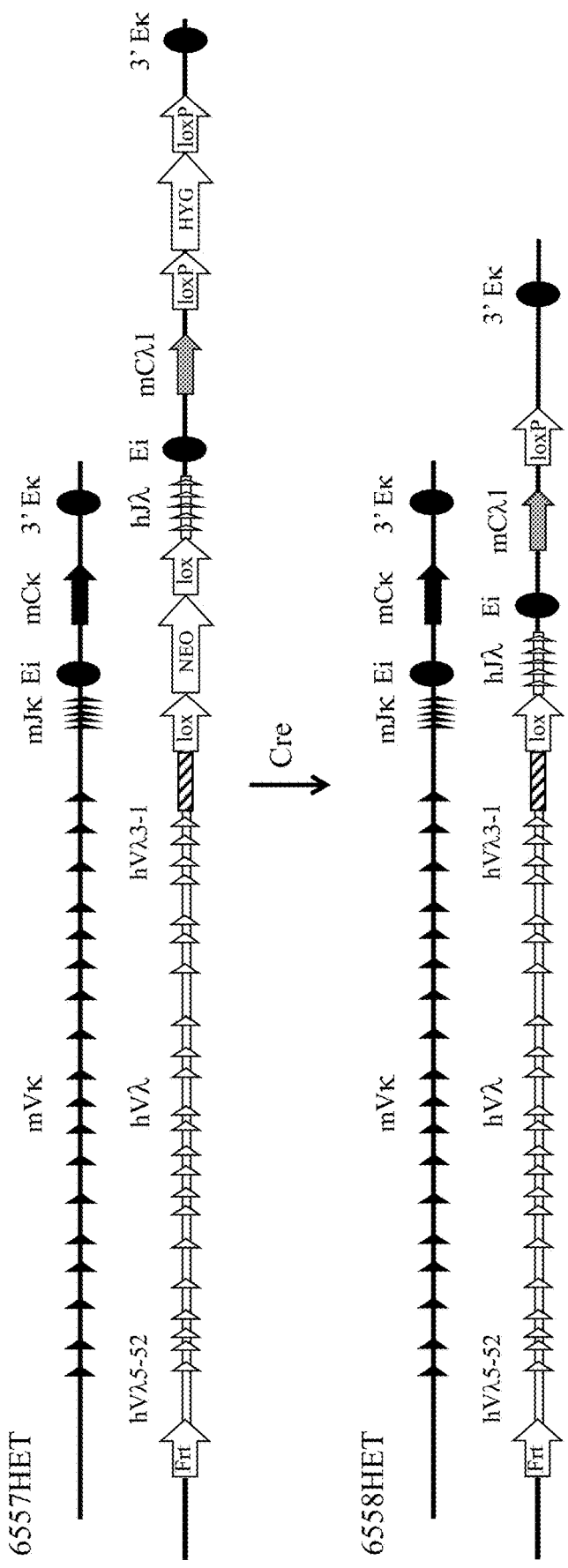
FIG. 2B shows an illustration of an exemplary embodiment, not to scale, of recombinase-mediated removal of selection cassette(s) in an engineered Igκ light chain locus resulting from the insertion of a targeting vector (described in Example 1.1) used in generating an embodiment of the rodent according to the present disclosure.
Figure 3:
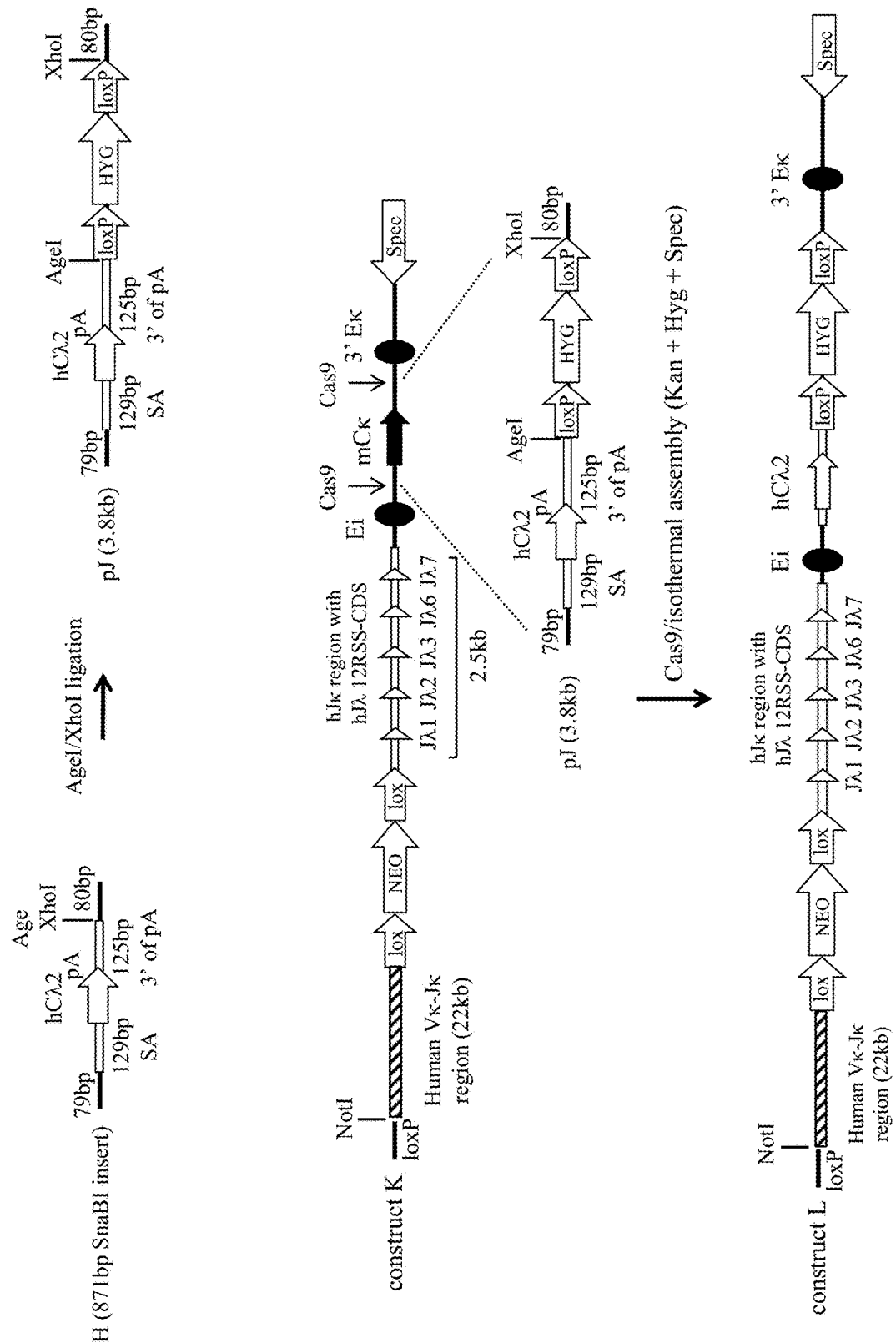
FIG. 3 shows an illustration of an exemplary embodiment, not to scale, of a strategy for constructing a targeting vector (described in Example 1.2) used in generating an embodiment of the rodent according to the present disclosure.

Schematic illustrations (not to scale) of exemplary methods for constructing an engineered Igκ light chain locus as described herein are provided in FIGS. 1A, 1B, 2A, 2B, 3, 4A and 4B. In particular, FIGS. 1A and 1B sets forth an exemplary strategy for construction of an engineered Igκ light chain locus characterized by insertion of nucleotide sequences containing a plurality of human Vλ and Jλ gene segments. As illustrated in FIGS. 1A and 1B, a DNA fragment containing a human Vκ-Jκ intergenic region (see U.S. Pat. Nos. 9,006,511, 9,012,717, 9,029,628, 9,035,128, 9,066,502, 9,150,662 and 9,163,092) and engineered fragment containing a set of human Jλ gene segments (e.g., human Jλ1, Jλ2, Jλ3, Jλ6 and Jλ7) is operably linked to a rodent Igκ intronic enhancer region (or enhancer sequence) via a series of steps using various molecular biology techniques described in Example 1. This engineered fragment is also engineered to contain a rodent Igλ light chain constant region that is operably linked to the human Jλ gene segments. Selection cassettes (e.g., Neomycin and Hygromycin) are included in the targeting vector to allow for selection of positive clones in bacteria and mammalian cells (e.g., embryonic stem cells). As illustrated a Neomycin resistance gene is flanked by lox2372 site-specific recombination sites (lox) and positioned between the human Vκ-Jκ region and the set of human Jλ gene segments, while the Hygromycin selection cassette is flanked by loxP site-specific recombination sites and positioned 3' of the rodent Igλ light chain constant region (mCλ1) gene. The DNA fragment is then combined with a DNA fragment containing a rodent Igκ light chain 3' enhancer to create the final targeting vector (FIG. 1B). The resulting targeting vector (construct G) is linearized and electroporated into rodent embryonic stem (ES) cells to create a rodent whose germline genome comprises the engineered Igκ light chain locus. As described in the examples section below, the rodent ES cells employed in electroporation of the targeting vector contained an engineered Igκ light chain locus as previously described in U.S. Pat. Nos. 9,006,511, 9,012,717, 9,029,628, 9,035,128, 9,066,502, 9,150,662 and 9,163,092; incorporated herein by reference in their entireties. Homologous recombination with the targeting vector as depicted in FIG. 3 results in an engineered Igκ light chain locus characterized by a plurality of human Vλ and Jλ gene segments operably linked to a murine Cλ1 gene, which murine Cλ1 gene is located in place of a murine Cκ gene that naturally appears in a wild-type Igκ light chain locus. The human Jλ gene segments are uniquely engineered into a sequence that naturally appears in a genomic human Jκ region yet has human Jλ coding sequences and associated 12RSS in the place of human Jκ coding sequences and associated 23RSS. Positive rodent ES cell clones are confirmed using screening methods described herein and/or known in the art. Any remaining selection cassette may be deleted as desired via recombinase-mediated deletion (see Example 2).

Alternatively, a human Cλ gene may be employed in a targeting vector instead of a mouse Cλ gene. To give but one example, FIG. 3 illustrates a targeting vector that was constructed in a similar manner as described above except that a sequence encoding a human Cλ2 gene was engineered into the targeting vector and in operable linkage with five human Jλ gene segments. Using such an approach provides an added benefit in developing human antibody therapeutics as DNA encoding the variable and constant regions of light chains may be isolated together, thereby eliminating any subsequent cloning step linking to a human light chain constant region for the preparation of fully-human antibodies.

Targeting vectors for constructing an engineered Igκ light chain locus as described herein may be incorporated into the germline genome of a non-human cell (e.g., a rodent embryonic stem cell). In some embodiments, targeting vectors as described herein are incorporated into a wild-type Igλ light chain locus in the germline genome of a non-human cell that further contains human $V_H$, $D_H$ and $J_H$ genomic DNA (e.g., containing a plurality of human $V_H$, $D_H$ and $J_H$ gene segments) operably linked with one or more immunoglobulin heavy chain constant region genes (e.g., see U.S. Pat. Nos. 8,502,018, 8,642,835, 8,697,940 and 8,791,323, each of which is incorporated herein by reference in its entirety). In some embodiments, targeting vectors as described herein are incorporated into a modified or engineered immunoglobulin κ light chain locus in the germline genome of a non-human cell that further contains human $V_H$, $D_H$ and $J_H$ genomic DNA (e.g., containing a plurality of human $V_H$, $D_H$ and $J_H$ gene segments) operably linked with one or more immunoglobulin heavy chain constant region genes (e.g., see U.S. Pat. Nos. 8,502,018, 8,642,835, 8,697,940, 8,791,323, 9,006,511, 9,012,717, 9,029,628, 9,035,128, 9,066,502, 9,150,662 and 9,163,092, each of which is incorporated herein by reference in its entirety).

A targeting vector is introduced into rodent (e.g., mouse) embryonic stem cells by electroporation so that the sequence contained in the targeting vector results in the capacity of a non-human cell or non-human animal (e.g., a mouse) that expresses antibodies having light chains that include human Vλ domains and non-human or human Cλ domains, and which light chains are expressed from an endogenous engineered immunoglobulin κ light chain locus. As described herein, a genetically engineered rodent is generated where an engineered immunoglobulin κ light chain locus has been created in the germline genome of the rodent (e.g., an endogenous immunoglobulin κ light chain locus containing a human Igλ light chain sequence (i.e., a plurality of human Vλ and Jλ gene segments) operably linked to a rodent or human Cλ gene in the place of an endogenous rodent Cκ gene). Antibodies are expressed on the surface of rodent B cells and in the serum of said rodent, which antibodies are characterized by light chains having human Vλ domains and non-human or human Cλ domains. When an endogenous immunoglobulin κ light chain locus in the germline genome of the rodent is not targeted by the targeting vector, an engineered immunoglobulin κ light chain transgene is preferably inserted at a location other than that of an endogenous rodent immunoglobulin κ light chain locus (e.g., randomly inserted transgene).

Creation of an engineered immunoglobulin κ light chain locus in a non-human animal as described above provides an engineered rodent strain that produces antibodies that include immunoglobulin λ light chains expressed from such an engineered immunoglobulin κ light chain locus having a human Vλ domain and a non-human or human Cλ domain.

Leveraged with the presence of an engineered immunoglobulin heavy chain locus that includes a plurality of human $V_H$, $D_H$ and $J_H$ gene segments operably linked to immunoglobulin heavy chain constant region genes, an engineered rodent strain that produces antibodies and antibody components for the development of human antibody-based therapeutics is created. Thus, a single engineered rodent strain is realized that has the capacity to provide an alternative in vivo system for exploiting human Vλ domains for the development of new antibody-based medicines to treat human disease.

In some embodiments, a method of making a non-human animal whose germline genome comprises an engineered endogenous immunoglobulin κ light chain locus is provided, the method comprising (a) introducing a DNA fragment into a non-human embryonic stem cell, said DNA fragment comprising a nucleotide sequence that includes (i) one or more human Vλ gene segments, (ii) one or more human Jλ gene segments and (iii) a Cλ gene (e.g., non-human or human), wherein (i)-(iii) are operably linked, and wherein the nucleotide sequence further comprises an immunoglobulin k light chain sequence between (i) and (ii), (b) obtaining the non-human embryonic stem cell generated in (a); and (c) creating a rodent using the rodent embryonic stem cell of (b).

In some embodiments, a method of making a non-human animal whose germline genome comprises an engineered endogenous immunoglobulin κ light chain locus is provided, the method comprising (a) introducing a DNA fragment into a non-human embryonic stem cell, said DNA fragment comprising a nucleotide sequence that includes one or more human Jλ gene segments, one or more non-human immunoglobulin κ light chain enhancers, and a non-human or human Cλ gene, which human Jλ gene segments are operably linked to said one or more non-human immunoglobulin κ light chain enhancers and said non-human or human Cλ gene, (b) obtaining the non-human embryonic stem cell generated in (a); and (c) creating a rodent using the rodent embryonic stem cell of (b).

In some embodiments, a method of making a non-human animal whose germline genome comprises an engineered endogenous immunoglobulin κ light chain locus, which engineered endogenous immunoglobulin κ light chain locus comprises insertion of one or more human Vλ gene segments, one or more human Jλ gene segments and a non-human or human Cλ gene, which human Vλ and Jλ gene segments are operably linked to said non-human or human Cλ gene, and which non-human or human Cλ gene is inserted in the place of a non-human Cκ gene at the endogenous immunoglobulin κ locus, is provided, the method comprising modifying the germline genome of a non-human animal so that it comprises an engineered endogenous immunoglobulin κ light chain locus that includes insertion of one or more human Vλ gene segments, one or more human Jλ gene segments and a non-human or human Cλ gene, which human Vλ and Jλ gene segments are operably linked to said non-human or human Cλ gene, and which non-human or human Cλ gene is inserted in the place of a non-human Cκ gene at the endogenous immunoglobulin κ locus.

In some embodiments of a method of making a non-human animal, one or more human Vλ gene segments includes at least 24, at least 34, at least 52, at least 61, or at least 70 human Vλ gene segments. In some embodiments of a method of making a non-human animal, one or more human Vλ gene segments include 39 human Vλ gene segments. In some certain embodiments of a method of making a non-human animal, one or more human Vλ gene segments include human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1 or any combination thereof. In some certain embodiments, one or more human Vλ gene segments include human non-coding DNA that naturally appears adjacent to the relevant human Vλ gene segments in an endogenous human λ light chain locus.

In some embodiments of a method of making a non-human animal, one or more human Jλ gene segments includes at least 1, at least 2, at least 3, at least 4 or at least 5 human Jλ gene segments. In some embodiments of a method of making a non-human animal, one or more human Jλ gene segments includes 5 human Jλ gene segments. In some embodiments of a method of making a non-human animal, one or more human Jλ gene segments comprise human Jλ1, Jλ2, Jλ3, Jλ6, Jλ7, or any combination thereof. In some certain embodiments, one or more human Jλ gene segments include human non-coding DNA, in whole or in part, that naturally appears adjacent to the relevant human Jλ gene segments in an endogenous human λ light chain locus. In some embodiments, one or more human Jλ gene segments include human non-coding DNA that naturally appears adjacent to a human Jκ1-Jκ5 in an endogenous human κ light chain locus.

In some embodiments of a method of making a non-human animal, a DNA fragment includes intergenic DNA that contains non-coding immunoglobulin DNA (e.g., DNA that naturally appears between the coding sequence of two V gene segments, a V and J gene segment or between two J gene segments). In many embodiments, said non-coding immunoglobulin DNA is non-coding immunoglobulin light chain DNA (e.g., human or murine). In some embodiments, non-coding immunoglobulin light chain DNA is immunoglobulin κ light chain DNA, immunoglobulin λ light chain DNA or combinations thereof.

In some embodiments of a method of making a non-human animal, a DNA fragment further comprises one or more selection markers. In some embodiments of a method of making a non-human animal, a DNA fragment further comprises one or more site-specific recombination sites. In some certain embodiments of a method of making a non-human animal, a DNA fragment further comprises one or more sets of site-specific recombination sites that recombine with the same recombinase. In some certain embodiments of a method of making a non-human animal, a DNA fragment further comprises one or more sets of site-specific recombination sites that recombine with different recombinases.

In some embodiments of a method of making a non-human animal, a DNA fragment comprises an engineered sequence that includes immunoglobulin κ light chain sequence and immunoglobulin λ light chain sequence together in a continuous sequence. In some embodiments of a method of making a non-human animal, a DNA fragment comprises an engineered sequence that includes immunoglobulin κ light chain sequence and immunoglobulin λ light chain sequence together in a single sequence yet interrupted by a non-immunoglobulin sequence (e.g., a recombination signal sequence, a resistance gene, and combinations thereof). In some certain embodiments of a method of making a non-human animal, an engineered sequence includes portions of a Jκ region and portions of a Jλ region. In some embodiments, an engineered sequence includes portions of a human Jκ region and portions of a human Jλ region. In some certain embodiments, portions of a human Jκ region include non-coding sequences of a human Jκ region that naturally appear in a human immunoglobulin κ light chain locus of a human cell. In some certain embodiments, portions of a human Jλ region include coding sequences and recombination signal sequences (RSS) of one or more human Jλ gene segments. In some certain embodiments of a method of making a non-human animal, a DNA fragment comprises an engineered sequence that is characterized, in some embodiments, by the presence of coding sequences and recombination signal sequences (RSS) of one or more human Jλ gene segments that positionally replace or substitute (i.e., positioned in the place of) the corresponding coding sequences and recombination signal sequences (RSS) of human Jκ gene segments so that said coding sequences and recombination signal sequences (RSS) of said one or more human Jλ gene segments are within, adjacent to, contiguous with or juxtaposed by said non-coding sequences of said one or more human Jκ gene segments.

In some embodiments of a method of making a non-human animal, a DNA fragment is introduced into a non-human embryonic stem cell whose germline genome comprises one or more engineered immunoglobulin loci (e.g., immunoglobulin heavy chain, immunoglobulin κ light chain, immunoglobulin λ light chain, and combinations thereof). In some certain embodiments, engineered immunoglobulin loci are endogenous engineered immunoglobulin loci.

In some embodiments of a method of making a non-human animal, a DNA fragment is introduced into a non-human embryonic stem cell whose germline genome comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region.

In some embodiments of a method of making a non-human animal, a DNA fragment is introduced into a non-human embryonic stem cell whose germline genome comprises an endogenous immunoglobulin κ light chain locus comprising insertion of one or more human Vλ and one or more human Jλ gene segments, which human Vλ and Jλ gene segments are operably linked to a non-human immunoglobulin κ light chain constant region gene. In some certain embodiments of a method of making a non-human animal, a DNA fragment is introduced into a non-human embryonic stem cell whose germline genome comprises an endogenous immunoglobulin κ light chain locus comprising insertion of one or more human Vλ and one or more human Jλ gene segments, and a human immunoglobulin κ light chain sequence positioned, placed or located between said one or more human Vλ gene segments and said one or more human Jλ gene segments, which human Vλ and Jλ gene segments are operably linked to a non-human immunoglobulin κ light chain constant region gene.

In some embodiments of a method of making a non-human animal, modifying the germline genome of a non-human animal so that it comprises an engineered immunoglobulin κ light chain locus is carried out in a non-human embryonic stem cell whose germline genome comprises an endogenous immunoglobulin heavy chain locus comprising insertion of one or more human $V_H$ gene segments, one or more human $D_H$ gene segments and one or more human $J_H$ gene segments, which human $V_H$, $D_H$ and $J_H$ gene segments are operably linked to a non-human immunoglobulin heavy chain constant region.

In some embodiments of a method of making a non-human animal, modifying the germline genome of a non-human animal so that it comprises an engineered immunoglobulin κ light chain locus is carried out in a non-human embryonic stem cell whose germline genome comprises an endogenous immunoglobulin κ light chain locus comprising insertion of one or more human Vλ and one or more human Jλ gene segments, which human Vλ and Jλ gene segments are operably linked to a non-human immunoglobulin κ light chain constant region gene. In some embodiments of a method of making a non-human animal, modifying the germline genome of a non-human animal so that it comprises an engineered immunoglobulin κ light chain locus is carried out in a non-human embryonic stem cell whose germline genome comprises an endogenous immunoglobulin κ light chain locus comprising insertion of one or more human Vλ and one or more human Jλ gene segments, and a human immunoglobulin κ light chain sequence positioned, placed or located between said one or more human Vλ gene segments and said one or more human Jλ gene segments, which human Vλ and Jλ gene segments are operably linked to a non-human immunoglobulin κ light chain constant region gene.

In some embodiments of a method of making a non-human animal, insertion of one or more human $V_H$ gene segments, one or more human $D_H$ gene segments and one or more human $J_H$ gene segments includes human non-coding DNA that naturally appears adjacent to the human $V_H$ gene segments, human non-coding DNA that naturally appears adjacent to the human $D_H$ gene segments and human non-coding DNA that naturally appears adjacent to the human $J_H$ gene segments in an endogenous human immunoglobulin locus.

In some embodiments, a non-human animal made, generated, produced, obtained or obtainable from a method as described herein is provided.

In some embodiments, the genome of a non-human animal as described herein further comprises one or more human immunoglobulin heavy variable regions as described in U.S. Pat. Nos. 8,502,018, 8,642,835, 8,697,940 and 8,791,323, each of which is incorporated herein by reference in its entirety. Alternatively, an engineered immunoglobulin κ light chain locus as described herein can be engineered into an embryonic stem cell of a different modified strain such as, e.g., a VELOCIMMUNE® strain (see, e.g., U.S. Pat. Nos. 8,502,018 and/or 8,642,835; incorporated herein by reference in their entireties). Homozygosity of the engineered Igκ light chain locus as described herein can subsequently be achieved by breeding. Alternatively, in the case of a randomly inserted engineered immunoglobulin κ light chain transgene (described above), rodent strains can be selected based on, among other things, expression of human Vλ domains from the transgene. In some embodiments, a VELOCIMMUNE® mouse can be a VELOCIMMUNE® 1 (VI-1) mouse, which includes eighteen human $V_H$ gene segments, all of the human $D_H$ gene segments, and all of the $J_H$ gene segments. A VI-1 mouse can also include sixteen human Vκ gene segments and all of the human Jκ gene segments. In some embodiments, a VELOCIMMUNE® mouse can be a VELOCIMMUNE® 2 (VI-2) mouse, which includes thirty-nine human $V_H$ gene segments, all of the human $D_H$ gene segments, and all of the $J_H$ gene segments. A VI-2 mouse can also include human thirty Vκ gene segments and all of the human Jκ gene segments. In some embodiments, a VELOCIMMUNE® mouse can be a VELOCIMMUNE® 3 (VI-3) mouse, which includes eighty human $V_H$ gene segments, all of the human $D_H$ gene segments, and all of the $J_H$ gene segments. A VI-3 mouse can also include human forty Vκ gene segments and all of the human Jκ gene segments.

Alternatively, and/or additionally, in some embodiments, the germline genome of a non-human animal as described herein further comprises a deleted, inactivated, functionally silenced or otherwise non-functional endogenous immunoglobulin λ light chain locus. Genetic modifications to delete or render non-functional a gene or genetic locus may be achieved using methods described herein and/or methods known in the art.

A genetically engineered founder non-human animal can be identified based upon the presence of an engineered Igκ light chain locus in its germline genome and/or expression of antibodies having a human Vλ domain and a non-human or human Cλ domain in tissues or cells of the non-human animal. A genetically engineered founder non-human animal can then be used to breed additional non-human animals carrying the engineered immunoglobulin κ light chain locus thereby creating a cohort of non-human animals each carrying one or more copies of an engineered immunoglobulin κ light chain locus. Moreover, genetically engineered non-human animals carrying an engineered immunoglobulin κ light chain locus as described herein can further be bred to other genetically engineered non-human animals carrying other transgenes (e.g., human immunoglobulin genes) or engineered immunoglobulin loci as desired.

Genetically engineered non-human animals may also be produced to contain selected systems that allow for regulated, directed, inducible and/or cell-type specific expression of the transgene or integrated sequence(s). For example, non-human animals as described herein may be engineered to contain one or more sequences encoding a human Vλ domain of an antibody that is/are conditionally expressed (e.g., reviewed in Rajewski, K. et al., 1996, J. Clin. Invest. 98(3):600-3, incorporated herein by reference in its entirety). Exemplary systems include the Cre/loxP recombinase system of bacteriophage P1 (see, e.g., Lakso, M. et al., 1992, Proc. Natl. Acad. Sci. U.S.A. 89:6232-6, incorporated herein by reference in its entirety) and the FLP/Frt recombinase system of S. cerevisiae (O'Gorman, S. et al, 1991, Science 251:1351-5, incorporated herein by reference in its entirety). Such animals can be provided through the construction of "double" genetically engineered animals, e.g., by mating two genetically engineered animals, one containing a transgene comprising a selected modification (e.g., an engineered Igκ light chain locus as described herein) and the other containing a transgene encoding a recombinase (e.g., a Cre recombinase).

Non-human animals as described herein may be prepared as described above, or using methods known in the art, to comprise additional human, humanized or otherwise engineered genes, oftentimes depending on the intended use of the non-human animal. Genetic material of such human, humanized or otherwise engineered genes may be introduced through the further alteration of the genome of cells (e.g., embryonic stem cells) having the genetic modifications or alterations as described above or through breeding techniques known in the art with other genetically modified or engineered strains as desired. In some embodiments, non-human animals as described herein are prepared to further comprise human IgH and/or Igκ light chain genes or gene segments (see e.g., Murphy, A. J. et al., (2014) Proc. Natl. Acad. Sci. U.S.A. 111(14):5153-5158; U.S. Pat. Nos. 8,502,018, 8,642,835, 8,697,940 and 8,791,323; 8,791,323; and U.S. Patent Application Publication No. 2013/0096287 A1; each of which is incorporated herein by reference in its entirety).

In some embodiments, non-human animals as described herein may be prepared by introducing a targeting vector described herein into a cell from a modified or engineered strain. For example, a targeting vector as described herein may be introduced into a VELOCIMMUNE® mouse. VELOCIMMUNE® mice express antibodies that have fully human variable regions and mouse constant regions. In another example, a targeting vector as described herein may be introduced into an engineered mouse as described in any one of U.S. Pat. Nos. 9,006,511, 9,012,717, 9,029,628, 9,035,128, 9,066,502, 9,150,662 and 9,163,092, incorporated herein by reference in their entireties. In some embodiments, non-human animals as described herein are prepared to further comprise human immunoglobulin genes (variable and/or constant region genes). In some embodiments, non-human animals as described herein comprise an engineered Igκ light chain locus as described herein and genetic material from a heterologous species (e.g., humans), wherein the genetic material encodes, in whole or in part, one or more human heavy and/or Igκ light chain variable regions.

For example, as described herein, non-human animals comprising an engineered Igκ light chain locus as described herein may further comprise (e.g., via cross-breeding or multiple gene targeting strategies) one or more modifications as described in Murphy, A. J. et al., (2014) Proc. Natl. Acad. Sci. U.S.A. 111(14):5153-8; Macdonald, L. E. et al., 2014, Proc. Natl. Acad. Sci. U.S.A. 111(14):5147-52; U.S. Pat. Nos. 8,502,018, 8,642,835, 8,697,940 and 8,791,323; all of which are incorporated herein by reference in their entireties. In some embodiments, a rodent comprising an engineered immunoglobulin κ light chain locus as described herein is crossed to a rodent comprising a humanized immunoglobulin heavy chain and/or immunoglobulin κ light chain variable region locus (see, e.g., U.S. Pat. Nos. 8,502,018, 8,642,835, 8,697,940 and/or 8,791,323; incorporated herein by reference in their entireties). In some embodiments, a rodent comprising an engineered immunoglobulin κ light chain locus as described herein is crossed to a rodent comprising a humanized immunoglobulin heavy chain variable region locus (see, e.g., U.S. Pat. Nos. 8,502, 018, 8,642,835, 8,697,940 and/or 8,791,323; incorporated herein by reference) and an inactivated endogenous immunoglobulin λ light chain locus (see, e.g., U.S. Pat. Nos. 9,006,511, 9,012,717, 9,029,628, 9,035,128, 9,066,502, 9,150,662 and 9,163,092, incorporated herein by reference in their entireties).

Although embodiments describing the construction of an engineered immunoglobulin κ light chain locus in a mouse (i.e., a mouse with an engineered immunoglobulin κ light chain locus characterized by the presence of a plurality of human Vλ and Jλ gene segments operably linked with a mouse or human Cλ gene, which mouse or human Cλ gene is located in the place of a mouse Cκ gene, so that antibodies containing human Vλ domains and mouse or human Cλ domains are expressed) are extensively discussed herein, other non-human animals that comprise an engineered immunoglobulin κ light chain locus are also provided. Such non-human animals include any of those which can be genetically modified to express antibodies as described herein, including, e.g., mammals, e.g., mouse, rat, rabbit, pig, bovine (e.g., cow, bull, buffalo), deer, sheep, goat, chicken, cat, dog, ferret, primate (e.g., marmoset, rhesus monkey), etc. For example, for those non-human animals for which suitable genetically modifiable ES cells are not readily available, other methods are employed to make a non-human animal comprising the genetic modification. Such methods include, e.g., modifying a non-ES cell genome (e.g., a fibroblast or an induced pluripotent cell) and employing somatic cell nuclear transfer (SCNT) to transfer the genetically modified genome to a suitable cell, e.g., an enucleated oocyte, and gestating the modified cell (e.g., the modified oocyte) in a non-human animal under suitable conditions to form an embryo.

Methods for modifying the germline genome of a non-human animal (e.g., a pig, cow, rodent, chicken, etc. genome) include, e.g., employing a zinc finger nuclease (ZFN), a transcription activator-like effector nuclease (TALEN), or a Cas protein (i.e., a CRISPR/Cas system) to include an engineered immunoglobulin κ light chain locus as described herein. Guidance for methods for modifying the germline genome of a non-human animal can be found in, e.g., U.S. patent application Ser. No. 14/747,461 (filed Jun. 23, 2015), Ser. No. 14/948,221 (filed Nov. 20, 2015) and Ser. No. 14/974,623 (filed Dec. 18, 2015); incorporated herein by reference in their entireties.

In some embodiments, a non-human animal as described herein is a mammal. In some embodiments, a non-human animal as described herein is a small mammal, e.g., of the superfamily Dipodoidea or Muroidea. In some embodiments, a genetically modified animal as described herein is a rodent. In some embodiments, a rodent as described herein is selected from a mouse, a rat, and a hamster. In some embodiments, a rodent as described herein is selected from the superfamily Muroidea. In some embodiments, a genetically modified animal as described herein is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rats, bamboo rats, and zokors). In some certain embodiments, a genetically modified rodent as described herein is selected from a true mouse or rat (family Muridae), a gerbil, a spiny mouse, and a crested rat. In some certain embodiments, a genetically modified mouse as described herein is from a member of the family Muridae. In some embodiment, a non-human animal as described herein is a rodent. In some certain embodiments, a rodent as described herein is selected from a mouse and a rat. In some embodiments, a non-human animal as described herein is a mouse.

In some embodiments, a non-human animal as described herein is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse as described herein is a 129-strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach, W. et al., 2000, Biotechniques 29(5):1024-1028, 1030, 1032, each of which is incorporated herein by reference in its entirety). In some certain embodiments, a genetically modified mouse as described herein is a mix of an aforementioned 129 strain and an aforementioned C57BL/6 strain. In some certain embodiments, a mouse as described herein is a mix of aforementioned 129 strains, or a mix of aforementioned BL/6 strains. In some certain embodiments, a 129 strain of the mix as described herein is a 129S6 (129/SvEvTac) strain. In some embodiments, a mouse as described herein is a BALB strain, e.g., BALB/c strain. In some embodiments, a mouse as described herein is a mix of a BALB strain and another aforementioned strain.

In some embodiments, a non-human animal as described herein is a rat. In some certain embodiments, a rat as described herein is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

A rat pluripotent and/or totipotent cell can be from any rat strain, including, for example, an ACI rat strain (an inbred strain originally derived from August and Copenhagen strains), a Dark Agouti (DA) rat strain, a Wistar rat strain, a LEA rat strain, a Sprague Dawley (SD) rat strain, or a Fischer rat strain such as Fisher F344 or Fisher F6. Rat pluripotent and/or totipotent cells can also be obtained from a strain derived from a mix of two or more strains recited above. For example, the rat pluripotent and/or totipotent cell can be from a DA strain or an ACI strain. The ACI rat strain is characterized as having black agouti, with white belly and feet and an RT1av1 haplotype. Such strains are available from a variety of sources including Harlan Laboratories. An example of a rat ES cell line from an ACI rat is an ACI.G1 rat ES cell. The DA rat strain is characterized as having an agouti coat and an RT1av1 haplotype. Such rats are available from a variety of sources including Charles River and Harlan Laboratories. Examples of a rat ES cell line from a DA rat are the DA.2B rat ES cell line and the DA.2C rat ES cell line. In some embodiments, the rat pluripotent and/or totipotent cells are from an inbred rat strain (see, e.g., U.S. Patent Application Publication No. 2014-0235933 A1, published Aug. 21, 2014, incorporated herein by reference in its entirety). Guidance for making modifications in a rat genome (e.g., in a rat ES cell) using methods and/or constructs as described herein can be found in, e.g., in U.S. Patent Application Publication Nos. 2014-0310828 and 2017-0204430; both of which are incorporated herein by reference in their entireties.

Specific Exemplary
Embodiments—Immunoglobulin Heavy Chain Loci

In some embodiments, provided non-human animals comprise an engineered immunoglobulin κ light chain locus as described herein and further comprise engineered IgH loci (or alleles) characterized by the presence of a plurality of human $V_H$, $D_H$ and $J_H$ gene segments arranged in germline configuration and operably linked to non-human immunoglobulin heavy chain constant region genes, enhancers and regulatory regions. In some embodiments, an engineered immunoglobulin heavy chain locus (or allele) as described herein comprises one or more human $V_H$ gene segments, one or more human $D_H$ gene segments and one or more human $J_H$ gene segments operably linked to a non-human immunoglobulin heavy chain constant region. In some certain embodiments, an engineered immunoglobulin heavy chain locus (or allele) comprises at least human $V_H$ gene segments $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H4$-23, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, or any combination thereof. In some certain embodiments, an engineered IgH locus (or allele) comprises at least human $D_H$ gene segments $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof. In some certain embodiments, an engineered immunoglobulin heavy chain locus (or allele) comprises at least human $J_H$ gene segments $J_H1$, $J_H2$, $J_H3$, $J_H4$, $J_H5$, $J_H6$, or any combination thereof.

The present disclosure recognizes that a non-human animal as described herein will utilize human heavy chain variable region gene segments comprised in its genome in its antibody selection and generation mechanisms (e.g., recombination and somatic hypermutation). As such, in various embodiments, human immunoglobulin heavy chain variable domains generated by non-human animals described herein are encoded by the human heavy chain variable region gene segments included in their genome or somatically hypermutated variants thereof.

In some embodiments, a non-human animal is provided whose genome comprises an engineered immunoglobulin κ light chain locus, where the non-human animal includes a B cell that includes a human heavy variable region sequence, a human λ light chain variable region sequence, and/or a human κ light chain variable region sequence that is somatically hypermutated. In some embodiments, a human heavy variable region sequence, a human λ light chain variable region sequence, and/or a human κ light chain variable region sequence present in a B cell of a mouse of the present disclosure has 1, 2, 3, 4, 5, or more somatic hypermutations. Those skilled in the art are aware of methods for identifying source gene segments in a mature antibody sequence. For example, various tools are available to aid in this analysis, such as, for example, DNAPLOT, IMGT/V-QUEST, JOIN-SOLVER, SoDA, and Ab-origin.

In some embodiments, a non-human immunoglobulin heavy chain constant region includes one or more non-human immunoglobulin heavy chain constant region genes such as, for example, immunoglobulin M (IgM), immunoglobulin D (IgD), immunoglobulin G (IgG), immunoglobulin E (IgE) and immunoglobulin A (IgA). In some certain embodiments, a non-human immunoglobulin heavy chain constant region includes a rodent IgM, rodent IgD, rodent IgG3, rodent IgG1, rodent IgG2b, rodent IgG2a, rodent IgE and rodent IgA constant region genes. In some embodiments, said human $V_H$, $D_H$ and $J_H$ gene segments are operably linked to one or more non-human immunoglobulin heavy chain enhancers (i.e., enhancer sequences or enhancer regions). In some embodiments, said human $V_H$, $D_H$ and $J_H$ gene segments are operably linked to one or more non-human immunoglobulin heavy chain regulatory regions (or regulatory sequences). In some embodiments, said human $V_H$, $D_H$ and $J_H$ gene segments are operably linked to one or more non-human immunoglobulin heavy chain enhancers (or enhancer sequence) and one or more non-human immunoglobulin heavy chain regulatory regions (or regulatory sequence).

In some embodiments, an engineered immunoglobulin heavy chain locus as described herein does not contain an endogenous Adam6 gene. In some embodiments, an engineered immunoglobulin heavy chain locus as described herein does not contain an endogenous Adam6 gene (or Adam6-encoding sequence) in the same germline genomic position as found in a germline genome of a wild-type non-human animal of the same species. In some embodiments, an engineered immunoglobulin heavy chain locus as described herein does not contain a human Adam6 pseudogene. In some embodiments, an engineered immunoglobulin heavy chain locus as described herein comprises insertion of at least one nucleotide sequence that encodes one or more non-human (e.g., rodent) Adam6 polypeptides, functional orthologs, functional homologs, or functional fragments thereof. In some embodiments, said insertion may be outside of an engineered immunoglobulin heavy chain locus as described herein (e.g., but not limited to, upstream of a 5' most $V_H$ gene segment), within an engineered immunoglobulin heavy chain locus or elsewhere in the germline genome of a non-human animal (e.g., but not limited to, a randomly introduced non-human Adam6-encoding sequence), cell or tissue.

In various embodiments, a provided non-human animal, non-human cell or non-human tissue as described herein does not detectably express, in whole or in part, an endogenous non-human $V_H$ region in an antibody molecule. In various embodiments, a provided non-human animal, non-human cell or non-human tissue as described herein does not contain (or lacks, or contains a deletion of) one or more nucleotide sequences that encode, in whole or in part, an endogenous non-human $V_H$ region (e.g., $V_H$, $D_H$ and/or $J_H$) in an antibody molecule. In various embodiments, a provided non-human animal, non-human cell or non-human tissue as described herein has a germline genome that includes a deletion of endogenous non-human $V_H$, $D_H$ and $J_H$ gene segments, in whole or in part. In various embodiments, a provided non-human animal is fertile.

Guidance for the creation of targeting vectors, non-human cells and animals harboring such engineered immunoglobulin heavy chain loci (or alleles) can be found in U.S. Pat. Nos. 8,502,018, 8,642,835, 8,697,940 and 8,791,323, each of which is incorporated herein by reference in its entirety. Persons skilled in the art are aware of a variety of technologies, known in the art, for accomplishing such genetic engineering and/or manipulation of non-human (e.g., mammalian) genomes or for otherwise preparing, providing, or manufacturing such sequences for introducing into the germline genome of non-human animals.

Specific Exemplary
Embodiments—Immunoglobulin κ Light Chain
Loci

In some embodiments, provided non-human animals comprise an engineered immunoglobulin κ light chain locus characterized by the presence of a plurality of human Vλ and Jλ gene segments arranged in germline configuration (i.e., not rearranged and associated with recombination signal sequences) and inserted upstream of, and operably linked to, a non-human or human Cλ gene, which non-human or human Cλ gene is inserted in the place of a non-human Cκ gene. As described herein, such engineered immunoglobulin κ light chain locus further includes non-human immunoglobulin κ light chain enhancer regions (or enhancer sequences). In some embodiments, an engineered immunoglobulin κ light chain locus comprises one or more human Vλ gene segments and one or more human Jλ gene segments operably linked to a non-human or human Cλ gene. In some certain embodiments, an engineered immunoglobulin κ light chain locus (or allele) comprises human Vλ gene segments that appear in at least cluster A of a human immunoglobulin λ light chain locus; in some embodiments, cluster A and cluster B of a human immunoglobulin λ light chain locus; in some certain embodiments, cluster A, cluster B and cluster C of a human immunoglobulin λ light chain locus. In some certain embodiments, an engineered immunoglobulin κ light chain locus (or allele) comprises at least human Vλ gene segments Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1 or any combination thereof. In some certain embodiments, an engineered Igκ light chain locus (or allele) comprises at least human Jλ gene segments Jλ1, Jλ2, Jλ3, Jλ6 Jλ7, or any combination thereof.

The present disclosure recognizes that a non-human animal as described herein will utilize human λ light chain variable region gene segments included in its genome in its antibody selection and generation mechanisms (e.g., recombination and somatic hypermutation). As such, in various embodiments, human immunoglobulin λ light chain variable domains generated by non-human animals described herein are encoded by the human λ light chain variable region gene segments included in their genome or somatically hypermutated variants thereof.

In some embodiments, a non-human animal is provided whose genome comprises an engineered immunoglobulin κ light chain locus, where the non-human animal includes a B cell that includes a human heavy variable region sequence, a human λ light chain variable region sequence, and/or a human κ light chain variable region sequence that is somatically hypermutated. In some embodiments, a human heavy variable region sequence, a human λ light chain variable region sequence, and/or a human κ light chain variable region sequence present in a B cell of a mouse of the present disclosure has 1, 2, 3, 4, 5, or more somatic hypermutations. Those skilled in the art are aware of methods for identifying source gene segments in a mature antibody sequence. For example, various tools are available to aid in this analysis, such as, for example, DNAPLOT, IMGT/V-QUEST, JOIN-SOLVER, SoDA, and Ab-origin.

In many embodiments, an engineered immunoglobulin κ light chain locus (or allele) contains the same non-human immunoglobulin κ light chain enhancer regions (or enhancer sequences) that appear in a wild-type immunoglobulin κ light chain locus (or allele). In some embodiments, an engineered immunoglobulin κ light chain locus (or allele) contains non-human immunoglobulin κ light chain enhancer regions (or enhancer sequences) that appear in a wild-type immunoglobulin κ light chain locus (or allele) of a different species (e.g., a different rodent species).

In some embodiments, said human Vλ and Jλ gene segments are operably linked to one or more non-human immunoglobulin κ light chain enhancers (i.e., enhancer sequences or enhancer regions). In some certain embodiments, said human Vλ and Jλ gene segments are operably linked to a murine immunoglobulin κ light chain intronic enhancer region (Igκ Ei or Eiκ). In some certain embodiments, said human Vλ and Jλ gene segments are operably linked to a murine immunoglobulin κ light chain 3' enhancer region (Igκ 3'E or 3'Eκ). In some certain embodiments, said human Vλ and Jλ gene segments are operably linked to a murine Eiκ and operably linked to a murine 3'Eκ.

In some embodiments, an engineered immunoglobulin κ light chain locus (or allele) as described herein does not contain (i.e., lacks) a human VpreB gene (or human VpreB gene-encoding sequence).

In some embodiments, a non-human Cλ gene of an engineered immunoglobulin κ light chain locus (or allele) includes a rodent Cλ gene such as, for example, a mouse Cλ gene or a rat Cλ gene. In some certain embodiments, a non-human Cλ gene of an engineered Igκ light chain locus (or allele) is or comprises a mouse Cλ gene from a genetic background that includes a 129 strain, a BALB/c strain, a C57BL/6 strain, a mixed 129xC57BL/6 strain or combinations thereof.

In some embodiments, a non-human Cλ gene of an engineered Igκ light chain locus (or allele) as described herein comprises a sequence that is at least 80%, at least 85%, at least 90%, at least 95%, or at least 98% identical to SEQ ID NO: 1 (mouse Cλ1), SEQ ID NO:3 (mouse Cλ2) or SEQ ID NO:5 (mouse Cλ3). In some embodiments, a non-human Cλ gene of an engineered Igκ light chain locus (or allele) as described herein comprises a sequence that is substantially identical or identical to SEQ ID NO: 1 (mouse Cλ1), SEQ ID NO:3 (mouse Cλ2) or SEQ ID NO:5 (mouse Cλ3). In some embodiments, a non-human Cλ gene of an engineered Igκ light chain locus (or allele) as described herein is or comprises the sequence of a mouse Cλ1 gene.

In some embodiments, a non-human Cλ domain encoded by a sequence positioned at an engineered Igκ light chain locus (or allele) as described herein comprises a sequence that is at least 80%, at least 85%, at least 90%, at least 95%, or at least 98% identical to SEQ ID NO:2 (mouse Cλ1), SEQ ID NO:4 (mouse Cλ2) or SEQ ID NO:6 (mouse Cλ3). In some embodiments, a non-human Cλ domain encoded by a sequence positioned at an engineered Igκ light chain locus (or allele) as described herein comprises a sequence that is substantially identical or identical to SEQ ID NO:2 (mouse Cλ1), SEQ ID NO:4 (mouse Cλ2) or SEQ ID NO:6 (mouse Cλ3). In some embodiments, a non-human Cλ gene encoded by a sequence positioned at an engineered Igκ light chain locus (or allele) as described herein is or comprises a mouse Cλ1 domain polypeptide.

In some embodiments, a non-human Cλ gene of an engineered Igκ light chain locus (or allele) as described herein comprises a sequence that is at least 80%, at least 85%, at least 90%, at least 95%, or at least 98% identical to SEQ ID NO:7 (rat Cλ1), SEQ ID NO:9 (rat Cλ2), SEQ ID NO: 11 (rat Cλ3) or SEQ ID NO: 13 (rat Cλ4). In some certain embodiments, a non-human Cλ gene of an engineered Igκ light chain locus (or allele) as described herein comprises a sequence that is substantially identical or identical to SEQ ID NO:7 (rat Cλ1), SEQ ID NO:9 (rat Cλ2), SEQ ID NO: 11 (rat Cλ3) or SEQ ID NO: 13 (rat Cλ4). In some certain embodiments, a non-human Cλ gene of an engineered Igκ light chain locus (or allele) as described herein is or comprises the sequence of a rat Cλ1 gene.

In some embodiments, a non-human Cλ domain encoded by a sequence positioned at an engineered Igκ light chain locus (or allele) as described herein comprises a sequence that is at least 80%, at least 85%, at least 90%, at least 95%, or at least 98% identical to SEQ ID NO:8 (rat Cλ1), SEQ ID NO:10 (rat Cλ2), SEQ ID NO:12 (rat Cλ3) or SEQ ID NO:14 (rat Cλ4). In some embodiments, a non-human Cλ domain encoded by a sequence positioned at an engineered Igκ light chain locus (or allele) as described herein comprises a sequence that is substantially identical or identical to SEQ ID NO:8 (rat Cλ1), SEQ ID NO: 10 (rat Cλ2), SEQ ID NO: 12 (rat Cλ3) or SEQ ID NO:14 (rat Cλ4). In some embodiments, a non-human Cλ domain encoded by a sequence positioned at an engineered Igκ light chain locus (or allele) as described herein is or comprises a rat Cλ1 domain polypeptide.

In some embodiments, a human Cλ gene of an engineered Igκ light chain locus (or allele) includes a human Cλ gene such as, for example, a human Cλ1 gene, a human Cλ2 gene, a human Cλ3 gene, a human Cλ6 gene or a human Cλ7 gene. In some certain embodiments, a human Cλ gene of an engineered Igκ light chain locus (or allele) is or comprises a human Cλ2 gene.

In some embodiments, a human Cλ gene of an engineered Igκ light chain locus (or allele) as described herein comprises a sequence that is at least 80%, at least 85%, at least 90%, at least 95%, or at least 98% identical to SEQ ID NO:15 (human Cλ1), SEQ ID NO:17 (human Cλ2), SEQ ID NO: 19 (human Cλ3), SEQ ID NO:21 (human Cλ6) or SEQ ID NO:23 (human Cλ7). In some embodiments, a human Cλ gene of an engineered Igκ light chain locus (or allele) as described herein comprises a sequence that is substantially identical or identical to SEQ ID NO:15 (human Cλ1), SEQ ID NO: 17 (human Cλ2), SEQ ID NO: 19 (human Cλ3), SEQ ID NO:21 (human Cλ6) or SEQ ID NO:23 (human Cλ7). In some embodiments, a human Cλ gene of an engineered Igκ light chain locus (or allele) as described herein is or comprises the sequence of a human Cλ2 gene.

In some embodiments, a human Cλ domain encoded by a sequence positioned at an engineered Igκ light chain locus (or allele) as described herein comprises a sequence that is at least 80%, at least 85%, at least 90%, at least 95%, or at least 98% identical to SEQ ID NO: 16 (human Cλ1), SEQ ID NO:18 (human Cλ2), SEQ ID NO:20 (human Cλ3), SEQ ID NO:22 (human Cλ6) or SEQ ID NO:24 (human Cλ7). In some embodiments, a human Cλ domain encoded by a sequence positioned at an engineered Igκ light chain locus (or allele) as described herein comprises a sequence that is substantially identical or identical to SEQ ID NO: 16 (human Cλ1), SEQ ID NO: 18 (human Cλ2), SEQ ID NO:20 (human Cλ3), SEQ ID NO:22 (human Cλ6) or SEQ ID NO:24 (human Cλ7). In some embodiments, a human Cλ domain encoded by a sequence positioned at an engineered Igκ light chain locus (or allele) as described herein is or comprises a human Cλ2 domain polypeptide.

Among other things, the present disclosure demonstrates that the presence of human Vλ and Jλ gene segments at Igκ light chain loci (or alleles) increases the diversity of the light chain repertoire of a provided non-human animal as compared to the diversity of the light chains in the expressed antibody repertoire of a non-human animal that does not comprise such engineered Igκ light chain loci.

Specific Exemplary Embodiments—Immunoglobulin λ Light Chain Loci

In some embodiments, provided non-human animals comprise an engineered immunoglobulin κ light chain locus as described herein and further comprise wild-type or inactivated immunoglobulin λ light chain loci (or alleles).

In some embodiments, provided non-human animals, non-human cells and/or non-human tissues as described herein comprise a deletion, in whole or in part, of an endogenous immunoglobulin λ light chain locus. In some embodiments, provided non-human animals, non-human cells and/or non-human tissues as described herein comprise an insertion within an endogenous immunoglobulin λ light chain locus, wherein said insertion renders the endogenous immunoglobulin λ light chain locus non-functional. In some embodiments, provided non-human animals, non-human cells and/or non-human tissues as described herein comprise a deletion of one or more gene segments of an endogenous immunoglobulin λ light chain locus such that the endogenous immunoglobulin λ light chain locus is unable to recombine and/or express a functional light chain of an antibody.

In some embodiments, a provided non-human animal, non-human cell or non-human tissue as described herein does not detectably express, in whole or in part, an endogenous non-human Vλ region in an antibody molecule. In some embodiments, a provided non-human animal, non-human cell or non-human tissue as described herein does not contain (or lacks, or contains a deletion of) one or more nucleotide sequences that encode, in whole or in part, an endogenous non-human Vλ region in an antibody molecule. In some embodiments, a provided non-human animal, non-human cell or non-human tissue as described herein has a germline genome that includes a deletion of endogenous non-human Vλ and Jλ gene segments, in whole or in part. In some embodiments, a provided non-human animal, non-human cell or non-human tissue as described herein as a germline genome that includes a deletion of endogenous non-human Vλ, Jλ and Cλ gene segments, in whole or in part.

Guidance for the creation of targeting vectors, non-human cells and animals harboring inactivated Igλ light chain loci (or alleles) can be found in, e.g., U.S. Pat. Nos. 9,006,511, 9,012,717, 9,029,628, 9,035,128, 9,066,502, 9,150,662 and 9,163,092, which are incorporated herein by reference in their entireties. Those skilled in the art are aware of a variety of technologies, known in the art, for accomplishing genetic inactivation of specific loci and/or manipulation of non-human (e.g., mammalian) genomes or for otherwise preparing, providing, or manufacturing such genetic inactivation (e.g., gene deletions) for introducing into the germline genome of non-human animals.

Specific Exemplary Embodiments—Combinations of Immunoglobulin Loci

In some embodiments, provided non-human animals comprise an engineered immunoglobulin κ light chain locus as described herein and further comprise one or more additional human or humanized genes (e.g., via crossbreeding or multiple gene targeting strategies). Such non-human animals may be prepared as described above, or using methods known in the art, to achieve a desired engineered genotype depending on the intended use of the non-human animal. Genetic material of such additional human or humanized genes may be introduced through the further alteration of the genome of cells (e.g., embryonic stem cells) having the genetic modifications as described above or through breeding techniques known in the art with other genetically modified strains as desired.

In some embodiments, provided non-human animals are prepared to further comprise a human or humanized immunoglobulin heavy chain locus (e.g., including but not limited to, a plurality of human $V_H$, $D_H$ and $J_H$ gene segments operably linked to one or more rodent immunoglobulin heavy chain constant region genes at an endogenous immunoglobulin heavy chain locus). In some embodiments, provided non-human animals are heterozygous for an engineered immunoglobulin κ light chain locus as described herein and heterozygous for a human or humanized immunoglobulin heavy chain locus. In some embodiments, provided non-human animals are homozygous for an engineered immunoglobulin κ light chain locus as described herein and homozygous for a human or humanized immunoglobulin heavy chain locus.

In some embodiments, provided non-human animals are prepared to further comprise a human or humanized immunoglobulin heavy chain locus (e.g., including but not limited to, a plurality of human $V_H$, $D_H$ and $J_H$ gene segments operably linked to one or more rodent immunoglobulin heavy chain constant region genes at an endogenous immunoglobulin heavy chain locus) and a humanized immunoglobulin κ light chain locus (e.g., including but not limited to, a plurality of human Vκ and Jκ gene segments operably linked to a rodent immunoglobulin κ light chain constant region gene at an endogenous immunoglobulin κ light chain locus. In some embodiments, provided non-human animals are heterozygous for a human or humanized immunoglobulin heavy chain locus and further comprise one endogenous immunoglobulin κ light chain locus that contains a plurality of human Vλ and Jλ gene segments operably linked to a rodent immunoglobulin λ light chain constant region gene (i.e., an engineered Igκ light chain locus as described herein), and another endogenous immunoglobulin κ light chain locus having a plurality of human Vκ and Jκ gene segments operably linked to a rodent immunoglobulin κ light chain constant region gene. In some embodiments, provided non-human animals are homozygous for a human or humanized immunoglobulin heavy chain locus and further comprise an endogenous immunoglobulin κ light chain locus that contains a plurality of human Vλ and Jλ gene segments operably linked to a rodent immunoglobulin λ light chain constant region gene (i.e., an engineered Igκ light chain locus as described herein), and another endogenous immunoglobulin κ light chain locus having a plurality of human Vκ and Jκ gene segments operably linked to a rodent immunoglobulin κ light chain constant region gene.

In some embodiments, provided non-human animals have a genome comprising (a) a homozygous or heterozygous human or humanized immunoglobulin heavy chain locus comprising human $V_H$, $D_H$ and $J_H$ gene segments operably linked to one or more endogenous non-human immunoglobulin heavy chain constant regions such that the non-human animal expresses an immunoglobulin heavy chain that comprises a human $V_H$ domain sequence fused with a non-human $C_H$ domain sequence; (b) a first immunoglobulin κ light chain locus comprising human Vλ and Jλ gene segments operably linked to a non-human immunoglobulin Cλ gene such that the non-human animal expresses an immunoglobulin light chain that comprises a human Vλ domain sequence fused with a non-human Cλ domain sequence; and (c) a second immunoglobulin κ light chain locus comprising human Vκ and Jκ gene segments operably linked to an endogenous non-human Cκ gene such that the non-human animal expresses an immunoglobulin light chain that comprises a human Vκ domain sequence fused with a mouse Cκ domain sequence.

In some embodiments, provided non-human animals have a genome comprising (a) a homozygous or heterozygous human or humanized immunoglobulin heavy chain locus comprising human $V_H$, $D_H$ and $J_H$ gene segments operably linked to one or more endogenous non-human immunoglobulin heavy chain constant regions such that the non-human animal expresses an immunoglobulin heavy chain that comprises a human $V_H$ domain sequence fused with a non-human $C_H$ domain sequence; (b) a first immunoglobulin κ light chain locus comprising human Vλ and Jλ gene segments operably linked to a non-human immunoglobulin Cλ gene such that the non-human animal expresses an immunoglobulin light chain that comprises a human Vλ domain sequence fused with a non-human Cλ domain sequence; (c) a second immunoglobulin κ light chain locus comprising human Vκ and Jκ gene segments operably linked to an endogenous non-human Cκ gene such that the non-human animal expresses an immunoglobulin light chain that comprises a human Vκ domain sequence fused with a mouse Cκ domain sequence; and (d) a homozygous or heterozygous functionally inactivated or deleted, in whole or in part, endogenous immunoglobulin λ light chain locus.

For example, as described herein, non-human animals comprising an engineered immunoglobulin κ light chain locus as described herein may further comprise (e.g., via cross-breeding or multiple gene targeting strategies) one or more modifications as described in U.S. Pat. Nos. 8,642,835, 8,697,940, 9,006,511, 9,035,128, 9,066,502, 9,150,662 and 9,163,092; each of which is incorporated by reference in its entirety. In some embodiments, provided non-human animals further comprise a humanized immunoglobulin heavy chain locus (e.g., an immunoglobulin heavy chain locus comprising human $V_H$, $D_H$ and $J_H$ gene segments operably linked to one or more non-human immunoglobulin heavy chain constant region genes). In some embodiments, provided non-human animals further comprise a humanized immunoglobulin heavy chain locus and a non-functional endogenous immunoglobulin λ light chain locus (e.g., deleted in whole or in part, or otherwise rendered non-functional).

In some embodiments, provided non-human animals comprise an immunoglobulin κ light chain locus having human Vλ and Jλ gene segments operably linked to a human or non-human Cλ gene positioned in the place of a non-human Cκ gene and a second immunoglobulin κ light chain locus comprising human Vκ and Jκ gene segments operably linked to an endogenous non-human Cκ gene. In such embodiments, provided non-human animals are referred to as hemizygous for an engineered immunoglobulin κ light chain locus. In some embodiment, said hemizygous non-human animals provided herein further comprise a humanized immunoglobulin heavy chain locus. In some embodiments, said hemizygous non-human animals provided herein further comprise a humanized immunoglobulin heavy chain locus and a non-functional endogenous immunoglobulin λ light chain locus.

Methods of Using Provided Non-Human Animals, Cells or Tissues

Non-human animals as described herein can be used as a platform for the development of antibodies. In particular, the non-human animals described herein represent a particularly advantageous platform for the generation and identification of human lambda light chain variable domains and antibodies that include such human lambda light chain variable domains.

Accordingly, the present disclosure provides that non-human animals described herein can be used in methods of making antibodies. Antibodies made in accordance with the present disclosure can include, for example, human antibodies, chimeric antibodies, reverse chimeric antibodies, fragments of any of these antibodies, or combinations thereof.

In some embodiments, non-human animals as described herein may be employed for making a human antibody (e.g., a fully human antibody), which human antibody comprises variable regions derived from nucleic acid sequences encoded by genetic material of a cell of a non-human animal as described herein. In some embodiments, a non-human animal as described herein is immunized with an antigen of interest under conditions and for a time sufficient that the non-human animal develops an immune response to said antigen of interest. Antibodies and/or antibody sequences (i.e., sequences that encode for part of an antibody, e.g., a variable region sequence) are isolated and/or identified from the non-human animal (or one or more cells, for example, one or more B cells) so immunized and characterized using various assays measuring, for example, affinity, specificity, epitope mapping, ability for blocking ligand-receptor interaction, inhibition receptor activation, etc. In various embodiments, antibodies produced by non-human animals as described herein comprise one or more human variable regions that are derived from one or more human variable region nucleotide sequences isolated from the non-human animal. In some embodiments, anti-drug antibodies (e.g., anti-idiotype antibody) may be raised in non-human animals as described herein. In various embodiments, antibodies produced by non-human animals as described herein are reverse chimeric antibodies that include a human light chain variable domain and a non-human (e.g., rodent) light chain constant domain and/or a human heavy chain variable domain and a non-human (e.g. rodent) heavy chain constant domain.

In various embodiments, antibodies produced by non-human animals include heavy and light chains having a human variable domain and a non-human constant domain. In some embodiments, antibodies produced by non-human animals as described herein are reverse chimeric antibodies that include a human light chain variable domain and a non-human (e.g. rodent) light chain constant domain. In some embodiments, antibodies produced by non-human animals as described herein are reverse chimeric antibodies that include a human heavy chain variable domain and a non-human (e.g. rodent) heavy chain constant domain.

In some embodiments, provided methods include immunizing a non-human animal as described herein with an antigen of interest. In some embodiments, provided methods include identifying a lymphocyte (e.g., a clonally selected lymphocyte) from said non-human animal, where the lymphocyte expresses an antibody that binds (e.g., specifically binds) the antigen of interest. In some embodiments, a lymphocyte is a B cell. In some embodiments, a human heavy chain variable region sequence, a human lambda light chain variable region sequence, and/or a human kappa light chain variable region sequence is obtained from the lymphocyte (e.g., B cell) and/or identified (e.g., genotyped, e.g., sequenced). In some embodiments, an amino acid sequence of a human heavy chain variable domain, a human lambda light chain variable domain, and/or a human kappa light chain variable domain is obtained from the lymphocyte (e.g., B cell) and/or identified (e.g., sequenced). In some embodiments, a human heavy chain variable region sequence, a human lambda light chain variable region sequence, and/or a human kappa light chain variable region sequence from a B cell of a non-human animal is expressed in a host cell. In some embodiments, a variant of a human heavy chain variable region sequence, a human lambda light chain variable region sequence, and/or a human kappa light chain variable region sequence from a B cell of a non-human animal is expressed in a host cell. In some embodiments, a variant includes one or more mutations. In some embodiments, one or more mutations can improve a pharmacokinetic and/or a pharmacodynamic property of an antibody including a variant. In some embodiments, one or more mutations can improve the specificity, the affinity, and/or the immunogenicity of an antibody including a variant.

In some embodiments, methods of making a human antibody include identifying a nucleotide sequence encoding a human immunoglobulin heavy chain variable domain and/or a human immunoglobulin light chain variable domain from a non-human animal described herein; and (i) joining or ligating the nucleotide sequence encoding the human immunoglobulin heavy chain variable domain to a nucleotide sequence encoding a human immunoglobulin heavy chain constant domain, thereby forming a human immunoglobulin heavy chain sequence encoding a fully human immunoglobulin heavy chain, (ii) joining or ligating the nucleotide sequence encoding the human immunoglobulin λ light chain variable domain to a nucleotide sequence encoding a human immunoglobulin λ light chain constant domain, thereby forming a human immunoglobulin λ light chain sequence encoding a fully human immunoglobulin λ light chain, and/or (iii) joining or ligating the nucleotide sequence encoding the human immunoglobulin κ light chain variable domain to a nucleotide sequence encoding a human immunoglobulin κ light chain constant domain, thereby forming a human immunoglobulin κ light chain sequence encoding a fully human immunoglobulin κ light chain. In certain embodiments, a human immunoglobulin heavy chain sequence, and (i) a human immunoglobulin λ light chain sequence, or (ii) a human immunoglobulin κ light chain sequence are expressed in a cell (e.g., a host cell, a mammalian cell) so that fully human immunoglobulin heavy chains and (i) fully human immunoglobulin λ light chains or (ii) fully human immunoglobulin κ light chains are expressed and form human antibodies. In some embodiments, human antibodies are isolated from the cell or culture media including the cell.

Non-human animals as described herein may be employed for identifying a nucleotide or nucleic acid sequence encoding a human variable domain generated by a non-human animal described herein, e.g., as part of an antibody against an epitope or antigen.

Non-human animals as described herein may be employed for identifying an amino acid sequence of a human variable domain generated by a non-human animal described herein, e.g., as part of an antibody against an epitope or antigen.

Non-human animals as described herein provide an improved in vivo system and source of biological materials (e.g., cells, nucleotides, polypeptides, protein complexes) for producing human antibodies that are useful for a variety of assays. In various embodiments, non-human animals as described herein are used to develop therapeutics that target a polypeptide of interested (e.g., a transmembrane or secreted polypeptide) and/or modulate one or more activities associated with said polypeptide of interest and/or modulate interactions of said polypeptide of interest with other binding partners (e.g., a ligand or receptor polypeptide). For example, in various embodiments, non-human animals as described herein are used to develop therapeutics that target one or more receptor polypeptides, modulate receptor polypeptide activity and/or modulate receptor polypeptide interactions with other binding partners. In various embodiments, non-human animals as described herein are used to identify, screen and/or develop candidate therapeutics (e.g., antibodies, siRNA, etc.) that bind one or more polypeptides of interest. In various embodiments, non-human animals as described herein are used to screen and develop candidate therapeutics (e.g., antibodies, siRNA, etc.) that block activity of one or more polypeptides of interest or that block the activity of one or more receptor polypeptides of interest. In various embodiments, non-human animals as described herein are used to determine the binding profile of antagonists and/or agonists of one or more polypeptides of interest. In some embodiments, non-human animals as described herein are used to determine the epitope or epitopes of one or more candidate therapeutic antibodies that bind one or more polypeptides of interest.

In various embodiments, non-human animals as described herein are used to determine the pharmacokinetic profiles of one or more human antibody candidates. In various embodiments, one or more non-human animals as described herein and one or more control or reference non-human animals are each exposed to one or more human antibody candidates at various doses (e.g., 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/mg, 7.5 mg/kg, 10 mg/kg, 15 mg/kg, 20 mg/kg, 25 mg/kg, 30 mg/kg, 40 mg/kg, or 50 mg/kg or more). Candidate therapeutic antibodies may be dosed via any desired route of administration including parenteral and non-parenteral routes of administration. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Blood is isolated from non-human animals (humanized and control) at various time points (e.g., 0 hr, 6 hr, 1 day, 2 days, 3 days, 4 days, 5 days, 6 days, 7 days, 8 days, 9 days, 10 days, 11 days, or up to 30 or more days). Various assays may be performed to determine the pharmacokinetic profiles of administered candidate therapeutic antibodies using samples obtained from non-human animals as described herein including, but not limited to, total IgG, anti-therapeutic antibody response, agglutination, etc.

In various embodiments, non-human animals as described herein are used to measure the therapeutic effect of blocking or modulating the activity of a polypeptide of interest and the effect on gene expression as a result of cellular changes or, in the context of a receptor polypeptide, the density of a receptor polypeptide on the surface of cells in the non-human animals. In various embodiments, a non-human animal as described herein or cells isolated therefrom are exposed to a candidate therapeutic that binds a polypeptide of interest and, after a subsequent period of time, analyzed for effects on specific cellular processes that are associated with said polypeptide of interest, for example, ligand-receptor interactions or signal transduction.

Non-human animals as described herein express human antibody variable regions, thus cells, cell lines, and cell cultures can be generated to serve as a source of human antibody variable regions for use in binding and functional assays, e.g., to assay for binding or function of an antagonist or agonist, particularly where the antagonist or agonist is specific for a human antigen of interest or specific for an epitope that functions in ligand-receptor interaction (binding). In various embodiments, epitopes bound by candidate therapeutic antibodies or siRNAs can be determined using cells isolated from non-human animals as described herein.

Cells from provided non-human animals can be isolated and used on an ad hoc basis, or can be maintained in culture for many generations. In various embodiments, cells from a provided non-human animal are immortalized (e.g., via use of a virus) and maintained in culture indefinitely (e.g., in serial cultures).

In some embodiments, a non-human cell is a non-human lymphocyte. In some embodiments, a non-human cell is selected from a B cell, dendritic cell, macrophage, monocyte and a T cell. In some embodiments, a non-human cell is an immature B cell, a mature naïve B cell, an activated B cell, a memory B cell, and/or a plasma cell.

In some embodiments, a non-human cell is a non-human embryonic stem (ES) cell. In some embodiments, a non-human ES cell is a rodent ES cell. In some certain embodiments, a rodent ES cell is a mouse ES cell and is from a 129 strain, C57BL strain, BALB/c or a mixture thereof. In some certain embodiments, a rodent embryonic stem cell is a mouse embryonic stem cell and is a mixture of 129 and C57BL strains. In some certain embodiments, a rodent embryonic stem cell is a mouse embryonic stem cell and is a mixture of 129, C57BL and BALB/c strains.

In some embodiments, use of a non-human ES cell as described herein to make a non-human animal is provided. In some certain embodiments, a non-human ES cell is a mouse ES cell and is used to make a mouse comprising engineered immunoglobulin κ light chain locus as described herein. In some certain embodiments, a non-human ES cell is a rat ES cell and is used to make a rat comprising engineered immunoglobulin κ light chain locus as described herein.

In some embodiments, a non-human tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, an immortalized cell made, generated, produced or obtained from an isolated non-human cell or tissue as described herein is provided.

In some embodiments, a non-human embryo made, generated, produced, or obtained from a non-human ES cell as described herein is provided. In some certain embodiments, a non-human embryo is a rodent embryo; in some embodiments, a mouse embryo; in some embodiments, a rat embryo.

Non-human animals as described herein provide an in vivo system for the generation of variants of human antibody variable regions that binds a polypeptide of interest (e.g., human Vλ domain variants). Such variants include human antibody variable regions having a desired functionality, specificity, low cross-reactivity to a common epitope shared by two or more variants of a polypeptide of interest. In some embodiments, non-human animals as described herein are employed to generate panels of human antibody variable regions that contain a series of variant variable regions that are screened for a desired or improved functionality.

Non-human animals as described herein provide an in vivo system for generating human antibody variable region libraries (e.g., a human Vλ domain library). Such libraries provide a source for heavy and/or light chain variable region sequences that may be grafted onto different Fc regions based on a desired effector function, used as a source for affinity maturation of the variable region sequence using techniques known in the art (e.g., site-directed mutagenesis, error-prone PCR, etc.) and/or used as a source of antibody components for the generation of antibody-based therapeutic molecules such as, for example, chimeric antigen receptors (i.e., a molecule engineered using antibody components, e.g., an scFv), multi-specific binding agents (e.g., bi-specific binding agents) and fusion proteins (e.g., single domain antibodies, scFvs, etc.).

In some embodiments, a method of producing an antibody in a non-human animal is provided, the method comprising the steps of (a) immunizing a non-human animal as described herein with an antigen of interest; (b) maintaining the non-human animal under conditions sufficient that the non-human animal produces an immune response to the antigen of interest; and (c) recovering an antibody from the non-human animal, or a non-human cell, that binds the antigen of interest.

In some embodiments of a method of producing an antibody in a non-human animal, a non-human cell is a B cell. In some embodiments of a method of producing an antibody in a non-human animal, a non-human cell is a hybridoma.

In some embodiments, a non-human animal is provided whose germline genome comprises a homozygous endogenous immunoglobulin κ light chain locus comprising (i) human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1 or any combination thereof, (ii) human J Jλ1, Jλ2, Jλ3, Jλ6, Jλ7 or any combination thereof, and (iii) a non-human or human Cλ gene, wherein (i)-(iii) are operably linked to each other, the non-human or human Cλ gene is inserted in the place of a non-human Cκ gene of the endogenous immunoglobulin κ light chain locus, the human Vλ gene segment(s) include human non-coding DNA that naturally appears adjacent to the corresponding human Vλ gene segments in an endogenous human λ light chain locus, and the human Jλ gene segment(s) include human non-coding DNA that naturally appears adjacent to the corresponding human Vλ gene segments in an endogenous human λ light chain locus. In some certain embodiments of a provided non-human animal, a non-human Cλ gene is or comprises a mouse Cλ1 gene. In some certain embodiments of a provided non-human animal, a human Cλ gene is or comprises a human Cλ2 gene. In some certain embodiments of a provided non-human animal, the endogenous immunoglobulin κ light chain locus further comprises non-human immunoglobulin κ light chain enhancers Eκi and 3' Eκ. In some certain embodiments of a provided non-human animal, the endogenous immunoglobulin κ light chain locus includes a deletion of non-human Vκ and Jκ gene segments.

In some embodiments, an antibody prepared by a method is provided, comprising the steps of: (a) providing a non-human animal as described herein; (b) immunizing the non-human animal with an antigen of interest; (c) maintaining the non-human animal under conditions sufficient that the non-human animal produces an immune response to the antigen of interest; and (d) recovering an antibody from the non-human animal, or a non-human cell, that binds the antigen of interest, wherein the antibody of (d) includes human $V_H$ and Vλ domains.

In some embodiments of an antibody prepared by a method, a human $V_H$ domain encoded by a rearranged human heavy chain variable region comprising a human $V_H$3-74, $V_H$3-73, $V_H$3-72, $V_H$2-70, $V_H$1-69, $V_H$3-66, $V_H$3-64, $V_H$4-61, $V_H$4-59, $V_H$1-58, $V_H$3-53, $V_H$5-51, $V_H$3-49, $V_H$3-48, $V_H$1-46, $V_H$1-45, $V_H$3-43, $V_H$4-39, $V_H$4-34, $V_H$3-33, $V_H$4-31, $V_H$3-30, $V_H$4-28, $V_H$2-26, $V_H$1-24, $V_H$3-23, $V_H$3-21, $V_H$3-20, $V_H$1-18, $V_H$3-15, $V_H$3-13, $V_H$3-11, $V_H$3-9, $V_H$1- 8, $V_H$3-7, $V_H$2-5, $V_H$7-4-1, $V_H$4-4, $V_H$1-3, $V_H$1-2 $V_H$6-1, or somatically hypermutated variant thereof.

In some embodiments of an antibody prepared by a method, a human Vλ domain encoded by a rearranged human λ light chain variable region comprising a human Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 Vλ3-1, or somatically hypermutated variant thereof.

In some embodiments, a non-human animal, non-human cell or non-human tissue as described herein is provided for use in the manufacture and/or development of a drug (e.g., an antibody or fragment thereof) for therapy or diagnosis.

In some embodiments, a non-human animal, non-human cell or non-human tissue as described herein is provided for use in the manufacture of a medicament for the treatment, prevention or amelioration of a disease, disorder or condition.

In some embodiments, use of a non-human animal, non-human cell or non-human tissue as described herein in the manufacture and/or development of a drug or vaccine for use in medicine, such as use as a medicament, is provided.

In some embodiments, use of a non-human animal or cell as described herein in the manufacture and/or development of an antibody or fragment thereof is provided.

Non-human animals as described herein provide an in vivo system for the analysis and testing of a drug or vaccine. In various embodiments, a candidate drug or vaccine may be delivered to one or more non-human animals as described herein, followed by monitoring of the non-human animals to determine one or more of the immune response to the drug or vaccine, the safety profile of the drug or vaccine, or the effect on a disease or condition and/or one or more symptoms of a disease or condition. Exemplary methods used to determine the safety profile include measurements of toxicity, optimal dose concentration, antibody (i.e., anti-drug) response, efficacy of the drug or vaccine and possible risk factors. Such drugs or vaccines may be improved and/or developed in such non-human animals.

Vaccine efficacy may be determined in a number of ways. Briefly, non-human animals as described herein are vaccinated using methods known in the art and then challenged with a vaccine or a vaccine is administered to already-infected non-human animals. The response of a non-human animal(s) to a vaccine may be measured by monitoring of, and/or performing one or more assays on, the non-human animal(s) (or cells isolated therefrom) to determine the efficacy of the vaccine. The response of a non-human animal(s) to the vaccine is then compared with control animals, using one or more measures known in the art and/or described herein.

Vaccine efficacy may further be determined by viral neutralization assays. Briefly, non-human animals as described herein are immunized and serum is collected on various days post-immunization. Serial dilutions of serum are pre-incubated with a virus during which time antibodies in the serum that are specific for the virus will bind to it. The virus/serum mixture is then added to permissive cells to determine infectivity by a plaque assay or microneutralization assay. If antibodies in the serum neutralize the virus, there are fewer plaques or lower relative luciferase units compared to a control group.

Non-human animals as described herein produce human antibody variable regions and, therefore, provide an in vivo system for the production of human antibodies for use in diagnostic applications (e.g., immunology, serology, microbiology, cellular pathology, etc.). In various embodiments, non-human animals as described herein may be used to produce human antibody variable regions that bind relevant antigenic sites for identification of cellular changes such as, for example, expression of specific cell surface markers indicative of pathological changes. Such antibodies can be conjugated to various chemical entities (e.g., a radioactive tracer) and be employed in various in vivo and/or in vitro assays as desired.

Non-human animals as described herein provide an improved in vivo system for development and selection of human antibodies for use in oncology and/or infectious diseases. In various embodiments, non-human animals as described herein and control non-human animals (e.g., having a genetic modification that is different than as described herein or no genetic modification, i.e., wild-type) may be implanted with a tumor (or tumor cells) or infected with a virus (e.g., influenza, HIV, HCV, HPV, etc.). Following implantation of infection, non-human animals may be administered a candidate therapeutic. The tumor or virus may be allowed sufficient time to be established in one or more locations within the non-human animals prior to administration of a candidate therapeutic. Alternatively, and/or additionally, the immune response may be monitored in such non-human animals so as to characterize and select potential human antibodies that may be developed as a therapeutic.

Pharmaceutical Compositions

In some embodiments, an antibody, a nucleic acid, or a therapeutically relevant portion thereof produced by a non-human animal disclosed herein or derived from an antibody, a nucleic acid, or a therapeutically relevant portion thereof produced by a non-human animal disclosed herein can be administered to a subject (e.g., a human subject). In some embodiments, a pharmaceutical composition includes an antibody produced by a non-human animal disclosed herein. In some embodiments, a pharmaceutical composition can include a buffer, a diluent, an excipient, or any combination thereof. In some embodiments, a composition, if desired, can also contain one or more additional therapeutically active substances.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

For example, a pharmaceutical composition provided herein may be provided in a sterile injectable form (e.g., a form that is suitable for subcutaneous injection or intravenous infusion). For example, in some embodiments, a pharmaceutical compositions is provided in a liquid dosage form that is suitable for injection. In some embodiments, a pharmaceutical composition is provided as powders (e.g., lyophilized and/or sterilized), optionally under vacuum, which can be reconstituted with an aqueous diluent (e.g., water, buffer, salt solution, etc.) prior to injection. In some embodiments, a pharmaceutical compositionsis diluted and/or reconstituted in water, sodium chloride solution, sodium acetate solution, benzyl alcohol solution, phosphate buffered saline, etc. In some embodiments, a powder should be mixed gently with the aqueous diluent (e.g., not shaken).

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

In some embodiments, a pharmaceutical composition including an antibody produced by a non-human animal disclosed herein can be included in a container for storage or administration, for example, an vial, a syringe (e.g., an IV syringe), or a bag (e.g., an IV bag). A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100% (w/w) active ingredient.

A pharmaceutical composition may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

In some embodiments, a provided pharmaceutical composition comprises one or more pharmaceutically acceptable excipients (e.g., preservative, inert diluent, dispersing agent, surface active agent and/or emulsifier, buffering agent, etc.). In some embodiments, a pharmaceutical composition comprises one or more preservatives. In some embodiments, pharmaceutical compositions comprise no preservative.

In some embodiments, a pharmaceutical composition is provided in a form that can be refrigerated and/or frozen. In some embodiments, a pharmaceutical composition is provided in a form that cannot be refrigerated and/or frozen. In some embodiments, reconstituted solutions and/or liquid dosage forms may be stored for a certain period of time after reconstitution (e.g., 2 hours, 12 hours, 24 hours, 2 days, 5 days, 7 days, 10 days, 2 weeks, a month, two months, or longer). In some embodiments, storage of antibody compositions for longer than the specified time results in antibody degradation.

Liquid dosage forms and/or reconstituted solutions may comprise particulate matter and/or discoloration prior to administration. In some embodiments, a solution should not be used if discolored or cloudy and/or if particulate matter remains after filtration.

General considerations in the formulation and/or manufacture of pharmaceutical agents may be found, for example, in Remington: The Science and Practice of Pharmacy 21st ed., Lippincott Williams & Wilkins, 2005.

Kits

The present disclosure further provides a pack or kit comprising one or more containers filled with at least one non-human animal, non-human cell, DNA fragment, targeting vector, or any combination thereof, as described herein. Kits may be used in any applicable method (e.g., a research method). Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, and/or (c) a contract that governs the transfer of materials and/or biological products (e.g., a non-human animal or non-human cell as described herein) between two or more entities and combinations thereof.

In some embodiments, a kit comprising a non-human animal, non-human cell, non-human tissue, immortalized cell, non-human ES cell, or non-human embryo as described herein is provided. In some embodiments, a kit comprising an amino acid (e.g., an antibody or fragment thereof) from a non-human animal, non-human cell, non-human tissue, immortalized cell, non-human ES cell, or non-human embryo as described herein is provided. In some embodiments, a kit comprising a nucleic acid (e.g., a nucleic acid encoding an antibody or fragment thereof) from a non-human animal, non-human cell, non-human tissue, immortalized cell, non-human ES cell, or non-human embryo as described herein is provided. In some embodiments, a kit comprising a sequence (amino acid and/or nucleic acid sequence) identified from a non-human animal, non-human cell, non-human tissue, immortalized cell, non-human ES cell, or non-human embryo as described herein is provided.

In some embodiments, a kit as described herein for use in the manufacture and/or development of a drug (e.g., an antibody or fragment thereof) for therapy or diagnosis is provided.

In some embodiments, a kit as described herein for use in the manufacture and/or development of a drug (e.g., an antibody or fragment thereof) for the treatment, prevention or amelioration of a disease, disorder or condition is provided.

Other features of certain embodiments will become apparent in the course of the following descriptions of exemplary embodiments, which are given for illustration and are not intended to be limiting thereof.

EXAMPLES

The following examples are provided so as to describe to the skilled artisan how to make and use methods and compositions described herein, and are not intended to limit the scope of what the inventors of the present disclosure regard as their invention. Unless indicated otherwise, temperature is indicated in Celsius and pressure is at or near atmospheric.

Example 1. Construction of a Targeting Vectors for Generating a Rodent Expressing at Least One Lambda Light Chain from a Kappa Light Chain Locus Example 1.1. Engineering a Targeting Vector Comprising a Rodent Lambda Constant Region This example illustrates exemplary methods of constructing a targeting vector for insertion into the genome of a non-human animal such as a rodent (e.g., a mouse). Furthermore, this example demonstrates production of a non-human animal whose germline genome comprises an engineered immunoglobulin κ light chain locus. In particular, this example demonstrates construction of a targeting vector for engineering an endogenous immunoglobulin κ light chain locus in a rodent so that the rodent expresses and/or produces antibodies that include immunoglobulin λ light chains having human variable regions and non-human immunoglobulin λ constant (Cλ) regions from said immunoglobulin κ light chain locus in the germline genome of the non-human animal. As described below in Example 2, DNA fragments containing multiple human Jλ (e.g., Jλ1, Jλ2, Jλ3, Jλ6 and Jλ7) coding sequences and a rodent Cλ (e.g., a mouse Cλ1) coding sequence are inserted into an endogenous rodent immunoglobulin κ light chain locus. In particular exemplified embodiments, a mouse Cλ1 gene is inserted in the place of a mouse Cκ gene and in operable linkage with rodent Igκ enhancers (e.g., Eκi and 3'Eκ). An exemplary strategy for creation of a targeting vector for generating an engineered immunoglobulin κ light chain locus in a rodent characterized by the presence of a plurality of human Vλ and Jλ gene segments operably linked to a rodent (e.g., mouse) Cλ gene and operably linked to endogenous Igκ enhancers is set forth in FIG. 1 (FIG. 1A: initial steps of construction of targeting vector; FIG. 1B: additional subsequent steps of construction of a targeting vector; a human immunoglobulin κ light chain sequence between human Vλ and Jλ gene segments is indicated by an open bar filed with wide downward diagonal lines (e.g., see U.S. Pat. Nos. 9,006,511, 9,035,128, 9,066,502, 9,150,662 and 9,163,092), lox: lox2372; NEO: Neomycin resistance gene (neo$^R$) under transcriptional control of a ubiquitin promoter, HYG: Hygromycin resistance gene (hyg$^R$) under transcriptional control of a ubiquitin promoter, Spec: Spectinomycin resistance gene (Spec$^R$), R6κ: R6K origin of replication).

A targeting vector containing human Jλ and rodent Cλ coding sequences for insertion into a rodent immunoglobulin κ light chain locus was created using VELOCIGENE® technology (see, e.g., U.S. Pat. No. 6,586,251 and Valenzuela et al., 2003, Nature Biotech. 21(6):652-9; incorporated herein by reference in their entireties) and molecular biology techniques known in the art. Those of ordinary skill, reading the present example, will appreciate that the described technologies and approach can be employed to utilize any human Jλ and any Cλ coding sequences, or combination of coding sequences (or sequence fragments) as desired.

Briefly, a 2.7 kb DNA fragment containing human Jλ gene segments Jλ1, Jλ2, Jλ3, Jλ6 and Jλ7 and unique 5' and 3' overlap regions corresponding to a human Vκ-Jκ genomic (non-coding) sequence and a genomic sequence 5' of a mouse Cκ gene, respectively, was made by de novo DNA synthesis (pA; FIG. 1A, top left, Blue Heron Biotech, Bothell, Wash.). Various restriction enzyme recognition sites were included in the DNA fragment to facilitate subsequent cloning of selection markers and other DNA fragments (described below). The DNA fragment was uniquely designed to contain non-coding human Jκ sequences juxtaposed with human Jλ coding sequences and human Jλ recombination signal sequences (RSS). As in known in the art, an RSS consists of a conserved block of seven nucleotides (heptamer) followed by a spacer either 12 or 23 base pairs in length and followed by a second conserved block of nine nucleotides (nonamer). Thus, an RSS has a configuration of 7-12-9 (12RSS) or 7-23-9 (23RSS) depending on the associated gene segment (see, e.g., FIG. 5.4 in Murphy, Kenneth, et al. "Chapter 5." *Janeway's Immunobiology*, 8th ed., Garland Science/Taylor & Francis Group, L L C, 2012, which is incorporated herein by reference in its entirety). In particular, human Jλ gene segments (i.e., human Jλ coding sequences) and their associated 12RSS were substituted in the place of human Jκ gene segments (i.e., human Jκ coding sequences) and their associated 23RSS. Thus, this fragment contained human Jλ and Jκ DNA sequences. Inclusion of such sequences in targeting vectors described herein can provide for (or promote) efficient joining of human Vλ and Jλ gene segments within an engineered rodent Igκ light chain locus.

Plasmid A (pA) was digested with AgeI and EcoRI and ligated to a Neomycin selection cassette (i.e., a Neo$^R$ gene under control of a ubiquitin promoter flanked by lox2372 sites) containing compatible ends to create plasmid B (pB) (FIG. 1A). Separately, unique DNA fragments containing a mouse Igκ intronic enhancer (Ei), a mouse Cλ1 gene (from BAC clone RP23-60e14), a DNA fragment containing 316 bp of sequence immediately downstream of a mouse Cκ coding sequence and 80 bp of overlap sequence to facilitate isothermal assembly, and restriction enzyme recognition sites (NotI, MluI) to facilitate subsequent cloning steps, and an R6K-Spec (a Spectinomycin Adenylytransferase gene and a R6K origin of replication) were amplified by polymerase chain reaction (PCR) and combined together by isothermal assembly (see, e.g., Gibson, D. G. et. al., 2009, Nat. Meth. 6(5):343-5; Gibson, D. G. et al., 2010, Nat. Meth. 7:901-903; incorporated herein by reference in their entireties) to create plasmid C (pC), which was subsequently digested with NotI and MluI and ligated to a Hygromycin selection cassette (i.e., a Hyg$^R$ gene under control of a ubiquitin promoter flanked by loxP sites) containing compatible ends to create plasmid D (pD; FIG. 1A, top and middle right). This resulting plasmid (pD; FIG. 1A, middle) was then digested with PI-SceI and AscI and ligated with plasmid B (pB) containing compatible ends (FIG. 1A, bottom) to generate plasmid E (pE).

In a next step, a targeting vector containing human Vλ and Jλ gene segments operably linked to a mouse Cκ gene and a human immunoglobulin κ light chain sequence positioned between the human Vλ and Jλ gene segments (see, e.g., U.S. Pat. No. 9,006,511, which is incorporated herein by reference in its entirety) was separately digested with NotI and religated to remove the human Vλ region including a human immunoglobulin κ sequence (FIG. 1B, top), which resulted in a deletion of ~137 kb. The resulting construct (construct F) was combined with plasmid E (pE) using a CRISPR/Cas9 isothermal assembly method (see, e.g., U.S. Pat. No. 9,738,897, and U.S. Publication No. 2016/0145646; incorporated herein by reference in their entireties) so that the human Jκ region with human Jλ-12RSS coding sequence (CDS) was operably linked with a human Vκ-Jκ intergenic (non-coding) region (see, e.g., U.S. Pat. No. 9,006,511, which is incorporated herein by reference in its entirety) and a mouse Igκ 3' enhancer (FIG. 1B). Positive bacterial clones were selected on media containing Kanamycin, Hygromycin and Spectinomycin. The resulting targeting vector (construct G) contained, from 5' to 3', a loxP recognition site, a NotI site, a human Vκ-Jκ intergenic sequence (see, e.g., U.S. Pat. No. 9,006,511, which is incorporated by reference herein in its entirety), a Neomycin selection cassette flanked by lox2372 recognition sites, a human Jκ region with five human Jλ gene segments and their respective 12RSS, a mouse immunoglobulin κ intronic enhancer (Eiκ), a mouse Cλ1 gene, a Hygromycin selection cassette flanked by loxP recognition sites, a mouse immunoglobulin κ 3' enhancer (3' Eκ) and a Spectinomycin selection cassette (FIG. 1B).

Example 1.2. Engineering a Targeting Vector Comprising a Human Lambda Constant Region This example illustrates exemplary methods of constructing a targeting vector for insertion into the genome of a non-human animal such as a rodent (e.g., a mouse). Furthermore, this example demonstrates production of a non-human animal whose germline genome comprises an engineered immunoglobulin κ light chain locus. In particular, this example demonstrates construction of a targeting vector for engineering an endogenous immunoglobulin κ light chain locus in a rodent so that the rodent expresses and/or produces antibodies that include immunoglobulin λ light chains having human variable regions and human immunoglobulin λ constant (Cλ) regions from said immunoglobulin κ light chain locus in the germline genome of the non-human animal. As described below in Example 2, DNA fragments containing multiple human Jλ (e.g., Jλ1, Jλ2, Jλ3, Jλ6 and Jλ7) coding sequences and a human Cλ (e.g., a human Cλ2) coding sequence are inserted into an endogenous rodent immunoglobulin κ light chain locus. In particular, a human Cλ2 gene is inserted in the place of a mouse Cκ gene and in operable linkage with rodent immunoglobulin κ enhancers (e.g., Eiκ and 3'Eκ). An exemplary strategy for creation of a targeting vector is set forth in FIG. 3.

A targeting vector containing human Jλ and human Cλ coding sequences for insertion into a rodent Igκ light chain locus was created using VELOCIGENE® technology (see, e.g., U.S. Pat. No. 6,586,251 and Valenzuela et al., 2003, Nature Biotech. 21(6):652-9; incorporated herein by reference in their entireties) and molecular biology techniques known in the art. Those of ordinary skill, reading the present example, will appreciate that the described approach and technologies can be employed to utilize any human Jλ and Cλ coding sequences, or combination of coding sequences (or sequence fragments) as desired.

Briefly, an 871 bp DNA fragment containing a human Cλ coding sequence and unique 5' and 3' overlap regions corresponding to genomic sequences 5' and 3' of a mouse Cκ gene, respectively, was made by de novo DNA synthesis (pH; FIG. 3, top left, Blue Heron Biotech, Bothell, Wash.). Various restriction enzyme recognition sites were included in the DNA fragment to allow for subsequent cloning of selection markers and other DNA fragments (described below). Plasmid H (pH) was digested with AgeI and XhoI and ligated to a Hygromycin selection cassette (i.e., a Hyg$^R$ gene under control of a ubiquitin promoter flanked by loxP sites) containing compatible ends to create plasmid J (pJ; FIG. 3). An intermediate construct (construct K, generated from construct F and plasmid B using Cas9 and isothermal assembly) containing an engineered human Jκ region with human Jλ coding sequences (described above) operably linked to a mouse Cκ gene and mouse Igκ enhancers was combined with plasmid J using a CRISPR/Cas9 isothermal assembly method (see, e.g., U.S. Pat. No. 9,738,897, and U.S. Publication No. 2016/0145646; incorporated herein by reference in their entireties) so that the human Jκ region with human Jλ-12RSS coding sequence (CDS) was operably linked with the human Cλ2 coding sequence of plasmid J (FIG. 3). Positive bacterial clones were selected on media containing Kanamycin, Hygromycin and Spectinomycin. The resulting targeting vector (construct L) contained, from 5' to 3', a loxP recognition site, a NotI site, a human Vκ-Jκ intergenic sequence (see, e.g., U.S. Pat. No. 9,006,511, which is incorporated by reference herein in its entirety), a Neomycin selection cassette flanked by lox2372 recognition sites, a human Jκ region with five human Jλ gene segments and their respective 12RSS, a mouse Igκ intronic enhancer (Eiκ), a human Cλ2 gene, a Hygromycin selection cassette flanked by loxP recognition sites, a mouse immunoglobulin κ 3' enhancer (3' Eκ) and a Spectinomycin selection cassette (FIG. 3).

Example 2. Generation of Rodents Having an Engineered Light Chain Locus

This example demonstrates production of non-human animals (e.g., rodents) whose germline genome comprises an endogenous immunoglobulin κ light chain locus comprising insertion of a plurality of human Vλ and Jλ gene segments and a rodent or human Cλ gene, which human Vλ and Jλ gene segments are operably linked to said rodent or human Cλ gene, and which rodent or human Cλ gene is inserted in the place of a rodent Cκ gene of an endogenous immunoglobulin κ light chain locus. Such non-human animals are characterized, in some embodiments, by expression of immunoglobulin λ light chains (variable and constant domains) from an endogenous immunoglobulin κ light chain locus.

Targeted insertion of targeting vectors described in Examples 1.1 and 1.2 were confirmed by polymerase chain reaction. Targeted BAC DNA, confirmed by polymerase chain reaction, was introduced into $F^1$ hybrid (C57BL6NTac/129S6SvEvTac) mouse embryonic stem (ES) cells via electroporation followed by culturing in selection medium.

ES cells used for electroporation of construct G (mouse Cλ1) had a germline genome that included a heterozygous immunoglobulin κ light chain locus containing a plurality of human Vλ and Jλ gene segments operably linked to a rodent immunoglobulin κ light chain constant region gene including rodent immunoglobulin κ light chain enhancers, and a human immunoglobulin κ light chain sequence positioned between the human Vλ and Jλ gene segments and one wild-type rodent immunoglobulin κ light chain locus. ES cells before and after electroporation are depicted in FIG. 2A (1741HET: a rodent ES cell clone having a genome heterozygous for an engineered immunoglobulin κ light chain locus containing human Vλ and Jλ gene segments operably linked to a rodent immunoglobulin κ light chain constant region gene including rodent immunoglobulin κ light chain enhancers, and a human immunoglobulin κ light chain sequence positioned between the human Vλ and Jλ gene segments indicated by an open bar filed with wide downward diagonal lines, and wild-type immunoglobulin heavy and λ light chain loci, e.g., see U.S. Pat. Nos. 9,006,511, 9,035,128, 9,066,502, 9,150,662 and 9,163,092, which are hereby incorporated by reference in their entireties; 6557HET: a mouse ES cell clone after insertion of construct G resulting in a genome heterozygous for an engineered immunoglobulin κ light chain locus including rodent immunoglobulin κ light chain enhancers, which engineered immunoglobulin κ light chain locus is characterized by the presence of a plurality of human Vλ and Jλ gene segments, which human Jλ gene segments are contained within a human Jκ region sequence with human Jλ gene segment coding sequences and human Jλ 12RSS in place of the corresponding human Jκ gene segment coding sequences and human Jκ 23RSS, and which human Vλ and Jλ gene segments are operably linked to a rodent immunoglobulin λ light chain constant region gene (e.g., mCλ1); lox: lox2372; NEO: Neomycin resistance gene (neo$^R$) under transcriptional control of a ubiquitin promoter; HYG: Hygromycin resistance gene (hyg$^R$) under transcriptional control of a ubiquitin promoter; locations of selected primer/probe sets for screening ES cells clones are indicated near the locations of regions within the engineered Igκ light chain locus detected in an assay described below).

Figure 4A:
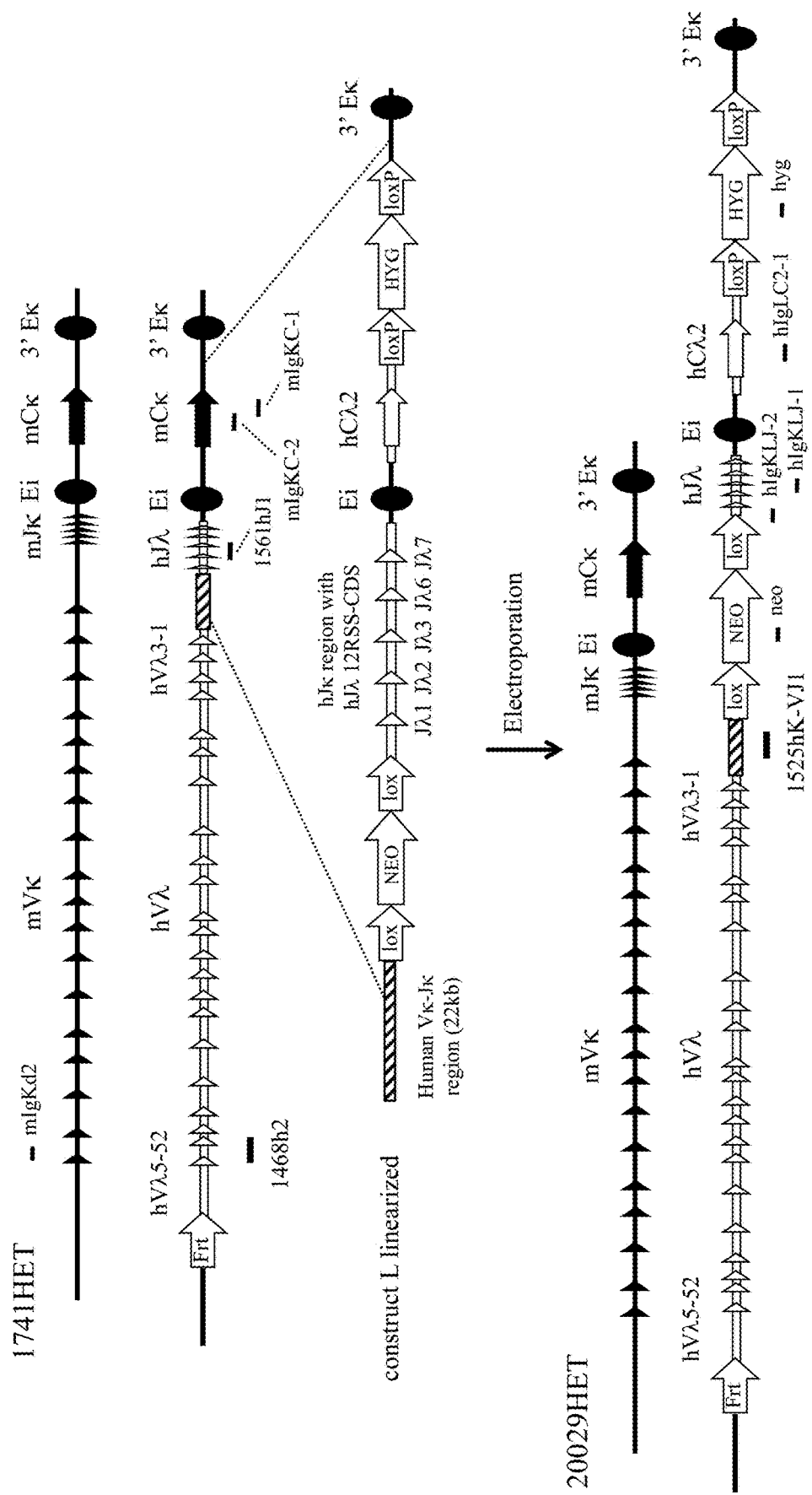
FIG. 4A shows an illustration, not to scale, of the insertion of a targeting vector (described in Example 1.2) into an engineered Igκ light chain locus of a rodent embryonic stem (ES) cell clone, which ES cell clone was used in generating an embodiment of the rodent according to the present disclosure.

ES cells used for electroporation of construct L (human Cλ2) had a germline genome that included a heterozygous immunoglobulin κ light chain locus containing a plurality of human Vλ and Jλ gene segments operably linked to a rodent immunoglobulin κ light chain constant region gene including rodent immunoglobulin κ light chain enhancers, and a human immunoglobulin κ light chain sequence positioned between the human Vλ and Jλ gene segments and one wild-type rodent Igκ locus. ES cells before and after electroporation are depicted in FIG. 4A (1741HET: supra; 20029HET: a mouse ES cell clone after insertion of a targeting vector having a genome heterozygous for an engineered Igκ light chain locus including rodent immunoglobulin κ light chain enhancers, which engineered Igκ light chain locus is characterized by the presence of a plurality of human Vλ and Jλ gene segments, which human Jλ gene segments are contained within a human Jκ region sequence with human Jλ gene segment coding sequences and human Jλ 12RSS in place of the corresponding human Jκ gene segment coding sequences and human Jκ 23RSS, and which human Vλ and Jλ gene segments are operably linked to a human Igλ light chain constant region gene (e.g., hCλ2); lox: lox2372; NEO: Neomycin resistance gene (neo$^R$) under transcriptional control of a ubiquitin promoter; HYG: Hygromycin resistance gene (hyg$^R$) under transcriptional control of a ubiquitin promoter; locations of selected primer/ probe sets for screening ES cells clones are indicated near the locations of regions within the engineered Igκ light chain locus detected in an assay described below).

Drug-resistant colonies were picked 10 days after electroporation and screened by TAQMAN™ and karyotyping for correct targeting as previously described (Valenzuela et al., supra; Frendewey, D. et al., 2010, Methods Enzymol. 476:295-307; incorporated herein by reference in their entireties). Table 1 sets forth exemplary primers/probes sets used for screening positive ES cell clones (F: forward; R: reverse; P: probe; GOA: gain of allele; *LOA*: loss of allele; WT: wild-type).

The VELOCIMOUSE® method (DeChiara, T. M. et al., 2010, Methods Enzymol. 476:285-294; DeChiara, T. M., 2009, Methods Mol. Biol. 530:311-324; Poueymirou et al., 2007, Nat. Biotechnol. 25:91-99; incorporated herein by reference in their entireties), in which targeted ES cells were injected into uncompacted 8-cell stage Swiss Webster embryos, was used to produce healthy fully ES cell-derived F0 generation mice heterozygous for the engineered Igκ light chain locus (FIGS. 2A and 4A). F0 generation heterozygous mice were crossed with C57Bl6/NTac mice to generate F1 heterozygotes that were intercrossed to produce homozygous F2 generation animals for phenotypic analyses.

Figure 4B:
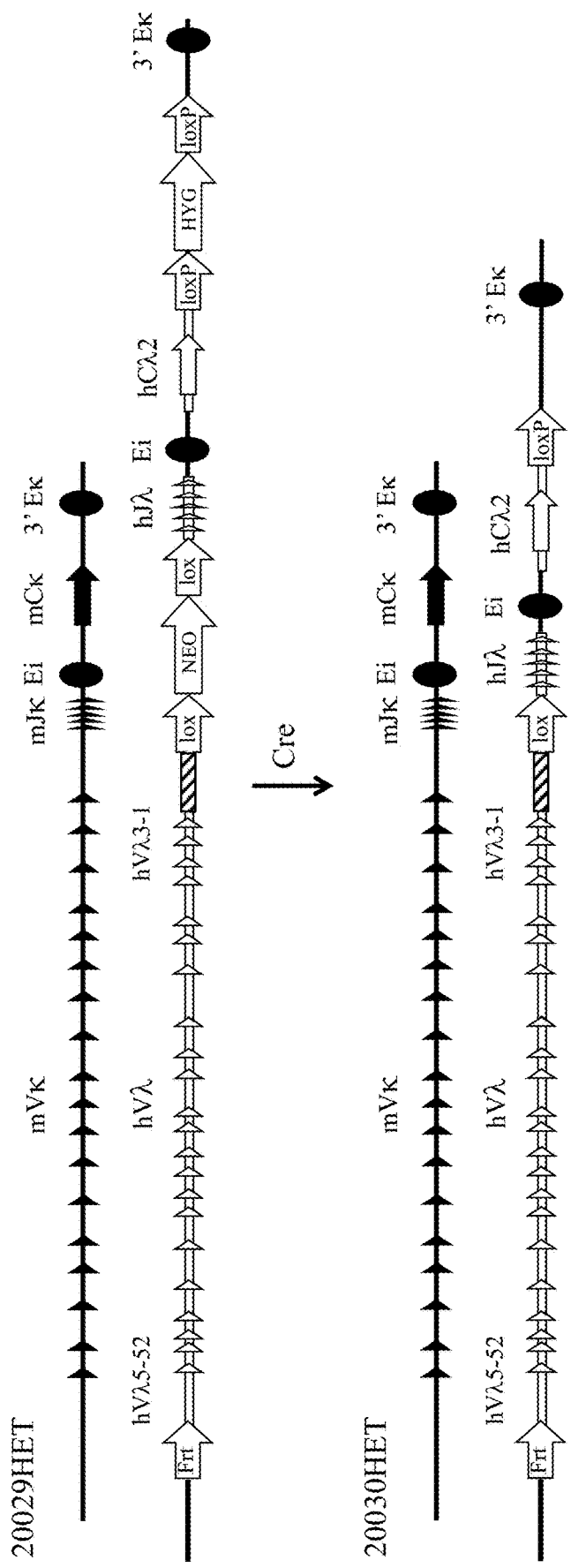
FIG. 4B shows an illustration of an exemplary embodiment, not to scale, of recombinase-mediated removal of selection cassette(s) in an engineered Igκ light chain locus resulting from the insertion of a targeting vector (described in Example 1.2) used in generating an embodiment of the rodent according to the present disclosure.

Alternatively, murine ES cells bearing an engineered immunoglobulin κ locus as described above can be modified to remove one or more selection cassettes introduced with a targeting vector as desired (FIG. 2B: 6557HET: supra; 6558HET: a mouse ES cell clone after recombinase-mediated excision of Neomycin and Hygromycin selection cassettes inserted after homologous recombination with a targeting vector; FIG. 4B: 20029HET: supra; 20030HET: a mouse ES cell clone after recombinase-mediated excision of Neomycin and Hygromycin selection cassettes inserted after homologous recombination with a targeting vector. Cre: Cre recombinase). For example, the Neomycin and Hygromycin cassette introduced by the targeting vectors may be removed in engineered ES cells (or embryos) by transient recombinase expression or by breeding to a recombinase-expressing genetically engineered strain (see e.g., Lakso, M. et al., 1992, Proc. Natl. Acad. Sci. USA 89: 6232-6; Orban, P. C. et al., 1992, Proc. Natl. Acad. Sci. U.S.A. 89:6861-5; Gu, H. et al., 1993, Cell 73(6):1155-64; Araki, K. et al., 1995, Proc. Natl. Acad. Sci. U.S.A. 92:160-4; Dymecki, S. M., 1996, Proc. Natl. Acad. Sci. U.S.A. 93(12):6191-6; all of which are incorporated herein by reference in their entireties).

Taken together, this example illustrates the generation of a rodent (e.g., a mouse) whose germline genome comprises an engineered Igκ light chain locus characterized by the presence of a plurality of human Vλ and Jλ gene segments operably linked to a rodent or human Cλ gene, which rodent or human Cλ gene is inserted in the place of a rodent Cκ gene of an endogenous Igκ light chain locus. An engineered Igκ light chain locus as described includes plurality of human Vλ and Jλ gene segments in a non-endogenous arrangement. The strategy described herein for inserting human Vλ and Jλ gene segments, and a rodent or human Cλ gene into the place of a rodent Cκ gene, enables the construction of a rodent that expresses antibodies that exclusively contain human Vλ domains. It was unclear if such an engineered Igκ light chain locus that includes exclusively λ gene segments (outside of the endogenous λ locus, in a non-endogenous orientation) would be able to produce functional light chains. As described herein, such human Vλ domains are expressed from endogenous Igκ light chain loci in the germline genome of provided rodents.

TABLE 1

Representative primer/probe sets for screening positive ES cell clones

| Name | | Sequence (5'-3') | Assay |
|---|---|---|---|
| mIgKC-1 | F | GTGGAAGATTGATGGCAGTGAAC (SEQ ID NO: 25) | LOA |
| | R | GTGCTGCTCATGCTGTAGGT (SEQ ID NO: 26) | |
| | P | AAATGGCGTCCTGAACAGTTGGACTGA (SEQ ID NO: 27) | |
| mIgKC-2 | F | CCATCCAGTGAGCAGTTAACATC (SEQ ID NO: 28) | LOA |
| | R | TGTCGTTCACTGCCATCAATC (SEQ ID NO: 29) | |
| | P | AGGTGCCTCAGTCGTGTGCTTC (SEQ ID NO: 30) | |
| mIgKLC1-1 | F | GGAGCCCTTCCTTGTTACTTCA (SEQ ID NO: 31) | GOA-6557 |
| | R | AGGTGGAAACAGGGTGACTGATG (SEQ ID NO: 32) | |
| | P | TCCTCTGTGCTTCCTTCCTCAGGC (SEQ ID NO: 33) | |
| mIgKLC1-2 | F | TCCTTGTTACTTCATACCATCCTCT (SEQ ID NO: 34) | GOA-6557 |
| | R | AGGGTGACTGATGGCGAAGACT (SEQ ID NO: 35) | |
| | P | TTCCTTCCTCAGGCCAGCCC (SEQ ID NO: 36) | |
| hIgKLJ-1 | F | GAGGCTTGCTGAGCTTTCAG (SEQ ID NO: 37) | GOA |
| | R | AGGACGGTCAGCTTGGTC (SEQ ID NO: 38) | |
| | P | TATGAGCCTGTGTCACAGTGTTGGG (SEQ ID NO: 39) | |
| hIgKLJ-2 | F | GCTGACCCAGGACTCTGTTC (SEQ ID NO: 40) | GOA |
| | R | TCCCAGTTCCGAAGACATAACAC (SEQ ID NO: 41) | |
| | P | CCCTTTGGTGAGAAGGGTTTTGGTC (SEQ ID NO: 42) | |
| hIgLC2-1 | F | TACGCGGCCAGCAGTAT (SEQ ID NO: 43) | GOA-20029 |
| | R | TGGCAGCTGTAGCTTCTGT (SEQ ID NO: 44) | |
| | P | CTGAGCCTGACGCCTGAGCAG (SEQ ID NO: 45) | |
| 1561hJ1 | F | TCAACCTTTCCCAGCCTGTCT (SEQ ID NO: 46) | LOA |
| | R | CCCCAGAGAGAGAAAACAGATTTT (SEQ ID NO: 47) | |
| | P | ACCCTCTGCTGTCCCT (SEQ ID NO: 49) | |
| Neo | F | GGTGGAGAGGCTATTCGGC (SEQ ID NO: 50) | GOA |
| | R | GAACACGGCGGCATCAG (SEQ ID NO: 51) | |
| | P | TGGGCACAACAGACAATCGGCTG (SEQ ID NO: 52) | |
| Hyg | F | TGCGGCCGATCTTAGCC (SEQ ID NO: 53) | GOA |
| | R | TTGACCGATTCCTTGCGG (SEQ ID NO: 54) | |
| | P | ACGAGCGGGTTCGGCCCATTC (SEQ ID NO: 55) | |
| 1468h2 | F | GGGCTACTTGAGGACCTTGCT (SEQ ID NO: 56) | Parental |
| | R | GACAGCCCTTACAGAGTTTGGAA (SEQ ID NO: 57) | |
| | P | CAGGGCCTCCATCCCAGGCA (SEQ ID NO: 58) | |

TABLE 1-continued

Representative primer/probe sets for screening positive ES cell clones

| Name | | Sequence (5'-3') | Assay |
|---|---|---|---|
| 1525hk-VJ1 | F | ATCTCCCTACTTCCTGGCTAATG (SEQ ID NO: 59) | Parental |
| | R | GCTTGGAACCTGATTGGTTGTC (SEQ ID NO: 60) | |
| | P | AGCCTTGATCCTTGGGAATCCAGGACA (SEQ ID NO: 61) | |
| mIgKd2 | F | GCAAACAAAAACCACTGGCC (SEQ ID NO: 62) | WT |
| | R | GGCCACATTCCATGGGTTC (SEQ ID NO: 63) | |
| | P | CTGTTCCTCTAAAACTGGACTCCACAGTAAATGGAAA (SEQ ID NO: 64) | |

Example 3. Characterization of Rodents Having an Engineered Immunoglobulin Light Chain Locus Example 3.1. Phenotypic Assessment of Immune Cells in Rodents Having an Engineered Immunoglobulin Light Chain Locus This example demonstrates the characterization of various immune cell populations in rodents (e.g., mice) engineered to contain a plurality of human Vλ and Jλ gene segments operably linked to a rodent Cλ gene, and rodent immunoglobulin κ light chain enhancer and regulatory regions, within an endogenous immunoglobulin κ light chain locus. In particular, this example specifically demonstrates that rodents having engineered immunoglobulin κ light chain loci described herein display a unique light chain expression profile as compared to wild-type rodents. This example also demonstrates that provided rodents express a broad repertoire of human V, regions from the engineered immunoglobulin κ light chain locus.

Briefly, spleens and femurs were harvested from wild-type (WT, 75% C57BL/6NTac 25% 129SvEvTac) and 6558HO (homozygous LiK, 75% C57BL/6NTac 25% 129SvEvTac) mice. Bone marrow was collected from femurs by flushing with 1× phosphate buffered saline (PBS, Gibco) with 2.5% fetal bovine serum (FBS). Red blood cells from spleen and bone marrow preparations were lysed with ACK lysis buffer (Gibco) followed by washing with 1×PBS with 2.5% FBS.

Isolated cells (1×10⁶) were incubated with selected antibody cocktails for 30 min at +4° C.: anti-mIgK-FITC (187.1, BD Biosciences), anti-mIgλ-PE (RML-42, BioLegend; 1060-09, Southern Biotech), anti-mIgλ-FITC (106002, Bio-Rad; ABIN303989, Antibodies-online), anti-mouse IgM-PeCy7 (II/41, eBioscience), anti-mouse IgD-PerCP/Cy5.5 (11-26c.2a, BioLegend), anti-mouse CD3-Pacific Blue (17A2, BioLegend), anti-mouse B220-APC (RA3-6B2, eBioscience), anti-mouse CD19-APC-H7 (ID3, BD Biosciences). Following staining, cells were washed and fixed in 2% formaldehyde. Data acquisition was performed on a BD LSRFORTESSA™ flow cytometer and analyzed with FLOWJO™ software. Representative results are set forth in FIGS. 5-7.

Figure 5:
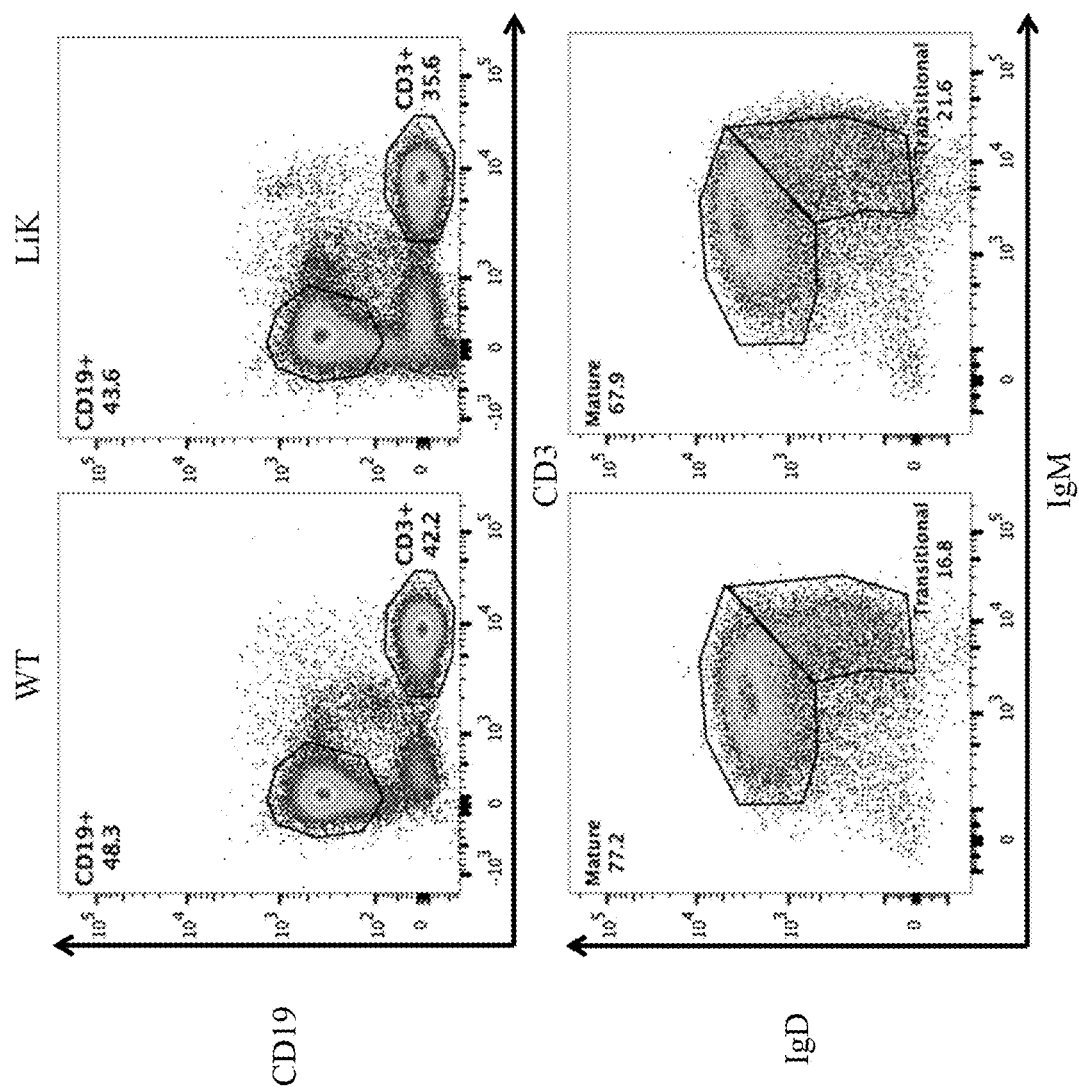
FIG. 5 shows results derived from a representative embodiment according to the present disclosure, showing single cell-gated splenocytes harvested from wild-type (WT) and 6558 HO (LiK, homozygous) mice, the top row illustrating expression of CD19 (y-axis) and CD3 (x-axis), and the bottom row illustrating CD19$^+$-gated splenocytes expressing immunoglobulin D (IgD, y-axis) and immunoglobulin M (IgM, x-axis).
Figure 6:
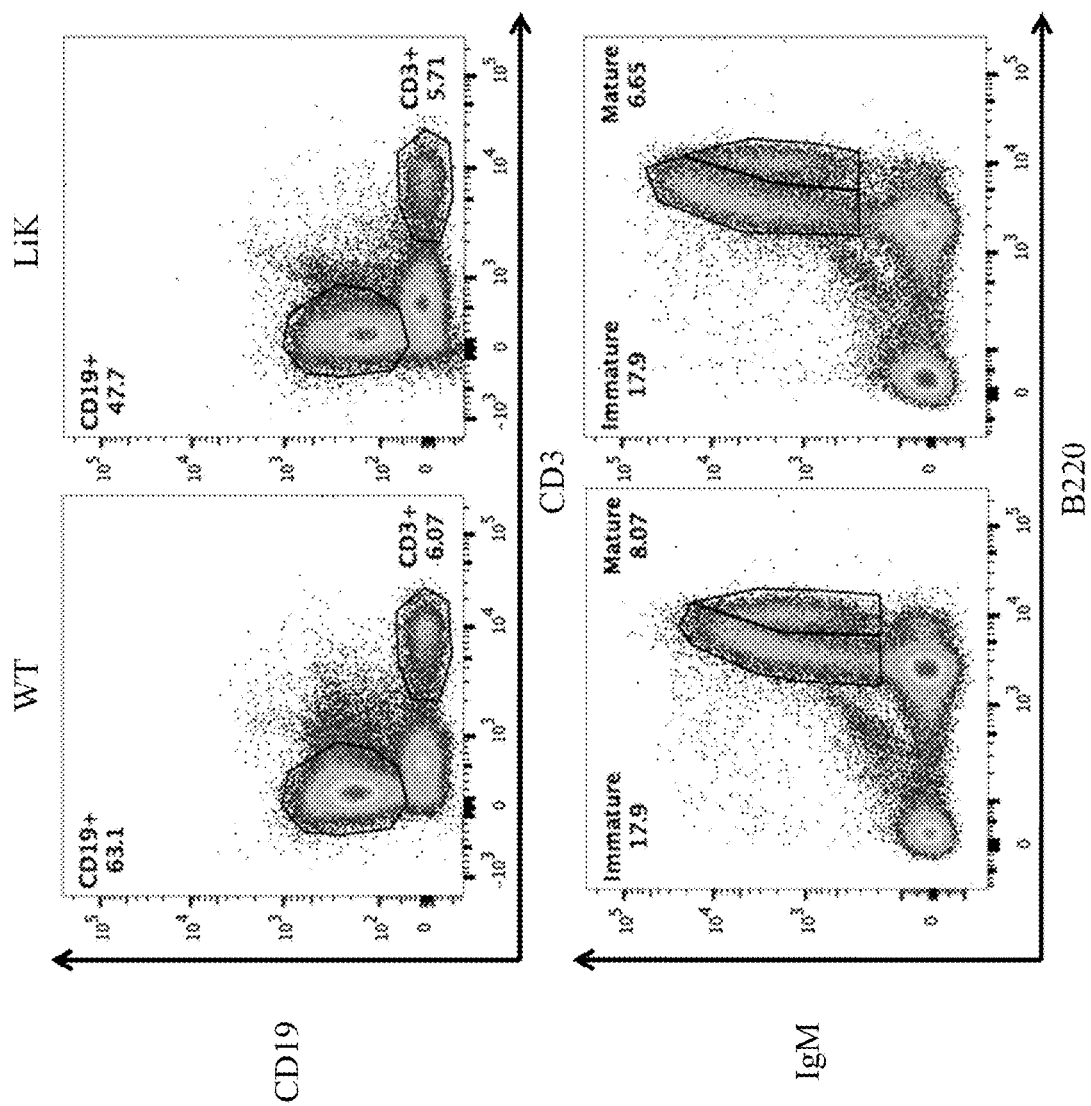
FIG. 6 shows results derived from a representative embodiment according to the present disclosure, including representative single cell-gated bone marrow harvested from wild-type (WT) and 6558HO (LiK, homozygous) mice, the top row illustrating expression of CD19 (y-axis) and CD3 (x-axis), and the bottom row illustrating expression of immunoglobulin M (IgD, y-axis) and B220 (x-axis).
Figure 7:
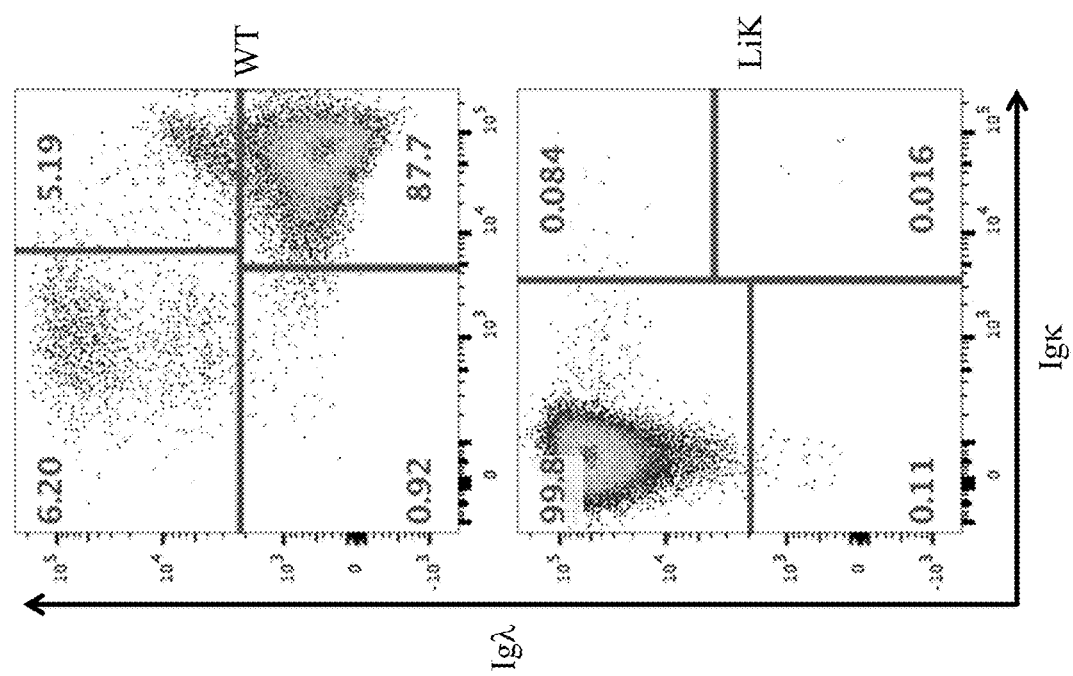
FIG. 7 shows results derived from a representative embodiment according to the present disclosure, including representative CD19$^+$-gated splenocytes harvested from wild-type (WT) and 6558HO (LiK, homozygous) mice illustrating expression of immunoglobulin light chains containing mouse Igλ (y-axis) or mouse Igκ (x-axis) constant regions.
Figure 8:
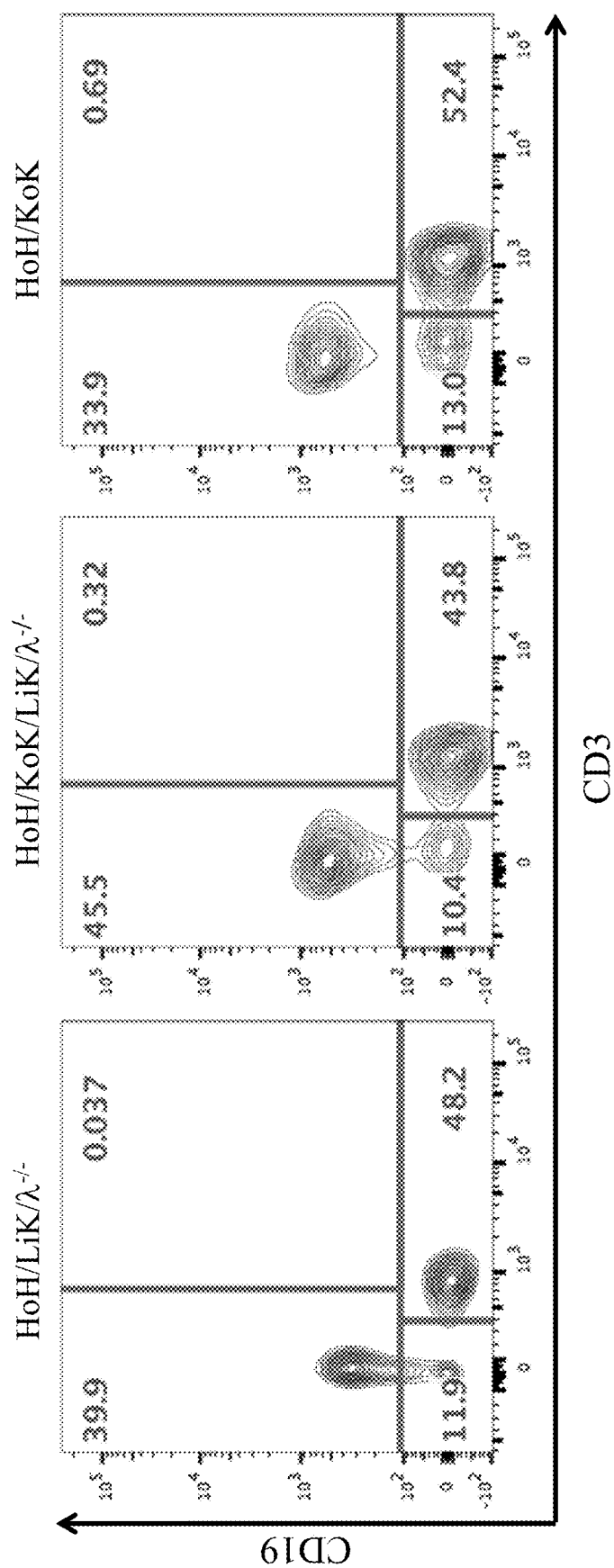
FIG. 8 shows results derived from a representative embodiment according to the present disclosure, including representative single cell-gated splenocytes harvested from various indicated humanized mice illustrating expression of CD19 (y-axis) and CD3 (x-axis). HOH/LiK/λ$^{-/-}$ mice-mice homozygous for humanized immunoglobulin heavy chain (see, e.g., U.S. Pat. Nos. 8,642,835 and 8,697,940), homozygous for LiK locus and homozygous for an inactivated endogenous immunoglobulin λ light chain locus; HOH/KoK/LiK/λ$^{-/-}$ mice-mice homozygous for humanized immunoglobulin heavy chain (see, e.g., U.S. Pat. Nos. 8,642,835 and 8,697,940), hemizygous for one kappa locus comprising LiK locus and a second kappa locus comprising humanized immunoglobulin kappa light chain locus, and homozygous for an inactivated endogenous immunoglobulin λ light chain locus; HOH/KoK mice-control mice homozygous for humanized immunoglobulin heavy chain and homozygous for humanized immunoglobulin kappa light chain.
Figure 9:
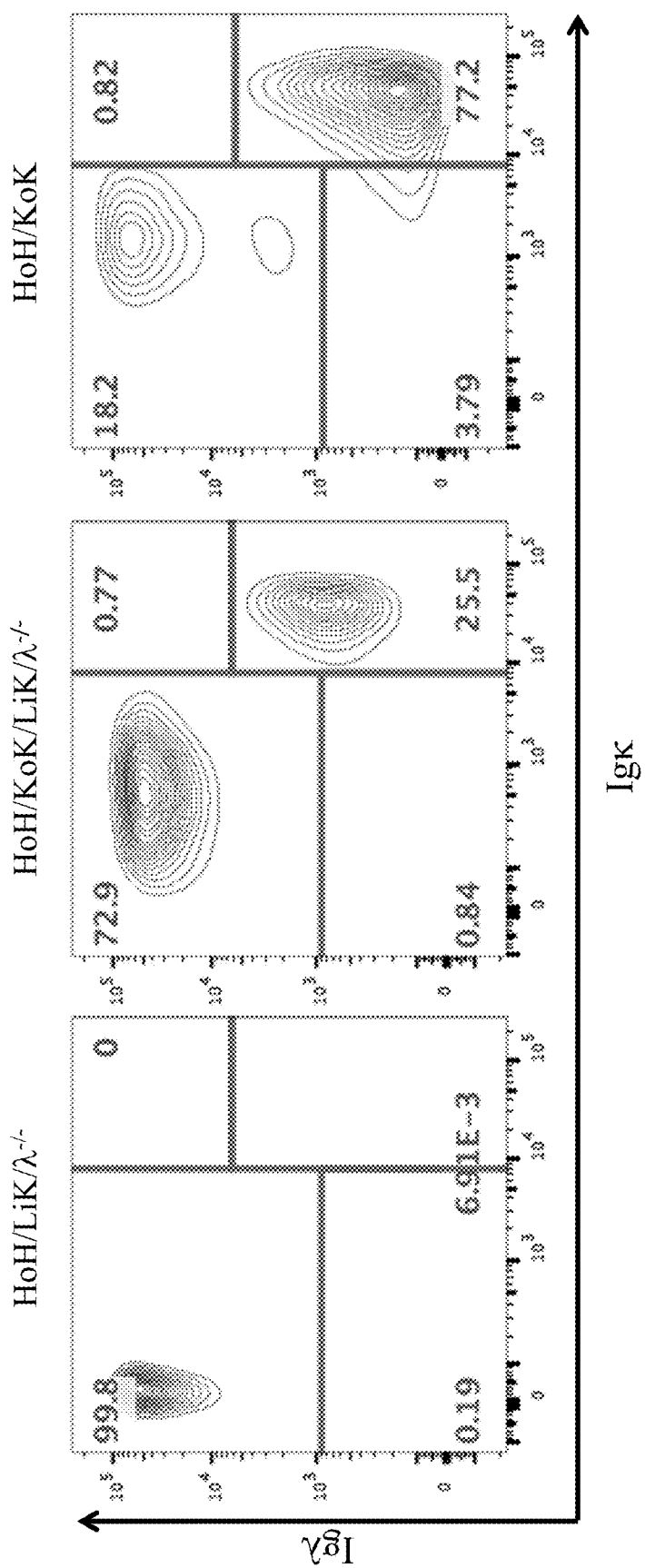
FIG. 9 shows results derived from a representative embodiment according to the present disclosure, including representative CD19$^+$-gated splenocytes harvested from various indicated humanized mice illustrating expression of immunoglobulin light chains containing mouse Igλ (y-axis) or mouse Igκ (x-axis) constant regions.
Figure 10:
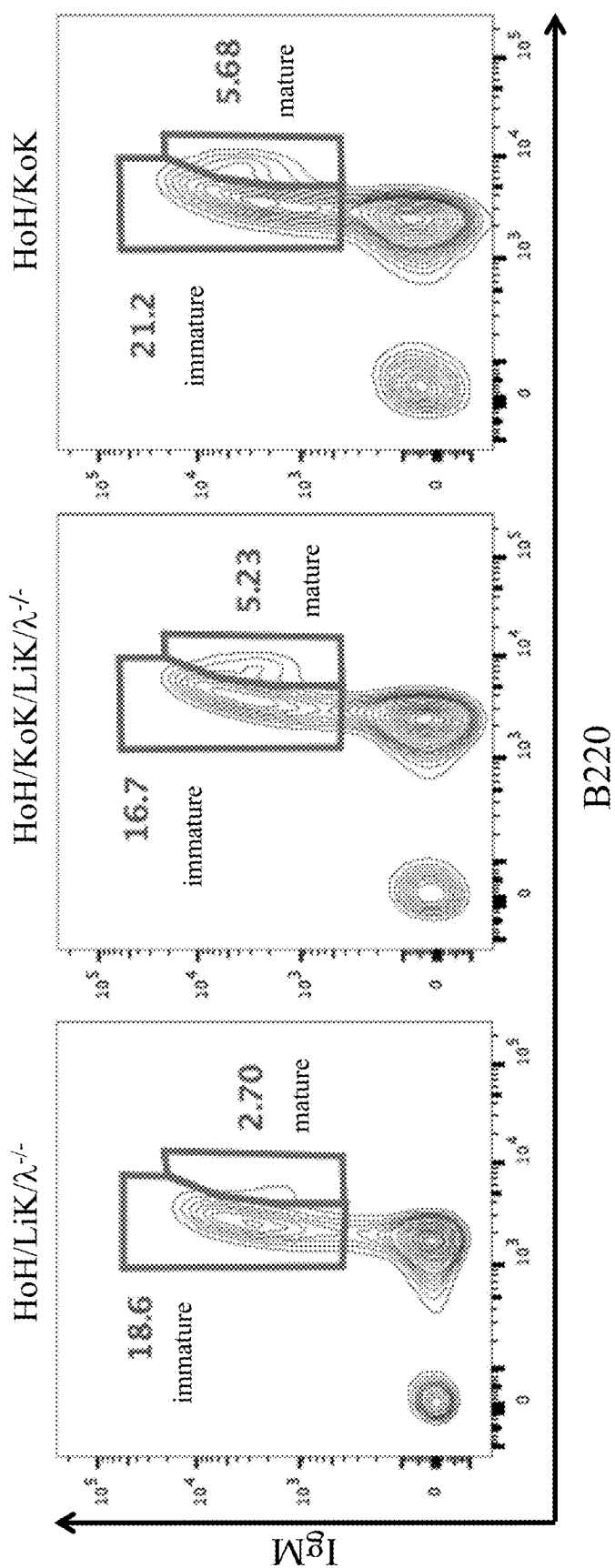
FIG. 10 shows results derived from a representative embodiment according to the present disclosure, including representative single cell-gated bone marrow harvested from various indicated humanized mice illustrating expression of immunoglobulin M (IgD, y-axis) and B220 (x-axis).

As shown in FIGS. 5 and 6, LiK mice demonstrate similar distributions of CD19⁺ and immature/mature B cells as compared to wild-type mice in the spleen and bone marrow compartments, respectively. However, LiK mice demonstrate a unique light chain expression as compared to wild-type mice in that only Igλ⁺ expression was observed in these mice (FIG. 7). In particular, >90% of CD19⁺ B cells in LiK mice express immunoglobulin, light chain thereby confirming proper recombination and expression at the engineered immunoglobulin κ locus. As expected given these mice lack a mouse Cκ gene, LiK mice demonstrate no detectable immunoglobulin κ expression by flow cytometry (i.e., the anti-mIgκ antibody detects the constant region). Similar levels of immunoglobulin λ light chain expression were observed from additional LiK mice littermates (data not shown). Expression of human Vλ regions in the context of a mouse Cλ region from the LiK locus was confirmed by, among other things, immunoglobulin repertoire analysis using Next Generation Sequencing techniques (described in Example 3.2 below).

Example 3.2. Immunoglobulin Repertoire in Rodents Having an Engineered Immunoglobulin Light Chain Locus Usage of human antibody genes (i.e., VDJ gene segments) in the engineered rodent strain described above was determined by Next Generation Sequencing antibody repertoire analysis. In particular, RT-PCR sequencing was conducted on RNA isolated from splenocytes of mice homozygous for the LiK locus (6558 HO) to confirm correct transcription and recombination of the LiK locus. A representative illustration of a rearranged LiK locus is set forth in FIG. 12 (LiK locus: engineered immunoglobulin κ light chain locus as described herein; rearranged LiK locus: representative rearrangement of engineered immunoglobulin κ light chain locus (referred to herein as "LiK locus") resulting in human Vλ-Jλ recombination; rearranged LiK mRNA: representative transcription and mRNA processing of rearranged LiK locus).

Briefly, splenic B cells were positively enriched from total splenocytes by magnetic cell sorting using mouse anti-CD19 magnetic beads and MACS® columns (Miltenyi Biotech). Total RNA was isolated from purified splenic B cells using an RNeasy Plus RNA isolation kit (Qiagen) according to manufacturer's specifications. Reverse transcription was performed to generate cDNA containing immunoglobulin, constant region gene sequence, using a SMARTer™ RACE cDNA Amplification Kit (Clontech) and immunoglobulin, specific primers (see below). During this process, a DNA sequence, reverse compliment to 3' of a template switching (TS) primer, was attached to the 3' end of newly synthesized cDNAs. Purified Igλ-specific cDNAs were then amplified by a 1$^{st}$ round PCR reaction using the TS specific primer and reverse primers specific to sequences of mouse Cλ1. PCR products ranging from ~450-700 bp were isolated using Pippin Prep (SAGE Science) and then these fragments were further amplified by a 2$^{nd}$ round PCR reaction. Table 2 sets forth the sequences of selected primers used for repertoire library construction (for: forward primer; rev: reverse primer). PCR products ranging from ~400 bp-700 bp were isolated, purified, and quantified by qPCR using a KAPA Library Quantification Kit (KAPA Biosystems) before loading onto a Miseq sequencer (Illumina) for sequencing using Miseq Reagent Kits v3 (2×300 cycles).

For bioinformatic analysis, Raw Illumina sequences were de-muliplexed and filtered based on quality, length and match to corresponding constant region gene primer. Overlapping paired-end reads were merged and analyzed using custom in-house pipeline. The pipeline used local installation of IgBLAST (NCBI, v2.2.25$^+$) to align rearranged light chain sequences to human germline Vλ and Jλ gene segment database, and denoted productive and non-productive joins along with the presence of stop codons. CDR3 sequences and expected non-template nucleotides were extracted using boundaries as defined in International Immunogenetics Information System (IMGT).

rodent Cλ gene, which human Vλ and Jλ gene segments are operably linked to said rodent Cλ gene, and which rodent Cλ gene is inserted in the place of a rodent Cκ gene of an endogenous rodent Igκ light chain locus.

Blood was drawn from wild-type (WT, 75% C57BL/6NTac 25% 129SvEvTac) and 6558 homozygous ("LiK", 75% C57BL/6NTac 25% 129SvEvTac) mice. Serum was separated from blood using Eppendorf tubes centrifuged at 9000 rpm for five minutes at 4° C. Collected serum was used for immunoblotting to identify expression of IgG antibodies.

Mouse sera were diluted 1:100 or 1:500 in PBS (without Cλ2$^+$ and Mg2$^+$) and run on 4-20% Novex Tris-Glycine gels

TABLE 2

Representative primers for repertoire library construction

| Primer Name | Sequence (5'-3') |
|---|---|
| TS primer | CACCATCGAT GTCGACACGC CTAGGG (SEQ ID NO: 65) |
| IgλC (RT primer) | CACCAGTGTG GCCTTGTTAG TCTC (SEQ ID NO: 66) |
| IgλC (1$^{st}$ PCR) | ACACTCTTTC CCTACACGAC GCTCTTCCGA TCTCAGGGTG ACTGATGGCG AAGAC (SEQ ID NO: 67) |
| TS specific (1$^{st}$ PCR) | GTGACTGGAG TTCAGACGTG TGCTCTTCCG ATCTCACCAT CGATGTCGAC ACGCCTA (SEQ ID NO: 68) |
| for (2$^{nd}$ PCR) | AATGATACGG CGACCACCGA GATCTACAC XXXXXX ACACTCTTTC CCTACACGAC GCTCTTCCGA TCT (SEQ ID NO: 69) |
| rev (2$^{nd}$ PCR) | CAAGCAGAAG ACGGCATACG AGAT XXXXXX GTGACTGGAG TTCAGACGTG TGCTCTTCCG ATCT (SEQ ID NO: 70) |

The majority of the functional human Vλ and Jλ gene segments included in the LiK locus in engineered mice exemplified herein were represented in the expressed antibody repertoire of LiK mice comprising a plurality of human Vλ and Jλ gene segments operably linked to a rodent Cλ gene at the endogenous kappa locus (data not shown). Overall, the inventors observed that the B cells of LiK mice expressed antibodies having light chains expressed from the LiK locus as expected. No altered splicing products, insertions, deletions or otherwise unexpected mutations were observed in the transcripts analyzed. These results confirm that recombination at the LiK locus generates functional light chains as part of the antibody repertoire of these mice. Similar analysis was performed in mice comprising a plurality of human Vλ and Jλ gene segments operably linked to a human Cλ gene at the endogenous kappa locus, where the expression of a plurality of human Vλ and Jλ gene segments was detected (data not shown).

Example 3.3. Antibody Expression in Rodents Having an Engineered Light Chain Locus This example demonstrates expression of antibodies (e.g., IgG) from non-human animals, which antibodies contain light chains characterized by the presence of human Vλ regions and rodent or human Cλ regions, and which light chains are expressed from an engineered endogenous rodent immunoglobulin κ light chain locus. Among other things, this example specifically demonstrates expression of IgG antibodies (in dimeric and monomeric forms) in the serum of non-human animals (e.g., rodents) whose germline genome comprises an endogenous immunoglobulin κ light chain locus comprising insertion of one or more human Vλ gene segments, one or more human Jλ gene segments and a under reducing and non-reducing conditions. Gels were transferred to Polyvinylidene difluoride (PVDF) membranes according to manufacturer's specifications. Blots were blocked overnight with 5% nonfat milk in Tris-Buffered Saline with 0.05% Tween-20 (TBST, Sigma). PVDF membranes were exposed to primary antibody (goat anti-mIgG1 conjugated to HRP, Southern Biotech) diluted 1:1000 in 0.1% nonfat milk in TBST for one hour at room temperature. Blots were washed four times for ten minutes per wash and developed for five minutes with Amersham ECL Western Blotting Detection Reagent (GE Healthcare Life Sciences) according to manufacturer's specifications. Blots were then imaged using GE Healthcare ImageQuant LAS-4000 Cooled CCD Camera Gel Documentation System. Images were captured at 15 second intervals until 20 images were captured or images were fully exposed, whichever came first. Representative results are set forth in FIG. 13 (lane numbers are indicated at the top of each gel image and lane assignments are the same for both images; top left: reduced samples; bottom left: non-reduced samples; LiK HO: 6558 homozygous; WT: wild-type; molecular weights are indicated on the left of each gel image).

Figure 13:
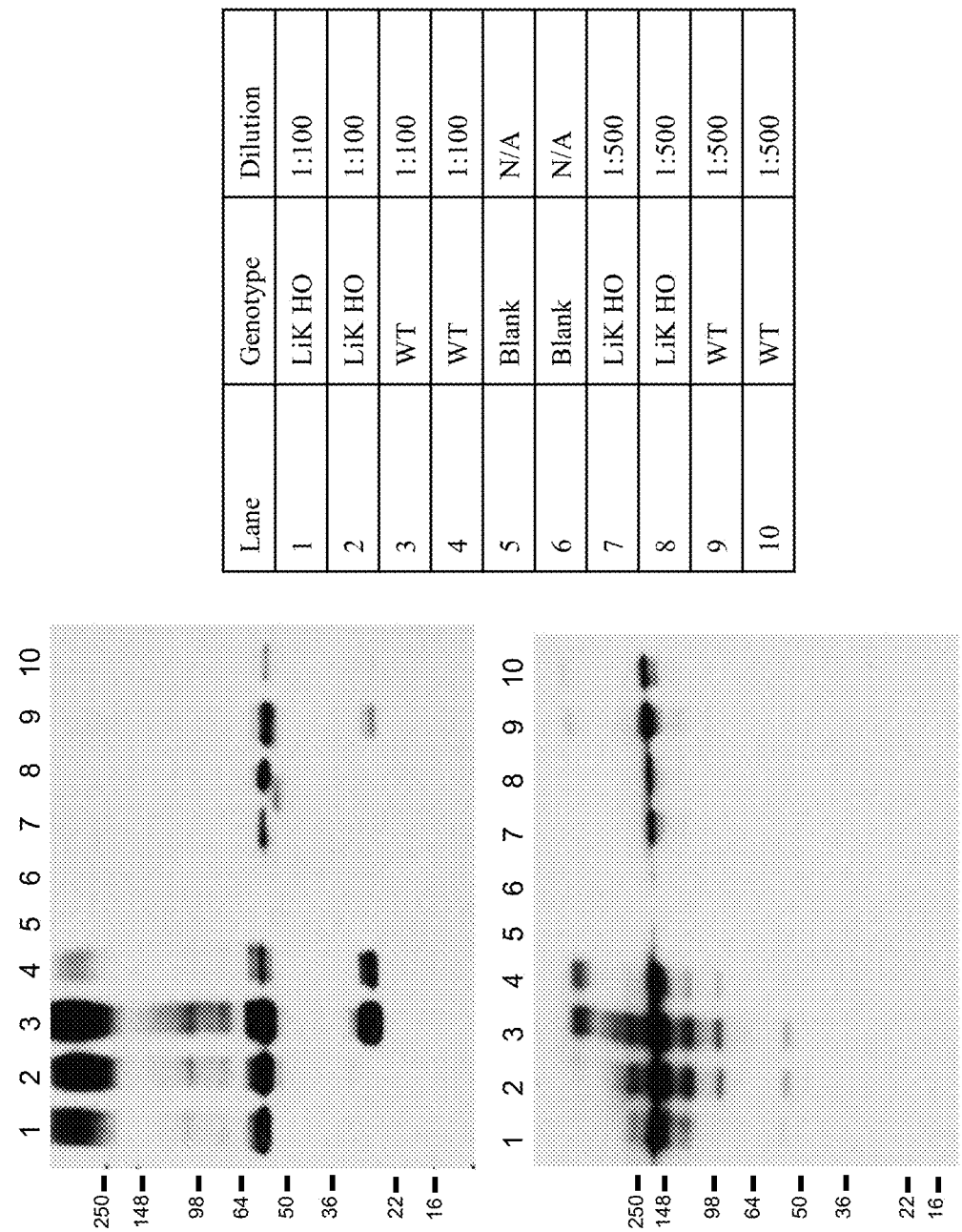
FIG. 13 shows results derived from a representative embodiment according to the present disclosure, including representative protein immunoblots (Western blots) of SDS-PAGE using serum isolated from wild-type (WT) and 6558 homozygous (LiK HO) mice as described in Example 3.3.
Figure 14:
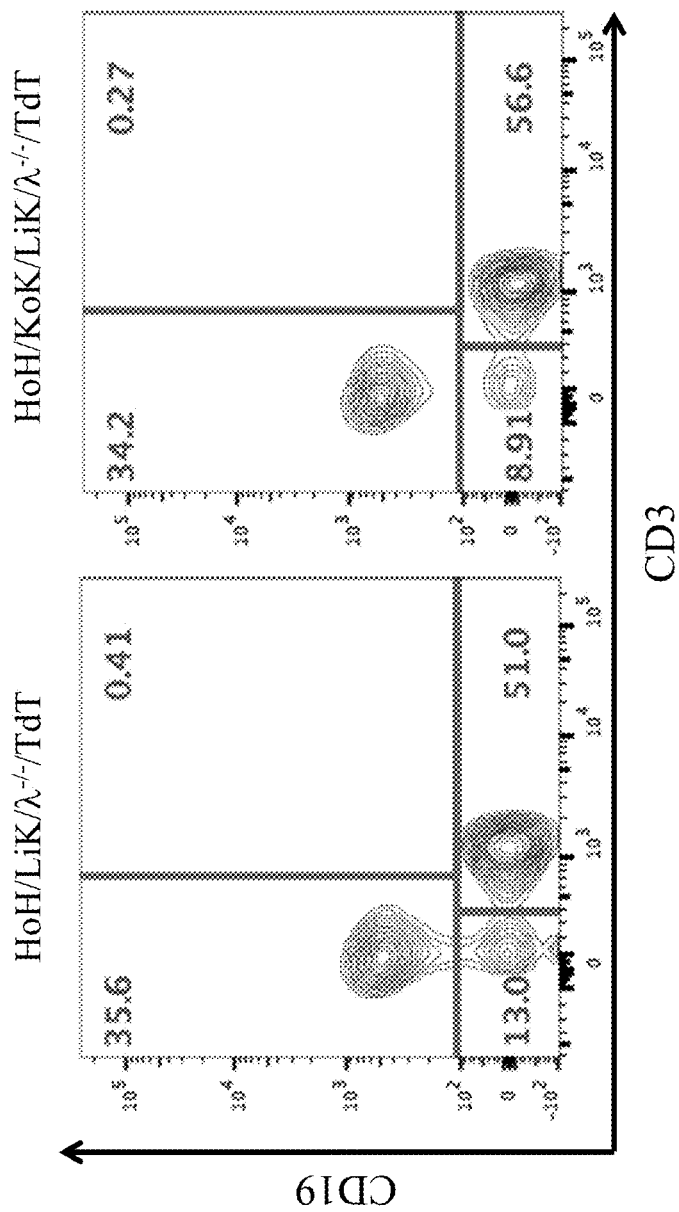
FIG. 14 shows results of testing an embodiment according to the present disclosure, showing representative single cell-gated splenocytes harvested from humanized mice illustrating expression of CD19 (y-axis) and CD3 (x-axis). HOH/LiK/λ$^{-/-}$/TdT mice-mice homozygous for humanized immunoglobulin heavy chain (see, e.g., U.S. Pat. Nos. 8,642,835 and 8,697,940), homozygous for LiK locus and homozygous for an inactivated endogenous immunoglobulin λ light chain locus that include a nucleic acid sequence encoding an exogenous terminal deoxynucleotidyltransferase (TdT); and HOH/KoK/LiK/λ$^{-/-}$/TdT mice-mice homozygous for humanized immunoglobulin heavy chain (see, e.g., U.S. Pat. Nos. 8,642,835 and 8,697,940), hemizygous for one kappa locus comprising an LiK locus and a second kappa locus comprising humanized immunoglobulin kappa light chain locus, and homozygous for an inactivated endogenous immunoglobulin λ light chain locus that include a nucleic acid sequence encoding an exogenous terminal deoxynucleotidyltransferase (TdT).
Figure 15:
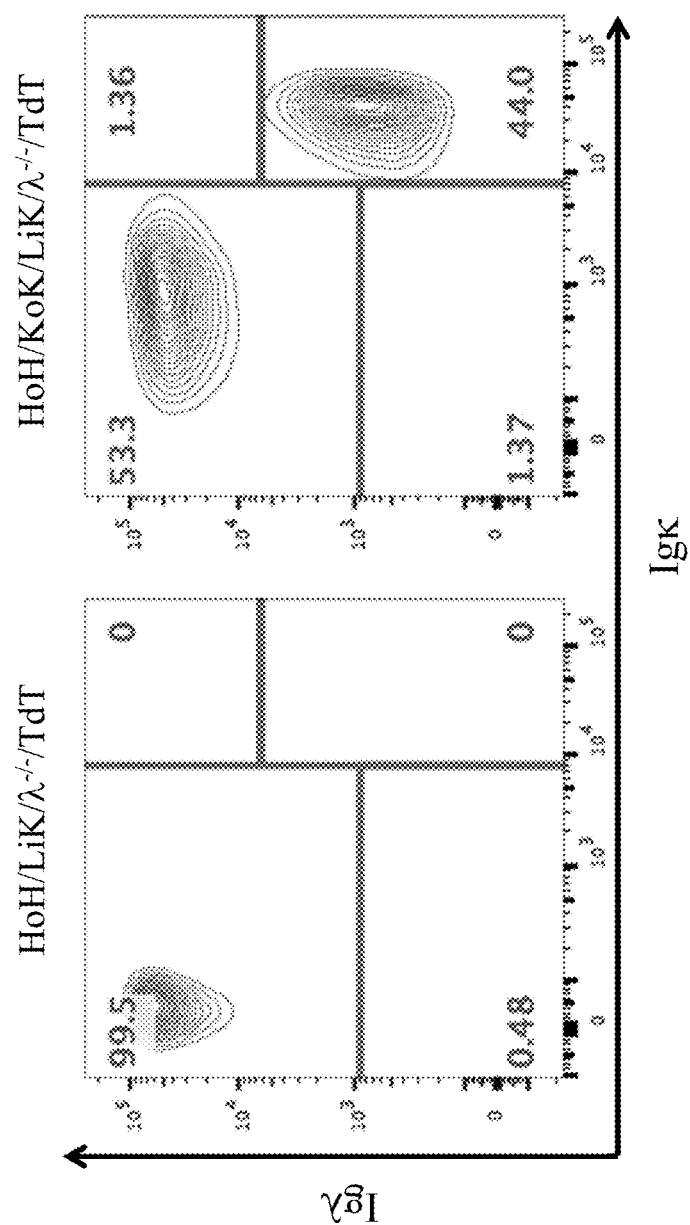
FIG. 15 shows results of testing an embodiment according to the present disclosure, showing representative CD19$^+$-gated splenocytes harvested from various indicated humanized mice illustrating expression of immunoglobulin light chains containing mouse Igλ (y-axis) or mouse Igκ (x-axis) constant regions.
Figure 16:
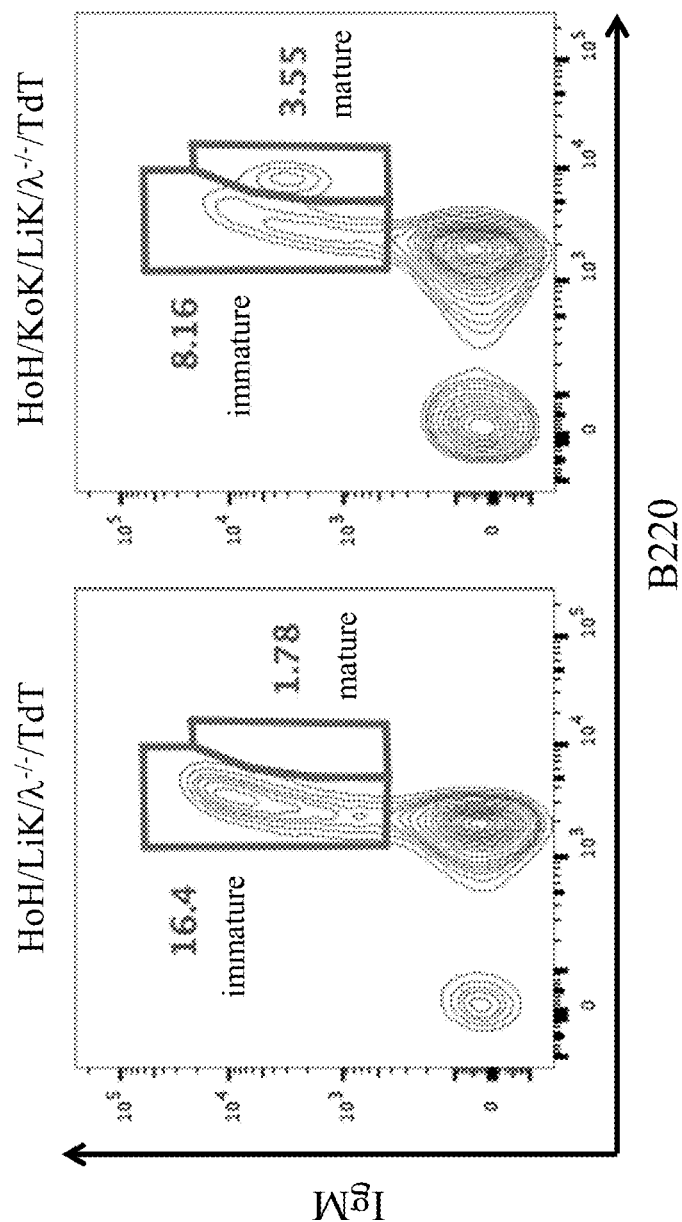
FIG. 16 shows results of testing an embodiment according to the present disclosure, showing representative single cell-gated bone marrow harvested from various indicated humanized mice illustrating expression of immunoglobulin M (IgM, y-axis) and B220 (x-axis).
Figure 17:
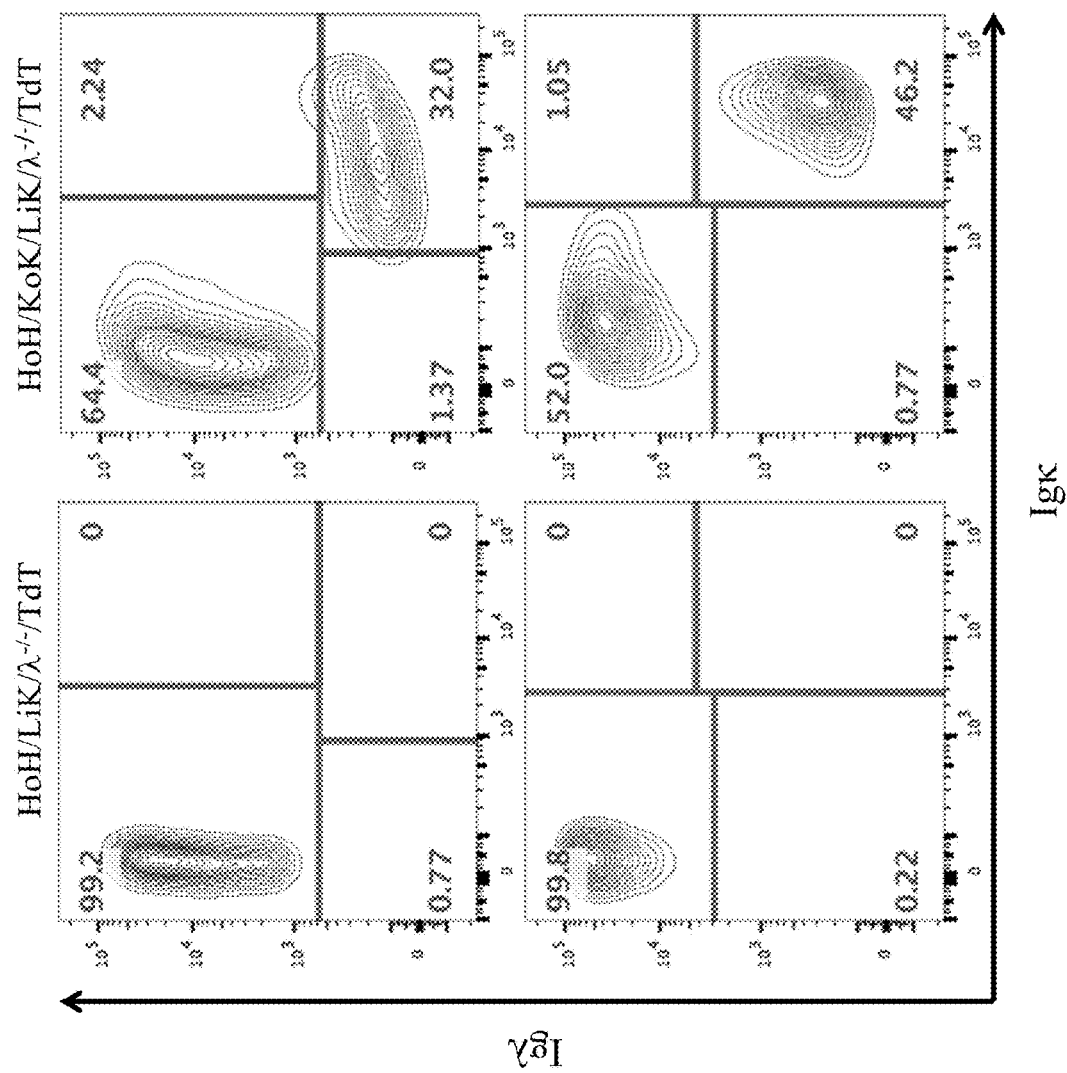
FIG. 17 shows results of testing an embodiment according to the present disclosure, showing representative single cell-gated bone marrow harvested from various indicated humanized mice illustrating expression of immunoglobulin light chains containing mouse Igλ (y-axis) or mouse Igκ (x-axis) constant regions in immature (top row) and mature (bottom row) B cells.

As shown in FIG. 13, the size of IgG antibodies expressed in LiK mice is similar to the size observed for IgG antibodies expressed in wild-type mice, which demonstrates that LiK mice produce functional antibodies that bind antigen and can be used as an in vivo system for the production of human antibodies and human antibody components for use in the treatment of human disease(s).

Example 4. Generation and Characterization of Rodents Comprising Several Engineered Immunoglobulin Loci LiK rodents as described herein are separately bred with multiple engineered rodent strains over multiple breedings using techniques known in the art to establish rodents strains containing the following engineered immunoglobulin loci: (1) a rodent strain homozygous for humanized immunoglobulin heavy chain (see, e.g., U.S. Pat. Nos. 8,642,835 and 8,697,940, each of which is incorporated herein by reference in its entirety), homozygous for an immunoglobulin κ light chain locus comprising human Vλ and Jλ gene segments operably linked to a Cλ gene as described herein and homozygous for an inactivated endogenous immunoglobulin λ light chain locus (see, e.g., U.S. Pat. No. 9,006,511, which is incorporated by reference herein in its entirety), in some embodiments referred to herein as HoH/LiK/λ$^{-/-}$ mice, (2) a rodent strain homozygous for a humanized immunoglobulin heavy chain locus (supra), homozygous for an inactivated endogenous immunoglobulin λ light chain locus (supra), and hemizygous for an immunoglobulin κ light chain locus having a first immunoglobulin κ light chain locus comprising human Vλ and Jλ gene segments operably linked to a Cλ gene as described herein and a second immunoglobulin κ light chain locus comprising human Vκ and Jκ gene segments operably linked to an endogenous mouse Cκ gene (see, e.g., U.S. Pat. Nos. 8,642,835 and 8,697,940, each of which is incorporated herein by reference in its entirety), in some embodiments referred to herein as HoH/KoK/LiK/λ$^{-/-}$ mice. Alternatively, such mice maybe generated by introducing targeting vectors comprising engineered loci into ES cells already comprising several engineered immunoglobulin loci. In some embodiments, the immunoglobulin heavy chain locus in said rodents comprises a functional and expressed rodent Adam6 gene.

Specifically, LiK mice were bred with multiple engineered mouse strains over multiple breedings to establish HoH/LiK/λ$^{-/-}$ and HoH/KoK/LiK/λ$^{-/-}$ mice.

Once established, various immune cell populations were characterized in these humanized mice by flow cytometry. Briefly, spleens and femurs were harvested from HoH/LiK/λ$^{-/-}$ (n=3), HoH/KoK/LiK/λ$^{-/-}$ (n=4) and VELOCIMMUNE® ("HoH/KoK"; n=3; see U.S. Pat. Nos. 8,642,835 and 8,697,940, each of which is incorporated herein by reference in its entirety) mice and prepared for flow cytometry analysis as described above. Representative results are set forth in FIGS. 8-11. Average light chain expression (κ:λ) observed in splenocytes of engineered mouse strains tested was approximately as follows: HoH/LiK/λ$^{-/-}$: 0:100, HoH/KoK/LiK/λ$^{-/-}$: 40:60, HoH/KoK: 85:15.

Example 5. Production of Antibodies in Engineered Rodents

This example demonstrates production of antibodies in a rodent that comprises an engineered endogenous immunoglobulin κ light chain locus as described above using an antigen of interest (e.g., a single-pass or multi-pass membrane protein, etc.). The methods described in this example, or immunization methods well known in the art, can be used to immunize rodents containing an engineered endogenous immunoglobulin κ light chain locus as described with various antigens (e.g., polypeptides, etc.). Any genetically modified rodents described herein above, e.g., LiK mice-mice comprising an immunoglobulin κ light chain locus comprising human Vλ and Jλ gene segments operably linked to a Cλ gene (such as mice homozygous for the LiK locus); HoH/LiK/λ$^{-/-}$ mice-mice comprising an LiK locus (such as mice homozygous for the LiK locus) and also comprising humanized immunoglobulin heavy chain locus (see, e.g., U.S. Pat. Nos. 8,642,835 and 8,697,940, each of which is incorporated herein by reference in its entirety) and an inactivated endogenous immunoglobulin λ light chain locus (see, e.g., U.S. Pat. No. 9,006,511, which is incorporated by reference herein in its entirety); and HoH/KoK/LiK/λ$^{-/-}$ mice-mice hemizygous for immunoglobulin κ light chain locus having a first immunoglobulin κ light chain locus comprising LiK and the second immunoglobulin κ light chain locus comprising human Vκ and Jκ gene segments operably linked to an endogenous mouse Cκ gene (see, e.g., U.S. Pat. Nos. 8,642,835 and 8,697,940), and also comprising humanized immunoglobulin heavy chain locus (see, e.g., U.S. Pat. Nos. 8,642,835 and 8,697,940, each of which is incorporated herein by reference in its entirety) and an inactivated endogenous immunoglobulin λ light chain locus (see, e.g., U.S. Pat. No. 9,006,511, which is incorporated herein by reference), may be used for production of antibodies after immunization with an antigen of interest. Such mice are suitable for immunization and production of human antibodies and/or human antibody fragments.

LiK mice that further include the engineered immunoglobulin loci described above are challenged with an antigen of interest using immunization methods known in the art. The antibody immune response is monitored by an ELISA immunoassay (i.e., serum titer). When a desired immune response is achieved, splenocytes (and/or other lymphatic tissue) are harvested and fused with mouse myeloma cells to preserve their viability and form immortal hybridoma cell lines. Generated hybridoma cell lines are screened (e.g., by an ELISA assay) and selected to identify hybridoma cell lines that produce antigen-specific antibodies. Hybridomas may be further characterized for relative binding affinity and isotype as desired. Using this technique, and the immunogen described above, several antigen-specific chimeric antibodies (i.e., antibodies possessing human variable domains and rodent constant domains) are obtained.

DNA encoding the variable regions of heavy chain and light chains may be isolated or otherwise prepared, and may be linked to human heavy chain and light chain constant regions (e.g., of a desired isotype) for the preparation of fully-human antibodies. Such fully-human antibodies (and/or heavy or light chains thereof) may be produced in a cell, typically a mammalian cell such as a CHO cell. Fully human antibodies may then be characterized for relative binding affinity and/or neutralizing activity of the antigen of interest.

DNA encoding antigen-specific chimeric antibodies produced by B cells of the engineered mice described and/or exemplified herein, and/or the variable domains of light and/or heavy chains thereof, may be isolated directly from antigen-specific lymphocytes. For example, high affinity chimeric antibodies having a human variable region and a rodent constant region may be isolated and characterized so that particular antibodies (and/or B cells that produce them) of interest are defined. To give but a few examples, assessed characteristics of such antibodies, and/or variable and/or constant regions thereof, may be or include one or more of affinity, selectivity, identity of epitope, etc.

Rodent constant regions are replaced with a desired human constant region to generate fully-human antibodies. While the constant region selected may vary according to specific use, high affinity antigen-binding and target specificity characteristics reside in the variable region. Alternatively, when employing LiK mice containing a human Cλ2 gene in the place of a rodent Cκ gene as described herein, a step of replacing a rodent constant region in an antibody isolated from an immunized mouse is omitted. Antigen-specific antibodies are also isolated directly from antigen-positive B cells (from immunized mice) without fusion to myeloma cells, as described in, e.g., U.S. Pat. No. 7,582, 298, specifically incorporated herein by reference in its entirety. Using this method, several fully human antigen-specific antibodies (i.e., antibodies possessing human variable domains and human constant domains) are made.

Example 6. Generation of Rodents Having an Engineered Light Chain Locus and Expressing Human Terminal Deoxynucleotidyl Transferase (TdT) Gene

Example 6.1. Generation of Rodents Having an Engineered Light Chain Locus and Expressing Human TDT This example illustrates the generation of mice whose germline genome comprises an engineered immunoglobulin κ light chain locus as described herein and further expressing human TdT. Mice expressing human TdT were made as described in Example 1.1. of WO 2017/210586, incorporated herein by reference in its entirety. Mice having a genome comprising both an engineered immunoglobulin κ light chain locus as described herein and further expressing human TdT were generated by multiple breedings to establish cohorts of mouse strains containing both modifications.

Example 6.2. Phenotypic Assessment of Rodents Having an Engineered Kappa Locus and Expressing Human TDT Once established, immune cell populations were characterized in these humanized mice by flow cytometry. Briefly, spleens and femurs were harvested from HoH/LiK/λ$^{-/-}$/TdT (n=4) and HoH/KoK/LiK/λ$^{-/-}$/TdT (n=6) mice and prepared for flow cytometry analysis as described above (see Example 3 above). Representative results are set forth in FIGS. 14-17. Average light chain expression (κ:λ) observed in splenocytes of engineered mouse strains tested was as follows: HoH/LiK/λ$^{-/-}$/TdT: 0:100, HoH/KoK/LiK/λ$^{-/-}$/TdT: 45:55.

Example 6.3. Human Immunoglobulin Kappa Junctional Diversity and Non-Germline Additions in LiK Mice Comprising Human TdTS As demonstrated in WO 2017/210586 (incorporated herein by reference in its entirety), mice comprising exogenously introduced TdT exhibited increases in both junctional diversity and non-germline nucleotide additions (also "non-template nucleotide additions" as used herein) in their light chains. The mice comprising HoH/LiK/λ$^{-/-}$/TdT and HoH/KoK/LiK/λ$^{-/-}$/TdT were assessed to determine their immunoglobulin repertoire sequence diversity and presence of non-template nucleotide additions in their CDR3 using Next Generation Sequencing technology.

Briefly, splenocytes were harvested from mice and B cells were positively enriched from total splenocytes by anti-mouse CD19 magnetic beads and MACS columns (Miltenyi Biotech). Total RNA was isolated from splenic B cells using the RNeasy Plus kit (Qiagen).

Reverse transcription with an oligo-dT primer followed by gene specific PCR was performed to generate cDNA containing mouse Cλ1 sequence, using SMARTer™ RACE cDNA Amplification Kit (Clontech). During reverse transcription, a specific DNA sequence (PIIA: 5'-CCCATGTACT CTGCGTTGAT ACCACTGCTT-3', SEQ ID NO:71) was attached to the 3' end of the newly synthesized cDNAs. The cDNAs were purified by the NucleoSpin Gel and PCR Clean-Up Kit (Clontech), then further amplified using a primer reverse compliment to PIIA (5'-AAGCAGTGGT ATCAACGCAG AGTACAT-3', SEQ ID NO:72) paired with mouse Cλ1 specific primer (5'-CACCAGTGTG GCCTTGTTAG TCTC-3', SEQ ID NO:73).

Purified amplicons were then amplified by PCR using a PIIA specific primer (5'-GTGACTGGAG TTCAGACGTG TGCTCTTCCG ATCTAAGCAG TGGTATCAAC GCAGAGT-3', SEQ ID NO:74 and a nested mouse Cλ1 specific primer (5'-ACACTCTTTC CCTACACGAC GCTCTTCCGA TCTAAGGTGG AAACAGGGTG ACTGATG-3', SEQ ID NO:75. PCR products between 450-690 bp were isolated and collected by Pippin Prep (SAGE Science). These fragments were further amplified by PCR using following primers: 5'-AATGATACGG CGACCACCGA GATCTACACλ XXXXXACACT CTTTCCCTAC ACGACGCTCT TCCGATC-3', SEQ ID NO:76 and 5'-CAAGCAGAAG ACGGCATACG AGATXXXXXX GTGACTGGAG TTCAGACGTG TGCTCTTCCG ATCT-3', SEQ ID NO:77 ("XXXXXX" represents a 6 bp index sequence to enable multiplexing samples for sequencing). PCR products between 490 bp-710 bp were isolated and collected by Pippin Prep, then quantified by qPCR using a KAPA Library Quantification Kit (KAPA Biosystems) before loading onto Miseq sequencer (Illumina) for sequencing (v3, 600-cycles).

For bioinformatic analysis, the resulting Illumina sequences were demultiplexed and trimmed for quality. Overlapping paired-end reads were then assembled and annotated using local installation of igblast (NCBI, v2.2.25+). Reads were aligned to human germline Vλ and Jλ segments database and sorted for the best hit. A sequence was marked as ambiguous and removed from analysis when multiple best hits with identical score were detected. A set of in-house perl scripts was developed to analyze results.

Lambda light chains from splenic B cells from HoH/LiK/λ$^{-/-}$/TdT mice, and both lambda and kappa light chains from splenic B cells from HoH/KoK/LiK/λ$^{-/-}$/TdT mice, were tested for an increase in non-template additions and junctional diversity at lambda and/or kappa loci. Light chains from HoH/LiK/λ$^{-/-}$/TdT and HoH/KoK/LiK/λ$^{-/-}$/TdT mice exhibited at least a 2 fold increase in junctional diversity as measured by number of unique CDR3/10,000 reads (data not shown). In addition, about 50% of light chains (lambda and/or kappa) from in HoH/LiK/λ$^{-/-}$/TdT and HoH/KoK/LiK/λ$^{-/-}$/TdT mice exhibited non-template additions as compared to light chains from control mice without TdT, which only exhibited about 10% non-template additions (data not shown).

Example 7. Immunization of Engineered Rodents and Analysis of Immune Response to Immunogens This example illustrates immunization of LiK/VI-3 and LiK/VI-3/TdT mice, and the analysis of serum antibody responses to the immunogens. Briefly, (1) VI-3/TdT (e.g., a positive control for human kappa light chain, which also has endogenous mouse lambda light chain loci) and VI-3 mice with human lambda light chains, (2) LiK/VI-3 and (3) LiK/VI-3/TdT, respectively, were immunized with protein immunogens using standard protocols and adjuvants. The mice were bled prior to the initiation of immunization and periodically bled following immunogen boosts. Anti-serum titers were assayed on respective antigens.

Antibody titers in serum against immunogens were determined using ELISA. Ninety six-well microtiter plates (Pierce) were coated with antigens at 2 µg/ml in phosphate-buffered saline (PBS, Irvine Scientific) overnight at 4° C. Plates were washed with PBS containing 0.05% Tween-20 (PBS-T, Sigma-Aldrich) and blocked with 250 µl of 0.5% bovine serum albumin (BSA, Sigma-Aldrich) in PBS for 1 hour at room temperature. The plates were washed with PBS-T. Pre-immune and immune anti-sera were serially diluted three-fold in 1% BSA-PBS and added to the plates for 1 hour at room temperature. The plates were washed and goat anti-mouse IgG-Fc-Horse Radish Peroxidase (HRP) conjugated secondary antibodies (Jackson Immunoresearch), goat anti-mouse Kappa-HRP (SouthernBiotech) or goat anti-mouse Lambda-HRP (SouthernBiotech) were added at 1:5000 dilution to the plates and incubated for 1 hour at room temperature. Plates were washed and developed using TMB/$H_2O_2$ as substrate by incubating for 15-20 minutes. The reaction was stopped with acid and plates read on a spectrophotometer (Victor, Perkin Elmer) at 450 nm. Antibody titers were computed using Graphpad PRISM software. The titer is defined as interpolated serum dilution factor of which the binding signal is 2-fold over background.

Figure 18:
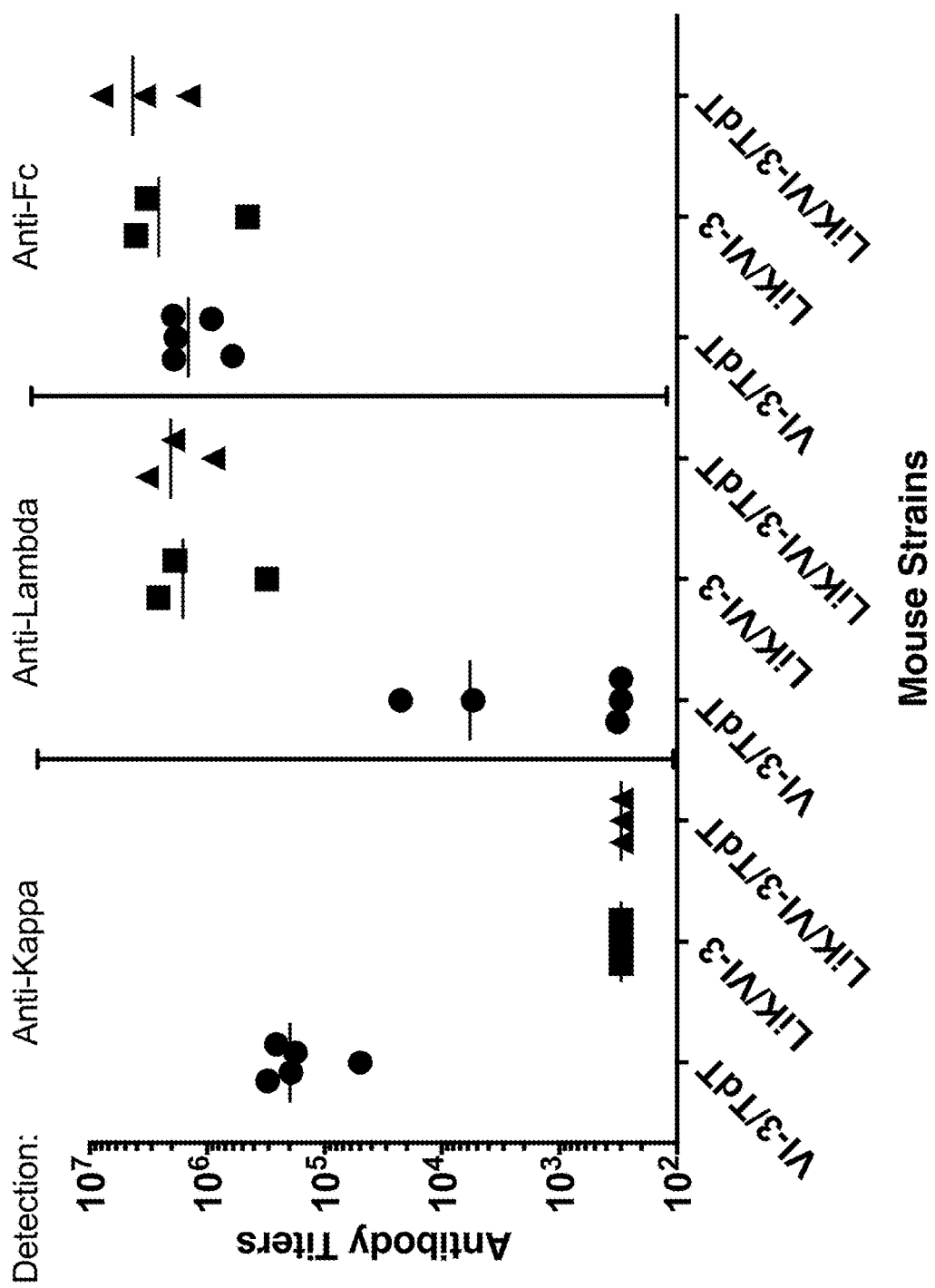
FIG. 18 shows results of testing an embodiment according to the present disclosure, showing a graph comparing immune responses in LiK/VI-3, LiK/VI-3/TdT and VI-3/TdT mice strains following immunization with a protein immunogen.
Figure 19:
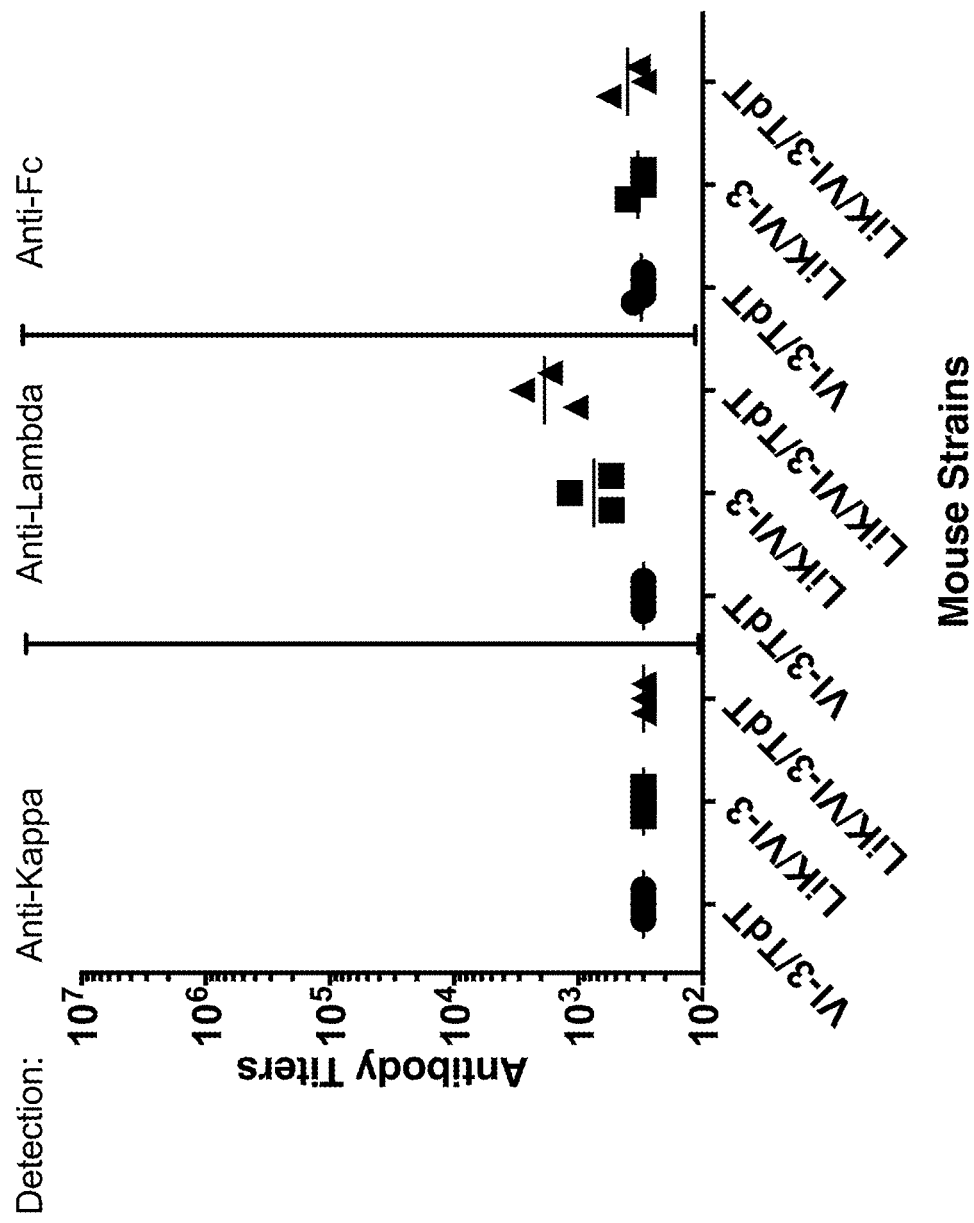
FIG. 19 shows results of testing an embodiment according to the present disclosure, showing a graph comparing immune responses against His tag in LiK/VI-3, LiK/VI-3/TdT and VI-3/TdT mice strains following immunization with an irrelevant protein antigen fused to a HIS tag.
Figure 20:
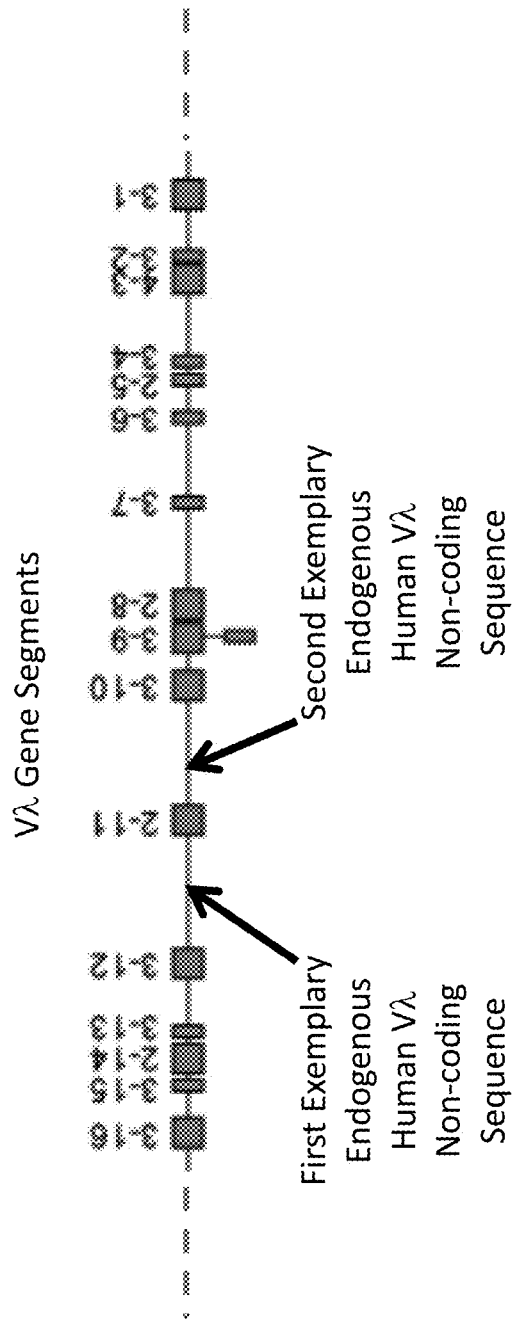
FIG. 20 shows an illustration, not to scale, of a portion of an endogenous human immunoglobulin λ light chain locus.
Figure 21:
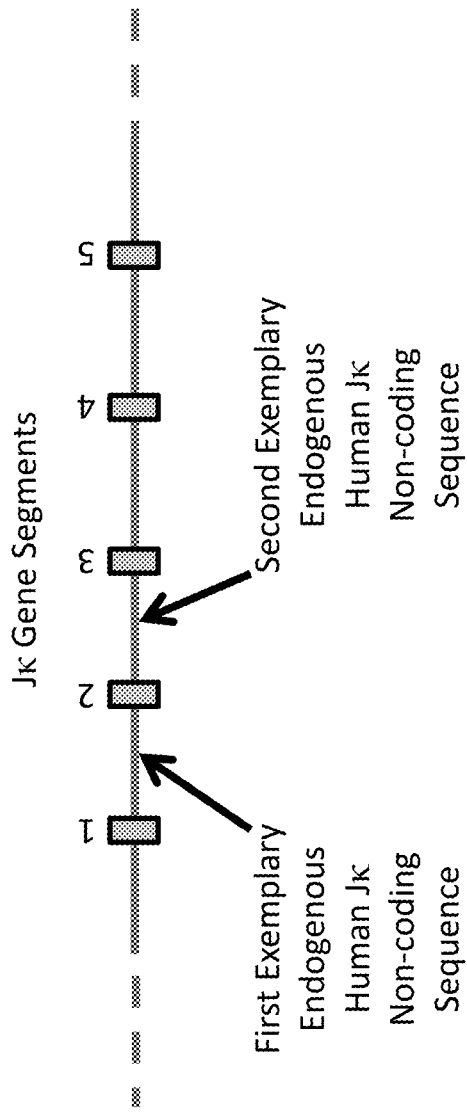
FIG. 21 shows an illustration, not to scale, of a portion of an endogenous human immunoglobulin κ light chain locus.

The humoral immune responses in LiK/VI-3, LiK/VI-3/TdT, and VI-3/TdT mice were investigated following immunization with a protein immunogen. Antisera from mice immunized with protein show high titers on antigen in LiK/VI-3 and LiK/VI-3/TdT strains comparable to VI-3/TdT strain (FIG. 18). High lambda titers were elicited in both LiK/VI-3 and LiK/VI-3/TdT mice. In VI-3/TdT strain mice, lambda titers were not observed in three mice, while low titers were observed in two mice, which corresponds to the low usage of mouse lambda variables in this strain. As expected, no kappa titers were elicited in LiK/VI-3 and LiK/VI-3/TdT mice as they lack the kappa light chain, while the VI-3/TdT showed high kappa titers. FIG. 19 shows baseline titers (lowest serum dilution) were observed on irrelevant protein antigen for His tag in all three mice strains with anti-Fc and anti-kappa detection, while very low titers were observed with anti-lambda detection in LiK/VI-3 and LiK/VI-3/TdT mice.

CERTAIN EMBODIMENTS

Embodiment 1

A genetically modified rodent, whose germline genome comprises:
a first engineered endogenous immunoglobulin κ light chain locus comprising:
(a) one or more human Vλ gene segments,
(b) one or more human Jλ gene segments, and
(c) a Cλ gene,
wherein the one or more human Vλ gene segments and the one or more human Jλ gene segments are operably linked to the Cλ gene; and
wherein the rodent lacks a rodent Cr gene at the first engineered endogenous immunoglobulin κ light chain locus.

Embodiment 2

The genetically modified rodent of embodiment 1, wherein the rodent is homozygous for the first engineered endogenous immunoglobulin κ light chain locus.

Embodiment 3

The genetically modified rodent of embodiment 1, wherein the rodent is heterozygous for the first engineered endogenous immunoglobulin κ light chain locus.

Embodiment 4

The genetically modified rodent of embodiment 3, wherein the germline genome of the rodent comprises a second engineered endogenous immunoglobulin κ light chain locus comprising:
(a) one or more human Vκ gene segments, and
(b) one or more human Jκ gene segments,
wherein the one or more human Vκ gene segments and the one or more human Jκ gene segments are operably linked to a Cκ gene.

Embodiment 5

The genetically modified rodent of embodiment 4, wherein the Cκ gene at the second engineered endogenous immunoglobulin κ light chain locus is an endogenous rodent Cκ gene.

Embodiment 6

The genetically modified rodent of any one of embodiments 1-5, wherein the rodent lacks a rodent Cκ gene at the first engineered endogenous immunoglobulin κ light chain locus.

Embodiment 7

A genetically modified rodent, whose germline genome comprises:
(a) a first engineered endogenous immunoglobulin κ light chain locus comprising:
(i) one or more human Vλ gene segments,
(ii) one or more human Jλ gene segments, and
(iii) a Cλ gene,
wherein the one or more human Vλ gene segments and the one or more human Jλ gene segments are operably linked to the Cλ gene, and
wherein the rodent lacks a rodent Cκ gene at the first engineered endogenous immunoglobulin κ light chain locus; and
(b) a second engineered endogenous immunoglobulin κ light chain locus comprising:
(i) one or more human Vκ gene segments, and
(ii) one or more human Jκ gene segments,
wherein the one or more human Vκ gene segments and the one or more human Jκ gene segments are operably linked to a Cκ gene.

Embodiment 8

The genetically modified rodent of embodiment 7, wherein the Cκ gene at the second engineered endogenous immunoglobulin κ light chain locus is an endogenous rodent Cκ gene.

Embodiment 9

The genetically modified rodent of any one of embodiments 1-8, wherein the Cλ gene at the first engineered endogenous immunoglobulin κ light chain locus comprises a rodent Cλ gene.

Embodiment 10

The genetically modified rodent of any one of embodiments 1-9, wherein the first engineered endogenous immunoglobulin κ light chain locus further comprises:

(i) one or more human Vλ non-coding sequences, each of which is adjacent to at least one of the one or more human Vλ gene segments, wherein the one or more human Vλ non-coding sequences naturally appears adjacent to a human Vλ gene segment in an endogenous human immunoglobulin λ light chain locus;

(ii) one or more human Jλ non-coding sequences, each of which is adjacent to at least one of the one or more human Jλ gene segments, wherein the one or more human Jλ non-coding sequences naturally appears adjacent to a human Jλ gene segment in an endogenous human immunoglobulin λ light chain locus; or (iii) any combination thereof.

Embodiment 11

The genetically modified rodent of any one of embodiments 1-10, wherein:

(i) the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and (ii) the one or more human Jλ gene segments comprise Jλ1, Jλ2, Jλ3, Jλ6, Jλ7, or any combination thereof.

Embodiment 12

The genetically modified rodent of embodiment 11, wherein the first engineered endogenous immunoglobulin κ light chain locus comprises:

(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jλ1, Jλ2, Jλ3, Jλ6 or Jλ7 of an endogenous human immunoglobulin λ light chain locus.

Embodiment 13

The genetically modified rodent of embodiment 11, wherein the first engineered endogenous immunoglobulin κ light chain locus comprises:

(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 14

The genetically modified rodent of any one of embodiments 1-13, wherein:

(i) the one or more human Vλ gene segments comprise Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and (ii) the one or more human Jλ gene segments comprise Jλ1, Jλ2, Jλ3, Jλ6, Jλ7, or any combination thereof.

Embodiment 15

The genetically modified rodent of embodiment 14, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 16

The genetically modified rodent of embodiment 14, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 17

A genetically modified rodent, whose germline genome comprises:

a first engineered endogenous immunoglobulin κ light chain locus comprising:
  (i) one or more human Vλ gene segments, wherein the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1, or any combination thereof,
  (ii) one or more human Jλ gene segments, wherein the one or more human Jλ gene segments comprise Jλ1, Jλ2, Jλ3, Jλ6, Jλ7, or any combination thereof,
  (iii) a rodent Cλ gene,
  (iv) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus,
  (v) one or more human Jκ non-coding sequences, wherein each of the one or more human Jκ non-coding sequences is adjacent to the Jλ1, Jλ2, Jλ3, Jλ6, or Jλ7 in the engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus, and
  (vi) a human κ light chain non-coding sequence between the one or more human Vλ gene segments and the one or more human Jλ gene segments that has a sequence that naturally appears between a human Vκ4-1 gene segment and a human Jκ1 gene segment in an endogenous human immunoglobulin κ light chain locus, wherein the one or more human Vλ gene segments, the one or more human Jλ gene segments, and the rodent Cλ gene are operably linked to each other, and wherein the rodent Cλ gene is in place of a rodent Cκ gene of the endogenous immunoglobulin κ light chain locus.

Embodiment 18

The genetically modified rodent of embodiment 17, wherein the germline genome of the rodent comprises a second engineered endogenous immunoglobulin κ light chain locus comprising:
  (a) one or more human Vκ gene segments, and
  (b) one or more human Jκ gene segments, wherein the one or more human Vκ gene segments and the one or more human Jκ gene segments are operably linked to a Cκ gene.

Embodiment 19

The genetically modified rodent of embodiment 18, wherein the Cκ gene at the second engineered endogenous immunoglobulin κ light chain locus is an endogenous rodent Cκ gene.

Embodiment 20

The genetically modified rodent of any one of embodiments 1-19, wherein the germline genome of the rodent further comprises:

an engineered endogenous immunoglobulin heavy chain locus, comprising:
  (a) one or more human $V_H$ gene segments,
  (b) one or more human $D_H$ gene segments, and
  (c) one or more human $J_H$ gene segments, wherein the one or more human $V_H$ gene segments, the one or more human $D_H$ gene segments, and the one or more human $J_H$ gene segments are operably linked to one or more rodent immunoglobulin heavy chain constant region genes at the engineered endogenous immunoglobulin heavy chain locus.

Embodiment 21

A genetically modified rodent whose germline genome comprises:

(a) an engineered endogenous immunoglobulin heavy chain locus comprising one or more human $V_H$ gene segments, one or more human $D_H$ gene segments, and one or more human $J_H$ gene segments operably linked to one or more endogenous immunoglobulin heavy chain constant region genes such that the rodent expresses immunoglobulin heavy chains that comprise a human heavy chain variable domain sequence and a rodent heavy chain constant domain sequence, wherein the germline genome is homozygous for the engineered endogenous immunoglobulin heavy chain locus;

(b) a first engineered endogenous immunoglobulin κ light chain locus comprising:

(i) one or more human Vλ gene segments, wherein the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1, or any combination thereof, (ii) one or more human Jλ gene segments, wherein the one or more human Jλ gene segments comprise Jλ1, Jλ2, Jλ3, Jλ6, Jλ7, or any combination thereof, (iii) a rodent Cλ gene, (iv) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the second engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus, (v) one or more human Jκ non-coding sequences, wherein each of the one or more human Jκ non-coding sequences is adjacent to the Jλ1, Jλ2, Jλ3, Jλ6 or Jλ7 in the second engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus, and (vi) a human κ light chain non-coding sequence between the one or more human Vλ gene segments and the one or more human Jλ gene segments that has a sequence that naturally appears between a human Vκ4-1 gene segment and a human Jκ1 gene segment in an endogenous human immunoglobulin κ light chain locus, wherein the one or more human Vλ gene segments, the one or more human Jλ gene segments, and the rodent Cλ gene are operably linked to each other, wherein the rodent Cλ gene is in place of a rodent Cκ gene at the second endogenous immunoglobulin κ light chain locus; and (c) a second engineered endogenous immunoglobulin κ light chain locus comprising one or more human Vκ gene segments and one or more Jκ gene segments operably linked to an endogenous rodent Cκ region gene such that the rodent expresses immunoglobulin light chains that comprise a human κ light chain variable domain sequence and a rodent κ light chain constant domain sequence, wherein the rodent expresses immunoglobulin light chains that comprise a human λ light chain variable domain sequence and a rodent λ light chain constant domain sequence.

Embodiment 22

The genetically modified rodent of embodiment 20 or 21, wherein the one or more human $V_H$ gene segments, one or more human $D_H$ gene segments, and one or more human $J_H$ gene segments are in place of one or more rodent $V_H$ gene segments, one or more rodent $D_H$ gene segments, one or more rodent $J_H$ gene segments, or a combination thereof.

Embodiment 23

The genetically modified rodent of any one of embodiments 20-22, wherein the one or more human $V_H$ gene segments, one or more human $D_H$ gene segments, and one or more human $J_H$ gene segments replace one or more rodent $V_H$ gene segments, one or more rodent $D_H$ gene segments, one or more rodent $J_H$ gene segments, or any combination thereof.

Embodiment 24

The genetically modified rodent of any one of embodiments 20-23, wherein the engineered endogenous immunoglobulin heavy chain locus further comprises:

(i) one or more human $V_H$ non-coding sequences, each of which is adjacent to at least one of the one or more human $V_H$ gene segments, wherein each of the one or more $V_H$ non-coding sequences naturally appears adjacent to a human $V_H$ gene segment in an endogenous human immunoglobulin heavy chain locus;

(ii) one or more human $D_H$ non-coding sequences, each of which is adjacent to at least one of the one or more human $D_H$ gene segments, wherein each of the one or more $D_H$ non-coding sequences naturally appears adjacent to a human $D_H$ gene segment in an endogenous human immunoglobulin heavy chain locus;

(iii) one or more human $J_H$ non-coding sequences, each of which is adjacent to at least one of the one or more human $J_H$ gene segments, wherein each of the one or more $J_H$ non-coding sequences naturally appears adjacent to a human $J_H$ gene segment in an endogenous human immunoglobulin heavy chain locus; or (iv) any combination thereof.

Embodiment 25

The genetically modified rodent of any one of embodiments 20-24, wherein the one or more rodent immunoglobulin heavy chain constant region genes are one or more endogenous rodent immunoglobulin heavy chain constant region genes.

Embodiment 26

The genetically modified rodent of any one of embodiments 20-25, wherein:

(i) the one or more human $V_H$ gene segments comprise $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, or any combination thereof, (ii) the one or more human $D_H$ gene segments comprise $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof, and (iii) the one or more human $J_H$ gene segments comprise $J_H1$, $J_H2$, $J_H3$, $J_H4$, $J_H5$, $J_H6$, or any combination thereof.

Embodiment 27

The genetically modified rodent of any one of embodiments 20-26, wherein the engineered endogenous immunoglobulin heavy chain locus lacks a functional endogenous rodent Adam6 gene.

Embodiment 28

The genetically modified rodent of any one of embodiments 20-27, wherein the germline genome further comprises one or more nucleotide sequences encoding one or more rodent ADAM6 polypeptides, functional orthologs, functional homologs, or functional fragments thereof.

Embodiment 29

The genetically modified rodent of embodiment 28, wherein the one or more rodent ADAM6 polypeptides, functional orthologs, functional homologs, or functional fragments thereof are expressed.

Embodiment 30

The genetically modified rodent of embodiment 28 or 29, wherein the one or more nucleotide sequences encoding one or more rodent ADAM6 polypeptides, functional orthologs, functional homologs, or functional fragments thereof are included on the same chromosome as the engineered endogenous immunoglobulin heavy chain locus.

Embodiment 31

The genetically modified rodent of any one of embodiments 28-30, wherein the one or more nucleotide sequences encoding one or more rodent ADAM6 polypeptides, functional orthologs, functional homologs, or functional fragments thereof are included in the engineered endogenous immunoglobulin heavy chain locus.

Embodiment 32

The genetically modified rodent of any one of embodiments 28-31, wherein the one or more nucleotide sequences encoding one or more rodent ADAM6 polypeptides, functional orthologs, functional homologs, or functional fragments thereof are in place of a human Adam6 pseudogene.

Embodiment 33

The genetically modified rodent of any one of embodiments 28-32, wherein the one or more nucleotide sequences encoding one or more rodent ADAM6 polypeptides, functional orthologs, functional homologs, or functional fragments thereof replace a human Adam6 pseudogene.

Embodiment 34

The genetically modified rodent of any one of embodiments 28-33, wherein the one or more nucleotide sequences encoding one or more rodent ADAM6 polypeptides, functional orthologs, functional homologs, or functional fragments thereof are between a first human $V_H$ gene segment and a second human $V_H$ gene segment.

Embodiment 35

The genetically modified rodent of embodiment 34, wherein the first human $V_H$ gene segment is $V_H1$-2 and the second human $V_H$ gene segment is $V_H6$-1.

Embodiment 36

The genetically modified rodent of any one of embodiments 28-31, wherein the one or more nucleotide sequences encoding one or more rodent ADAM6 polypeptides, functional orthologs, functional homologs, or functional fragments thereof are between a human $V_H$ gene segment and a human $D_H$ gene segment.

Embodiment 37

The genetically modified rodent of any one embodiments 20, and 22-36, wherein the rodent is homozygous for the engineered endogenous immunoglobulin heavy chain locus.

Embodiment 38

The genetically modified rodent of any one of embodiments 9-37, wherein the rodent Cλ gene has a sequence that is at least 80% identical to a mouse Cλ1, mouse Cλ2 or a mouse Cλ3 gene.

Embodiment 39

The genetically modified rodent of any one of embodiments 9-38, wherein the rodent Cλ gene comprises a mouse Cλ1 gene.

Embodiment 40

The genetically modified rodent of any one of embodiments 9-39, wherein the rodent Cλ gene comprises a rat Cλ gene.

Embodiment 41

The genetically modified rodent of embodiment 40, wherein the rat Cλ gene has a sequence that is at least 80% identical to a rat Cλ1, rat Cλ2, rat Cλ3 or a rat Cλ4 gene.

Embodiment 42

The genetically modified rodent of any one of embodiments 1-41, wherein the one or more human Vλ gene segments and the one or more human Jλ gene segments are in place of one or more rodent Vκ gene segments, one or more rodent Jκ gene segments, or any combination thereof.

Embodiment 43

The genetically modified rodent of any one of embodiments 1-42, wherein the one or more human Vλ gene segments and the one or more human Jλ gene segments replace one or more rodent Vκ gene segments, one or more rodent Jκ gene segments, or any combination thereof.

Embodiment 44

The genetically modified rodent of any one of embodiments 1-43, wherein the first engineered endogenous immunoglobulin κ light chain locus further comprises a κ light chain non-coding sequence between the one or more human Vλ gene segments and the one or more human Jλ gene segments.

Embodiment 45

The genetically modified rodent of embodiment 44, wherein the κ light chain non-coding sequence is a human κ light chain non-coding sequence.

Embodiment 46

The genetically modified rodent of embodiment 45, wherein the human K light chain non-coding sequence has a sequence that naturally appears between a human Vκ4-1 gene segment and a human Jκ1 gene segment in an endogenous human immunoglobulin κ light chain locus.

Embodiment 47

The genetically modified rodent of any one of embodiments 1-46, further comprising an inactivated endogenous immunoglobulin λ light chain locus.

Embodiment 48

The genetically modified rodent of embodiment 47, wherein the rodent is heterozygous for the inactivated endogenous immunoglobulin λ light chain locus.

Embodiment 49

The genetically modified rodent of embodiment 47, wherein the rodent is homozygous for the inactivated endogenous immunoglobulin λ light chain locus.

Embodiment 50

The genetically modified rodent of any one of embodiments 1-49, wherein the endogenous Vλ gene segments, the endogenous Jλ gene segments, and the endogenous Cλ genes are deleted in whole or in part.

Embodiment 51

The genetically modified rodent of any one of embodiments 1-50, wherein the rodent does not detectably express endogenous immunoglobulin λ light chain variable domains.

Embodiment 52

The genetically modified rodent of any one of embodiments 1-51, wherein the rodent does not detectably express endogenous immunoglobulin κ light chain variable domains.

Embodiment 53

The genetically modified rodent of any one of embodiments 1-52, wherein the rodent comprises a population of B cells that express antibodies, including immunoglobulin λ light chains that each include a human immunoglobulin λ light chain variable domain.

Embodiment 54

The genetically modified rodent of embodiment 53, wherein the human immunoglobulin λ light chain variable domain is encoded by a rearranged human immunoglobulin λ light chain variable region sequence comprising (i) one of the one or more human Vλ gene segments or a somatically hypermutated variant thereof, and (ii) one of the one or more human Jλ gene segments or a somatically hypermutated variant thereof.

Embodiment 55

The genetically modified rodent of any one of embodiments 1-54, wherein the germline genome of the rodent further comprises a nucleic acid sequence encoding an exogenous terminal deoxynucleotidyltransferase (TdT) operably linked to a transcriptional control element.

Embodiment 56

The genetically modified rodent of embodiment 55, wherein the TdT is a short isoform of TdT (TdTS).

Embodiment 57

The genetically modified rodent of embodiment 55 or 56, wherein the transcriptional control element comprises a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof.

Embodiment 58

The genetically modified rodent of any one of embodiments 55-57, wherein the nucleic acid sequence encoding an exogenous TdT is in the germline genome at an immunoglobulin κ light chain locus, an immunoglobulin λ light chain locus, an immunoglobulin heavy chain locus, a RAG1 locus, or a RAG2 locus.

Embodiment 59

A genetically modified rodent whose germline genome comprises
(a) a nucleic acid sequence encoding an exogenous terminal deoxynucleotidyltransferase (TdT) operably linked to a transcriptional control element;
(b) an engineered endogenous immunoglobulin heavy chain locus comprising one or more human $V_H$ gene segments, one or more human $D_H$ gene segments and one or more human $J_H$ gene segments operably linked to one or more endogenous immunoglobulin heavy chain constant region genes such that the rodent expresses immunoglobulin heavy chains that each comprise a human heavy chain variable domain sequence and a rodent heavy chain constant domain sequence, wherein the germline genome is homozygous for the engineered endogenous immunoglobulin heavy chain locus; and
(c) an engineered endogenous immunoglobulin κ light chain locus comprising:
(i) one or more human Vλ gene segments, wherein the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3, Vλ3-1 or any combination thereof, (ii) one or more human Jλ gene segments, wherein the one or more human Jλ gene segments comprise Jλ1, Jλ2, Jλ3, Jλ6, Jλ7 or any combination thereof,
(iii) a rodent Cλ gene,
(iv) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus,
(v) one or more human Jκ non-coding sequences, wherein each of the one or more human Jκ non-coding sequences is adjacent to the Jλ1, Jλ2, Jλ3, Jλ6 and Jλ7 in the engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus, and
(vi) a human κ light chain non-coding sequence between the one or more human Vλ gene segments and the one or more human Jλ gene segments that comprises a sequence that naturally appears between a human Vκ4-1 gene segment and a human Jκ1 gene segment in an endogenous human immunoglobulin κ light chain locus,
wherein the one or more human Vλ gene segments, the one or more human Jλ gene segments, and the rodent Cλ gene are operably linked to each other,
wherein the rodent Cλ gene is in place of a rodent Cκ gene of the endogenous immunoglobulin κ light chain locus,
wherein the germline genome is homozygous for the engineered endogenous immunoglobulin κ light chain locus, and
wherein the rodent expresses immunoglobulin light chains that comprise a human λ light chain variable domain sequence fused to a rodent λ light chain constant domain sequence.

Embodiment 60

The genetically modified rodent of any one of embodiments 1-59, wherein the rodent is a rat or a mouse.

Embodiment 61

An isolated rodent cell obtained from a rodent of any one of embodiments 1-60.

Embodiment 62

An immortalized cell generated from the isolated rodent cell of embodiment 61.

Embodiment 63

The isolated rodent cell of 61, wherein the rodent cell is a rodent embryonic stem (ES) cell.

Embodiment 64

A rodent embryo generated from the rodent ES cell of embodiment 63.

Embodiment 65

Use of a rodent of any one of embodiments 1-60 for making an antibody.

Embodiment 66

Use of a rodent of any one of embodiments 1-60 for making a light chain variable region sequence.

Embodiment 67

Use of a rodent of any one of embodiments 1-60 for making a light chain variable domain sequence.

Embodiment 68

An isolated B cell obtained from a rodent of any one embodiments 1-60, wherein the genome of the B cell comprises:
(a) a rearranged human lambda light chain variable region sequence operably linked to a lambda light chain variable region sequence, wherein the rearranged human lambda light chain variable region sequence comprises:
(i) one of the one or more human Vλ gene segments or a somatically hypermuted variant thereof, and
(ii) one of the one or more human Jλ gene segments or a somatically hypermuted variant thereof.

Embodiment 69

The isolated B cell of embodiment 68, further comprising:
(b) a rearranged human heavy chain variable region sequence operably linked to a rodent heavy chain variable region sequence, wherein the rearranged human heavy chain variable region sequence comprises:
(i) one of the one or more human $V_H$ gene segments or a somatically hypermuted variant thereof,
(ii) one of the one or more human $D_H$ gene segments or a somatically hypermuted variant thereof, and
(iii) one of the one or more human $J_H$ gene segments or a somatically hypermuted variant thereof.

Embodiment 70

An antibody prepared by a method comprising the steps of:
(a) providing a rodent of any one of embodiments 1-60;
(b) immunizing the rodent with an antigen of interest;
(c) maintaining the rodent under conditions sufficient for the rodent to produce an immune response to the antigen of interest; and
(d) recovering from the rodent:
(i) an antibody that binds the antigen of interest,
(ii) a nucleotide that encodes a human light or heavy chain variable domain, a light chain, or a heavy chain of an antibody that binds the antigen of interest, or
(iii) a cell that expresses an antibody that binds the antigen of interest,
wherein an antibody of (d) includes human heavy chain variable and human λ light chain variable domains.

Embodiment 71

An isolated rodent cell, whose genome comprises:
a first engineered endogenous immunoglobulin κ light chain locus comprising:
(a) one or more human Vλ gene segments,
(b) one or more human Jλ gene segments, and
(c) a Cλ gene,
wherein the one or more human Vλ gene segments and the one or more human Jλ gene segments are operably linked to the Cλ gene, and
wherein the isolated rodent cell lacks a rodent Cκ gene at the first engineered endogenous immunoglobulin κ light chain locus.

Embodiment 72

The isolated rodent cell of embodiment 71, wherein the isolated rodent cell is homozygous for the first engineered endogenous immunoglobulin κ light chain locus.

Embodiment 73

The isolated rodent cell of embodiment 71, wherein the isolated rodent cell is heterozygous for the first engineered endogenous immunoglobulin κ light chain locus.

Embodiment 74

The isolated rodent cell of embodiment 73, wherein the genome of the isolated rodent cell comprises a second engineered endogenous immunoglobulin κ light chain locus comprising:
(a) one or more human Vκ gene segments, and
(b) one or more human Jκ gene segments,
wherein the one or more human Vκ gene segments and the one or more human Jκ gene segments are operably linked to a Cκ gene.

Embodiment 75

The isolated rodent cell of embodiment 74, wherein the Cκ gene at the second engineered endogenous immunoglobulin κ light chain locus is an endogenous rodent Cκ gene.

Embodiment 76

The isolated rodent cell of any one of embodiments 71-75, wherein the isolated rodent cell lacks a rodent Cκ gene at the first engineered endogenous immunoglobulin κ light chain locus.

Embodiment 77

The isolated rodent cell of any one of embodiments 71-76, wherein the Cλ gene at the first engineered endogenous immunoglobulin κ light chain locus comprises a rodent Cλ gene.

Embodiment 78

The isolated rodent cell of any one of embodiments 71-77, wherein the first engineered endogenous immunoglobulin κ light chain locus further comprises:
(i) one or more human Vλ non-coding sequences, each of which is adjacent to at least one of the one or more human Vλ gene segments, wherein the one or more human Vλ non-coding sequences naturally appears adjacent to a human Vλ gene segment in an endogenous human immunoglobulin λ light chain locus;
(ii) one or more human Jλ non-coding sequences, each of which is adjacent to at least one of the one or more human Jλ gene segments, wherein the one or more human Jλ non-coding sequences naturally appears adjacent to a human Jλ gene segment in an endogenous human immunoglobulin λ light chain locus; or
(iii) any combination thereof.

Embodiment 79

The isolated rodent cell of any one of embodiments 71-78, wherein:
(i) the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and
(ii) the one or more human Jλ gene segments comprise Jλ1, Jλ2, Jλ3, Jλ6, Jλ7, or any combination thereof.

Embodiment 80

The isolated rodent cell of embodiment 79, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and
(ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jx non-coding sequences naturally appears adjacent to a Jλ1, Jλ2, Jλ3, Jλ6 or Jλ7 of an endogenous human immunoglobulin λ light chain locus.

Embodiment 81

The isolated rodent cell of embodiment 79, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus, (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 82

The isolated rodent cell of any one of embodiments 71-81, wherein:

(a) the one or more human Vλ gene segments comprise Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and (b) the one or more human Jλ gene segments comprise Jλ1, Jλ2, Jλ3, Jλ6, Jλ7, or any combination thereof.

Embodiment 83

The isolated rodent cell of embodiment 82, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 84

The isolated rodent cell of embodiment 82, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 85

The isolated rodent cell of any one of embodiments 71-84, wherein the genome of the rodent cell further comprises:
an engineered endogenous immunoglobulin heavy chain locus, comprising:
(a) one or more human $V_H$ gene segments,
(b) one or more human $D_H$ gene segments, and
(c) one or more human $J_H$ gene segments,
wherein the one or more human $V_H$ gene segments, the one or more human $D_H$ gene segments, and the one or more human $J_H$ gene segments are operably linked to one or more rodent immunoglobulin heavy chain constant region genes at the engineered endogenous immunoglobulin heavy chain locus.

Embodiment 86

The isolated rodent cell of embodiment 85, wherein the one or more human $V_H$ gene segments, one or more human $D_H$ gene segments, and one or more human $J_H$ gene segments are in place of one or more rodent $V_H$ gene segments, one or more rodent $D_H$ gene segments, one or more rodent $J_H$ gene segments, or a combination thereof.

Embodiment 87

The isolated rodent cell of embodiment 85 or 86, wherein the one or more human $V_H$ gene segments, one or more human $D_H$ gene segments, and one or more human $J_H$ gene segments replace one or more rodent $V_H$ gene segments, one or more rodent $D_H$ gene segments, one or more rodent $J_H$ gene segments, or any combination thereof.

Embodiment 88

The isolated rodent cell of any one of embodiments 85-87, wherein the engineered endogenous immunoglobulin heavy chain locus further comprises:
(i) one or more human $V_H$ non-coding sequences, each of which is adjacent to at least one of the one or more human $V_H$ gene segments, wherein each of the one or more $V_H$ non-coding sequences naturally appears adjacent to a human $V_H$ gene segment in an endogenous human immunoglobulin heavy chain locus;

(ii) one or more human $D_H$ non-coding sequences, each of which is adjacent to at least one of the one or more human $D_H$ gene segments, wherein each of the one or more $D_H$ non-coding sequences naturally appears adjacent to a human $D_H$ gene segment in an endogenous human immunoglobulin heavy chain locus;

(iii) one or more human $J_H$ non-coding sequences, each of which is adjacent to at least one of the one or more human $J_H$ gene segments, wherein each of the one or more $J_H$ non-coding sequences naturally appears adjacent to a human $J_H$ gene segment in an endogenous human immunoglobulin heavy chain locus; or (iv) any combination thereof.

Embodiment 89

The isolated rodent cell of any one of embodiments 85-88, wherein the one or more rodent immunoglobulin heavy chain constant region genes are one or more endogenous rodent immunoglobulin heavy chain constant region genes.

Embodiment 90

The isolated rodent cell of any one of embodiments 85-89, wherein:

(i) the one or more human $V_H$ gene segments comprise $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, or any combination thereof, (ii) the one or more human $D_H$ gene segments comprise $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof, and (iii) the one or more human $J_H$ gene segments comprise $J_H1$, $J_H2$, $J_H3$, $J_H4$, $J_H5$, $J_H6$, or any combination thereof.

Embodiment 91

The isolated rodent cell of any one of embodiments 85-90, wherein the engineered endogenous immunoglobulin heavy chain locus lacks a functional endogenous rodent Adam6 gene.

Embodiment 92

The isolated rodent cell of any one of embodiments 85-91, wherein the genome of the rodent cell further comprises one or more nucleotide sequences encoding one or more rodent ADAM6 polypeptides, functional orthologs, functional homologs, or functional fragments thereof.

Embodiment 93

The isolated rodent cell of embodiment 92, wherein the one or more nucleotide sequences encoding one or more rodent ADAM6 polypeptides, functional orthologs, functional homologs, or functional fragments thereof are included on the same chromosome as the engineered endogenous immunoglobulin heavy chain locus.

Embodiment 94

The isolated rodent cell of embodiment 92 or 93, wherein the one or more nucleotide sequences encoding one or more rodent ADAM6 polypeptides, functional orthologs, functional homologs, or functional fragments thereof are included in the engineered endogenous immunoglobulin heavy chain locus.

Embodiment 95

The isolated rodent cell of any one of embodiments 92-94, wherein the one or more nucleotide sequences encoding one or more rodent ADAM6 polypeptides, functional orthologs, functional homologs, or functional fragments thereof are in place of a human Adam6 pseudogene.

Embodiment 96

The isolated rodent cell of any one of embodiments 92-95, wherein the one or more nucleotide sequences encoding one or more rodent ADAM6 polypeptides, functional orthologs, functional homologs, or functional fragments thereof replace a human Adam6 pseudogene.

Embodiment 97

The isolated rodent cell of any one of embodiments 92-96, wherein the one or more nucleotide sequences encoding one or more rodent ADAM6 polypeptides, functional orthologs, functional homologs, or functional fragments thereof are between a first human $V_H$ gene segment and a second human $V_H$ gene segment.

Embodiment 98

The isolated rodent cell of embodiment 97, wherein the first human $V_H$ gene segment is $V_H1$-2 and the second human $V_H$ gene segment is $V_H6$-1.

Embodiment 99

The isolated rodent cell of any one of embodiments 92-94, wherein the one or more nucleotide sequences encoding one or more rodent ADAM6 polypeptides, functional orthologs, functional homologs, or functional fragments thereof are between a human $V_H$ gene segment and a human $D_H$ gene segment.

Embodiment 100

The isolated rodent cell of any one embodiments 85-99, wherein the isolated rodent cell is homozygous for the engineered endogenous immunoglobulin heavy chain locus.

Embodiment 101

The isolated rodent cell of any one of embodiments 71-100, wherein the genome of the isolated rodent cell further comprises a nucleic acid sequence encoding an exogenous terminal deoxynucleotidyltransferase (TdT) operably linked to a transcriptional control element.

Embodiment 102

The isolated rodent cell of embodiment 101, wherein the TdT is a short isoform of TdT (TdTS).

Embodiment 103

The isolated rodent cell of embodiment 101 or 102, wherein the transcriptional control element comprises a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof.

Embodiment 104

The isolated rodent cell of any one of embodiments 101-103, wherein the nucleic acid sequence encoding an exogenous TdT is in the genome of the rodent cell at an immunoglobulin κ light chain locus, an immunoglobulin λ light chain locus, an immunoglobulin heavy chain locus, a RAG1 locus, or a RAG2 locus.

Embodiment 105

The isolated rodent cell of any one of embodiments 71-104, wherein the rodent cell is a rat cell or a mouse cell.

Embodiment 106

An immortalized cell generated from the isolated rodent cell of any one of embodiments 71-105.

Embodiment 107

The isolated rodent cell of any one of embodiments 71-105, wherein the rodent cell is a rodent embryonic stem (ES) cell.

Embodiment 108

A rodent embryo generated from the rodent ES cell of embodiment 107.

Embodiment 109

A method of making a genetically modified rodent comprising the steps of:
(a) introducing one or more DNA fragments into the a first engineered immunoglobulin κ light chain locus in the genome of a rodent ES cell, wherein the one or more DNA fragments comprise:
  (i) one or more human Vλ gene segments,
  (ii) one or more human Jλ gene segments, and
  (iii) a Cλ gene,
  wherein the one or more human Vλ gene segments, the one or more human Jλ gene segments, and the Cλ gene are introduced into the genome of the rodent ES cell at the endogenous immunoglobulin κ light chain locus, and wherein the one or more human Vλ gene segments, the one or more human Jλ gene segments, and the Cλ gene are operably linked; and
(b) generating a rodent using the rodent ES cell generated in (a).

Embodiment 110

The method of embodiment 109, wherein the genome of the rodent ES cell comprises a second engineered endogenous immunoglobulin κ light chain locus comprising:
  (i) one or more human Vκ gene segments, and
  (ii) one or more human Jκ gene segments,
wherein the one or more human Vκ gene segments and the one or more human Jκ gene segments are operably linked to a Cκ gene.

Embodiment 111

The method of embodiment 109 or 110, wherein the genome of the rodent ES cell comprises an engineered endogenous immunoglobulin heavy chain locus comprising:
  (i) one or more human $V_H$ gene segments,
  (ii) one or more human $D_H$ gene segments, and
  (iii) one or more human $J_H$ gene segments,
wherein the one or more human $V_H$ gene segments, the one or more human $D_H$ gene segments, and the one or more human $J_H$ gene segments are operably linked to one or more rodent immunoglobulin heavy chain constant region genes at the engineered endogenous immunoglobulin heavy chain locus.

Embodiment 112

The method of any one of embodiments 109-111, wherein the one or more DNA fragments further comprise at least one selection marker.

Embodiment 113

The method of any one of embodiments 109-112, wherein the one or more DNA fragments further comprise at least one site-specific recombination site.

Embodiment 114

The method of any one of embodiments 109-113, further comprising introducing one or more human Vλ non-coding sequences and one or more human Vx non-coding sequences in the first engineered endogenous immunoglobulin κ light chain locus, wherein each of the one or more human Vλ non-coding sequences is adjacent to a human Vx gene segment, and each of the one or more human Jλ non-coding sequences is adjacent to a human Jx gene segment.

Embodiment 115

The method of any one of embodiments 109-114, further comprising introducing a κ light chain non-coding sequence into the genome of the rodent ES cell so that the K light chain non-coding sequence is between the one or more human Vλ gene segments and the one or more human Jλ gene segments in the first engineered endogenous immunoglobulin κ light chain locus.

Embodiment 116

The method of any one embodiments 109-115, wherein the rodent ES cell is a rat ES cell or a mouse ES cell.

Embodiment 117

A method of making a genetically modified rodent, comprising the step of:

(a) engineering a first endogenous immunoglobulin κ light chain locus in the germline genome of the rodent to include:
(i) one or more human Vλ gene segments,
(ii) one or more human Jλ gene segments, and
(iii) a Cλ gene,
wherein the one or more human Vλ gene segments and the one or more human Jλ gene segments are operably linked to the Cλ gene, and
wherein the Cλ gene is inserted at the first endogenous immunoglobulin κ light chain locus.

Embodiment 118

The method of embodiment 117, wherein the method further comprises the step of:
(b) engineering a second endogenous immunoglobulin κ light chain locus in the germline genome of the rodent to include:
(i) one or more human Vλ gene segments,
(ii) one or more human Jλ gene segments, and
(iii) a Cλ gene,
wherein the one or more human Vλ gene segments and the one or more human Jλ gene segments are operably linked to the Cλ gene, and
wherein the Cλ gene is inserted at the second endogenous immunoglobulin κ light chain locus.

Embodiment 119

The method of embodiment 117, wherein the method further comprises the step of:
(b) engineering a second engineered endogenous immunoglobulin κ light chain locus in the germline genome of the rodent to include:
(i) one or more human Vκ gene segments, and
(ii) one or more human Jκ gene segments,
wherein the one or more human Vκ gene segments and the one or more human Jκ gene segments are operably linked to a Cκ gene.

Embodiment 120

The method of embodiment 119, wherein the Cκ gene at the second engineered endogenous immunoglobulin κ light chain locus is an endogenous rodent Cκ gene.

Embodiment 121

The method of any one of embodiments 117-120, wherein the method further comprises the step of:
(c) engineering an engineered endogenous immunoglobulin heavy chain locus in the germline genome of the rodent to include:
(i) one or more human $V_H$ gene segments,
(ii) one or more human $D_H$ gene segments, and
(iii) one or more human $J_H$ gene segments,
wherein the one or more human $V_H$ gene segments, the one or more human $D_H$ gene segments, and the one or more human $J_H$ gene segments are operably linked to one or more rodent immunoglobulin heavy chain constant region genes.

Embodiment 122

The method of any one of embodiments 117-121, wherein the step of engineering a first endogenous immunoglobulin κ light chain locus in the germline genome of the rodent is carried out in a rodent ES cell whose genome comprises a second engineered endogenous immunoglobulin κ light chain locus comprising one or more human Vκ gene segments, and one or more human Jκ gene segments, wherein the one or more human Vκ gene segments and the one or more human Jκ gene segments are operably linked to a Cκ gene.

Embodiment 123

The method of embodiment 122, wherein the Cκ gene at the second engineered endogenous immunoglobulin κ light chain locus is an endogenous rodent Cκ gene.

Embodiment 124

The method of any one of embodiments 117-120, 122 and 123, wherein the step of engineering is carried out in a rodent ES cell whose genome comprises an engineered endogenous immunoglobulin heavy chain locus comprising one or more human $V_H$ gene segments, one or more human $D_H$ gene segments, and one or more human $J_H$ gene segments operably linked to one or more rodent immunoglobulin heavy chain constant region genes.

Embodiment 125

The method of any one of embodiments 121-124, wherein the engineered endogenous immunoglobulin heavy chain locus comprises one or more human $V_H$ non-coding sequences, each of which is adjacent to at least one of the one or more human $V_H$ gene segments, wherein each of the one or more human $V_H$ non-coding sequences naturally appears adjacent to a human $V_H$ gene segment in an endogenous human immunoglobulin heavy chain locus.

Embodiment 126

The method of any one of embodiments 121-125, wherein the engineered endogenous immunoglobulin heavy chain locus comprises one or more human $D_H$ non-coding sequences, each of which is adjacent to at least one of the one or more human $D_H$ gene segments, wherein each of the one or more $D_H$ non-coding sequences naturally appears adjacent to a human $D_H$ gene segment in an endogenous human immunoglobulin heavy chain locus.

Embodiment 127

The method of any one of embodiments 121-126, wherein the engineered endogenous immunoglobulin heavy chain locus comprises one or more human $J_H$ non-coding sequences, each of which is adjacent to at least one of the one or more human $J_H$ gene segments, wherein each of the one or more $J_H$ non-coding sequences naturally appears adjacent to a human $J_H$ gene segment in an endogenous human immunoglobulin heavy chain locus.

Embodiment 128

The method of any one of embodiments 109-127, wherein the first engineered endogenous immunoglobulin κ light chain locus lacks a rodent Cκ gene.

139

Embodiment 129

The method of any one of embodiments 110-115 and 119-128, wherein the Cκ gene at the second engineered endogenous immunoglobulin κ light chain locus is an endogenous rodent Cκ gene.

Embodiment 130

The method of any one of embodiments 109-129, wherein the Cλ gene at the first engineered endogenous immunoglobulin κ light chain locus comprises a rodent Cλ gene.

Embodiment 131

The method of any one of embodiments 109-130, wherein the first engineered endogenous immunoglobulin κ light chain locus further comprises:
(i) one or more human Vλ non-coding sequences, each of which is adjacent to at least one of the one or more human Vλ gene segments, wherein the one or more human Vλ non-coding sequences naturally appears adjacent to a human Vλ gene segment in an endogenous human immunoglobulin λ light chain locus;
(ii) one or more human Jλ non-coding sequences, each of which is adjacent to at least one of the one or more human Jλ gene segments, wherein the one or more human Jλ non-coding sequences naturally appears adjacent to a human Jλ gene segment in an endogenous human immunoglobulin λ light chain locus; or
(iii) any combination thereof.

Embodiment 132

The method of any one of embodiments 109-131, wherein:
(i) the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and
(ii) the one or more human Jλ gene segments comprise Jλ1, Jλ2, Jλ3, Jλ6, Jλ7, or any combination thereof.

Embodiment 133

The method of embodiment 132, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and
(ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 134

The method of embodiment 132, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and
(ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 135

The method of any one of embodiments 109-134, wherein:
(i) the one or more human Vλ gene segments comprise Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and
(ii) the one or more human Jλ gene segments comprise Jλ1, Jλ2, Jλ3, Jλ6, Jλ7, or any combination thereof.

Embodiment 136

The method of embodiment 135, wherein the first engineered endogenous immunoglobulin κ light chain locus comprises:
(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-

43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 137

The method of embodiment 135, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 138

The method of any one of embodiments 111-116 and 121-137, wherein the one or more human $V_H$ gene segments, one or more human $D_H$ gene segments, and one or more human $J_H$ gene segments are in place of one or more rodent $V_H$ gene segments, one or more rodent $D_H$ gene segments, one or more rodent $J_H$ gene segments, or a combination thereof.

Embodiment 139

The method of any one of embodiments 111-116 and 121-138, wherein the one or more human $V_H$ gene segments, one or more human $D_H$ gene segments, and one or more human $J_H$ gene segments replace one or more rodent $V_H$ gene segments, one or more rodent $D_H$ gene segments, one or more rodent $J_H$ gene segments, or any combination thereof.

Embodiment 140

The method of any one of embodiments 111-116 and 121-139, wherein the engineered endogenous immunoglobulin heavy chain locus further comprises:

(i) one or more human $V_H$ non-coding sequences, each of which is adjacent to at least one of the one or more human $V_H$ gene segments, wherein each of the one or more $V_H$ non-coding sequences naturally appears adjacent to a human $V_H$ gene segment in an endogenous human immunoglobulin heavy chain locus;

(ii) one or more human $D_H$ non-coding sequences, each of which is adjacent to at least one of the one or more human $D_H$ gene segments, wherein each of the one or more $D_H$ non-coding sequences naturally appears adjacent to a human $D_H$ gene segment in an endogenous human immunoglobulin heavy chain locus;

(iii) one or more human $J_H$ non-coding sequences, each of which is adjacent to at least one of the one or more human $J_H$ gene segments, wherein each of the one or more $J_H$ non-coding sequences naturally appears adjacent to a human $J_H$ gene segment in an endogenous human immunoglobulin heavy chain locus; or (iv) any combination thereof.

Embodiment 141

The method of any one of embodiments 111-116 and 121-140, wherein the one or more rodent immunoglobulin heavy chain constant region genes are one or more endogenous rodent immunoglobulin heavy chain constant region genes.

Embodiment 142

The method of any one of embodiments 111-116 and 121-141, wherein:

(i) the one or more human $V_H$ gene segments comprise $V_H3-7^4$, $V_H3-7^3$, $V_H3-7^2$, $V_H2-70$, $V_H1-69$, $V_H3-66$, $V_H3-64$, $V_H4-61$, $V_H4-59$, $V_H1-58$, $V_H3-53$, $V_H5-51$, $V_H3-49$, $V_H3-48$, $V_H1-46$, $V_H1-45$, $V_H3-43$, $V_H4-39$, $V_H4-34$, $V_H3-33$, $V_H4-31$, $V_H3-30$, $V_H4-28$, $V_H2-26$, $V_H1-24$, $V_H3-23$, $V_H3-21$, $V_H3-20$, $V_H1-18$, $V_H3-15$, $V_H3-13$, $V_H3-11$, $V_H3-9$, $V_H1-8$, $V_H3-7$, $V_H2-5$, $V_H7-4-1$, $V_H4-4$, $V_H1-3$, $V_H1-2$, $V_H6-1$, or any combination thereof;

(ii) the one or more human $D_H$ gene segments comprise $D_H1-1$, $D_H2-2$, $D_H3-3$, $D_H4-4$, $D_H5-5$, $D_H6-6$, $D_H1-7$, $D_H2-8$, $D_H3-9$, $D_H3-10$, $D_H5-12$, $D_H6-13$, $D_H2-15$, $D_H3-16$, $D_H4-17$, $D_H6-19$, $D_H1-20$, $D_H2-21$, $D_H3-22$, $D_H6-25$, $D_H1-26$, $D_H7-27$, or any combination thereof; and (iii) the one or more human $J_H$ gene segments comprise $J_H1$, $J_H2$, $J_H3$, $J_H4$, $J_H5$, $J_H6$, or any combination thereof.

Embodiment 143

The method of any one of embodiments 111-116 and 121-142, wherein the engineered endogenous immunoglobulin heavy chain locus lacks a functional endogenous rodent Adam6 gene.

Embodiment 144

The method of any one of embodiments 111-116 and 121-143, wherein the genome of the rodent ES cell or the germline genome of the rodent further comprises one or more nucleotide sequences encoding one or more rodent ADAM6 polypeptides, functional orthologs, functional homologs, or functional fragments thereof.

Embodiment 145

The method of embodiment 144, wherein the one or more nucleotide sequences encoding one or more rodent ADAM6

Embodiment 146

The method of embodiment 144 or 145, wherein the one or more nucleotide sequences encoding one or more rodent ADAM6 polypeptides, functional orthologs, functional homologs, or functional fragments thereof are included in the engineered endogenous immunoglobulin heavy chain locus.

Embodiment 147

The method of any one of embodiments 144-146, wherein the one or more nucleotide sequences encoding one or more rodent ADAM6 polypeptides, functional orthologs, functional homologs, or functional fragments thereof are in place of a human Adam6 pseudogene.

Embodiment 148

The method of any one of embodiments 144-147, wherein the one or more nucleotide sequences encoding one or more rodent ADAM6 polypeptides, functional orthologs, functional homologs, or functional fragments thereof replace a human Adam6 pseudogene.

Embodiment 149

The method of any one of embodiments 144-148, wherein the one or more nucleotide sequences encoding one or more rodent ADAM6 polypeptides, functional orthologs, functional homologs, or functional fragments thereof are between a first human $V_H$ gene segment and a second human $V_H$ gene segment.

Embodiment 150

The method of embodiment 149, wherein the first human $V_H$ gene segment is $V_H$1-2 and the second human $V_H$ gene segment is $V_H$6-1.

Embodiment 151

The method of any one of embodiments 144-146, wherein the one or more nucleotide sequences encoding one or more rodent ADAM6 polypeptides, functional orthologs, functional homologs, or functional fragments thereof are between a human $V_H$ gene segment and a human $D_H$ gene segment.

Embodiment 152

The method of any one embodiments 111-116 and 121-151, wherein the rodent is homozygous for the engineered endogenous immunoglobulin heavy chain locus.

Embodiment 153

The method of any one of embodiments 109-152, wherein the genome of the rodent ES cell or the germline genome of the rodent further comprises a nucleic acid sequence encoding an exogenous terminal deoxynucleotidyltransferase (TdT) operably linked to a transcriptional control element.

Embodiment 154

The method of embodiment 153, wherein the TdT is a short isoform of TdT (TdTS).

Embodiment 155

The method of embodiment 153 or 154, wherein the transcriptional control element comprises a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof.

Embodiment 156

The method of any one of embodiments 153-155, wherein the nucleic acid sequence encoding an exogenous TdT is at an immunoglobulin κ light chain locus, an immunoglobulin λ light chain locus, an immunoglobulin heavy chain locus, a RAG1 locus, or a RAG2 locus.

Embodiment 157

The method of any one embodiments 109-156, wherein the rodent is a rat or a mouse.

Embodiment 158

A method of producing an antibody in a genetically modified rodent, the method comprising the steps of:
(a) immunizing a rodent with an antigen of interest,
wherein the rodent has a germline genome comprising:
a first engineered endogenous immunoglobulin κ light chain locus, comprising:
(i) one or more human Vλ gene segments,
(ii) one or more human Jλ gene segments, and
(iii) a Cλ gene,
wherein the one or more human Vλ gene segments and the one or more human Jλ gene segments are operably linked to the Cλ gene, and
wherein the Cλ gene (c) is in the place of a rodent Cκ gene at the first engineered endogenous immunoglobulin κ light chain locus;
(b) maintaining the rodent under conditions sufficient for the rodent to produce an immune response to the antigen of interest; and
(c) recovering from the rodent:
(i) an antibody that binds the antigen of interest,
(ii) a nucleotide that encodes a human light or heavy chain variable domain, a light chain, or a heavy chain of an antibody that binds the antigen of interest, or
(iii) a cell that expresses an antibody that binds the antigen of interest.

Embodiment 159

The method of embodiment 158, wherein the cell of the rodent is a B cell.

Embodiment 160

The method of embodiment 159, further comprising producing a hybridoma from the B cell.

Embodiment 161

A method of making an antibody, comprising:
(a) expressing a first nucleotide sequence that encodes an immunoglobulin heavy chain in a host cell, wherein the first nucleotide sequence includes a human heavy chain variable region sequence;
(b) expressing a second nucleotide sequence that encodes an immunoglobulin λ light chain in a host cell, wherein the second nucleotide sequence includes a human λ light chain variable region sequence that was identified from a genetically modified rodent whose germline genome comprises:
  a first engineered endogenous immunoglobulin κ light chain locus comprising:
    (i) one or more human Vλ gene segment,
    (ii) one or more human Jλ gene segment, and
    (iii) a Cλ gene,
  wherein the one or more human Vλ gene segment and the one or more human Jλ gene segment are operably linked to the Cλ gene, and
  wherein the rodent lacks a rodent Cκ gene at the engineered endogenous immunoglobulin κ light chain locus;
(c) culturing the host cell so that immunoglobulin light chains and immunoglobulin heavy chains are expressed and form an antibody; and
(d) obtaining the antibody from the host cell or host cell culture.

Embodiment 162

The method of embodiment 161, wherein the first nucleotide further includes a human heavy chain constant region gene.

Embodiment 163

The method of embodiment 161 or 162, wherein the second nucleotide further includes a human λ light chain constant region gene.

Embodiment 164

The method of any one of embodiments 158-163, wherein the rodent is homozygous for the first engineered endogenous immunoglobulin κ light chain locus.

Embodiment 165

The method of any one of embodiments 158-163, wherein the rodent is heterozygous for the first engineered endogenous immunoglobulin κ light chain locus.

Embodiment 166

The method of embodiment 165, wherein the germline genome of the rodent comprises a second engineered endogenous immunoglobulin κ light chain locus comprising:
(a) one or more human Vκ gene segments, and
(b) one or more human Jκ gene segments,
wherein the one or more human Vκ gene segments and the one or more human Jκ gene segments are operably linked to a Cκ gene.

Embodiment 167

The method of embodiment 166, wherein the Cκ gene at the second engineered endogenous immunoglobulin κ light chain locus is an endogenous rodent Cκ gene.

Embodiment 168

The method of any one of embodiments 158-167, wherein the rodent lacks a rodent Cκ gene at the first engineered endogenous immunoglobulin κ light chain locus.

Embodiment 169

The method of any one of embodiments 158-168, wherein the Cλ gene at the first engineered endogenous immunoglobulin κ light chain locus comprises a rodent Cλ gene.

Embodiment 170

The method of any one of embodiments 158-169, wherein the first engineered endogenous immunoglobulin κ light chain locus further comprises:
(i) one or more human Vλ non-coding sequences, each of which is adjacent to at least one of the one or more human Vλ gene segments, wherein the one or more human Vλ non-coding sequences naturally appears adjacent to a human Vλ gene segment in an endogenous human immunoglobulin λ light chain locus;
(ii) one or more human Jλ non-coding sequences, each of which is adjacent to at least one of the one or more human Jλ gene segments, wherein the one or more human Jλ non-coding sequences naturally appears adjacent to a human Jλ gene segment in an endogenous human immunoglobulin λ light chain locus; or
(iii) any combination thereof.

Embodiment 171

The method of any one of embodiments 158-170, wherein:
(i) the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and
(ii) the one or more human Jλ gene segments comprise Jλ1, Jλ2, Jλ3, Jλ6, Jλ7, or any combination thereof.

Embodiment 172

The method of embodiment 171, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jλ1, Jλ2, Jλ3, Jλ6 or Jλ7 of an endogenous human immunoglobulin λ light chain locus.

Embodiment 173

The method of embodiment 171, wherein the first engineered endogenous immunoglobulin κ light chain locus comprises:

(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 174

The method of any one of embodiments 158-173, wherein:

(i) the one or more human Vλ gene segments comprise Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and (ii) the one or more human Jλ gene segments comprise Jλ1, Jλ2, Jλ3, Jλ6, Jλ7, or any combination thereof.

Embodiment 175

The method of embodiment 174, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 176

The method of embodiment 174, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus, (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 177

The method of any one of embodiments 158-176, wherein the germline genome of the rodent further comprises:

an engineered endogenous immunoglobulin heavy chain locus, comprising:
(a) one or more human $V_H$ gene segments,
(b) one or more human $D_H$ gene segments, and
(c) one or more human $J_H$ gene segments,
wherein the one or more human $V_H$ gene segments, the one or more human $D_H$ gene segments, and the one or more human $J_H$ gene segments are operably linked to one or more rodent immunoglobulin heavy chain constant region genes at the engineered endogenous immunoglobulin heavy chain locus.

Embodiment 178

The method of embodiment 177, wherein the one or more human $V_H$ gene segments, one or more human $D_H$ gene segments, and one or more human $J_H$ gene segments are in place of one or more rodent $V_H$ gene segments, one or more rodent $D_H$ gene segments, one or more rodent $J_H$ gene segments, or a combination thereof.

Embodiment 179

The method of embodiment 177 or 178, wherein the one or more human $V_H$ gene segments, one or more human $D_H$ gene segments, and one or more human $J_H$ gene segments replace one or more rodent $V_H$ gene segments, one or more rodent $D_H$ gene segments, one or more rodent $J_H$ gene segments, or any combination thereof.

Embodiment 180

The method of any one of embodiments 177-179, wherein the engineered endogenous immunoglobulin heavy chain locus further comprises:
(i) one or more human $V_H$ non-coding sequences, each of which is adjacent to at least one of the one or more human $V_H$ gene segments, wherein each of the one or more $V_H$ non-coding sequences naturally appears adjacent to a human $V_H$ gene segment in an endogenous human immunoglobulin heavy chain locus;
(ii) one or more human $D_H$ non-coding sequences, each of which is adjacent to at least one of the one or more human $D_H$ gene segments, wherein each of the one or more $D_H$ non-coding sequences naturally appears adjacent to a human $D_H$ gene segment in an endogenous human immunoglobulin heavy chain locus;
(iii) one or more human $J_H$ non-coding sequences, each of which is adjacent to at least one of the one or more human $J_H$ gene segments, wherein each of the one or more $J_H$ non-coding sequences naturally appears adjacent to a human $J_H$ gene segment in an endogenous human immunoglobulin heavy chain locus; or
(iv) any combination thereof.

Embodiment 181

The method of any one of embodiments 177-180, wherein the one or more rodent immunoglobulin heavy chain constant region genes are one or more endogenous rodent immunoglobulin heavy chain constant region genes.

Embodiment 182

The method of any one of embodiments 177-181, wherein:
(i) the one or more human $V_H$ gene segments comprise $V_H3-7^4$, $V_H3-7^3$, $V_H3-7^2$, $V_H2-70$, $V_H1-69$, $V_H3-66$, $V_H3-64$, $V_H4-61$, $V_H4-59$, $V_H1-58$, $V_H3-53$, $V_H5-51$, $V_H3-49$, $V_H3-48$, $V_H1-46$, $V_H1-45$, $V_H3-43$, $V_H4-39$, $V_H4-34$, $V_H3-33$, $V_H4-31$, $V_H3-30$, $V_H4-28$, $V_H2-26$, $V_H1-24$, $V_H3-23$, $V_H3-21$, $V_H3-20$, $V_H1-18$, $V_H3-15$, $V_H3-13$, $V_H3-11$, $V_H3-9$, $V_H1-8$, $V_H3-7$, $V_H2-5$, $V_H7-4-1$, $V_H4-4$, $V_H1-3$, $V_H1-2$, $V_H6-1$, or any combination thereof,
(ii) the one or more human $D_H$ gene segments comprise $D_H1-1$, $D_H2-2$, $D_H3-3$, $D_H4-4$, $D_H5-5$, $D_H6-6$, $D_H1-7$, $D_H2-8$, $D_H3-9$, $D_H3-10$, $D_H5-12$, $D_H6-13$, $D_H2-15$, $D_H3-16$, $D_H4-17$, $D_H6-19$, $D_H1-20$, $D_H2-21$, $D_H3-22$, $D_H6-25$, $D_H1-26$, $D_H7-27$, or any combination thereof, and
(iii) the one or more human $J_H$ gene segments comprise $J_H1$, $J_H2$, $J_H3$, $J_H4$, $J_H5$, $J_H6$, or any combination thereof.

Embodiment 183

The method of any one of embodiments 177-182, wherein the engineered endogenous immunoglobulin heavy chain locus lacks a functional endogenous rodent Adam6 gene.

Embodiment 184

The method of any one of embodiments 177-183, wherein the germline genome of the rodent further comprises one or more nucleotide sequences encoding one or more rodent ADAM6 polypeptides, functional orthologs, functional homologs, or functional fragments thereof.

Embodiment 185

The method of embodiment 184, wherein the one or more rodent ADAM6 polypeptides, functional orthologs, functional homologs, or functional fragments thereof are expressed.

Embodiment 186

The method of embodiment 184 or 185, wherein the one or more nucleotide sequences encoding one or more rodent ADAM6 polypeptides, functional orthologs, functional homologs, or functional fragments thereof are included on the same chromosome as the engineered endogenous immunoglobulin heavy chain locus.

Embodiment 187

The method of any one of embodiments 184-186, wherein the one or more nucleotide sequences encoding one or more rodent ADAM6 polypeptides, functional orthologs, functional homologs, or functional fragments thereof are included in the engineered endogenous immunoglobulin heavy chain locus.

Embodiment 188

The method of any one of embodiments 184-187, wherein the one or more nucleotide sequences encoding one or more rodent ADAM6 polypeptides, functional orthologs, functional homologs, or functional fragments thereof are in place of a human Adam6 pseudogene.

Embodiment 189

The method of any one of embodiments 184-188, wherein the one or more nucleotide sequences encoding one or more rodent ADAM6 polypeptides, functional orthologs, functional homologs, or functional fragments thereof replace a human Adam6 pseudogene.

Embodiment 190

The method of any one of embodiments 184-189, wherein the one or more nucleotide sequences encoding one or more rodent ADAM6 polypeptides, functional orthologs, functional homologs, or functional fragments thereof are between a first human $V_H$ gene segment and a second human $V_H$ gene segment.

Embodiment 191

The method of embodiment 190, wherein the first human $V_H$ gene segment is $V_H1-2$ and the second human $V_H$ gene segment is $V_H6-1$.

Embodiment 192

The method of any one of embodiments 184-187, wherein the one or more nucleotide sequences encoding one or more rodent ADAM6 polypeptides, functional orthologs, functional homologs, or functional fragments thereof are between a human $V_H$ gene segment and a human $D_H$ gene segment.

Embodiment 193

The method of any one embodiments 177-192, wherein the rodent is homozygous for the engineered endogenous immunoglobulin heavy chain locus.

Embodiment 194

The method of any one of embodiments 158-193, wherein the rodent comprises a population of B cells that express antibodies, including immunoglobulin λ light chains that each include a human immunoglobulin λ light chain variable domain.

Embodiment 195

The method of embodiment 194, wherein the human immunoglobulin λ light chain variable domain is encoded by a rearranged human immunoglobulin λ light chain variable region sequence comprising (i) one of the one or more human Vλ gene segments or a somatically hypermutated variant thereof, and (ii) one of the one or more human Jλ gene segments or a somatically hypermutated variant thereof.

Embodiment 196

The method of any one of embodiments 158-195, wherein the germline genome of the rodent further comprises a nucleic acid sequence encoding an exogenous terminal deoxynucleotidyltransferase (TdT) operably linked to a transcriptional control element.

Embodiment 197

The method of embodiment 196, wherein the TdT is a short isoform of TdT (TdTS).

Embodiment 198

The method of embodiment 196 or 197, wherein the transcriptional control element comprises a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof.

Embodiment 199

The method of any one of embodiments 196-198, wherein the nucleic acid sequence encoding an exogenous TdT is in the germline genome at an immunoglobulin κ light chain locus, an immunoglobulin λ light chain locus, an immunoglobulin heavy chain locus, a RAG1 locus, or a RAG2 locus.

Embodiment 200

The method any one of embodiments 158-199, wherein the rodent is a rat or a mouse.

Embodiment 201

A rodent embryonic stem (ES) cell, whose genome comprises:
a first engineered endogenous immunoglobulin κ light chain locus comprising:
(a) one or more human Vλ gene segments,
(b) one or more human Jλ gene segments, and
(c) a Cλ gene,
wherein the one or more human Vλ gene segments and the one or more human Jλ gene segments are operably linked to the Cλ gene, and
wherein the rodent ES cell lacks a rodent Cκ gene at the first engineered endogenous immunoglobulin κ light chain locus.

Embodiment 202

The rodent ES cell of embodiment 201, wherein the rodent ES cell is homozygous for the first engineered endogenous immunoglobulin κ light chain locus.

Embodiment 203

The rodent ES cell of embodiment 201, wherein the rodent ES cell is heterozygous for the first engineered endogenous immunoglobulin κ light chain locus.

Embodiment 204

The rodent ES cell of embodiment 203, wherein the genome of the rodent ES cell comprises a second engineered endogenous immunoglobulin κ light chain locus comprising:
(i) one or more human Vκ gene segments, and
(ii) one or more human Jκ gene segments,
wherein the one or more human Vκ gene segments and the one or more human Jκ gene segments are operably linked to a Cκ gene.

Embodiment 205

The rodent ES cell of embodiment 204, wherein the Cκ gene at the second engineered endogenous immunoglobulin κ light chain locus is an endogenous rodent Cκ gene.

Embodiment 206

The rodent ES cell of any one of embodiments 201-205, wherein the genome of the rodent ES cell comprises an engineered endogenous immunoglobulin heavy chain locus comprising:

(i) one or more human V$_H$ gene segments,
(ii) one or more human D$_H$ gene segments, and
(iii) one or more human J$_H$ gene segments,
wherein the one or more human V$_H$ gene segments, the one or more human D$_H$ gene segments, and the one or more human J$_H$ gene segments are operably linked to one or more rodent immunoglobulin heavy chain constant region genes at the engineered endogenous immunoglobulin heavy chain locus.

Embodiment 207

The rodent ES cell of embodiments 201-206, wherein the rodent lacks a rodent Cκ gene at the first engineered endogenous immunoglobulin κ light chain locus.

Embodiment 208

The rodent ES cell of any one of embodiments 201-207, wherein the Cλ gene at the first engineered endogenous immunoglobulin κ light chain locus comprises a rodent Cλ gene.

Embodiment 209

The rodent ES cell of any one of embodiments 201-208, wherein the first engineered endogenous immunoglobulin κ light chain locus further comprises:
(i) one or more human Vλ non-coding sequences, each of which is adjacent to at least one of the one or more human Vλ gene segments, wherein the one or more human Vλ non-coding sequences naturally appears adjacent to a human Vλ gene segment in an endogenous human immunoglobulin λ light chain locus;
(ii) one or more human Jλ non-coding sequences, each of which is adjacent to at least one of the one or more human Jλ gene segments, wherein the one or more human Jλ non-coding sequences naturally appears adjacent to a human Jλ gene segment in an endogenous human immunoglobulin λ light chain locus; or
(iii) any combination thereof.

Embodiment 210

The rodent ES cell of any one of embodiments 201-209, wherein:
(i) the one or more human Vλ gene segments comprise Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and
(ii) the one or more human Jλ gene segments comprise Jλ1, Jλ2, Jλ3, Jλ6, Jλ7, or any combination thereof.

Embodiment 211

The rodent ES cell of embodiment 210, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and
(ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 212

The rodent ES cell of embodiment 210, wherein the first engineered endogenous immunoglobulin κ light chain locus comprises:
(i) one or more human Vλ non-coding sequences, wherein each of the one or more human Vλ non-coding sequences is adjacent to the Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus,
(ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 213

The rodent ES cell of any one of embodiments 201-212, wherein:
(i) the one or more human Vλ gene segments comprise Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, Vλ3-1, or any combination thereof; and
(ii) the one or more human Jλ gene segments comprise Jλ1, Jλ2, Jλ3, Jλ6, Jλ7, or any combination thereof.

Embodiment 214

The rodent ES cell of embodiment 213, wherein the first engineered endogenous immunoglobulin κ light chain locus comprises:
(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ3-16, Vλ2-14, Vλ3-12, Vλ2-11, Vλ3-10, Vλ3-9, Vλ2-8, Vλ4-3, or Vλ3-1 of an endogenous human immunoglobulin λ light chain locus; and (ii) one or more human Jλ non-coding sequences, wherein each of the one or more human Jλ non-coding sequences is adjacent to the Jλ1, Jλ2, Jλ3, Jλ6 or Jλ7 in the first engineered endogenous immunoglobulin κ light chain locus, and wherein each of the one or more human Jλ non-coding sequences naturally appears adjacent to a Jλ1, Jλ2, Jλ3, Jλ6 or Jλ7 of an endogenous human immunoglobulin λ light chain locus.

Embodiment 215

The rodent ES cell of embodiment 213, wherein the first engineered endogenous immunoglobulin κ light chain locus comprises:

(i) one or more human Vλ non-coding sequences, wherein each of the one or more human Vλ non-coding sequences is adjacent to the Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 in the first engineered endogenous immunoglobulin κ light chain locus, and wherein each of the one or more human Vλ non-coding sequences naturally appears adjacent to a Vλ4-69, Vλ8-61, Vλ4-60, Vλ6-57, Vλ10-54, Vλ5-52, Vλ1-51, Vλ9-49, Vλ1-47, Vλ7-46, Vλ5-45, Vλ1-44, Vλ7-43, Vλ1-40, Vλ5-39, Vλ5-37, Vλ1-36, Vλ3-27, Vλ3-25, Vλ2-23, Vλ3-22, Vλ3-21, Vλ3-19, Vλ2-18, Vλ3-16, Vλ2-14, Vλ3-12, Vλ2-11, Vλ3-10, Vλ3-9, Vλ2-8, Vλ4-3 or Vλ3-1 of an endogenous human immunoglobulin λ light chain locus; and (ii) one or more human Jκ non-coding sequences, wherein each of the one or more human Jκ non-coding sequences is adjacent to the Jλ1, Jλ2, Jλ3, Jλ6 or Jλ7 in the first engineered endogenous immunoglobulin κ light chain locus, and wherein each of the one or more human Jκ non-coding sequences naturally appears adjacent to a Jκ1, Jκ2, Jκ3, Jκ4, or Jκ5 of an endogenous human immunoglobulin κ light chain locus.

Embodiment 216

The rodent ES cell of any one of embodiments 201-215, wherein the genome of the rodent ES cell further comprises:
an engineered endogenous immunoglobulin heavy chain locus, comprising:
(a) one or more human $V_H$ gene segments,
(b) one or more human $D_H$ gene segments, and
(c) one or more human $J_H$ gene segments,
wherein the one or more human $V_H$ gene segments, the one or more human $D_H$ gene segments, and the one or more human $J_H$ gene segments are operably linked to one or more rodent immunoglobulin heavy chain constant region genes at the engineered endogenous immunoglobulin heavy chain locus.

Embodiment 217

The rodent ES cell of embodiment 216, wherein the one or more human $V_H$ gene segments, one or more human $D_H$ gene segments, and one or more human $J_H$ gene segments are in place of one or more rodent $V_H$ gene segments, one or more rodent $D_H$ gene segments, one or more rodent $J_H$ gene segments, or a combination thereof.

Embodiment 218

The rodent ES cell of embodiment 216 or 217, wherein the one or more human $V_H$ gene segments, one or more human $D_H$ gene segments, and one or more human $J_H$ gene segments replace one or more rodent $V_H$ gene segments, one or more rodent $D_H$ gene segments, one or more rodent $J_H$ gene segments, or any combination thereof.

Embodiment 219

The rodent ES cell of any one of embodiments 216-218, wherein the engineered endogenous immunoglobulin heavy chain locus further comprises:
(i) one or more human $V_H$ non-coding sequences, each of which is adjacent to at least one of the one or more human $V_H$ gene segments, wherein each of the one or more $V_H$ non-coding sequences naturally appears adjacent to a human $V_H$ gene segment in an endogenous human immunoglobulin heavy chain locus;
(ii) one or more human $D_H$ non-coding sequences, each of which is adjacent to at least one of the one or more human $D_H$ gene segments, wherein each of the one or more $D_H$ non-coding sequences naturally appears adjacent to a human $D_H$ gene segment in an endogenous human immunoglobulin heavy chain locus;
(iii) one or more human $J_H$ non-coding sequences, each of which is adjacent to at least one of the one or more human $J_H$ gene segments, wherein each of the one or more $J_H$ non-coding sequences naturally appears adjacent to a human $J_H$ gene segment in an endogenous human immunoglobulin heavy chain locus; or
(iv) any combination thereof.

Embodiment 220

The rodent ES cell of any one of embodiments 216-219, wherein the one or more rodent immunoglobulin heavy chain constant region genes are one or more endogenous rodent immunoglobulin heavy chain constant region genes.

Embodiment 221

The rodent ES cell of any one of embodiments 216-220, wherein:
(i) the one or more human $V_H$ gene segments comprise $V_H3-74$, $V_H3-73$, $V_H3-72$, $V_H2-70$, $V_H1-69$, $V_H3-66$, $V_H3-64$, $V_H4-61$, $V_H4-59$, $V_H1-58$, $V_H3-53$, $V_H5-51$, $V_H3-49$, $V_H3-48$, $V_H1-46$, $V_H1-45$, $V_H3-43$, $V_H4-39$, $V_H4-34$, $V_H3-33$, $V_H4-31$, $V_H3-30$, $V_H4-28$, $V_H2-26$, $V_H1-24$, $V_H3-23$, $V_H3-21$, $V_H3-20$, $V_H1-1^8$, $V_H3-1^5$, $V_H3-1^3$, $V_H3-11$, $V_H3-9$, $V_H1-8$, $V_H3-7$, $V_H2-5$, $V_H7-4-1$, $V_H4-4$, $V_H1-3$, $V_H1-2$, $V_H6-1$, or any combination thereof, (ii) the one or more human $D_H$ gene segments comprise $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or any combination thereof, and (iii) the one or more human $J_H$ gene segments comprise $J_H1$, $J_H2$, $J_H3$, $J_H4$, $J_H5$, $J_H6$, or any combination thereof.

Embodiment 222

The rodent ES cell of any one of embodiments 216-221, wherein the engineered endogenous immunoglobulin heavy chain locus lacks a functional endogenous rodent Adam6 gene.

Embodiment 223

The rodent ES cell of any one of embodiments 216-222, wherein the genome of the rodent further comprises one or more nucleotide sequences encoding one or more rodent ADAM6 polypeptides, functional orthologs, functional homologs, or functional fragments thereof.

Embodiment 224

The rodent ES cell of embodiment 223, wherein the one or more nucleotide sequences encoding one or more rodent ADAM6 polypeptides, functional orthologs, functional homologs, or functional fragments thereof are included on the same chromosome as the engineered endogenous immunoglobulin heavy chain locus.

Embodiment 225

The rodent ES cell of embodiment 223 or 224, wherein the one or more nucleotide sequences encoding one or more rodent ADAM6 polypeptides, functional orthologs, functional homologs, or functional fragments thereof are included in the engineered endogenous immunoglobulin heavy chain locus.

Embodiment 226

The rodent ES cell of any one of embodiments 223-225, wherein the one or more nucleotide sequences encoding one or more rodent ADAM6 polypeptides, functional orthologs, functional homologs, or functional fragments thereof are in place of a human Adam6 pseudogene.

Embodiment 227

The rodent ES cell of any one of embodiments 223-226, wherein the one or more nucleotide sequences encoding one or more rodent ADAM6 polypeptides, functional orthologs, functional homologs, or functional fragments thereof replace a human Adam6 pseudogene.

Embodiment 228

The rodent ES cell of any one of embodiments 223-227, wherein the one or more nucleotide sequences encoding one or more rodent ADAM6 polypeptides, functional orthologs, functional homologs, or functional fragments thereof are between a first human $V_H$ gene segment and a second human $V_H$ gene segment.

Embodiment 229

The rodent ES cell of embodiment 228, wherein the first human $V_H$ gene segment is $V_H1$-2 and the second human $V_H$ gene segment is $V_H6$-1.

Embodiment 230

The rodent ES cell of any one of embodiments 223-225, wherein the one or more nucleotide sequences encoding one or more rodent ADAM6 polypeptides, functional orthologs, functional homologs, or functional fragments thereof are between a human $V_H$ gene segment and a human $D_H$ gene segment.

Embodiment 231

The rodent ES cell of any one embodiments 216-230, wherein the rodent cell is homozygous for the engineered endogenous immunoglobulin heavy chain locus.

Embodiment 232

The rodent ES cell of any one of embodiments 201-231, wherein the genome of the rodent ES cell further comprises a nucleic acid sequence encoding an exogenous terminal deoxynucleotidyltransferase (TdT) operably linked to a transcriptional control element.

Embodiment 233

The rodent ES cell of embodiment 232, wherein the TdT is a short isoform of TdT (TdTS).

Embodiment 234

The rodent ES cell of embodiment 232 or 233, wherein the transcriptional control element comprises a RAG1 transcriptional control element, a RAG2 transcriptional control element, an immunoglobulin heavy chain transcriptional control element, an immunoglobulin κ light chain transcriptional control element, an immunoglobulin λ light chain transcriptional control element, or any combination thereof.

Embodiment 235

The rodent ES cell of any one of embodiments 232-234, wherein the nucleic acid sequence encoding an exogenous TdT is at an immunoglobulin κ light chain locus, an immunoglobulin λ light chain locus, an immunoglobulin heavy chain locus, a RAG1 locus, or a RAG2 locus.

Embodiment 236

The rodent ES cell of any one of embodiments 201-235, wherein the rodent ES cell is a rat ES cell or a mouse ES cell.

Embodiment 237

A method of making a fully human antibody specific against an antigen comprising the steps of:
  (a) immunizing a rodent according to any one of embodiments 1-60 with the antigen;
  (b) determining a nucleotide sequence that encodes a human heavy chain variable domain of an antibody that specifically binds the antigen and that was generated by the genetically modified mouse and/or determining a nucleotide sequence that encodes a human λ light chain variable domain of an antibody that specifically binds the antigen and that was generated by the genetically modified mouse; and
(c) expressing a fully human antibody by employing:
  (i) the nucleotide sequence encoding a human heavy chain variable domain of (b) operably linked to a human heavy chain constant region gene, and/or
  (ii) the nucleotide sequence encoding a human λ light chain variable domain of (b) operably linked to a human light chain constant region gene.

Embodiment 238

A method of making a fully human antibody specific against an antigen comprising the steps of:
(a) expressing in a mammalian cell a fully human antibody comprising two human λ light chains and two human heavy chains, wherein each human λ light chain includes a human λ light chain variable domain encoded by a human λ light chain variable region and each human heavy chain includes a human heavy chain variable domain encoded by a human heavy chain variable region, wherein the nucleotide sequence of at least one human heavy or λ light chain variable region was obtained from a rodent according to any one of embodiments 1-60; and
(b) obtaining the fully human antibody.

Embodiment 239

A method of making a fully human antibody specific against an antigen comprising the steps of:
(a) immunizing a rodent according to any one of embodiments 1-60;
(b) determining a human heavy chain variable domain sequence of an antibody that specifically binds the antigen and that was generated by the genetically modified mouse and/or determining of a human λ light chain variable domain sequence of an antibody that specifically binds the antigen and that was generated by the genetically modified mouse; and
(c) expressing a fully human antibody by employing:
  (i) the human heavy chain variable domain sequence of (b) operably linked to a human heavy chain constant domain sequence, and/or
  (ii) the human λ light chain variable domain sequence of (b) operably linked to a human light chain constant domain sequence.

Embodiment 240

The method of embodiment 239, wherein employing the human heavy chain variable domain sequence of (b) operably linked to a human heavy chain constant domain sequence comprises expressing a nucleotide sequence that encodes the human heavy chain variable domain sequence of (b) and the human heavy chain constant domain sequence.

Embodiment 241

The method of embodiment 239 or 240, wherein employing the human λ light chain variable domain sequence of (b) operably linked to a human light chain constant domain sequence comprises expressing a nucleotide sequence that encodes the human λ light chain variable domain sequence of (b) and the human light chain constant domain sequence.

Embodiment 242

A method of making a fully human antibody specific against an antigen comprising the steps of:
(a) expressing in a mammalian cell said fully human antibody comprising two human λ light chains and two human heavy chains, wherein each human λ light chain includes a human light chain variable domain and each human heavy chain includes a human heavy chain variable domain, wherein the amino acid sequence of at least one human heavy or λ light chain variable domain was obtained from a rodent of any one of embodiments 1-60; and
(b) obtaining the fully human antibody.

Embodiment 243

A method for generating a human heavy or λ light chain variable domain sequence comprising the steps of:
(a) immunizing a rodent of any one of embodiments 1-60; and
(b) determining a human heavy or λ light chain variable domain sequence of an antibody that specifically binds the antigen and that was generated by the genetically modified mouse.

Embodiment 244

The method of embodiment 243, wherein determining a human heavy or λ light chain variable domain sequence comprises determining a nucleotide sequence that encodes the human heavy or λ light chain variable domain sequence.

Embodiment 245

A method of making a fully human heavy chain or a fully human light chain comprising the steps of:
(a) immunizing a rodent of any one of embodiments 1-60;
(b) determining a human heavy or λ light chain variable domain sequence of an antibody that specifically binds the antigen and that was generated by the genetically modified mouse; and
(c) operably linking the human heavy or λ light chain variable domain sequence to a human heavy or light chain constant domain sequence, respectively, to form a fully human heavy chain or a fully human light chain.

Embodiment 246

The method of embodiment 245, wherein operably linking the human heavy or λ light chain variable domain sequence to a human heavy or light chain constant domain sequence, respectively, comprises operably linking a nucleotide sequence encoding the human heavy or λ light chain variable domain sequence to a nucleotide sequence encoding the human heavy or light chain constant domain sequence.

Embodiment 247

A method for generating a human heavy or λ light chain variable region sequence comprising the steps of:
(a) immunizing a rodent of any one of embodiments 1-60; and
(b) determining a human heavy or λ light chain variable region sequence that encodes a human heavy or λ light chain variable domain, respectively, of an antibody that specifically binds the antigen and that was generated by the genetically modified mouse.

Embodiment 248

A method of making a nucleotide sequence encoding a fully human heavy chain or a fully human light chain comprising the steps of:
(a) immunizing a rodent of any one of embodiments 1-60;
(b) determining a human heavy or λ light chain variable region sequence that encodes a human heavy or λ light chain variable domain, respectively, of an antibody that specifically binds the antigen and that was generated by the genetically modified mouse; and
(c) operably linking the human heavy or λ light chain variable region sequence to a human heavy or light chain constant region gene, respectively, to form a nucleotide sequence encoding a fully human heavy chain or a fully human light chain.

EQUIVALENTS

It is to be appreciated by those skilled in the art that various alterations, modifications, and improvements to the present disclosure will readily occur to those skilled in the art. Such alterations, modifications, and improvements are intended to be part of the present disclosure, and are intended to be within the spirit and scope of the invention. Accordingly, the foregoing description and drawing are by way of example only and any invention described in the present disclosure if further described in detail by the claims that follow.

Those skilled in the art will appreciate typical standards of deviation or error attributable to values obtained in assays or other processes as described herein. The publications, websites and other reference materials referenced herein to describe the background of the invention and to provide additional detail regarding its practice are hereby incorporated by reference in their entireties.

The invention claimed is:

1. A genetically modified mouse, whose germline genome comprises:
   a first engineered endogenous immunoglobulin κ light chain locus comprising:
   (a) one or more unrearranged human Vλ gene segments,
   (b) one or more unrearranged human Jλ gene segments, and
   (c) a single mouse Cλ gene,
   wherein the one or more unrearranged human Vλ gene segments of (a) and the one or more unrearranged human Jλ gene segments of (b) are in place of one or more endogenous mouse Vκ gene segments and one or more endogenous mouse Jκ gene segments;
   wherein the one or more unrearranged human Vλ gene segments of (a) and the one or more unrearranged human Jλ gene segments of (b) are operably linked to the single mouse Cλ gene;
   wherein the single mouse Cλ gene of (c) is operably linked to a mouse kappa enhancer;
   wherein the genetically modified mouse lacks a mouse Cκ gene at the first engineered endogenous immunoglobulin κ light chain locus;
   wherein the genetically modified mouse comprises a population of B cells that express antibodies,
   wherein the antibodies include immunoglobulin λ light chains that each include:
   (i) a human immunoglobulin λ light chain variable domain encoded by one of the one or more unrearranged human Vλ gene segments of (a) or a somatically hypermuated variant thereof rearranged with one of one or more unrearranged human Jλ gene segments of (b) or a somatically hypermuated variant thereof, and
   (ii) a mouse Cλ domain encoded by the single mouse Cλ gene of (c), and
   wherein the mouse Cλ domain of each immunoglobulin λ light chain of the antibodies is expressed from the single mouse Cλ gene of (c).

2. The genetically modified mouse of claim 1, wherein the genetically modified mouse is homozygous for the first engineered endogenous immunoglobulin κ light chain locus.

3. The genetically modified mouse of claim 1, wherein the genetically modified mouse is heterozygous for the first engineered endogenous immunoglobulin κ light chain locus.

4. The genetically modified mouse of claim 1, wherein the germline genome of the genetically modified mouse comprises a second engineered endogenous immunoglobulin κ light chain locus comprising:

(a) one or more human Vκ gene segments, and
(b) one or more human Jκ gene segments,
wherein the one or more human Vκ gene segments of (a) and the one or more human Jκ gene segments of (b) are operably linked to a Cκ gene.

5. The genetically modified mouse of claim 1, wherein the germline genome of the mouse further comprises:
   an engineered endogenous immunoglobulin heavy chain locus, comprising:
   (a) one or more human $V_H$ gene segments,
   (b) one or more human $D_H$ gene segments, and
   (c) one or more human $J_H$ gene segments,
   wherein the one or more human $V_H$ gene segments of (a), the one or more human $D_H$ gene segments of (b), and the one or more human $J_H$ gene segments of (c) are operably linked to one or more mouse immunoglobulin heavy chain constant region genes at the engineered endogenous immunoglobulin heavy chain locus.

6. The genetically modified mouse of claim 5, wherein the one or more human $V_H$ gene segments of (a), one or more human $D_H$ gene segments of (b), and one or more human $J_H$ gene segments of (c) are in place of one or more mouse $V_H$ gene segments, one or more mouse $D_H$ gene segments, one or more mouse $J_H$ gene segments, or a combination thereof.

7. The genetically modified mouse of claim 5, wherein the engineered endogenous immunoglobulin heavy chain locus further comprises:
   (i) one or more human $V_H$ non-coding sequences, each of which is adjacent to at least one of the one or more human $V_H$ gene segments of (a), wherein each of the one or more $V_H$ non-coding sequences naturally appears adjacent to a human $V_H$ gene segment in an endogenous human immunoglobulin heavy chain locus;
   (ii) one or more human $D_H$ non-coding sequences, each of which is adjacent to at least one of the one or more human $D_H$ gene segments of (b), wherein each of the one or more $D_H$ non-coding sequences naturally appears adjacent to a human $D_H$ gene segment in an endogenous human immunoglobulin heavy chain locus;
   (iii) one or more human $J_H$ non-coding sequences, each of which is adjacent to at least one of the one or more human $J_H$ gene segments of (c), wherein each of the one or more $J_H$ non-coding sequences naturally appears adjacent to a human $J_H$ gene segment in an endogenous human immunoglobulin heavy chain locus; or
   (iv) any combination thereof.

8. The genetically modified mouse of claim 5, wherein the one or more mouse immunoglobulin heavy chain constant region genes are one or more endogenous mouse immunoglobulin heavy chain constant region genes.

9. The genetically modified mouse of claim 5, wherein:

(i) the one or more human $V_H$ gene segments comprise $V_H3$-74, $V_H3$-73, $V_H3$-72, $V_H2$-70, $V_H1$-69, $V_H3$-66, $V_H3$-64, $V_H4$-61, $V_H4$-59, $V_H1$-58, $V_H3$-53, $V_H5$-51, $V_H3$-49, $V_H3$-48, $V_H1$-46, $V_H1$-45, $V_H3$-43, $V_H4$-39, $V_H4$-34, $V_H3$-33, $V_H4$-31, $V_H3$-30, $V_H4$-28, $V_H2$-26, $V_H1$-24, $V_H3$-23, $V_H3$-21, $V_H3$-20, $V_H1$-18, $V_H3$-15, $V_H3$-13, $V_H3$-11, $V_H3$-9, $V_H1$-8, $V_H3$-7, $V_H2$-5, $V_H7$-4-1, $V_H4$-4, $V_H1$-3, $V_H1$-2, $V_H6$-1, or a combination thereof, (ii) the one or more human $D_H$ gene segments comprise $D_H1$-1, $D_H2$-2, $D_H3$-3, $D_H4$-4, $D_H5$-5, $D_H6$-6, $D_H1$-7, $D_H2$-8, $D_H3$-9, $D_H3$-10, $D_H5$-12, $D_H6$-13, $D_H2$-15, $D_H3$-16, $D_H4$-17, $D_H6$-19, $D_H1$-20, $D_H2$-21, $D_H3$-22, $D_H6$-25, $D_H1$-26, $D_H7$-27, or a combination thereof, and (iii) the one or more human $J_H$ gene segments comprise $J_H1$, $J_H2$, $J_H3$, $J_H4$, $J_H5$, $J_H6$, or a combination thereof.

10. The genetically modified mouse of claim 5, wherein the mouse is homozygous for the engineered endogenous immunoglobulin heavy chain locus.

11. The genetically modified mouse of claim 1, wherein the first engineered endogenous immunoglobulin κ light chain locus further comprises a κ light chain non-coding sequence between the one or more unrearranged human Vλ, gene segments and the one or more unrearranged human Jλ, gene segments.

12. The genetically modified mouse of claim 11, wherein the κ light chain non-coding sequence has a sequence that naturally appears between a human Vκ4-1 gene segment and a human Jκ1 gene segment in an endogenous human immunoglobulin κ light chain locus.

13. The genetically modified mouse of claim 1, wherein endogenous Vλ, gene segments, endogenous Jλ, gene segments, and endogenous Cλ, genes are deleted in whole or in part.

14. The genetically modified mouse of claim 1, wherein the germline genome of the genetically modified mouse further comprises a nucleic acid sequence encoding an exogenous terminal deoxynucleotidyltransferase (TdT) operably linked to a transcriptional control element.

\* \* \* \* \*

UNITED STATES PATENT AND TRADEMARK OFFICE
CERTIFICATE OF CORRECTION

PATENT NO.         : 11,051,498 B2
APPLICATION NO.    : 16/209820
DATED              : July 6, 2021
INVENTOR(S)        : Murphy et al.

Page 1 of 1

It is certified that error appears in the above-identified patent and that said Letters Patent is hereby corrected as shown below:

In the Claims

In Claim 1, Column 193, Line 24, please replace "Vλ," with "Vλ";
In Claim 1, Column 193, Line 26, replace "Jλ," with "Jλ";
In Claim 1, Column 193, Line 27, replace "Cλ," with "Cλ";
In Claim 1, Column 193, Line 28, replace "Vλ," with "Vλ";
In Claim 1, Column 193, Line 30, replace "Jλ," with "Jλ";
In Claim 1, Column 193, Line 33, replace "Vλ," with "Vλ";
In Claim 1, Column 193, Line 35, replace "Jλ," with "Jλ";
In Claim 1, Column 193, Line 36, replace "Cλ," with "Cλ";
In Claim 1, Column 193, Line 37, replace "Cλ," with "Cλ";
In Claim 1, Column 193, Line 44, replace "λ," with "λ";
In Claim 1, Column 193, Line 46, replace "λ," with "λ";
In Claim 1, Column 193, Line 48, replace "Vλ," with "Vλ";
In Claim 1, Column 193, Line 50, replace "Jλ," with "Jλ";
In Claim 1, Column 193, Line 53, replace "Cλ," with "Cλ";
In Claim 1, Column 193, Line 54, replace "Cλ," with "Cλ";
In Claim 1, Column 193, Line 55, replace "Cλ," with "Cλ";
In Claim 1, Column 193, Line 56, replace "λ," with "λ";
In Claim 1, Column 193, Line 57, replace "Cλ," with "Cλ";
In Claim 4, Column 194, Line 19, replace "Vιc" with "Vκ";
In Claim 4, Column 194, Line 21, replace "Vιc" with "Vκ";
In Claim 11, Column 196, Line 7, replace "Vλ," with "Vλ";
In Claim 11, Column 196, Line 8, replace "Jλ," with "Jλ";
In Claim 13, Column 196, Line 16, replace "Vλ," with "Vλ";
In Claim 13, Column 196, Line 16, replace "Jλ," with "Jλ"; and
In Claim 13, Column 196, Line 17, replace "Cλ," with "Cλ".

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 77

<210> SEQ ID NO 1
<211> LENGTH: 317
<212> TYPE: DNA
<213> ORGANISM: Mus sp.

<400> SEQUENCE: 1
gccagcccaa gtcttcgcca tcagtcaccc tgtttccacc ttcctctgaa gagctcgaga      60
ctaacaaggc cacactggtg tgtacgatca ctgatttcta cccaggtgtg gtgacagtgg     120
actggaaggt agatggtacc cctgtcactc agggtatgga gacaacccag ccttccaaac     180
agagcaacaa caagtacatg gctagcagct acctgaccct gacagcaaga gcatgggaaa     240
ggcatagcag ttacagctgc caggtcactc atgaaggtca cactgtggag aagagtttgt     300
cccgtgctga ctgttcc                                                    317

<210> SEQ ID NO 2
<211> LENGTH: 106
<212> TYPE: PRT
<213> ORGANISM: Mus sp.

<400> SEQUENCE: 2

Gly Gln Pro Lys Ser Ser Pro Ser Val Thr Leu Phe Pro Pro Ser Ser
1               5                   10                  15

Glu Glu Leu Glu Thr Asn Lys Ala Thr Leu Val Cys Thr Ile Thr Asp
            20                  25                  30

Phe Tyr Pro Gly Val Val Thr Val Asp Trp Lys Val Asp Gly Thr Pro
        35                  40                  45

Val Thr Gln Gly Met Glu Thr Thr Gln Pro Ser Lys Gln Ser Asn Asn
    50                  55                  60

Lys Tyr Met Ala Ser Ser Tyr Leu Thr Leu Thr Ala Arg Ala Trp Glu
65                  70                  75                  80

Arg His Ser Ser Tyr Ser Cys Gln Val Thr His Glu Gly His Thr Val
                85                  90                  95

Glu Lys Ser Leu Ser Arg Ala Asp Cys Ser
            100                 105

<210> SEQ ID NO 3
<211> LENGTH: 314
```

```
<212> TYPE: DNA
<213> ORGANISM: Mus sp.

<400> SEQUENCE: 3
gtcagcccaa gtccactccc actctcaccg tgtttccacc ttcctctgag gagctcaagg      60
aaaacaaagc cacactggtg tgtctgattt ccaacttttc cccgagtggt gtgacagtgg     120
cctggaaggc aaatggtaca cctatcaccc agggtgtgga cacttcaaat cccaccaaag     180
agggcaacaa gttcatggcc agcagcttcc tacatttgac atcggaccag tggagatctc     240
acaacagttt tacctgtcaa gttacacatg aaggggacac tgtggagaag agtctgtctc     300
ctgcagaatg tctc                                                      314

<210> SEQ ID NO 4
<211> LENGTH: 105
<212> TYPE: PRT
<213> ORGANISM: Mus sp.

<400> SEQUENCE: 4

Gly Gln Pro Lys Ser Thr Pro Thr Leu Thr Val Phe Pro Pro Ser Ser
1               5                   10                  15

Glu Glu Leu Lys Glu Asn Lys Ala Thr Leu Val Cys Leu Ile Ser Asn
            20                  25                  30

Phe Ser Pro Ser Gly Val Thr Val Ala Trp Lys Ala Asn Gly Thr Pro
        35                  40                  45

Ile Thr Gln Gly Val Asp Thr Ser Asn Pro Thr Lys Glu Gly Asn Lys
    50                  55                  60

Phe Met Ala Ser Ser Phe Leu His Leu Thr Ser Asp Gln Trp Arg Ser
65                  70                  75                  80

His Asn Ser Phe Thr Cys Gln Val Thr His Glu Gly Asp Thr Val Glu
                85                  90                  95

Lys Ser Leu Ser Pro Ala Glu Cys Leu
            100                 105

<210> SEQ ID NO 5
<211> LENGTH: 314
<212> TYPE: DNA
<213> ORGANISM: Mus sp.

<400> SEQUENCE: 5
gtcagcccaa gtccactccc acactcacca tgtttccacc ttcccctgag gagctccagg      60
aaaacaaagc cacactcgtg tgtctgattt ccaattttc cccaagtggt gtgacagtgg      120
cctggaaggc aaatggtaca cctatcaccc agggtgtgga cacttcaaat cccaccaaag     180
aggacaacaa gtacatggcc agcagcttct tacatttgac atcggaccag tggagatctc     240
acaacagttt tacctgccaa gttacacatg aaggggacac tgtggagaag agtctgtctc     300
ctgcagaatg tctc                                                      314

<210> SEQ ID NO 6
<211> LENGTH: 105
<212> TYPE: PRT
<213> ORGANISM: Mus sp.

<400> SEQUENCE: 6

Gly Gln Pro Lys Ser Thr Pro Thr Leu Thr Met Phe Pro Pro Ser Pro
1               5                   10                  15

Glu Glu Leu Gln Glu Asn Lys Ala Thr Leu Val Cys Leu Ile Ser Asn
            20                  25                  30
```

```
Phe Ser Pro Ser Gly Val Thr Val Ala Trp Lys Ala Asn Gly Thr Pro
            35                  40                  45

Ile Thr Gln Gly Val Asp Thr Ser Asn Pro Thr Lys Glu Asp Asn Lys
         50                  55                  60

Tyr Met Ala Ser Ser Phe Leu His Leu Thr Ser Asp Gln Trp Arg Ser
 65                  70                  75                  80

His Asn Ser Phe Thr Cys Gln Val Thr His Glu Gly Asp Thr Val Glu
                 85                  90                  95

Lys Ser Leu Ser Pro Ala Glu Cys Leu
                100                 105

<210> SEQ ID NO 7
<211> LENGTH: 314
<212> TYPE: DNA
<213> ORGANISM: Rattus sp.

<400> SEQUENCE: 7
gtcagcccaa gtccactccc acactcacag tatttccacc ttcaactgag gagctccagg      60
gaaacaaagc cacactggtg tgtctgattt ctgatttcta cccgagtgat gtggaagtgg     120
cctggaaggc aaatggtgca cctatctccc agggtgtgga cactgcaaat cccaccaaac     180
agggcaacaa atacatcgcc agcagcttct tacgtttgac agcagaacag tggagatctc     240
gcaacagttt tacctgccaa gttacacatg aagggaacac tgtggagaag agtctgtctc     300
ctgcagaatg tgtc                                                       314

<210> SEQ ID NO 8
<211> LENGTH: 105
<212> TYPE: PRT
<213> ORGANISM: Rattus sp.

<400> SEQUENCE: 8

Gly Gln Pro Lys Ser Thr Pro Thr Leu Thr Val Phe Pro Pro Ser Thr
 1               5                  10                  15

Glu Glu Leu Gln Gly Asn Lys Ala Thr Leu Val Cys Leu Ile Ser Asp
             20                  25                  30

Phe Tyr Pro Ser Asp Val Glu Val Ala Trp Lys Ala Asn Gly Ala Pro
            35                  40                  45

Ile Ser Gln Gly Val Asp Thr Ala Asn Pro Thr Lys Gln Gly Asn Lys
         50                  55                  60

Tyr Ile Ala Ser Ser Phe Leu Arg Leu Thr Ala Glu Gln Trp Arg Ser
 65                  70                  75                  80

Arg Asn Ser Phe Thr Cys Gln Val Thr His Glu Gly Asn Thr Val Glu
                 85                  90                  95

Lys Ser Leu Ser Pro Ala Glu Cys Val
                100                 105

<210> SEQ ID NO 9
<211> LENGTH: 314
<212> TYPE: DNA
<213> ORGANISM: Rattus sp.

<400> SEQUENCE: 9
accaacccaa ggctacgccc tcagtcaccc tgttcccacc ttcctctgaa gagctcaaga      60
ctgacaaggc tacactggtg tgtatggtga cagatttcta ccctggtgtt atgacagtgg     120
tctggaaggc agatggtacc cctatcactc agggtgtgga gactacccag cctttcaaac     180
```

```
agaacaacaa gtacatggct accagctacc tgcttttgac agcaaaagca tgggagactc    240
atagcaatta cagctgccag gtcactcacg aagagaacac tgtggagaag agtttgtccc    300
gtgctgagtg ttcc                                                     314
```

<210> SEQ ID NO 10
<211> LENGTH: 105
<212> TYPE: PRT
<213> ORGANISM: Rattus sp.

<400> SEQUENCE: 10

```
Asp Gln Pro Lys Ala Thr Pro Ser Val Thr Leu Phe Pro Pro Ser Ser
1               5                   10                  15

Glu Glu Leu Lys Thr Asp Lys Ala Thr Leu Val Cys Met Val Thr Asp
            20                  25                  30

Phe Tyr Pro Gly Val Met Thr Val Val Trp Lys Ala Asp Gly Thr Pro
        35                  40                  45

Ile Thr Gln Gly Val Glu Thr Thr Gln Pro Phe Lys Gln Asn Asn Lys
    50                  55                  60

Tyr Met Ala Thr Ser Tyr Leu Leu Leu Thr Ala Lys Ala Trp Glu Thr
65                  70                  75                  80

His Ser Asn Tyr Ser Cys Gln Val Thr His Glu Gly Asn Thr Val Glu
                85                  90                  95

Lys Ser Leu Ser Arg Ala Glu Cys Ser
            100                 105
```

<210> SEQ ID NO 11
<211> LENGTH: 314
<212> TYPE: DNA
<213> ORGANISM: Rattus sp.

<400> SEQUENCE: 11

```
gtcagcccaa gtccactccc acactcacag tatttccacc ttcaactgag gagctccagg     60
gaaacaaagc cacactggtg tgtctgattt ctgatttcta cccgagtgat gtggaagtgg    120
cctggaaggc aaatggtgca cctatctccc agggtgtgga cactgcaaat cccaccaaac    180
agggcaacaa atacatcgcc agcagcttct tacgtttgac agcagaacag tggagatctc    240
gcaacagttt tacctgccaa gttacacatg aagggaacac tgtggaaaag agtctgtctc    300
ctgcagagtg tgtc                                                     314
```

<210> SEQ ID NO 12
<211> LENGTH: 105
<212> TYPE: PRT
<213> ORGANISM: Rattus sp.

<400> SEQUENCE: 12

```
Gly Gln Pro Lys Ser Thr Pro Thr Leu Thr Val Phe Pro Pro Ser Thr
1               5                   10                  15

Glu Glu Leu Gln Gly Asn Lys Ala Thr Leu Val Cys Leu Ile Ser Asp
            20                  25                  30

Phe Tyr Pro Ser Asp Val Glu Val Ala Trp Lys Ala Asn Gly Ala Pro
        35                  40                  45

Ile Ser Gln Gly Val Asp Thr Ala Asn Pro Thr Lys Gln Gly Asn Lys
    50                  55                  60

Tyr Ile Ala Ser Ser Phe Leu Arg Leu Thr Ala Glu Gln Trp Arg Ser
65                  70                  75                  80

Arg Asn Ser Phe Thr Cys Gln Val Thr His Glu Gly Asn Thr Val Glu
```

Lys Ser Leu Ser Pro Ala Glu Cys Val
            100                 105

<210> SEQ ID NO 13
<211> LENGTH: 314
<212> TYPE: DNA
<213> ORGANISM: Rattus sp.

<400> SEQUENCE: 13
accaacccaa ggctacgccc tcagtcaccc tgttcccacc ttcctctgaa gagctcaaga    60
ctgacaaggc tacactggtg tgtatggtga cagatttcta ccctggtgtt atgacagtgg   120
tctggaaggc agatggtacc cctatcactc agggtgtgga gactacccag cctttcaaac   180
agaacaacaa gtacatggct accagctacc tgcttttgac agcaaaagca tgggagactc   240
atagcaatta cagctgccag gtcactcacg aagagaacac tgtggagaag agtttgtccc   300
gtgctgagtg ttcc                                                    314

<210> SEQ ID NO 14
<211> LENGTH: 105
<212> TYPE: PRT
<213> ORGANISM: Rattus sp.

<400> SEQUENCE: 14

Asp Gln Pro Lys Ala Thr Pro Ser Val Thr Leu Phe Pro Pro Ser Ser
1               5                   10                  15

Glu Glu Leu Lys Thr Asp Lys Ala Thr Leu Val Cys Met Val Thr Asp
            20                  25                  30

Phe Tyr Pro Gly Val Met Thr Val Val Trp Lys Ala Asp Gly Thr Pro
        35                  40                  45

Ile Thr Gln Gly Val Glu Thr Thr Gln Pro Phe Lys Gln Asn Asn Lys
    50                  55                  60

Tyr Met Ala Thr Ser Tyr Leu Leu Leu Thr Ala Lys Ala Trp Glu Thr
65                  70                  75                  80

His Ser Asn Tyr Ser Cys Gln Val Thr His Glu Glu Asn Thr Val Glu
                85                  90                  95

Lys Ser Leu Ser Arg Ala Glu Cys Ser
            100                 105

<210> SEQ ID NO 15
<211> LENGTH: 315
<212> TYPE: DNA
<213> ORGANISM: Homo sapiens

<400> SEQUENCE: 15
cccaaggcca accccacggt cactctgttc ccgccctcct ctgaggagct ccaagccaac    60
aaggccacac tagtgtgtct gatcagtgac ttctacccgg gagctgtgac agtggcttgg   120
aaggcagatg gcagccccgt caaggcggga gtggagacga ccaaaccctc aaacagagag   180
aacaacaagt acgcggccag cagctacctg agcctgacgc ccgagcagtg gaagtcccac   240
agaagctaca gctgccaggt cacgcatgaa gggagcaccg tggagaagac agtggcccct   300
acagaatgtt catag                                                   315

<210> SEQ ID NO 16
<211> LENGTH: 104
<212> TYPE: PRT
<213> ORGANISM: Homo sapiens

<400> SEQUENCE: 16

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 17
<211> LENGTH: 317
<212> TYPE: DNA
<213> ORGANISM: Homo sapiens

<400> SEQUENCE: 17
gtcagcccaa ggctgccccc tcggtcactc tgttcccgcc ctcctctgag gagcttcaag    60
ccaacaaggc cacactggtg tgtctcataa gtgacttcta cccgggagcc gtgacagtgg   120
cttggaaagc agatagcagc cccgtcaagg cgggagtgga gaccaccaca ccctccaaac   180
aaagcaacaa caagtacgcg gccagcagct atctgagcct gacgcctgag cagtggaagt   240
cccacagaag ctacagctgc caggtcacgc atgaagggag caccgtggag aagacagtgg   300
cccctacaga atgttca                                                  317

<210> SEQ ID NO 18
<211> LENGTH: 105
<212> TYPE: PRT
<213> ORGANISM: Homo sapiens

<400> SEQUENCE: 18

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 19
<211> LENGTH: 315
<212> TYPE: DNA
<213> ORGANISM: Homo sapiens

<400> SEQUENCE: 19

```
cccaaggctg ccccctcggt cactctgttc ccaccctcct ctgaggagct tcaagccaac      60
aaggccacac tggtgtgtct cataagtgac ttctacccgg gagccgtgac agttgcctgg     120
aaggcagata gcagcccgt caaggcgggg gtggagacca ccacaccctc caaacaaagc      180
aacaacaagt acgcggccag cagctacctg agcctgacgc tgagcagtg gaagtcccac      240
aaaagctaca gctgccaggt cacgcatgaa gggagcaccg tggagaagac agttgcccct    300
acggaatgtt catag                                                      315
```

<210> SEQ ID NO 20
<211> LENGTH: 104
<212> TYPE: PRT
<213> ORGANISM: Homo sapiens

<400> SEQUENCE: 20

```
Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 21
<211> LENGTH: 321
<212> TYPE: DNA
<213> ORGANISM: Homo sapiens

<400> SEQUENCE: 21

```
ggtcagccca aggctgcccc atcggtcact ctgttcccgc cctcctctga ggagcttcaa      60
gccaacaagg ccacactggt gtgcctgatc agtgacttct acccgggagc tgtgaaagtg    120
gcctggaagg cagatggcag ccccgtcaac acgggagtgg agaccaccac acctccaaa     180
cagagcaaca acaagtacgc ggccagcagc tacctgagcc tgacgcctga gcagtggaag    240
tcccacagaa gctacagctg ccaggtcacg catgaaggga gcaccgtgga agacagtg      300
gcccctgcag aatgttcata g                                               321
```

<210> SEQ ID NO 22
<211> LENGTH: 105
<212> TYPE: PRT
<213> ORGANISM: Homo sapiens

<400> SEQUENCE: 22

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Lys Val Ala Trp Lys Ala Asp Gly Ser Pro Val
        35                  40                  45
```

```
Asn Thr Gly Val Glu Thr Thr Thr Pro Ser Lys Gln Ser Asn Asn Lys
         50                  55                  60

Tyr Ala Ala Ser Ser Tyr Leu Ser Leu Thr Pro Glu Gln Trp Lys Ser
 65                  70                  75                  80

His Arg Ser Tyr Ser Cys Gln Val Thr His Glu Gly Ser Thr Val Glu
                 85                  90                  95

Lys Thr Val Ala Pro Ala Glu Cys Ser
            100                 105

<210> SEQ ID NO 23
<211> LENGTH: 317
<212> TYPE: DNA
<213> ORGANISM: Homo sapiens

<400> SEQUENCE: 23
gtcagcccaa ggctgccccc tcggtcactc tgttcccacc ctcctctgag gagcttcaag     60
ccaacaaggc cacactggtg tgtctcgtaa gtgacttcta cccggggagcc gtgacagtgg   120 cctggaaggc agatggcagc ccgtcaagg tgggagtgga gaccaccaaa ccctccaaac   180
aaagcaacaa caagtatgcg ccagcagct acctgagcct gacgcccgag cagtggaagt   240
cccacagaag ctacagctgc cgggtcacgc atgaagggag caccgtggag aagacagtgg   300
cccctgcaga atgctct                                                  317

<210> SEQ ID NO 24
<211> LENGTH: 105
<212> TYPE: PRT
<213> ORGANISM: Homo sapiens

<400> SEQUENCE: 24

Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Val Ser Asp Phe
             20                  25                  30

Tyr Pro Gly Ala Val Thr Val Ala Trp Lys Ala Asp Gly Ser Pro Val
         35                  40                  45

Lys Val Gly Val Glu Thr Thr Lys Pro Ser Lys Gln Ser Asn Asn Lys
     50                  55                  60

Tyr Ala Ala Ser Ser Tyr Leu Ser Leu Thr Pro Glu Gln Trp Lys Ser
 65                  70                  75                  80

His Arg Ser Tyr Ser Cys Arg Val Thr His Glu Gly Ser Thr Val Glu
                 85                  90                  95

Lys Thr Val Ala Pro Ala Glu Cys Ser
            100                 105

<210> SEQ ID NO 25
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 25
gtggaagatt gatggcagtg aac                                            23

<210> SEQ ID NO 26
<211> LENGTH: 20
<212> TYPE: DNA
<213> ORGANISM: Artificial Sequence
```

```
<220> FEATURE:
<223> OTHER INFORMATION: Chemically synthesized nucleotide

<400> SEQUENCE: 26
gtgctgctca tgctgtaggt                                          20

<210> SEQ ID NO 27
<211> LENGTH: 27
<212> TYPE: DNA
<213> ORGANISM: Artificial Sequence
<220> FEATURE:
<223> OTHER INFORMATION: Chemically synthesized nucleotide

<400> SEQUENCE: 27
aaatggcgtc ctgaacagtt ggactga                                  27

<210> SEQ ID NO 28
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 28
ccatccagtg agcagttaac atc                                      23

<210> SEQ ID NO 29
<211> LENGTH: 21
<212> TYPE: DNA
<213> ORGANISM: Artificial Sequence
<220> FEATURE:
<223> OTHER INFORMATION: Chemically synthesized nucleotide

<400> SEQUENCE: 29
tgtcgttcac tgccatcaat c                                        21

<210> SEQ ID NO 30
<211> LENGTH: 22
<212> TYPE: DNA
<213> ORGANISM: Artificial Sequence
<220> FEATURE:
<223> OTHER INFORMATION: Chemically synthesized nucleotide

<400> SEQUENCE: 30
aggtgcctca gtcgtgtgct tc                                       22

<210> SEQ ID NO 31
<211> LENGTH: 22
<212> TYPE: DNA
<213> ORGANISM: Artificial Sequence
<220> FEATURE:
<223> OTHER INFORMATION: Chemically synthesized nucleotide

<400> SEQUENCE: 31
ggagcccttc cttgttactt ca                                       22

<210> SEQ ID NO 32
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 32
aggtggaaac agggtgactg atg                                      23
```

<210> SEQ ID NO 33
<211> LENGTH: 24
<212> TYPE: DNA
<213> ORGANISM: Artificial Sequence
<220> FEATURE:
<223> OTHER INFORMATION: Chemically synthesized nucleotide

<400> SEQUENCE: 33
tcctctgtgc ttccttcctc aggc                                    24

<210> SEQ ID NO 34
<211> LENGTH: 25
<212> TYPE: DNA
<213> ORGANISM: Artificial Sequence
<220> FEATURE:
<223> OTHER INFORMATION: Chemically synthesized nucleotide

<400> SEQUENCE: 34
tccttgttac ttcataccat cctct                                   25

<210> SEQ ID NO 35
<211> LENGTH: 22
<212> TYPE: DNA
<213> ORGANISM: Artificial Sequence
<220> FEATURE:
<223> OTHER INFORMATION: Chemically synthesized nucleotide

<400> SEQUENCE: 35
agggtgactg atggcgaaga ct                                      22

<210> SEQ ID NO 36
<211> LENGTH: 20
<212> TYPE: DNA
<213> ORGANISM: Artificial Sequence
<220> FEATURE:
<223> OTHER INFORMATION: Chemically synthesized nucleotide

<400> SEQUENCE: 36
ttccttcctc aggccagccc                                         20

<210> SEQ ID NO 37
<211> LENGTH: 20
<212> TYPE: DNA
<213> ORGANISM: Artificial Sequence
<220> FEATURE:
<223> OTHER INFORMATION: Chemically synthesized nucleotide

<400> SEQUENCE: 37
gaggcttgct gagctttcag                                         20

<210> SEQ ID NO 38
<211> LENGTH: 18
<212> TYPE: DNA
<213> ORGANISM: Artificial Sequence
<220> FEATURE:
<223> OTHER INFORMATION: Chemically synthesized nucleotide

<400> SEQUENCE: 38
aggacggtca gcttggtc                                           18

<210> SEQ ID NO 39
<211> LENGTH: 25
<212> TYPE: DNA
<213> ORGANISM: Artificial Sequence
<220> FEATURE:
<223> OTHER INFORMATION: Chemically synthesized nucleotide -continued

```
<400> SEQUENCE: 39
tatgagcctg tgtcacagtg ttggg                                            25

<210> SEQ ID NO 40
<211> LENGTH: 20
<212> TYPE: DNA
<213> ORGANISM: Artificial Sequence
<220> FEATURE:
<223> OTHER INFORMATION: Chemically synthesized nucleotide

<400> SEQUENCE: 40
gctgacccag gactctgttc                                                  20

<210> SEQ ID NO 41
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 41
tcccagttcc gaagacataa cac                                              23

<210> SEQ ID NO 42
<211> LENGTH: 25
<212> TYPE: DNA
<213> ORGANISM: Artificial Sequence
<220> FEATURE:
<223> OTHER INFORMATION: Chemically synthesized nucleotide

<400> SEQUENCE: 42
ccctttggtg agaagggttt tggtc                                            25

<210> SEQ ID NO 43
<211> LENGTH: 18
<212> TYPE: DNA
<213> ORGANISM: Artificial Sequence
<220> FEATURE:
<223> OTHER INFORMATION: Chemically synthesized nucleotide

<400> SEQUENCE: 43
tacgcggcca gcagctat                                                    18

<210> SEQ ID NO 44
<211> LENGTH: 19
<212> TYPE: DNA
<213> ORGANISM: Artificial Sequence
<220> FEATURE:
<223> OTHER INFORMATION: Chemically synthesized nucleotide

<400> SEQUENCE: 44
tggcagctgt agcttctgt                                                   19

<210> SEQ ID NO 45
<211> LENGTH: 21
<212> TYPE: DNA
<213> ORGANISM: Artificial Sequence
<220> FEATURE:
<223> OTHER INFORMATION: Chemically synthesized nucleotide

<400> SEQUENCE: 45
ctgagcctga cgcctgagca g                                                21

<210> SEQ ID NO 46
```

-continued

```
<211> LENGTH: 21
<212> TYPE: DNA
<213> ORGANISM: Artificial Sequence
<220> FEATURE:
<223> OTHER INFORMATION: Chemically synthesized nucleotide

<400> SEQUENCE: 46
tcaacctttc ccagcctgtc t                                              21

<210> SEQ ID NO 47
<211> LENGTH: 24
<212> TYPE: DNA
<213> ORGANISM: Artificial Sequence
<220> FEATURE:
<223> OTHER INFORMATION: Chemically synthesized nucleotide

<400> SEQUENCE: 47
ccccagagag agaaaacaga tttt                                           24

<210> SEQ ID NO 48

<400> SEQUENCE: 48

000

<210> SEQ ID NO 49
<211> LENGTH: 16
<212> TYPE: DNA
<213> ORGANISM: Artificial Sequence
<220> FEATURE:
<223> OTHER INFORMATION: Chemically synthesized nucleotide

<400> SEQUENCE: 49
accctctgct gtccct                                                    16

<210> SEQ ID NO 50
<211> LENGTH: 19
<212> TYPE: DNA
<213> ORGANISM: Artificial Sequence
<220> FEATURE:
<223> OTHER INFORMATION: Chemically synthesized nucleotide

<400> SEQUENCE: 50
ggtggagagg ctattcggc                                                 19

<210> SEQ ID NO 51
<211> LENGTH: 17
<212> TYPE: DNA
<213> ORGANISM: Artificial Sequence
<220> FEATURE:
<223> OTHER INFORMATION: Chemically synthesized nucleotide

<400> SEQUENCE: 51
gaacacggcg gcatcag                                                   17

<210> SEQ ID NO 52
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 52
tgggcacaac agacaatcgg ctg                                            23

<210> SEQ ID NO 53
```

```
<211> LENGTH: 17
<212> TYPE: DNA
<213> ORGANISM: Artificial Sequence
<220> FEATURE:
<223> OTHER INFORMATION: Chemically synthesized nucleotide

<400> SEQUENCE: 53
tgcggccgat cttagcc                                                    17

<210> SEQ ID NO 54
<211> LENGTH: 18
<212> TYPE: DNA
<213> ORGANISM: Artificial Sequence
<220> FEATURE:
<223> OTHER INFORMATION: Chemically synthesized nucleotide

<400> SEQUENCE: 54
ttgaccgatt ccttgcgg                                                   18

<210> SEQ ID NO 55
<211> LENGTH: 21
<212> TYPE: DNA
<213> ORGANISM: Artificial Sequence
<220> FEATURE:
<223> OTHER INFORMATION: Chemically synthesized nucleotide

<400> SEQUENCE: 55
acgagcgggt tcggcccatt c                                               21

<210> SEQ ID NO 56
<211> LENGTH: 21
<212> TYPE: DNA
<213> ORGANISM: Artificial Sequence
<220> FEATURE:
<223> OTHER INFORMATION: Chemically synthesized nucleotide

<400> SEQUENCE: 56
gggctacttg aggaccttgc t                                               21

<210> SEQ ID NO 57
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 57 gacagcccctt acagagtttg gaa                                            23

<210> SEQ ID NO 58
<211> LENGTH: 20
<212> TYPE: DNA
<213> ORGANISM: Artificial Sequence
<220> FEATURE:
<223> OTHER INFORMATION: Chemically synthesized nucleotide

<400> SEQUENCE: 58
cagggcctcc atcccaggca                                                 20

<210> SEQ ID NO 59
<211> LENGTH: 23
<212> TYPE: DNA
<213> ORGANISM: Artificial Sequence
<220> FEATURE:
<223> OTHER INFORMATION: Chemically synthesized nucleotide

<400> SEQUENCE: 59
```
atctccctac ttcctggcta atg                                           23

<210> SEQ ID NO 60
<211> LENGTH: 22
<212> TYPE: DNA
<213> ORGANISM: Artificial Sequence
<220> FEATURE:
<223> OTHER INFORMATION: Chemically synthesized nucleotide

<400> SEQUENCE: 60
gcttggaacc tgattggttg tc                                            22

<210> SEQ ID NO 61
<211> LENGTH: 27
<212> TYPE: DNA
<213> ORGANISM: Artificial Sequence
<220> FEATURE:
<223> OTHER INFORMATION: Chemically synthesized nucleotide

<400> SEQUENCE: 61
agccttgatc cttgggaatc caggaca                                       27

<210> SEQ ID NO 62
<211> LENGTH: 20
<212> TYPE: DNA
<213> ORGANISM: Artificial Sequence
<220> FEATURE:
<223> OTHER INFORMATION: Chemically synthesized nucleotide

<400> SEQUENCE: 62
gcaaacaaaa accactggcc                                               20

<210> SEQ ID NO 63
<211> LENGTH: 19
<212> TYPE: DNA
<213> ORGANISM: Artificial Sequence
<220> FEATURE:
<223> OTHER INFORMATION: Chemically synthesized nucleotide

<400> SEQUENCE: 63
ggccacattc catgggttc                                                19

<210> SEQ ID NO 64
<211> LENGTH: 37
<212> TYPE: DNA
<213> ORGANISM: Artificial Sequence
<220> FEATURE:
<223> OTHER INFORMATION: Chemically synthesized nucleotide

<400> SEQUENCE: 64
ctgttcctct aaaactggac tccacagtaa atggaaa                            37

<210> SEQ ID NO 65
<211> LENGTH: 26
<212> TYPE: DNA
<213> ORGANISM: Artificial Sequence
<220> FEATURE:
<223> OTHER INFORMATION: Chemically synthesized nucleotide

<400> SEQUENCE: 65
caccatcgat gtcgacacgc ctaggg                                        26

<210> SEQ ID NO 66
<211> LENGTH: 24
<212> TYPE: DNA

<213> ORGANISM: Artificial Sequence
<220> FEATURE:
<223> OTHER INFORMATION: Chemically synthesized nucleotide

<400> SEQUENCE: 66
caccagtgtg gccttgttag tctc                                            24

<210> SEQ ID NO 67
<211> LENGTH: 55
<212> TYPE: DNA
<213> ORGANISM: Artificial Sequence
<220> FEATURE:
<223> OTHER INFORMATION: Chemically synthesized nucleotide

<400> SEQUENCE: 67
acactctttc cctacacgac gctcttccga tctcagggtg actgatggcg aagac          55

<210> SEQ ID NO 68
<211> LENGTH: 57
<212> TYPE: DNA
<213> ORGANISM: Artificial Sequence
<220> FEATURE:
<223> OTHER INFORMATION: Chemically synthesized nucleotide

<400> SEQUENCE: 68
gtgactggag ttcagacgtg tgctcttccg atctcaccat cgatgtcgac acgccta        57

<210> SEQ ID NO 69
<211> LENGTH: 68
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: modified_base
<222> LOCATION: (30)..(35)
<223> OTHER INFORMATION: a, c, t, g, unknown or other
<220> FEATURE:
<221> NAME/KEY: misc_feature
<222> LOCATION: (30)..(35)
<223> OTHER INFORMATION: n is a, c, g, or t

<400> SEQUENCE: 69
aatgatacgg cgaccaccga gatctacacn nnnnnacact ctttccctac acgacgctct     60
tccgatct                                                              68

<210> SEQ ID NO 70
<211> LENGTH: 64
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: modified_base
<222> LOCATION: (25)..(30)
<223> OTHER INFORMATION: a, c, t, g, unknown or other
<220> FEATURE:
<221> NAME/KEY: misc_feature
<222> LOCATION: (25)..(30)
<223> OTHER INFORMATION: n is a, c, g, or t

<400> SEQUENCE: 70
caagcagaag acggcatacg agatnnnnnn gtgactggag ttcagacgtg tgctcttccg     60
atct                                                                  64

<210> SEQ ID NO 71
<211> LENGTH: 30

```
<212> TYPE: DNA
<213> ORGANISM: Artificial Sequence
<220> FEATURE:
<223> OTHER INFORMATION: Chemically synthesized nucleotide

<400> SEQUENCE: 71
cccatgtact ctgcgttgat accactgctt                                    30

<210> SEQ ID NO 72
<211> LENGTH: 27
<212> TYPE: DNA
<213> ORGANISM: Artificial Sequence
<220> FEATURE:
<223> OTHER INFORMATION: Chemically synthesized nucleotide

<400> SEQUENCE: 72
aagcagtggt atcaacgcag agtacat                                       27

<210> SEQ ID NO 73
<211> LENGTH: 24
<212> TYPE: DNA
<213> ORGANISM: Artificial Sequence
<220> FEATURE:
<223> OTHER INFORMATION: Chemically synthesized nucleotide

<400> SEQUENCE: 73
caccagtgtg gccttgttag tctc                                          24

<210> SEQ ID NO 74
<211> LENGTH: 57
<212> TYPE: DNA
<213> ORGANISM: Artificial Sequence
<220> FEATURE:
<223> OTHER INFORMATION: Chemically synthesized nucleotide

<400> SEQUENCE: 74
gtgactggag ttcagacgtg tgctcttccg atctaagcag tggtatcaac gcagagt      57

<210> SEQ ID NO 75
<211> LENGTH: 57
<212> TYPE: DNA
<213> ORGANISM: Artificial Sequence
<220> FEATURE:
<223> OTHER INFORMATION: Chemically synthesized nucleotide

<400> SEQUENCE: 75
acactctttc cctacacgac gctcttccga tctaaggtgg aaacagggtg actgatg      57

<210> SEQ ID NO 76
<211> LENGTH: 67
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: modified_base
<222> LOCATION: (30)..(35)
<223> OTHER INFORMATION: a, c, t, g, unknown or other
<220> FEATURE:
<221> NAME/KEY: MISC_FEATURE
<222> LOCATION: (30)..(35)
<223> OTHER INFORMATION: a, c, t, g, unknown or other

<400> SEQUENCE: 76
aatgatacgg cgaccaccga gatctacacn nnnnnacact ctttccctac acgacgctct   60
tccgatc                                                             67
```

```
<210> SEQ ID NO 77
<211> LENGTH: 64
<212> TYPE: DNA
<213> ORGANISM: Artificial Sequence
<220> FEATURE:
<223> OTHER INFORMATION: Chemically synthesized nucleotide
<220> FEATURE:
<221> NAME/KEY: MISC_FEATURE
<222> LOCATION: (25)..(30)
<223> OTHER INFORMATION: a, c, t, g, unknown or other

<400> SEQUENCE: 77
caagcagaag acggcatacg agatnnnnnn gtgactggag ttcagacgtg tgctcttccg       60
atct                                                                   64
```